United States Patent
Binch et al.

(10) Patent No.: US 8,633,189 B2
(45) Date of Patent: Jan. 21, 2014

(54) MODULATORS OF CYSTIC FIBROSIS TRANSMEMBRANE CONDUCTANCE REGULATOR

(71) Applicant: Vertex Pharmaceuticals Incorporated, Cambridge, MA (US)

(72) Inventors: Hayley Binch, Encinitas, CA (US); Dennis Hurley, San Marcos, CA (US); Lev T. D. Fanning, San Marcos, CA (US); Peter D. J. Grootenhuis, San Diego, CA (US); Martyn Botfield, Concord, MA (US); Fredrick VanGoor, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/718,539

(22) Filed: Dec. 18, 2012

(65) Prior Publication Data

US 2013/0196983 A1 Aug. 1, 2013

Related U.S. Application Data

(62) Division of application No. 12/643,188, filed on Dec. 21, 2009, now Pat. No. 8,367,660.

(60) Provisional application No. 61/141,631, filed on Dec. 30, 2008.

(51) Int. Cl.
*A61K 31/538* (2006.01)

(52) U.S. Cl.
USPC ........................ 514/230.5; 544/105

(58) Field of Classification Search
USPC ..................................... 514/230.5
See application file for complete search history.

(56) References Cited

FOREIGN PATENT DOCUMENTS

| WO | 2006002421 A1 | 1/2006 |
|---|---|---|
| WO | 2008133274 A1 | 11/2008 |
| WO | 2008147952 A1 | 12/2008 |
| WO | 2009079008 A1 | 6/2009 |
| WO | 2009089057 A1 | 7/2009 |
| WO | 2010068881 A1 | 6/2010 |
| WO | 2010078103 A1 | 7/2010 |

OTHER PUBLICATIONS

Hooker et al., "Interior Surface Modification of Bacteriophage MS2", J.Am. Chem Soc. 2004. 126, 3718-3719.
Ma et al., "High-affinity Activators of Cystic Fibrosis Transmembrane Conductance Regulator (CFTR) Chloride Conductance Identified by High-throughput Screening", The Journal of Biological Chemistry vol. 277, No. 40, Issue of Oct. 4. pp. 37235-37241, 2002.
International Search Report PCT/US2009/068939 dated Feb. 24, 2010.
Cristina Bombieri et al., "Complete mutational screening of the CFTR gene in 120 patients with pulmonary disease" Human Genet (1998) 103: 718-722.
Marc H. Levin et al., "CFTR-Regulated Chloride Transport at the Ocular Surface in Living Mice Measured by Potential Differences" Investigative Ophthamology & Visual Science, Apr. 2005, vol. 46., No. 4.

*Primary Examiner* — Kahsay Habte
(74) *Attorney, Agent, or Firm* — Nancy K. Brennan

(57) ABSTRACT

The present invention relates to modulators of ATP-Binding Cassette ("ABC") transporters or fragments thereof, including Cystic Fibrosis Transmembrane Conductance Regulator, compositions thereof, and methods therewith. The present invention also relates to methods of treating diseases using such CFTR modulators.

24 Claims, No Drawings

MODULATORS OF CYSTIC FIBROSIS TRANSMEMBRANE CONDUCTANCE REGULATOR

CROSS-REFERENCE TO RELATED APPLICATIONS

The present application claims priority under 35 U.S.C. §119 to U.S. Provisional Application No. 61/141,631, filed Dec. 30, 2008 and entitled "MODULATORS OF CYSTIC FIBROSIS TRANSMEMBRANE CONDUCTANCE REGULATOR," the entire contents of which is incorporated herein by reference.

TECHNICAL FIELD OF THE INVENTION

The present invention relates to modulators of cystic fibrosis transmembrane conductance regulator ("CFTR"), compositions thereof, and methods therewith. The present invention also relates to methods of treating diseases using modulators of CFTR.

BACKGROUND OF THE INVENTION

ATP cassette transporters are a family of membrane transporter proteins that regulate the transport of a wide variety of pharmacological agents, potentially toxic drugs, and xenobiotics, as well as anions. They are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 such transporters have been identified and grouped into 7 families based on their sequence identity and function.

One member of the ATP cassette transporters family commonly associated with disease is the cAMP/ATP-mediated anion channel, CFTR. CFTR is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, more than 1000 disease causing mutations in the CF gene have been identified (http://www.genet.sickkids.on.calcftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dolmans et al. (1991), Nature Lond. 354: 526-528; Denning et al., supra; Pasyk and Foskett (1995), J. Cell. Biochem. 270: 12347-50). In addition to ΔF508-CFTR, R117H-CFTR and G551D-CFTR, other disease causing mutations in CFTR that result in defective trafficking, synthesis, and/or channel gating, could be up- or down-regulated to alter anion secretion and modify disease progression and/or severity.

Although CFTR transports a variety of molecules in addition to anions, it is clear that this role (the transport of anions, chloride and bicarbonate) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl- channels expressed on the basolateral surface of the cell. Secondary active transport of chloride from the luminal side leads to the accumulation of intracellular chloride, which can then passively leave the cell via $Cl^-$ ion channels, resulting in a vectorial transport. Arrangement of $Na^+/2Cl^-/K^+$ co-transporter, $Na^+$—$K^+$-ATPase pump and the basolateral membrane K⁺ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Defective bicarbonate transport due to mutations in CFTR is hypothesized to cause defects in certain secretory functions. See, e.g., "Cystic fibrosis: impaired bicarbonate secretion and mucoviscidosis," Paul M. Quinton, Lancet 2008; 372: 415-417.

Mutations in CFTR that are associated with moderate CFTR dysfunction are also evident in patients with conditions that share certain disease manifestations with CF but do not meet the diagnostic criteria for CF. These include congenital bilateral absence of the vas deferens, idiopathic chronic pancreatitis, chronic bronchitis, and chronic rhinosinusitis. Other diseases in which mutant CFTR is believed to be a risk factor along with modifier genes or environmental factors include primary sclerosing cholangitis, allergic bronchopulmonary aspergillosis, and asthma.

Cigarette smoke, hypoxia, and environmental factors that induce hypoxic signaling have also been demonstrated to impair CFTR function and may contribute to certain forms of respiratory disease, such as chronic bronchitis. Diseases that may be due to defective CFTR function but do not meet the diagnostic criteria for CF are characterized as CFTR-related diseases.

In addition to cystic fibrosis, modulation of CFTR activity may be beneficial for other diseases not directly caused by mutations in CFTR, such as secretory diseases and other protein folding diseases mediated by CFTR. CFTR regulates chloride and bicarbonate flux across the epithelia of many cells to control fluid movement, protein solubilization, mucus viscosity, and enzyme activity. Defects in CFTR can cause blockage of the airway or ducts in many organs, including the liver and pancreas. Potentiators are compounds that enhance the gating activity of CFTR present in the cell membrane. Any disease which involves thickening of the mucus, impaired fluid regulation, impaired mucus clearance, or blocked ducts leading to inflammation and tissue destruction could be a candidate for potentiators.

These include, but are not limited to, chronic obstructive pulmonary disease (COPD), asthma, smoke induced COPD, chronic bronchitis, rhinosinusitis, constipation, dry eye disease, and Sjögren's Syndrome, gastro-esophageal reflux disease, gallstones, rectal prolapse, and inflammatory bowel disease. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. In addition, by preventing ongoing infection and inflammation due to improved airway clearance, CFTR modulators may prevent or slow the parenchymal destruction of the airway that characterizes emphysema and reduce or reverse the increase in mucus secreting cell number and size that underlyses mucus hypersecretion in airway diseases. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and may help to alleviate the associated symptoms. Individuals with cystic fibrosis have recurrent episodes of intestinal obstruction and higher incidences of rectal polapse, gallstones, gastro-esophageal reflux disease, GI malignancies, and inflammatory bowel disease, indicating that CFTR function may play an important role in preventing such diseases.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of CFTR by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5 (7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyctransferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to α1-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear palsy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome (due to Prp processing defect), infertility pancreatitis, pancreatic insufficiency, osteoporosis, osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, and liver disease.

Other diseases implicated by a mutation in CFTR include male infertility caused by congenital bilateral absence of the vas deferens (CBAVD), mild pulmonary disease, idiopathic pancreatitis, and allergic bronchopulmonary aspergillosis (ABPA). See, "CFTR-opathies: disease phenotypes associated with cystic fibrosis transmembrane regulator gene mutations," Peader G. Noone and Michael R. Knowles, Respir. Res. 2001, 2: 328-332 (incorporated herein by reference).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR. Although there are numerous causes of diarrhea, the major consequences of diarrheal diseases, resulting from excessive chloride transport are common to all, and include dehydration, acidosis, impaired growth and death. Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients with acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Accordingly, there is a need for potent and selective CFTR potentiators of wild-type and mutant forms of human CFTR. These mutant CFTR forms include, but are not limited to, ΔF508del, G551D, R117H, 2789+5G->A.

There is also a need for modulators of CFTR activity, and compositions thereof, which can be used to modulate the activity of the CFTR in the cell membrane of a mammal.

There is a need for methods of treating diseases caused by mutation in CFTR using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of CFTR activity. These compounds have the general Formula I:

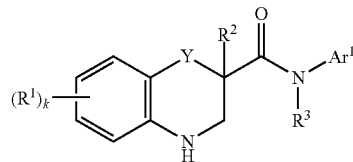

I or a pharmaceutically acceptable salt thereof, wherein $R^1$, $R^2$, $R^3$, Y, and $Ar^1$ are described generally and in classes and subclasses below.

These compounds and pharmaceutically acceptable compositions are useful for treating or lessening the severity of a variety of diseases, disorders, or conditions associated with mutations in CFTR.

DETAILED DESCRIPTION OF THE INVENTION

I. General Description of Compounds of the Invention

The present invention relates to compounds of Formula I useful as modulators of CFTR activity:

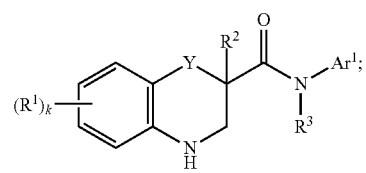

I or pharmaceutically acceptable salts thereof, wherein:

Y is O, S, S(O) or $S(O)_2$;

$Ar^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic ring, wherein each ring contains 0-4 heteroatoms independently selected from nitrogen, oxygen, or sulfur, wherein $Ar^1$ has m substituents, each independently selected from $—WR^W$;

W is a bond or is an optionally substituted $C_1$-$C_6$ alkylidene chain wherein up to two methylene units of W are optionally and independently replaced by O, —CO—, —CS—, —COCO—, —CONR'—, —CONR'NR'—, —$CO_2$—, —OCO—, —$NR'CO_2$—, —O—, —NR'CONR'—, —C(O)NR'—, —OCONR'—, —NR'NR', —NR'NR'CO—, —NR'CO—, —S—, —SO, —$SO_2$—, NR'—, —$SO_2NR'$—, $NR'SO_2$—, or —$NR'SO_2NR'$—;

$R^W$ is independently R', halo, $NO_2$, CN, $CF_3$, $OCF_3$, an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or a 7-12 membered saturated, partially unsaturated, or fully unsaturated bicyclic ring system having 0-5 heteroatoms independently selected from nitrogen, oxygen, or sulfur;

m is 0-5;

k is 0-3;

each of $R^1$ is independently —X—$R^X$;

X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —$CO_2$—, —OCO—, —$NR'CO_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

R$^X$ is independently halo, NO$_2$, CN, CF$_3$, OCF$_3$, OCH$_3$, an optionally substituted group selected from a C$_1$-C$_8$ aliphatic group, a 3-8-membered saturated, partially unsaturated, or fully unsaturated monocyclic ring having 0-3 heteroatoms independently selected from nitrogen, oxygen, or sulfur, or a 7-12 membered saturated, partially unsaturated, or fully unsaturated bicyclic ring system having 0-5 heteroatoms independently selected from nitrogen, oxygen, or sulfur;

R$^2$ is hydrogen, halo, or a C$_1$-C$_6$aliphatic group optionally substituted with —X—R$^X$;

R$^3$ is hydrogen or a C$_1$-C$_6$ aliphatic group optionally substituted with —X—R$^X$;

R' is independently selected from hydrogen, an optionally substituted group selected from a C$_1$-C$_8$ aliphatic group, a 3-8-membered saturated, partially unsaturated, or fully unsaturated monocyclic ring having 0-3 heteroatoms independently selected from nitrogen, oxygen, or sulfur, or a 7-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

provided that when Y is oxygen, R$^2$ is hydrogen and m is 0, Ar$^1$ is not phenyl, pyridyl or pyrimidinyl;

when Y is oxygen, R$^2$ is hydrogen, m is 1, and Ar$^1$ is phenyl or pyridyl, —WR$^W$ is not halo, —C$_1$-C$_3$ aliphatic, —SMe, —OC$_1$-C$_3$ aliphatic, —CN, —NH$_2$ or —CONH$_2$;

when Y is oxygen, R$^2$ is hydrogen, R$^3$ is hydrogen, m is 2, Ar$^1$ is phenyl, pyridyl or pyrimidinyl, and one instance of —WR$^W$ is halo, —CH$_3$, —CH$_2$CH$_3$, or —OCH$_3$, the second instance of —WR$^W$ is not —CH$_3$, —CH$_2$CH$_3$, —OCH$_3$, or halo; and when Y is oxygen, R$^2$ is hydrogen, R$^3$ is hydrogen, m is 3 and Ar$^1$ is phenyl, all instances of —WR$^W$ are not simultaneously halo or C$_1$-C$_3$ aliphatic.

2. Compounds and Definitions

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "CFTR" as used herein means cystic fibrosis transmembrane conductance regulator or a mutation thereof capable of regulator activity, including, but not limited to, ΔF508 CFTR, R117H CFTR, and G551D CFTR (see, e.g., http://www.genet.sickkids.on.ca/cftr/, for CFTR mutations).

The term "modulating" as used herein means increasing or decreasing by a measurable amount.

The term "normal CFTR" or "normal CFTR function" as used herein means wild-type like CFTR without any impairment due to environmental factors such as smoking, pollution, or anything that produces inflammation in the lungs.

The term "reduced CFTR" or "reduced CFTR function" as used herein means less than normal CFTR or less than normal CFTR function.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. In some embodiments, "cycloaliphatic" (or "carbocycle" or "cycloalkyl") refers to a monocyclic C$_3$-C$_8$ hydrocarbon or bicyclic or tricyclic C$_8$-C$_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic," as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle," "heterocyclyl," "heterocycloaliphatic," or "heterocyclic" groups.

The term "heterocycle," "heterocyclyl," "heterocycloaliphatic," or "heterocyclic" as used herein means non-aromatic, monocyclic, bicyclic, or tricyclic ring systems in which one or more ring members is an independently selected heteroatom. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "alkoxy" or "thioalkyl," as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —$CHF_2$, —$CH_2F$, —$CF_3$, —$CF_2$—, or perhaloalkyl, such as, —$CF_2CF_3$.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring." The term "aryl" also refers to heteroaryl ring systems as defined hereinbelow.

The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic."

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halo; —$R^o$; —$OR^o$; —$SR^o$; 1,2-methylene-dioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(O)N$ $(R^o)_2$; —$NR^oCO_2R^o$; —$NR^oNR^oC(O)R^o$; —$NR^oNR^oC(O)$ $N(R^o)_2$; —$NR^oNR^oCO_2R^o$; —$C(O)C(O)R^o$; —$C(O)CH_2C$ $(O)R^o$; —$CO_2R^o$; —$C(O)R^o$; —$C(O)N(R^o)_2$; —$OC(O)N$ $(R^o)_2$; —$S(O)_2R^o$; —$SO_2N(R^o)_2$; —$S(O)R^o$; —$NR^oSO_2N$ $(R^o)_2$; —$NR^oSO_2R^o$; —C(=S)$N(R^o)_2$; —C(=NH)— $N(R^o)_2$; or —$(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^o$ are selected from $NH_2$, $NH(C_{1-4}aliphatic)$, $N(C_{1-4}aliphatic)_2$, halo, $C_{1-4}$aliphatic, OH, $O(C_{1-4}aliphatic)$, $NO_2$, CN, $CO_2H$, $CO_2(C_{1-4}aliphatic)$, $O(haloC_{1-4}$ aliphatic), or halo$C_{1-4}$aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halo, $C_{1-4}$ aliphatic, OH, $O(C_{1-4}$ aliphatic), $NO_2$, CN, $CO_2H$, $CO_2(C_{1-4}$ aliphatic), $O(halo C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —$R^+$, —$N(R^+)_2$, —C(O) $R^+$, —$CO_2R^+$, —$C(O)C(O)R^+$, —$C(O)CH_2C(O)R^+$, —$SO_2R^+$, —$SO_2N(R^+)_2$, —C(=S)$N(R^+)_2$, —C(=NH)—N $(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$ (Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halo, $C_{1-4}$ aliphatic, OH, $O(C_{1-4}$ aliphatic), $NO_2$, CN, $CO_2H$, $CO_2(C_{1-4}$ aliphatic), $O(halo C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

The term "protecting group," as used herein, refers to an agent used to temporarily to block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis," Third Edition, John Wiley & Sons, New York: 1999, and other editions of this book, the entire contents of which are hereby incorporated by reference.

As detailed above, in some embodiments, two independent occurrences of $R^o$ (or $R^+$, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

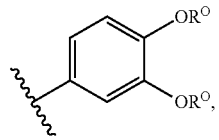

these two occurrences of $R^o$ are taken together with the oxygen atoms to which they are bound to form a fused 6-membered oxygen containing ring:

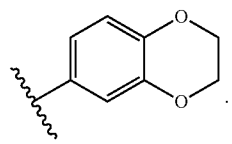 [SMILES: *c1ccc2c(c1)OCCO2 ; "."]

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

A substituent bond in, e.g., a bicyclic ring system, as shown below, means that the substituent can be attached to any substitutable ring atom on either ring of the bicyclic ring system:

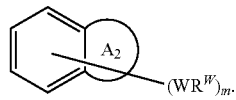

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. e.g., compounds of Formula I may exist as tautomers.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds

According to one embodiment, the present invention provides compounds of Formula IA:

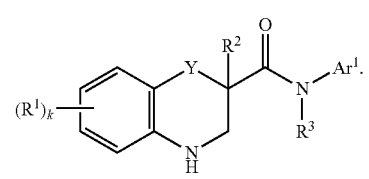

IA

According to one embodiment, the present invention provides compounds of Formula IB:

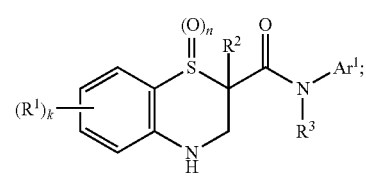

IB wherein n is 0, 1, or 2.

In some embodiments of the present invention, $Ar^1$ is selected from:

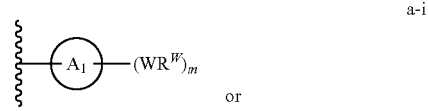

a-i or

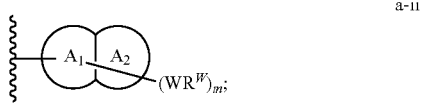

a-ii wherein ring $A_1$ is a 5-6 membered aromatic monocyclic ring having 0-4 heteroatoms independently selected from nitrogen, oxygen, or sulfur; or $A_1$ and $A_2$, together, is an 8-14 membered aromatic, bicyclic or tricyclic aryl ring, wherein each ring contains 0-4 heteroatoms independently selected from nitrogen, oxygen, or sulfur.

In some embodiments, $A_1$ is a 6 membered aromatic ring having 0-4 heteroatoms, wherein said heteroatom is nitrogen. In some embodiments, $A_1$ is phenyl. Or, $A_1$ is pyridyl, pyrimidinyl, pyrazinyl or triazinyl. Or, $A_1$ is an optionally substituted pyrazinyl or triazinyl.

In some embodiments, $A_1$ is an optionally substituted 5-membered aromatic ring having 0-3 heteroatoms, wherein said heteroatom is nitrogen, oxygen, or sulfur. In some embodiments, $A_1$ is an optionally substituted 5-membered aromatic ring having 1-2 nitrogen atoms.

In some embodiments, $A_2$ is an optionally substituted 6 membered aromatic ring having 0-4 heteroatoms, wherein said heteroatom is nitrogen. In some embodiments, $A_2$ is an optionally substituted phenyl. Or, $A_2$ is an optionally substituted pyridyl, pyrimidinyl, pyrazinyl, or triazinyl.

In some embodiments, $A_2$ is an optionally substituted 5-membered aromatic ring having 0-3 heteroatoms, wherein said heteroatom is nitrogen, oxygen, or sulfur. In some embodiments, $A_2$ is an optionally substituted 5-membered aromatic ring having 1-2 nitrogen atoms. In certain embodiments, $A_2$ is an optionally substituted pyrrolyl.

In some embodiments, $A_2$ is an optionally substituted 5-7 membered saturated or unsaturated heterocyclic ring having 1-3 heteroatoms independently selected from nitrogen, sulfur, or oxygen. Exemplary such rings include piperidyl, piperazyl, morpholinyl, thiomorpholinyl, pyrrolidinyl, tetrahydrofuranyl, etc.

In some embodiments, $A_2$ is an optionally substituted 5-10 membered saturated or unsaturated carbocyclic ring. In one embodiment, $A_2$ is an optionally substituted 5-10 membered saturated carbocyclic ring. Exemplary such rings include cyclohexyl, cyclopentyl, etc.

In some embodiments, ring $A_2$ is selected from:

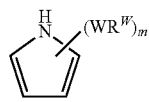

i

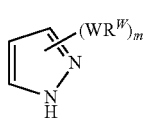

ii

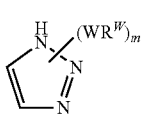

iii

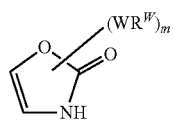

iv

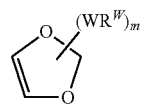

v

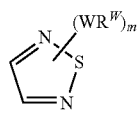

vi

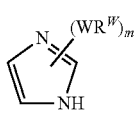

vii

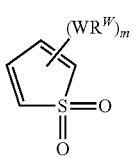

viii

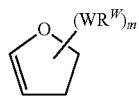

ix

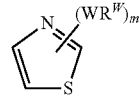

x

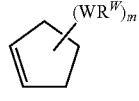

xi

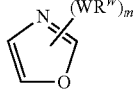

xii

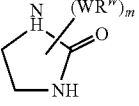

xiii

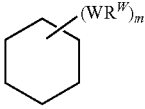

xiv

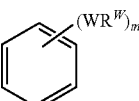

xv

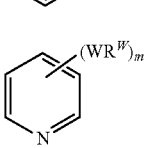

xvi

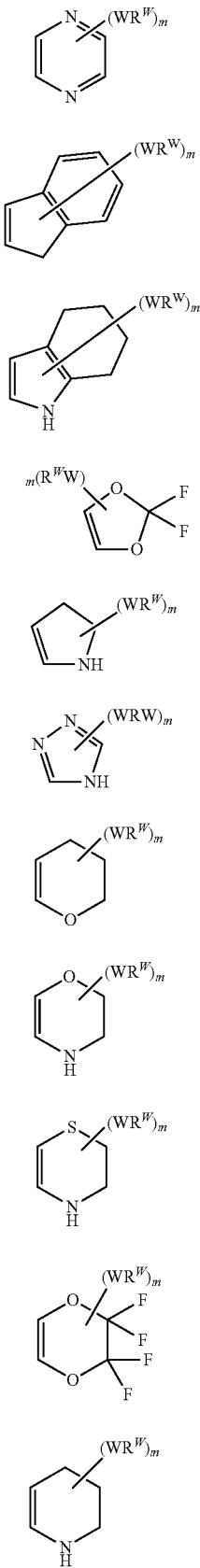
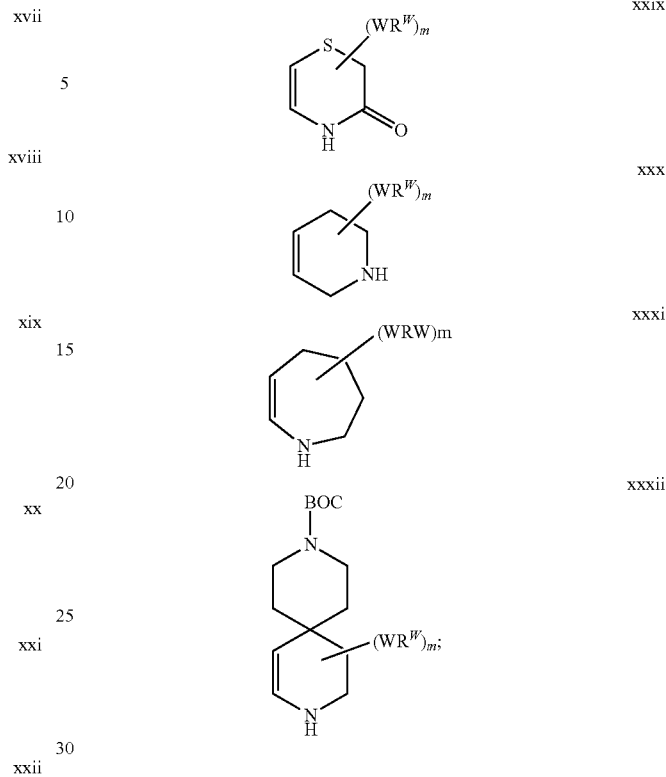

wherein ring $A_2$ is fused to ring $A_1$ through two adjacent ring atoms.

In other embodiments, W is a bond or is an optionally substituted $C_1$-$C_6$ alkylidene chain wherein up to two methylene units of W are optionally and independently replaced by O, —CO—, —CS—, —COCO—, —CONR'—, —CONR'NR'—, —CO$_2$—, —OCO—, —NR'CO$_2$—, —O—, —NR'CONR'—, —C(O)NR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—, and $R^W$ is R' or halo.

In still other embodiments, each occurrence of $WR^W$ is independently $C_1$-$C_3$ alkyl, t-butyl, $C_1$-$C_3$ perhaloalkyl, —OH, —O($C_1$-$C_3$alkyl), —CF$_3$, —OCF$_3$, —SCF$_3$, —F, —Cl, —Br, —COOR', —COR', —O(CH$_2$)$_2$N(R')(R'), —O(CH$_2$)N(R')(R'), —CON(R')(R'), —(CH$_2$)$_2$OR', —(CH$_2$)OR', optionally substituted 5-7 membered heterocylic ring, optionally substituted 5-7 membered cycloaliphatic group, optionally substituted monocyclic or bicyclic aromatic ring, optionally substituted arylsulfone, optionally substituted 5-membered heteroaryl ring, —N(R')(R'), —(CH$_2$)$_2$N(R')(R'), —(CH$_2$)$_3$N(R')(R'), —C≡CCH$_2$N(R')(R') or —(CH$_2$)N(R')(R')

In some embodiments, m is 0. Or, m is 1. Or, m is 2. In some embodiments, m is 3. In yet other embodiments, m is 4.

In some embodiments, k is 0. Or, k is 1. Or, k is 2. Or, k is 3.

In one embodiment, k is 1 and $R^1$ is halo.
In one embodiment, k is 1 and $R^1$ is $C_1$-$C_4$ alkyl.
In one embodiment, k is 1 and $R^1$ is Me.
In one embodiment, k is 1 and $R^1$ is —CF$_3$.
In one embodiment, k is 1 and $R^1$ is —OCF$_3$.
In one embodiment, k is 1 and $R^1$ is —OCH$_3$.
In one embodiment, k is 1 and $R^1$ is —F.
In one embodiment, k is 1 and $R^1$ is —SO$_2$Me.

In another embodiment of the present invention, k is 1 or 2 and each $R^1$ is independently $C_1$-$C_4$ alkyl, or halo.

In some embodiments, $R^2$ is hydrogen.

In one embodiment, $R^2$ is halo. In other embodiments, $R^2$ is a $C_1$-$C_6$ aliphatic group optionally substituted with —X—$R^X$.

In some embodiments, $R^3$ is hydrogen.

In further embodiments, $R^2$ and $R^3$ are hydrogen.

In some embodiments, $R^3$ is a $C_1$-$C_6$ aliphatic group optionally substituted with —X—$R^X$.

In one embodiment, $R^3$ is methyl. In another embodiment, $R^3$ is ethyl.

In some embodiments, X is a bond or is an optionally substituted $C_1$-$C_6$ alkylidene chain wherein one or two non-adjacent methylene units are optionally and independently replaced by O, NR', S, $SO_2$, or COO, CO, and $R^X$ is R' or halo. In still other embodiments, each occurrence of $XR^X$ is independently —$C_1$-$C_3$alkyl, —$CF_3$, —$OCF_3$, —$SCF_3$, —F, —Cl, —Br, OH, —COOR', —COR', —O($CH_2$)$_2$N(R')(R'), —O($CH_2$)N(R')(R'), —CON(R')(R'), —($CH_2$)$_2$OR', —($CH_2$)OR', optionally substituted phenyl, —N(R')(R'), —($CH_2$)$_2$N(R')(R'), or —($CH_2$)N(R')(R').

In one embodiment, $R^1$ is H, $C_1$-$C_4$ aliphatic, halo, or $C_3$-$C_6$ cycloaliphatic.

In some embodiments, $R^W$ is selected from halo, cyano, $CF_3$, $CHF_2$, $OCHF_2$, Me, Et, CH(Me)$_2$, CHMeEt, n-propyl, t-butyl, —OH, OMe, OEt, OPh, O-fluorophenyl, O-difluorophenyl, O-methoxyphenyl, O-tolyl, O-benzyl, SMe, $SCF_3$, $SCHF_2$, SEt, $CH_2CN$, $NH_2$, NHMe, N(Me)$_2$, NHEt, N(Et)$_2$, C(O)$CH_3$, C(O)Ph, C(O)$NH_2$, SPh, $SO_2$—(amino-pyridyl), $SO_2NH_2$, $SO_2$Ph, $SO_2$NHPh, $SO_2$—N-morpholino, $SO_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2yl, furan-2-yl, 4-methyl-4H-[1,2,4]triazol-3-yl, 3-(4'-chlorophenyl)-[1,2,4]oxadiazol-5-yl, NHC(O)Me, NHC(O)Et, NHC(O)Ph, $NHSO_2$Me, 2-indolyl, 5-indolyl, —$CH_2CH_2$OH, —$OCF_3$, O-(2,3-dimethylphenyl), 5-methylfuryl, —$SO_2$—N-piperidyl, 2-tolyl, 3-tolyl, 4-tolyl, O-butyl, $NHCO_2$C(Me)$_3$, $CO_2$C(Me)$_3$, isopropenyl, n-butyl, O-(2,4-dichlorophenyl), $NHSO_2$PhMe, O-(3-chloro-5-trifluoromethyl-2-pyridyl), phenylhydroxymethyl, 2-methylpyrrolyl, 3-fluoropyrrolyl, 3,3-difluoropyrrolyl, 3,3-dimethylpyrrolyl, 2,5-dimethylpyrrolyl, $NHCOCH_2$C(Me)$_3$, O-(2-tert-butyl)phenyl, 2,3-dimethylphenyl, 3,4-dimethylphenyl, 4-hydroxymethyl phenyl, 4-dimethylaminophenyl, 2-trifluoromethylphenyl, 3-trifluoromethylphenyl, 4-trifluoromethylphenyl, 4-cyanomethylphenyl, 4-isobutylphenyl, 3-pyridyl, 4-pyridyl, 4-isopropylphenyl, 3-isopropylphenyl, 2-methoxyphenyl, 3-methoxyphenyl, 4-methoxyphenyl, 3,4-methylenedioxyphenyl, 2-ethoxyphenyl, 3-ethoxyphenyl, 4-ethoxyphenyl, 2-methylthiophenyl, 4-methylthiophenyl, 2,4-dimethoxyphenyl, 2,5-dimethoxyphenyl, 2,6-dimethoxyphenyl, 3,4-dimethoxyphenyl, 5-chloro-2-methoxyphenyl, 2-$OCF_3$-phenyl, 3-trifluoromethoxy-phenyl, 4-trifluoromethoxyphenyl, 2-phenoxyphenyl, 4-phenoxyphenyl, 2-fluoro-3-methoxyphenyl, 2,4-dimethoxy-5-pyrimidyl, 5-isopropyl-2-methoxyphenyl, 2-fluorophenyl, 3-fluorophenyl, 4-fluorophenyl, 3-cyanophenyl, 3-chlorophenyl, 4-chlorophenyl, 2,3-difluorophenyl, 2,4-difluorophenyl, 2,5-difluorophenyl, 3,4-difluorophenyl, 3,5-difluorophenyl, 3-chloro-4-fluoro-phenyl, 3,5-dichlorophenyl, 2,5-dichlorophenyl, 2,3-dichlorophenyl, 3,4-dichlorophenyl, 2,4-dichlorophenyl, 3-methoxycarbonylphenyl, 4-methoxycarbonyl phenyl, 3-isopropyloxycarbonylphenyl, 3-acetamidophenyl, 4-fluoro-3-methylphenyl, 4-methanesulfinyl-phenyl, 4-methanesulfonyl-phenyl, 4-N-(2-N,N-dimethylaminoethyl)carbamoylphenyl, 5-acetyl-2-thienyl, 2-benzothienyl, 3-benzothienyl, furan-3-yl, 4-methyl-2-thienyl, 5-cyano-2-thienyl, N'-phenylcarbonyl-N-piperazinyl, —$NHCO_2$Et, —$NHCO_2$Me, N-pyrrolidinyl, —$NHSO_2(CH_2)_2$N-piperidine, —$NHSO_2(CH_2)_2$N-morpholine, $NHSO_2(CH_2)_2$N(Me)$_2$, $COCH_2$N(Me)$COCH_2$NHMe, —$CO_2$Et, O-propyl, —$CH_2CH_2NHCO_2$C(Me)$_3$, aminomethyl, pentyl, adamantyl, cyclopentyl, ethoxyethyl, C(Me)$_2$$CH_2$OH, C(Me)$_2$$CO_2$Et, —CHOHMe, $CH_2CO_2$Et, —C(Me)$_2$$CH_2$$NHCO_2$C(Me)$_3$, O($CH_2$)$_2$OEt, O($CH_2$)$_2$OH, $CO_2$Me, hydroxymethyl, 1-methyl-1-cyclohexyl, 1-methyl-1-cyclooctyl, 1-methyl-1-cycloheptyl, C(Et)$_2$C(Me)$_3$, C(Et)$_3$, $CONHCH_2$CH(Me)$_2$, 2-aminomethyl-phenyl, ethenyl, 1-piperidinylcarbonyl, ethynyl, cyclohexyl, 4-methylpiperidinyl, —$OCO_2$Me, —C(Me)$_2$$CH_2NHCO_2CH_2$CH(Me)$_2$, —C(Me)$_2$$CH_2NHCO_2CH_2CH_2CH_3$, —C(Me)$_2$$CH_2NHCO_2$Et, —C(Me)$_2$$CH_2NHCO_2$Me, —C(Me)$_2$$CH_2NHCO_2CH_2$C(Me)$_3$, —$CH_2NHCOCF_3$, —$CH_2NHCO_2$C(Me)$_3$, —C(Me)$_2$$CH_2NHCO_2(CH_2)_3CH_3$, C(Me)$_2$$CH_2NHCO_2(CH_2)_2$OMe, C(OH) (CF$_3$)$_2$, —C(Me)$_2$$CH_2NHCO_2CH_2$-tetrahydrofurane-3-yl, C(Me)$_2CH_2$O($CH_2)_2$OMe, or 3-ethyl-2,6-dioxopiperidin-3-yl.

In one embodiment, R' is hydrogen.

In one embodiment, R' is a $C_1$-$C_8$ aliphatic group, optionally substituted with up to 3 substituents selected from halo, CN, $CF_3$, $CHF_2$, $OCF_3$, or $OCHF_2$, wherein up to two methylene units of said $C_1$-$C_8$ aliphatic is optionally replaced with —CO—, —CONH($C_1$-$C_4$ alkyl)-, —$CO_2$—, —OCO—, —N($C_1$-$C_4$alkyl)$CO_2$—, —O—, —N($C_1$-$C_4$alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, N($C_1$-$C_4$ alkyl)$SO_2$—, or —N($C_1$-$C_4$ alkyl)$SO_2$N($C_1$-$C_4$ alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or $C_1$-$C_6$ alkyl, wherein up to two methylene units of said $C_1$-$C_6$ alkyl is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, N($C_1$-$C_4$ alkyl)$SO_2$—, or —N($C_1$-$C_4$ alkyl)$SO_2$N($C_1$-$C_4$ alkyl)-.

In one embodiment, R' is a 7-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, CN, $CF_3$, $CHF_2$, $OCF_3$, $OCHF_2$, or $C_1$-$C_6$ alkyl, wherein up to two methylene units of said $C_1$-$C_6$ alkyl is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, N($C_1$-$C_4$ alkyl)$SO_2$—, or —N($C_1$-$C_4$ alkyl)$SO_2$N($C_1$-$C_4$ In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, CN, $CF_3$, $CHF_2$, $OCF_3$, $OCHF_2$, or $C_1$-$C_6$ alkyl, wherein up to two methylene units of said $C_1$-$C_6$ alkyl is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N(C$_1$-C$_4$ alkyl)-, —SO$_2$N(C$_1$-C$_4$ alkyl)-, N(C$_1$-C$_4$ alkyl)SO$_2$—, or —N(C$_1$-C$_4$ alkyl)SO$_2$N(C$_1$-C$_4$ alkyl)-.

According to one embodiment, the present invention provides compounds of Formula IIA:

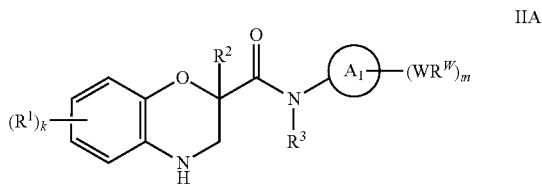

IIA

According to one embodiment, the present invention provides compounds of Formula IIB:

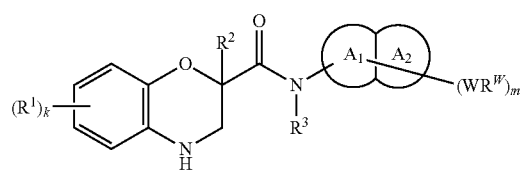

IIB

According to one embodiment, the present invention provides compounds of Formula IIIA:

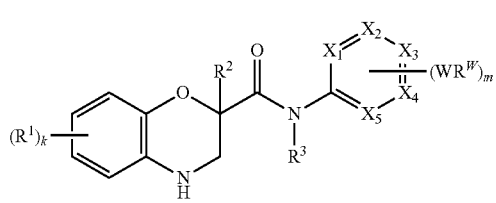

IIIA wherein each of X$_1$, X$_2$, X$_3$, X$_4$, and X$_5$ is independently selected from CH or N.

According to one embodiment, the present invention provides compounds of Formula IIIA-1:

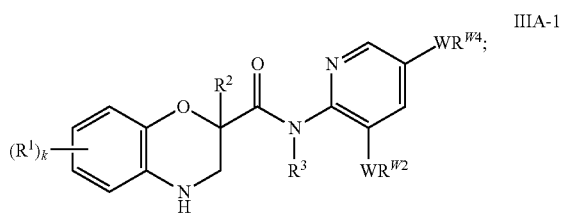

IIIA-1 wherein each of WR$^{W2}$ and WR$^{W4}$ is independently selected from CN, CF$_3$, OCF$_3$, —OC$_1$-C$_3$ aliphatic, —C≡CCH$_2$N(R')(R'), halo, C$_1$-C$_6$ straight or branched aliphatic, 3-12 membered cycloaliphatic, phenyl, 3-12 membered bicyclic, C$_5$-C$_{10}$ heteroaryl or C$_3$-C$_7$ heterocyclic, wherein said bicyclic, heteroaryl or heterocyclic has up to 3 heteroatoms selected from O, S, or N, wherein said WR$^{W2}$ and WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, —N(R')(R'), —NR'C(O)OR', —NR'C(O)R', —(CH$_2$)$_2$N(R')(R'), —(CH$_2$)N(R')(R') optionally substituted phenyl or phenoxy, or optionally substituted C$_3$-C$_7$ heterocyclic, wherein said heterocyclic has up to 3 heteroatoms selected from O, S, or N.

According to one embodiment, the present invention provides compounds of Formula IIIA-2:

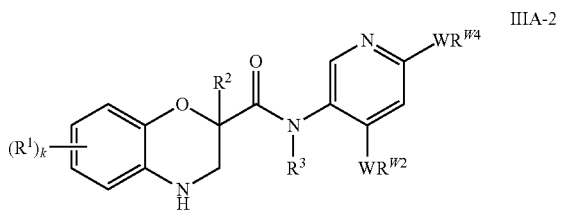

IIIA-2 wherein each of WR$^{W2}$ and WR$^{W4}$ is independently selected from CN, CF$_3$, OCF$_3$, —OC$_1$-C$_3$ aliphatic, —C≡CCH$_2$N(R')(R'), halo, C$_1$-C$_6$ straight or branched aliphatic, 3-12 membered cycloaliphatic, phenyl, 3-12 membered bicyclic, C$_5$-C$_{10}$ heteroaryl or C$_3$-C$_7$ heterocyclic, wherein said bicyclic, heteroaryl or heterocyclic has up to 3 heteroatoms selected from O, S, or N, wherein said WR$^{W2}$ and WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, —N(R')(R'), —NR'C(O)OR', —NR'C(O)R', —(CH$_2$)$_2$N(R')(R'), —(CH$_2$)N(R')(R') optionally substituted phenyl or phenoxy, or optionally substituted C$_3$-C$_7$ heterocyclic, wherein said heterocyclic has up to 3 heteroatoms selected from O, S, or N.

According to one embodiment, the present invention provides compounds of Formula IIIA-3:

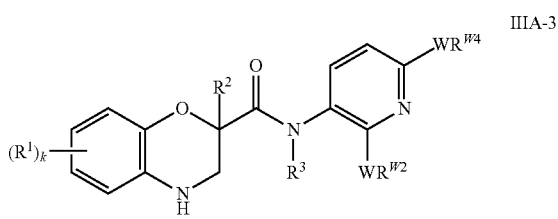

IIIA-3 wherein each of WR$^{W2}$ and WR$^{W4}$ is independently selected from CN, CF$_3$, OCF$_3$, —OC$_1$-C$_3$ aliphatic, —C≡CCH$_2$N(R')(R'), halo, C$_1$-C$_6$ straight or branched aliphatic, 3-12 membered cycloaliphatic, phenyl, 3-12 membered bicyclic, C$_5$-C$_{10}$ heteroaryl or C$_3$-C$_7$ heterocyclic, wherein said bicyclic, heteroaryl or heterocyclic has up to 3 heteroatoms selected from O, S, or N, wherein said WR$^{W2}$ and WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, —N(R')(R'), —NR'C(O)OR', —NR'C(O)R', —(CH$_2$)$_2$N(R')(R'), —(CH$_2$)N(R')(R') optionally substituted phenyl or phenoxy, or optionally substituted C$_3$-C$_7$ heterocyclic, wherein said heterocyclic has up to 3 heteroatoms selected from O, S, or N.

According to one embodiment, the present invention provides compounds of Formula IIIB:

IIIB

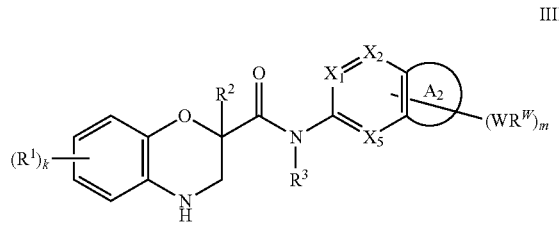

wherein each of $X_1$, $X_2$, and $X_5$ is independently selected from CH or N.

According to one embodiment, the present invention provides compounds of Formula IIIC:

IIIC

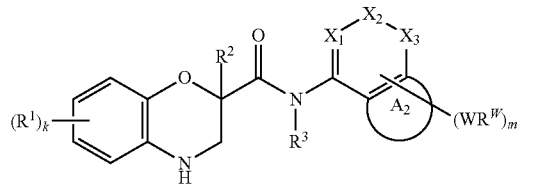

wherein each of $X_1$, $X_2$, and $X_3$ is independently selected from CH or N.

According to one embodiment, the present invention provides compounds of Formula IIID:

IIID

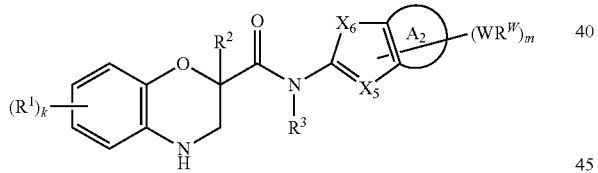

wherein $X_5$ is independently selected from CH or N and $X_6$ is O, S, or NR'.

According to one embodiment, the present invention provides compounds of Formula IIIE:

IIIE

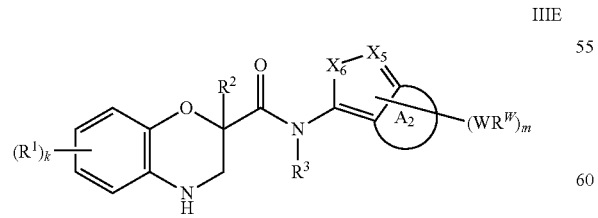

wherein $X_5$ is independently selected from CH or N and $X_6$ is O, S, or NR'.

In some embodiments of Formula IIIA, each of $X_1$, $X_2$, $X_3$, $X_4$, and $X_5$ is CH.

In some embodiments of Formula IIIA, $X_1$, $X_2$, $X_3$, $X_4$, and $X_5$ taken together is an optionally substituted ring selected from pyridyl, pyrazinyl, or pyrimidinyl.

In some embodiments of Formula IIIB, or Formula IIIC, $X_1$, $X_2$, $X_3$, or, $X_5$, taken together with ring $A_2$ is an optionally substituted ring selected from:

b-i

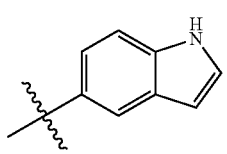

b-ii

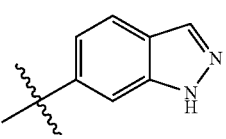

b-iii

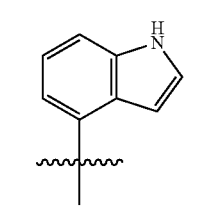

b-iv

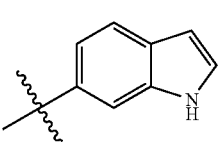

b-v

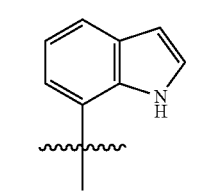

b-vi

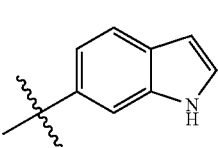

b-vii

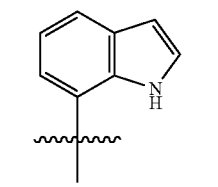

b-viii

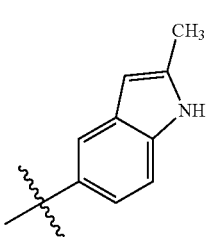

US 8,633,189 B2
23
-continued
b-ix
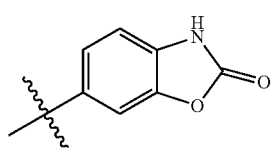
b-x
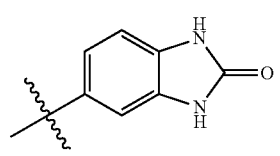
b-xi
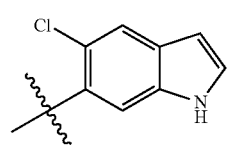
b-xii
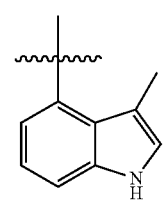
b-xiii
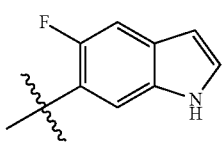
b-xiv
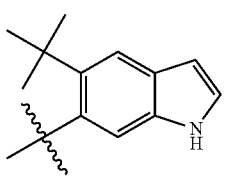
b-xv
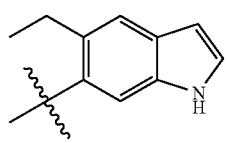
b-xvi
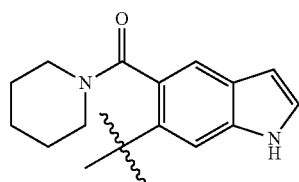
b-xvii
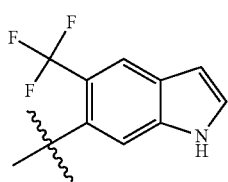
24
-continued
b-xviii
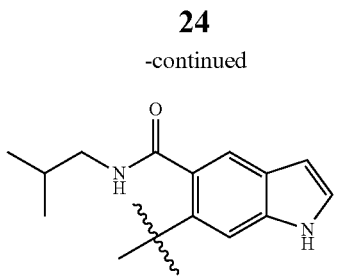
b-xix
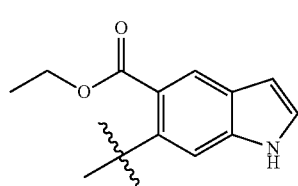
b-xx
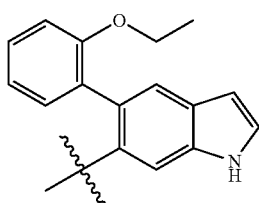
b-xxi
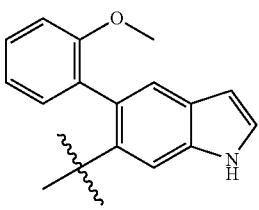
b-xxii
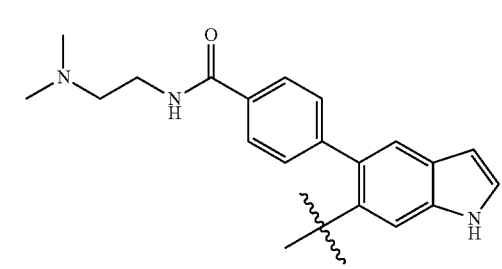
b-xxiii
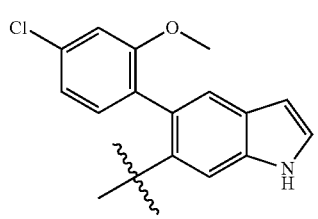
b-xxiv
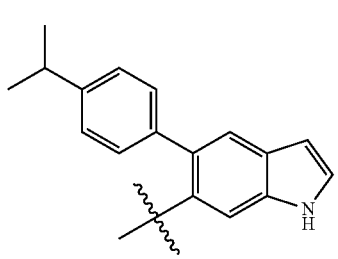

b-xxv
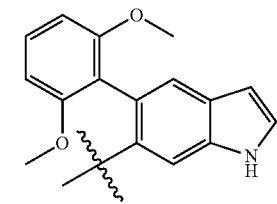
b-xxvi
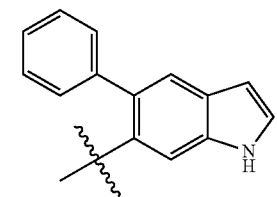
b-xxvii
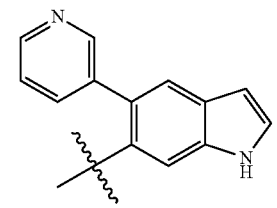
b-xxviii
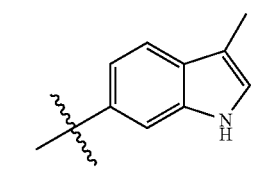
b-xxix
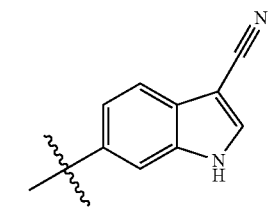
b-xxx
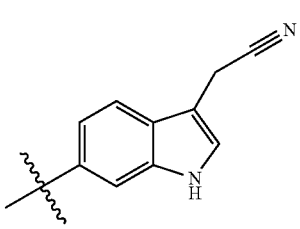
bxxxi
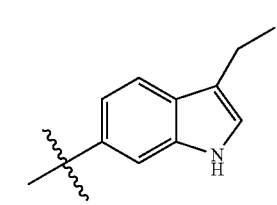
b-xxxii
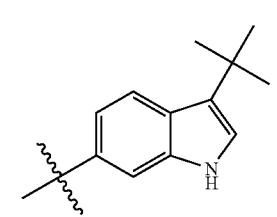
b-xxxiii
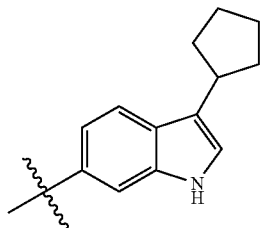
b-xxxiv
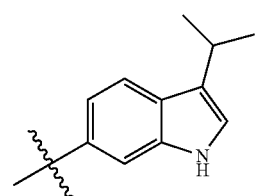
b-xxxv
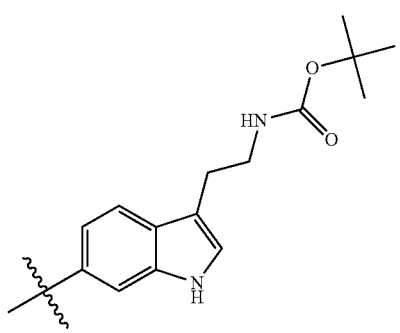
b-xxxvi
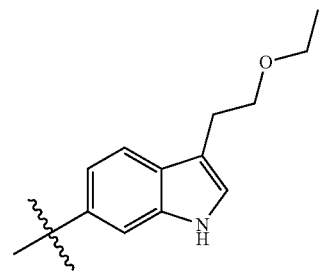
b-xxxvii
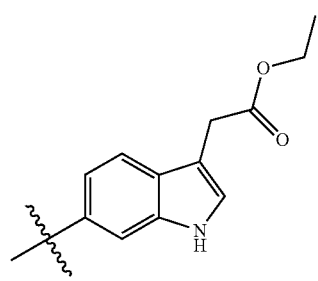
b-xxxviii
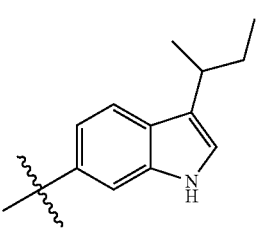

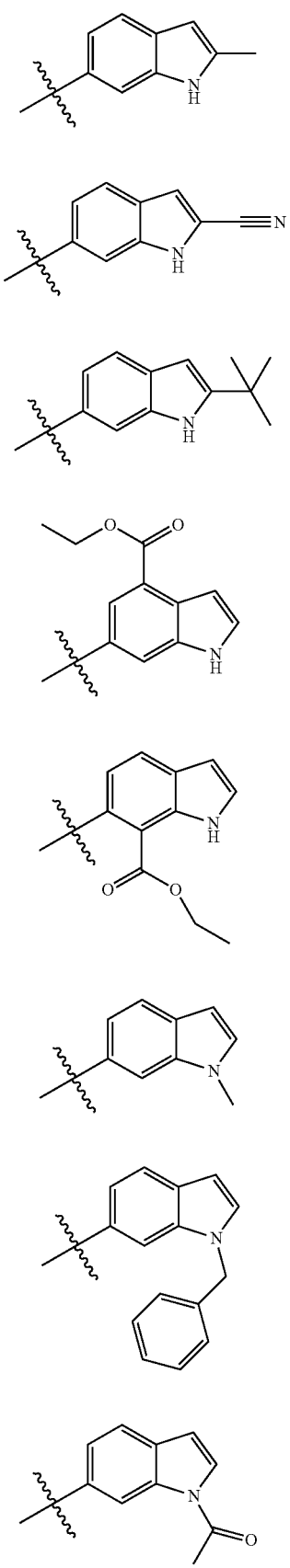
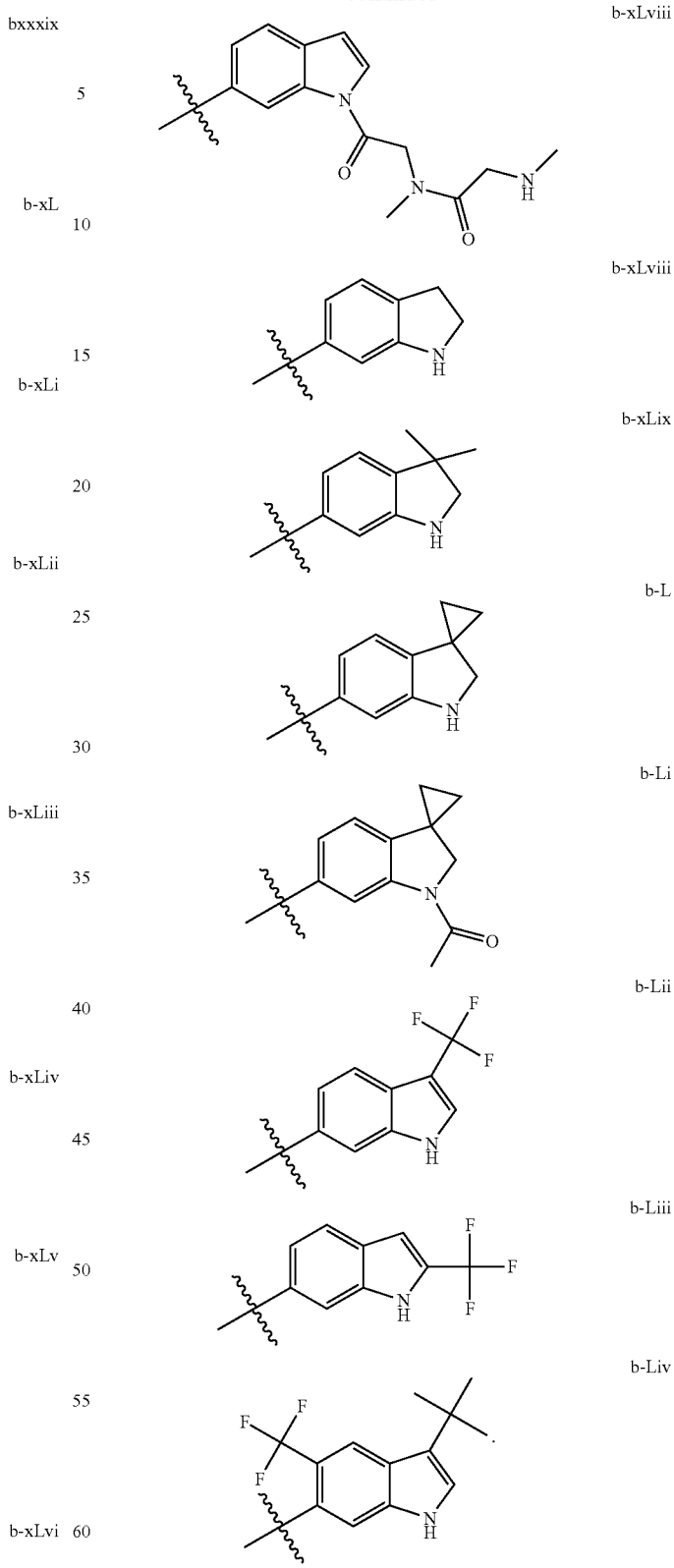
In some embodiments, $R^W$ is selected from halo, cyano, $CF_3$, $CHF_2$, $OCHF_2$, Me, Et, $CH(Me)_2$, CHMeEt, n-propyl, t-butyl, OH, OMe, OEt, OPh, O-fluorophenyl, O-difluorophenyl, O-methoxyphenyl, O-tolyl, O-benzyl, SMe, $SCF_3$, SCHF$_2$, SEt, CH$_2$CN, NH$_2$, NHMe, N(Me)$_2$, NHEt, N(Et)$_2$, C(O)CH$_3$, C(O)Ph, C(O)NH$_2$, SPh, SO$_2$—(amino-pyridyl), SO$_2$NH$_2$, SO$_2$Ph, SO$_2$NHPh, SO$_2$—N-morpholino, SO$_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2yl, furan-2-yl, 4-methyl-4H-[1,2,4]triazol-3-yl, 3-(4'-chlorophenyl)-[1,2,4] oxadiazol-5-yl, NHC(O)Me, NHC(O)Et, NHC(O)Ph, or NHSO$_2$Me.

In some embodiments, X and R$^X$, taken together, is Me, Et, halo, CN, CF$_3$, OH, OMe, OEt, SO$_2$N(Me)(fluorophenyl), SO$_2$-(4-methyl-piperidin-1-yl), or SO$_2$—N-pyrrolidinyl.

According to one embodiment, the present invention provides compounds of Formula IIIF:

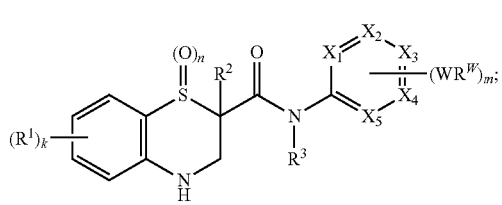

IIIF wherein n is 0, 1, or 2;

and each of X$_1$, X$_2$, X$_3$, X$_4$, and X$_5$ is independently selected from CH or N.

According to one embodiment, the present invention provides compounds of Formula IIIF-1:

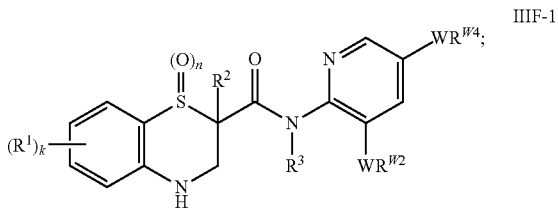

IIIF-1 wherein each of WR$^{W2}$ and WR$^{W4}$ is independently selected from CN, CF$_3$, OCF$_3$, —OC$_1$-C$_3$ aliphatic, —C≡CCH$_2$N(R')(R'), halo, C$_1$-C$_6$ straight or branched aliphatic, 3-12 membered cycloaliphatic, phenyl, 3-12 membered bicyclic, C$_5$-C$_{10}$ heteroaryl or C$_3$-C$_7$ heterocyclic, wherein said bicyclic, heteroaryl or heterocyclic has up to 3 heteroatoms selected from O, S, or N, wherein said WR$^{W2}$ and WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, —N(R')(R'), —NR'C(O)OR', —NR'C(O)R', —(CH$_2$)$_2$N(R')(R'), —(CH$_2$)N(R')(R') optionally substituted phenyl or phenoxy, or optionally substituted C$_3$-C$_7$ heterocyclic, wherein said heterocyclic has up to 3 heteroatoms selected from O, S, or N.

According to one embodiment, the present invention provides compounds of Formula IIIF-2:

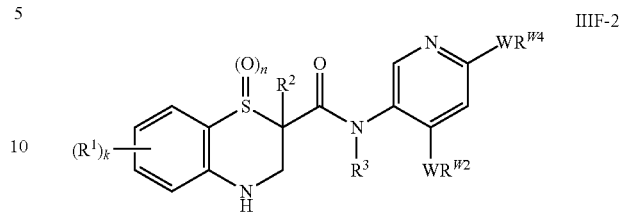

IIIF-2 wherein each of WR$^{W2}$ and WR$^{W4}$ is independently selected from CN, CF$_3$, OCF$_3$, —OC$_1$-C$_3$ aliphatic, —C≡CCH$_2$N(R')(R'), halo, C$_1$-C$_6$ straight or branched aliphatic, 3-12 membered cycloaliphatic, phenyl, 3-12 membered bicyclic, C$_5$-C$_{10}$ heteroaryl or C$_3$-C$_7$ heterocyclic, wherein said bicyclic, heteroaryl or heterocyclic has up to 3 heteroatoms selected from O, S, or N, wherein said WR$^{W2}$ and WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, —N(R')(R'), —NR'C(O)OR', —NR'C(O)R', —(CH$_2$)$_2$N(R')(R'), —(CH$_2$)N(R')(R') optionally substituted phenyl or phenoxy, or optionally substituted C$_3$-C$_7$ heterocyclic, wherein said heterocyclic has up to 3 heteroatoms selected from O, S, or N.

According to one embodiment, the present invention provides compounds of Formula IIIF-3:

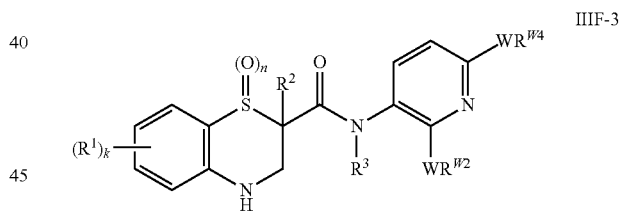

IIIF-3 wherein each of WR$^{W2}$ and WR$^{W4}$ is independently selected from CN, CF$_3$, OCF$_3$, —OC$_1$-C$_3$ aliphatic, —C≡CCH$_2$N(R')(R'), halo, C$_1$-C$_6$ straight or branched aliphatic, 3-12 membered cycloaliphatic, phenyl, 3-12 membered bicyclic, C$_5$-C$_{10}$ heteroaryl or C$_3$-C$_7$ heterocyclic, wherein said bicyclic, heteroaryl or heterocyclic has up to 3 heteroatoms selected from O, S, or N, wherein said WR$^{W2}$ and WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, —N(R')(R'), —NR'C(O)OR', —NR'C(O)R', —(CH$_2$)$_2$N(R')(R'), —(CH$_2$)N(R')(R') optionally substituted phenyl or phenoxy, or optionally substituted C$_3$-C$_7$ heterocyclic, wherein said heterocyclic has up to 3 heteroatoms selected from O, S, or N.

According to one embodiment, the present invention provides compounds of Formula IIIG:

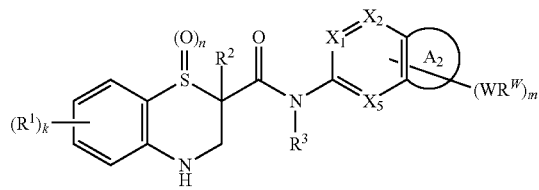

wherein n is 0, 1, or 2; and
each of $X_1$, $X_2$, and $X_5$ is independently selected from CH or N.

According to one embodiment, the present invention provides compounds of Formula IIIH:

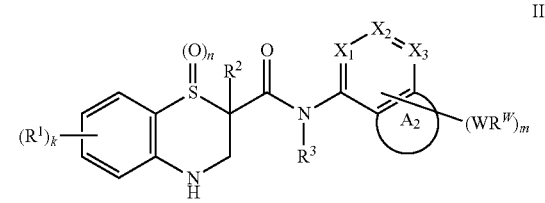

wherein n is 0, 1, or 2; and
each of $X_1$, $X_2$, and $X_3$ is independently selected from CH or N.

According to one embodiment, the present invention provides compounds of Formula IIIJ:

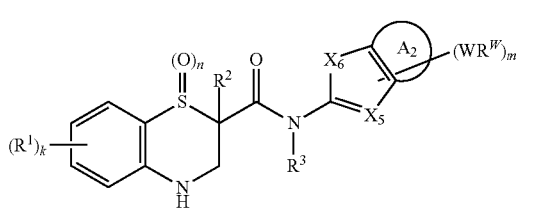

wherein n is 0, 1, or 2; and
$X_5$ is independently selected from CH or N and $X_6$ is O, S, or NR'.

According to one embodiment, the present invention provides compounds of Formula IIIK:

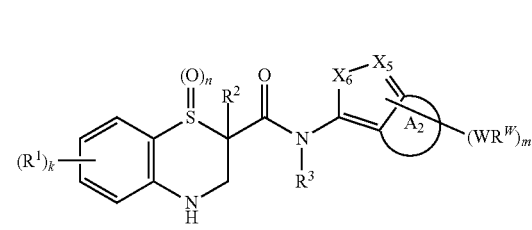

wherein n is 0, 1, or 2; and
$X_5$ is independently selected from CH or N and $X_6$ is O, S, or NR'.

In some embodiments of Formula IIIF, each of $X_1$, $X_2$, $X_3$, $X_4$, and $X_5$ is CH.

In some embodiments of Formula IIIF, $X_1$, $X_2$, $X_3$, $X_4$, and $X_5$ taken together is an optionally substituted ring selected from pyridyl, pyrazinyl, or pyrimidinyl.

In some embodiments of Formula IIIG, or Formula IIIH, $X_1$, $X_2$, $X_3$, or, $X_5$, taken together with ring $A_2$ is an optionally substituted ring selected from:

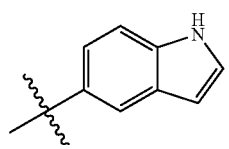
b-i

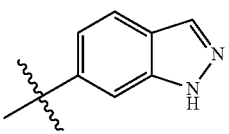
b-ii

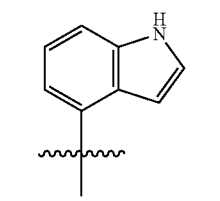
b-iii

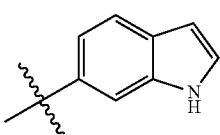
b-iv

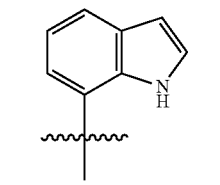
b-v

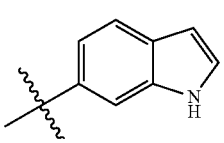
b-vi

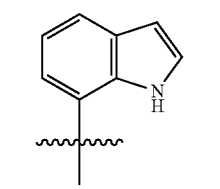
b-vii

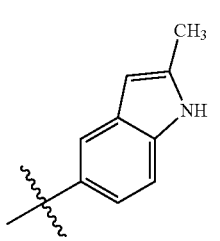
b-viii

33
-continued
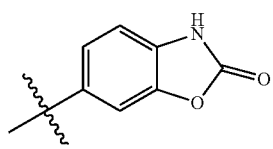
b-ix
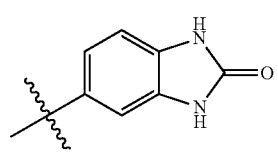
b-x
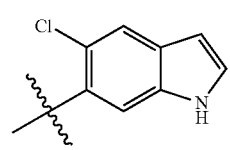
b-xi
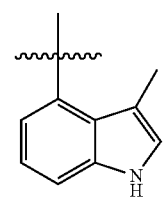
b-xii
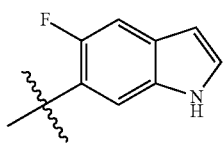
b-xiii
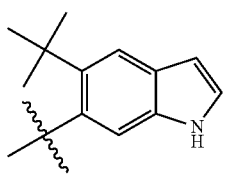
b-xiv
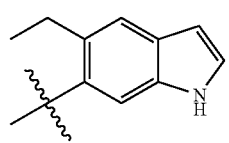
b-xv
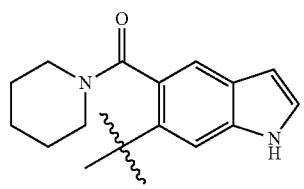
b-xvi
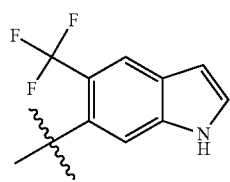
b-xvii
34
-continued
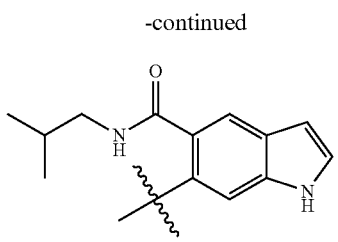
b-xviii
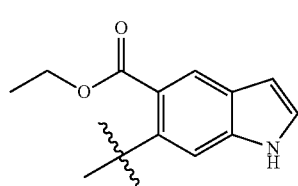
b-xix
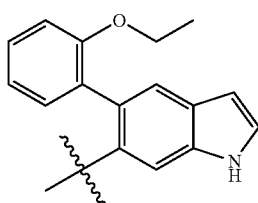
b-xx
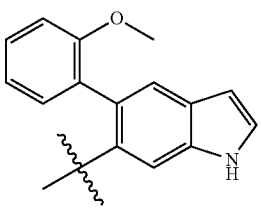
b-xxi
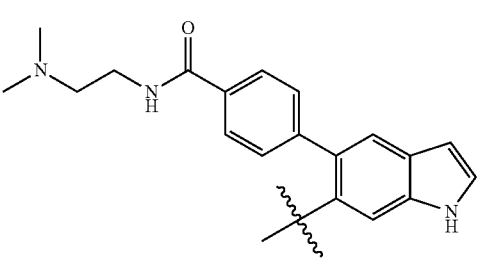
b-xxii
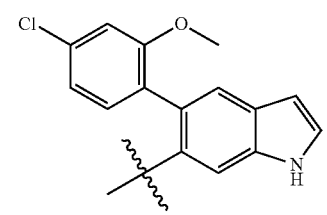
b-xxiii
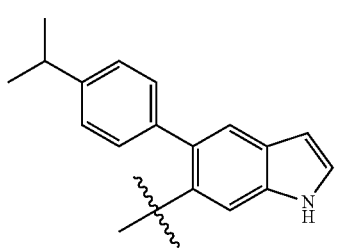
b-xxiv -continued
b-xxv
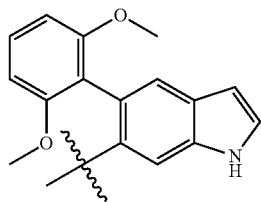
b-xxvi
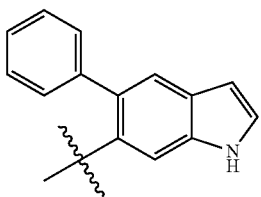
b-xxvii
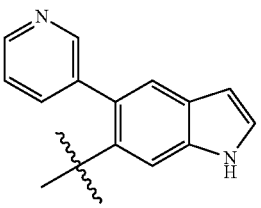
b-xxviii
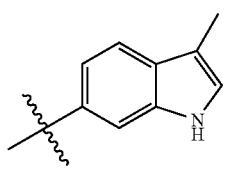
b-xxix
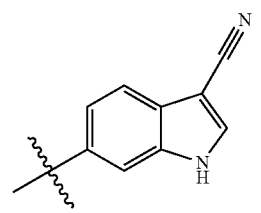
b-xxx
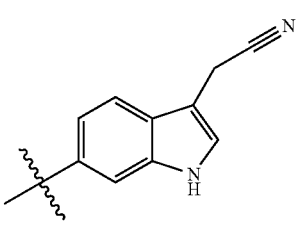
bxxxi
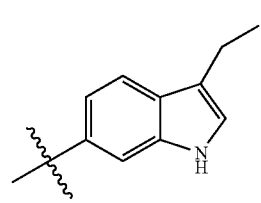
b-xxxii
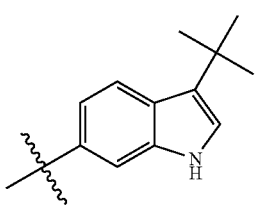
-continued
b-xxxiii
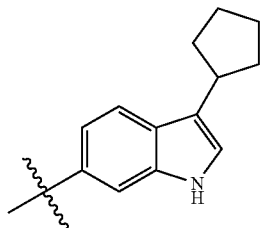
b-xxxiv
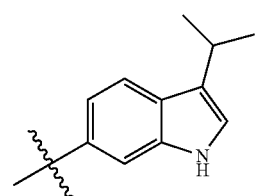
b-xxxv
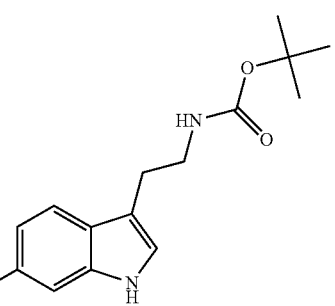
b-xxxvi
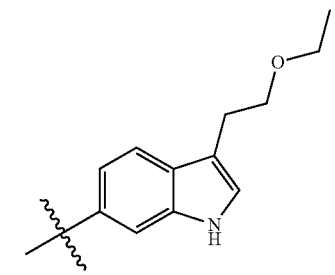
b-xxxvii
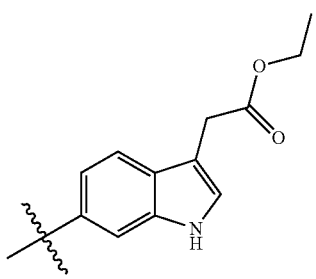
b-xxxviii
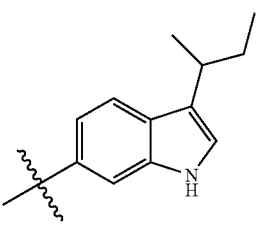

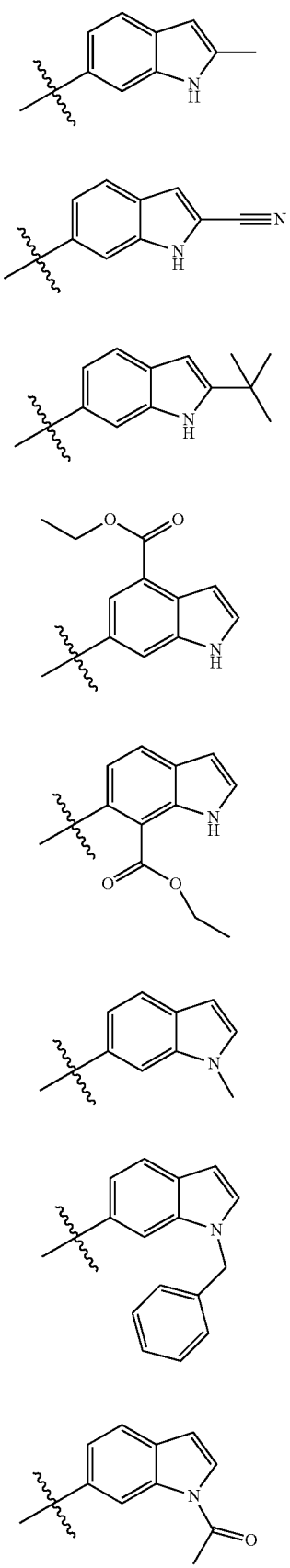
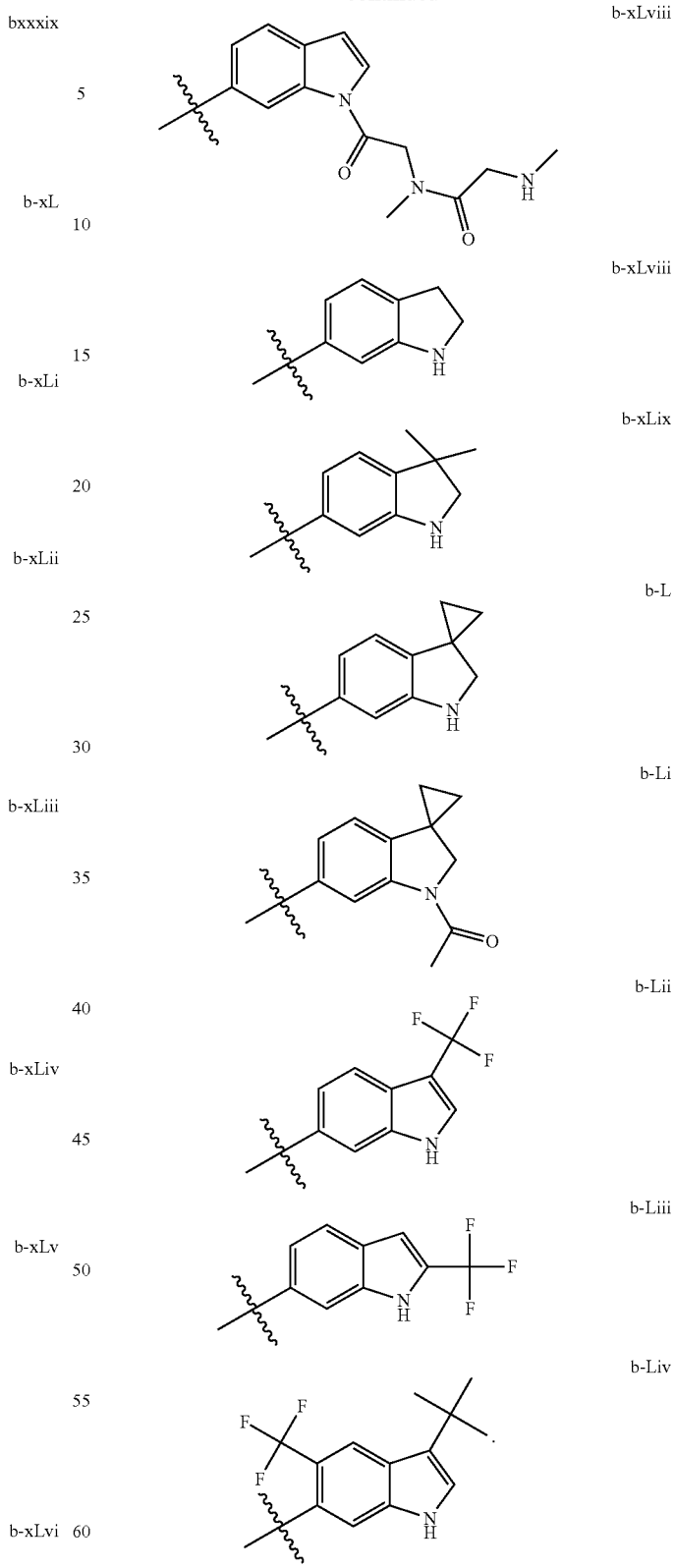
In some embodiments, $R^W$ is selected from halo, cyano, $CF_3$, $CHF_2$, $OCHF_2$, Me, Et, $CH(Me)_2$, CHMeEt, n-propyl, t-butyl, OH, OMe, OEt, OPh, O-fluorophenyl, O-difluorophenyl, O-methoxyphenyl, O-tolyl, O-benzyl, SMe, $SCF_3$, SCHF$_2$, SEt, CH$_2$CN, NH$_2$, NHMe, N(Me)$_2$, NHEt, N(Et)$_2$, C(O)CH$_3$, C(O)Ph, C(O)NH$_2$, SPh, SO$_2$—(amino-pyridyl), SO$_2$NH$_2$, SO$_2$Ph, SO$_2$NHPh, SO$_2$—N-morpholino, SO$_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2yl, furan-2-yl, 4-methyl-4H-[1,2,4]triazol-3-yl, 3-(4'-chlorophenyl)-[1,2,4]oxadiazol-5-yl, NHC(O)Me, NHC(O)Et, NHC(O)Ph, or NHSO$_2$Me.

In some embodiments, X and R$^x$, taken together, is Me, Et, halo, CN, CF$_3$, OH, OMe, OEt, SO$_2$N(Me)(fluorophenyl), SO$_2$-(4-methyl-piperidin-1-yl), or SO$_2$—N-pyrrolidinyl.

According to another embodiment, the present invention provides compounds of Formula IVA:

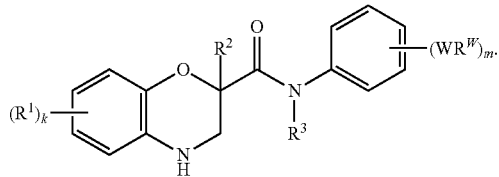

IVA

According to another embodiment, the present invention provides compounds of Formula IVB:

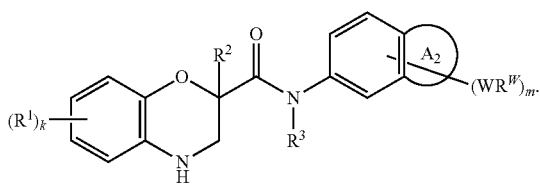

IVB

According to another embodiment, the present invention provides compounds of Formula IVC:

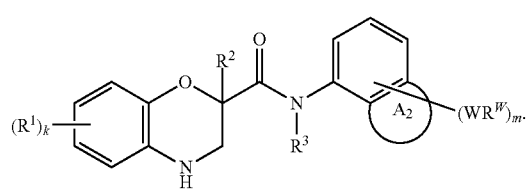

IVC

In one embodiment, the present invention provides compounds of Formula IVA, Formula IVB, or Formula IVC, wherein k is 1, and R$^1$ is H, Me, —OCH$_3$, —OCF$_3$, —SO$_2$Me or halo. In another embodiment, k is 1 and R$^1$ is Me.

In one embodiment, the present invention provides compounds of Formula IVB, or Formula IVC, wherein ring A$_2$ is an optionally substituted, saturated, unsaturated, or aromatic seven membered ring with 0-3 heteroatoms selected from O, S, or N. Exemplary rings include azepanyl, 5,5-dimethyl azepanyl, etc.

In one embodiment, the present invention provides compounds of Formula IVB, or Formula IVC, wherein ring A$_2$ is an optionally substituted, saturated, unsaturated, or aromatic six membered ring with 0-3 heteroatoms selected from O, S, or N. Exemplary rings include piperidinyl, 4,4-dimethylpiperidinyl, etc.

In one embodiment, the present invention provides compounds of Formula IVB, or Formula IVC, wherein ring A$_2$ is an optionally substituted, saturated, unsaturated, or aromatic five membered ring with 0-3 heteroatoms selected from O, S, or N.

In one embodiment, the present invention provides compounds of Formula IVB, or Formula IVC, wherein ring A$_2$ is an optionally substituted five membered ring with one nitrogen atom, e.g., pyrrolyl or pyrrolidinyl.

According to another embodiment, the present invention provides compounds of Formula IVD:

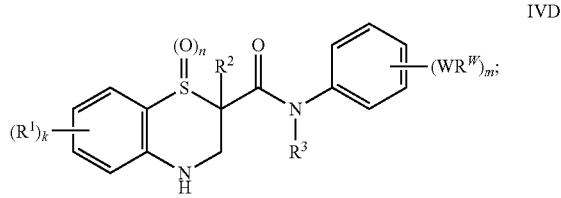

IVD wherein n is 0, 1, or 2.

According to another embodiment, the present invention provides compounds of Formula IVE:

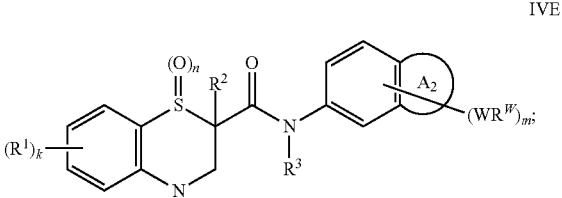

IVE wherein n is 0, 1, or 2.

According to another embodiment, the present invention provides compounds of Formula IVF:

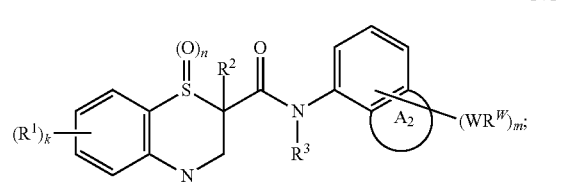

IVF wherein n is 0, 1, or 2.

In one embodiment, the present invention provides compounds of Formula IVD, Formula IVE, or Formula IVF, wherein k is 1, and R$^1$ is H, Me, —OCH$_3$, —OCF$_3$, —SO$_2$Me or halo. In another embodiment, k is 1 and R$^1$ is Me.

In one embodiment, the present invention provides compounds of Formula IVE, or Formula IVF, wherein ring A$_2$ is an optionally substituted, saturated, unsaturated, or aromatic seven membered ring with 0-3 heteroatoms selected from O, S, or N. Exemplary rings include azepanyl, 5,5-dimethyl azepanyl, etc.

In one embodiment, the present invention provides compounds of Formula IVE, or Formula IVF, wherein ring A$_2$ is an optionally substituted, saturated, unsaturated, or aromatic six membered ring with 0-3 heteroatoms selected from O, S, or N. Exemplary rings include piperidinyl, 4,4-dimethylpiperidinyl, etc.

In one embodiment, the present invention provides compounds of Formula IVE, or Formula IVF, wherein ring $A_2$ is an optionally substituted, saturated, unsaturated, or aromatic five membered ring with 0-3 heteroatoms selected from O, S, or N.

In one embodiment, the present invention provides compounds of Formula IVE, or Formula IVF, wherein ring $A_2$ is an optionally substituted five membered ring with one nitrogen atom, e.g., pyrrolyl or pyrrolidinyl.

According to one embodiment of Formula IVA, the following compound of Formula VA-1A is provided:

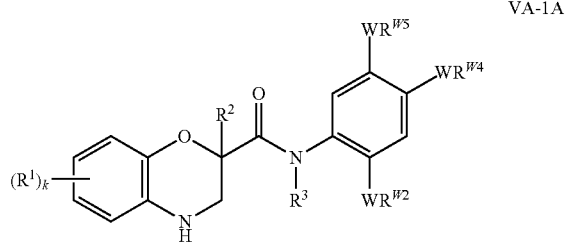

VA-1A wherein each of $WR^{W2}$ and $WR^{W4}$ is independently selected from hydrogen, CN, $CF_3$, $OCF_3$, —$SO_2R'$, —$OC_1$-$C_3$ aliphatic, —C≡$CCH_2N(R')(R')$, halo, $C_1$-$C_6$ straight or branched aliphatic, 3-12 membered cycloaliphatic, phenyl, $C_5$-$C_{10}$ heteroaryl or $C_3$-$C_7$ heterocyclic, wherein said heteroaryl or heterocyclic has up to 3 heteroatoms selected from O, S, or N; wherein each $WR^{W2}WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')(R')$, —$(CH_2)_2OR'$, —$(CH_2)OR'$, $CH_2CN$, —$N(R')(R')$, —NR'C(O)OR', —NR'C(O)R', $(CH_2)_3N(R')(R')$, —$(CH_2)_2N(R')(R')$, —$(CH_2)N(R')(R')$, optionally substituted phenyl or phenoxy, or optionally substituted $C_3$-$C_7$ heterocyclic, wherein said heterocyclic has up to 3 heteroatoms selected from O, S, or N and $WR^{W5}$ is selected from hydrogen, halo, —OH, OR', —$OCF_3$, $NH_2$, CN, $CHF_2$, $N(R')_2$, —NHC(O)R', —NHC(O)OR', $NHSO_2R'$, —OR', $CH_2OH$, $CH_2N(R')_2$, $C(O)OR'$, $C(O)N(R')_2$, $SO_2NHR'$, $SO_2N(R')_2$, $OSO_2N(R')_2$, $OSO_2CF_3$, optionally substituted $C_1$-$C_6$ straight or branched aliphatic, optionally substituted 3-12 membered cycloaliphatic, or $CH_2NHC(O)OR'$.

In one embodiment, the present invention provides compounds of Formula VA-1A, wherein k is 0.

In one embodiment, the present invention provides compounds of Formula VA-1A, wherein k is 1 and $R^1$ is halo.

In one embodiment, the present invention provides compounds of Formula VA-1A, wherein k is 1 and $R^1$ is $C_1$-$C_4$ alkyl.

In one embodiment, the present invention provides compounds of Formula VA-1A, wherein k is 1 and $R^1$ is Me.

In one embodiment, the present invention provides compounds of Formula VA-1A, wherein k is 1 and $R^1$ is —$CF_3$.

In one embodiment, the present invention provides compounds of Formula VA-1A, wherein k is 1 and $R^1$ is —$OCF_3$ In one embodiment, the present invention provides compounds of Formula VA-1A, wherein k is 1 and $R^1$ is —$OCH_3$.

In one embodiment, the present invention provides compounds of Formula VA-1A, wherein k is 1 and $R^1$ is —F.

In one embodiment, the present invention provides compounds of Formula VA-1A, wherein k is 1 and $R^1$ is —$SO_2Me$.

In one embodiment, the present invention provides compounds of Formula VA-1A, wherein k is 2 and each $R^1$ is independently $C_1$-$C_4$ alkyl, or halo.

In some embodiments of Formula VA-1A, $WR^{W4}$ is a $C_1$-$C_6$ straight or branched aliphatic, or a 3-12 membered cycloaliphatic.

In some embodiments of Formula VA-1A, $WR^{W5}$ is —OH or OR'.

In some embodiments of Formula VA-1A, $WR^{W2}$ is —C≡$CCH_2N(R')(R')$, —$(CH_2)_3N(R')(R')$, —$(CH_2)_2N(R')(R')$, —$(CH_2)N(R')(R')$ or —$N(R')(R')$.

According to one embodiment of Formula IVA, the following compound of Formula VA-1B is provided:

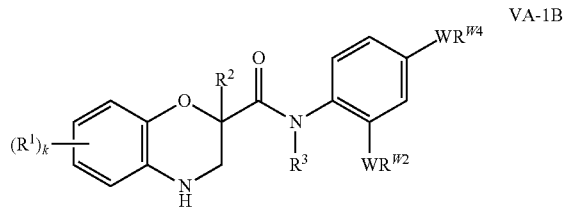

VA-1B wherein each of $WR^{W2}$ and $WR^{W4}$ is independently selected from hydrogen, CN, $CF_3$, $OCF_3$, —$OC_1$-$C_3$ aliphatic, —C≡$CCH_2N(R')(R')$, halo, $C_1$-$C_6$ straight or branched aliphatic, 3-12 membered cycloaliphatic, phenyl, 3-12 membered bicyclic, $C_5$-$C_{10}$ heteroaryl or $C_3$-$C_7$ heterocyclic, wherein said bicyclic, heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')(R')$, —$(CH_2)_2OR'$, —$(CH_2)OR'$, $CH_2CN$, —$N(R')(R')$, —NR'C(O)OR', —NR'C(O)R', —$(CH_2)_2N(R')(R')$, —$(CH_2)N(R')(R')$ optionally substituted phenyl or phenoxy, or optionally substituted $C_3$-$C_7$ heterocyclic, wherein said heterocyclic has up to 3 heteroatoms selected from O, S, or N.

In one embodiment, the present invention provides compounds of Formula VA-1B, wherein k is 1 and $R^1$ is halo.

In one embodiment, the present invention provides compounds of Formula VA-1B, wherein k is 1 and $R^1$ is $C_1$-$C_4$ alkyl.

In one embodiment, the present invention provides compounds of Formula VA-1B, wherein k is 1 and $R^1$ is Me.

In one embodiment, the present invention provides compounds of Formula VA-1B, wherein k is 1 and $R^1$ is —$CF_3$.

In one embodiment, the present invention provides compounds of Formula VA-1B, wherein k is 1 and $R^1$ is —$OCF_3$.

In one embodiment, the present invention provides compounds of Formula VA-1B, wherein k is 1 and $R^1$ is —$OCH_3$.

In one embodiment, the present invention provides compounds of Formula VA-1B, wherein k is 1 and $R^1$ is —F.

In one embodiment, the present invention provides compounds of Formula VA-1B, wherein k is 1 and $R^1$ is —$SO_2Me$.

In one embodiment, the present invention provides compounds of Formula VA-1B, wherein k is 2 and each $R^1$ is independently $C_1$-$C_4$ alkyl, or halo.

In some embodiments of Formula VA-1B, WR$^{W4}$ is a substituted $C_1$-$C_6$ straight or branched aliphatic, $C_3$-$C_7$ heterocyclic, 3-12 membered cycloaliphatic, or 3-12 membered bicyclic.

In some embodiments of Formula VA-1B, WR$^{W2}$ is —C≡CCH$_2$N(R')(R'), —(CH$_2$)$_3$N(R')(R'), —(CH$_2$)$_2$N(R')(R'), —(CH$_2$)N(R')(R') or —N(R')(R').

In one embodiment, the present invention provides compounds of Formula VA-1B, wherein k is 0.

According to one embodiment of Formula IVA, the following compound of Formula VA-1C is provided:

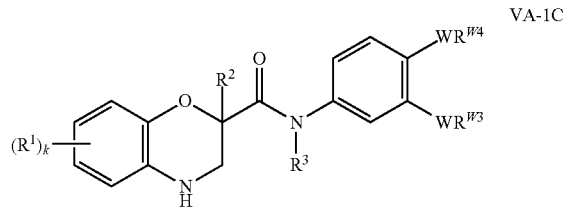

VA-1C wherein WR$^{W3}$ is selected from hydrogen, halo, —OH, —OCF$_3$, NH$_2$, CN, CHF$_2$, NHR', N(R')$_2$, —NHC(O)R', —NHC(O)OR', NHSO$_2$R', —OR', CH$_2$OH, CH$_2$N(R')$_2$, C(O)OR', C(O)N(R')$_2$, SO$_2$NHR', SO$_2$N(R')$_2$, OSO$_2$N(R')$_2$, OSO$_2$CF$_3$, $C_1$-$C_6$ straight or branched aliphatic, 3-12 membered cycloaliphatic, or CH$_2$NHC(O)OR' and
WR$^{W4}$ is independently selected from hydrogen, CN, CF$_3$, OCF$_3$, —SO$_2$R', —OC$_1$-C$_3$ aliphatic, halo, $C_1$-$C_6$ straight or branched aliphatic, 3-12 membered cycloaliphatic, phenyl, $C_5$-$C_{10}$ heteroaryl or $C_3$-$C_7$ heterocyclic, wherein said heteroaryl or heterocyclic has up to 3 heteroatoms selected from O, S, or N, wherein said WR$^{W4}$ is independently and optionally substituted with up to three substituents selected from —OR', —CF$_3$, —OCF$_3$, SR', S(O)R', SO$_2$R', —SCF$_3$, halo, $C_1$-$C_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, optionally substituted phenyl or phenoxy, —N(R')(R'), —NR'C(O)OR', —NR'C(O)R', —(CH$_2$)$_2$N(R')(R'), or —(CH$_2$)N(R')(R').

In one embodiment, the present invention provides compounds of Formula VA-1C, wherein k is 0.

In one embodiment, the present invention provides compounds of Formula VA-1C, wherein k is 1 and R$^1$ is halo.

In one embodiment, the present invention provides compounds of Formula VA-1C, wherein k is 1 and R$^1$ is $C_1$-$C_4$ alkyl.

In one embodiment, the present invention provides compounds of Formula VA-1C, wherein k is 1 and R$^1$ is Me.

In one embodiment, the present invention provides compounds of Formula VA-1C, wherein k is 1 and R$^1$ is —CF$_3$.

In one embodiment, the present invention provides compounds of Formula VA-1C, wherein k is 1 and R$^1$ is —OCF$_3$ In one embodiment, the present invention provides compounds of Formula VA-1C, wherein k is 1 and R$^1$ is —OCH$_3$.

In one embodiment, the present invention provides compounds of Formula VA-1C, wherein k is 1 and R$^1$ is —F.

In one embodiment, the present invention provides compounds of Formula VA-1C, wherein k is 1 and R$^1$ is —SO$_2$Me.

In one embodiment, the present invention provides compounds of Formula VA-1C, wherein k is 2 and each R$^1$ is independently $C_1$-$C_4$ alkyl, or halo.

In some embodiments of Formula VA-1C, WR$^{W4}$ is a substituted $C_1$-$C_6$ straight or branched aliphatic, $C_3$-$C_7$ heterocyclic, 3-12 membered cycloaliphatic, or 3-12 membered bicyclic.

In some embodiments of Formula VA-1C, WR$^{W2}$ is —C≡CCH$_2$N(R')(R'), —(CH$_2$)$_3$N(R')(R'), —(CH$_2$)$_2$N(R')(R'), —(CH$_2$)N(R')(R') or —N(R')(R').

According to one embodiment of Formula IVA, the following compound of Formula VA-1D is provided:

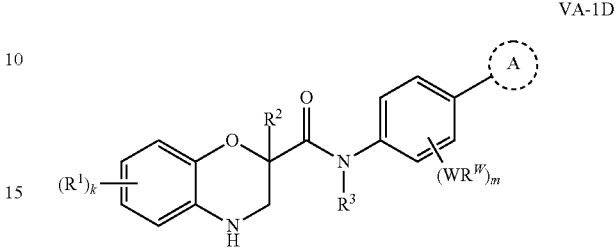

VA-1D ring A is a 5-7 membered monocyclic or bicyclic, heterocyclic or heteroaryl ring optionally substituted with up to p occurrences of -Q-R$^Q$,
Q is W;
R$^Q$ is R$^W$; and
m is 0-4
p is 0-4
and R$^1$, k, W, and R$^W$ are as defined above.

In one embodiment, the present invention provides compounds of Formula VA-1D, wherein k is 0.

In one embodiment, the present invention provides compounds of Formula VA-1D, wherein k is 1 and R$^1$ is halo.

In one embodiment, the present invention provides compounds of Formula VA-1D, wherein k is 1 and R$^1$ is $C_1$-$C_4$ alkyl.

In one embodiment, the present invention provides compounds of Formula VA-1D, wherein k is 1 and R$^1$ is Me.

In one embodiment, the present invention provides compounds of Formula VA-1D, wherein k is 1 and R$^1$ is —CF$_3$.

In one embodiment, the present invention provides compounds of Formula VA-1D, wherein k is 1 and R$^1$ is —OCF$_3$.

In one embodiment, the present invention provides compounds of Formula VA-1D, wherein k is 1 and R$^1$ is —OCH$_3$.

In one embodiment, the present invention provides compounds of Formula VA-1D, wherein k is 1 and R$^1$ is —F.

In one embodiment, the present invention provides compounds of Formula VA-1D, wherein k is 1 and R$^1$ is —SO$_2$Me In one embodiment, the present invention provides compounds of Formula VA-1D, wherein k is 2 and each R$^1$ is independently $C_1$-$C_4$ alkyl, or halo.

In another embodiment, ring A is a 5-7 membered monocyclic, heterocyclic ring having up to 2 heteroatoms selected from O, S, or N, optionally substituted with up to p occurrences of -Q-R$^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring A is a 5-6 membered monocyclic, heteroaryl ring having up to 3 heteroatoms selected from O, S, or N, optionally substituted with up to p occurrences of -Q-R$^Q$. Exemplary such rings include benzimidazol-2-yl, 5-methyl-furan-2-yl, 2,5-dimethyl-pyrrol-1-yl, pyridine-4-yl, 1,2,4-oxadiazol-3-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl, 1,2,4-oxadiazol-5-yl.

According to one embodiment of Formula IVD, the following compound of Formula VA-1E is provided:

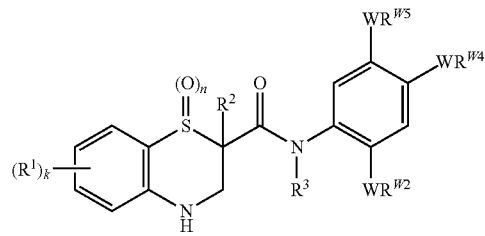

VA-1E wherein each of $WR^{W2}$ and $WR^{W4}$ is independently selected from hydrogen, CN, $CF_3$, $OCF_3$, —$SO_2R'$, —$OC_1$-$C_3$ aliphatic, —C≡$CCH_2N(R')(R')$, halo, $C_1$-$C_6$ straight or branched aliphatic, 3-12 membered cycloaliphatic, phenyl, $C_5$-$C_{10}$ heteroaryl or $C_3$-$C_7$ heterocyclic, wherein said heteroaryl or heterocyclic has up to 3 heteroatoms selected from O, S, or N, wherein each $WR^{W2}WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —CON(R')(R'), —$(CH_2)_2OR'$, —$(CH_2)OR'$, $CH_2CN$, —N(R')(R'), —NR'C(O)OR', —NR'C(O)R', —$(CH_2)_3N(R')(R')$, —$(CH_2)_2N(R')(R')$, —$(CH_2)N(R')(R')$, optionally substituted phenyl or phenoxy, or optionally substituted $C_3$-$C_7$ heterocyclic, wherein said heterocyclic has up to 3 heteroatoms selected from O, S, or N and $WR^{W5}$ is selected from hydrogen, halo, —OH, OR', —$OCF_3$, $NH_2$, CN, $CHF_2$, NHR', $N(R')_2$, —NHC(O)R', —NHC(O)OR', $NHSO_2R'$, —OR', $CH_2OH$, $CH_2N(R')_2$, C(O)OR', $C(O)N(R')_2$, $SO_2NHR'$, $SO_2N(R')_2$, $OSO_2N(R')_2$, $OSO_2CF_3$, optionally substituted $C_1$-$C_6$ straight or branched aliphatic, optionally substituted 3-12 membered cycloaliphatic, or $CH_2NHC(O)OR'$.

In one embodiment, the present invention provides compounds of Formula VA-1E, wherein k is 0.

In one embodiment, the present invention provides compounds of Formula VA-1E, wherein k is 1 and $R^1$ is halo.

In one embodiment, the present invention provides compounds of Formula VA-1E, wherein k is 1 and $R^1$ is $C_1$-$C_4$ alkyl.

In one embodiment, the present invention provides compounds of Formula VA-1E, wherein k is 1 and $R^1$ is Me.

In one embodiment, the present invention provides compounds of Formula VA-1E, wherein k is 1 and $R^1$ is —$CF_3$.

In one embodiment, the present invention provides compounds of Formula VA-1E, wherein k is 1 and $R^1$ is —$OCF_3$.

In one embodiment, the present invention provides compounds of Formula VA-1E, wherein k is 1 and $R^1$ is —$OCH_3$.

In one embodiment, the present invention provides compounds of Formula VA-1E, wherein k is 1 and $R^1$ is —F.

In one embodiment, the present invention provides compounds of Formula VA-1E, wherein k is 1 and $R^1$ is —$SO_2Me$.

In one embodiment, the present invention provides compounds of Formula VA-1E, wherein k is 2 and each $R^1$ is independently $C_1$-$C_4$ alkyl, or halo.

In some embodiments of Formula VA-1E, $WR^{W4}$ is a $C_1$-$C_6$ straight or branched aliphatic, or a 3-12 membered cycloaliphatic.

In some embodiments of Formula VA-1E, $WR^{W5}$ is —OH or OR'.

In some embodiments of Formula VA-1E, $WR^{W2}$ is —C≡$CCH_2N(R')(R')$, —$(CH_2)_3N(R')(R')$, —$(CH_2)_2N(R')(R')$, —$(CH_2)N(R')(R')$ or —N(R')(R').

According to one embodiment of Formula IVD, the following compound of Formula VA-1F is provided:

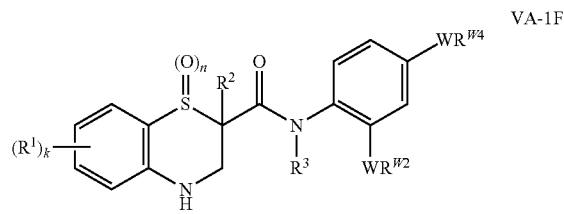

VA-1F wherein each of $WR^{W2}$ and $WR^{W4}$ is independently selected from hydrogen, CN, $CF_3$, $OCF_3$, —$OC_1$-$C_3$ aliphatic, —C≡$CCH_2N(R')(R')$, halo, $C_1$-$C_6$ straight or branched aliphatic, 3-12 membered cycloaliphatic, phenyl, 3-12 membered bicyclic, $C_5$-$C_{10}$ heteroaryl or $C_3$-$C_7$ heterocyclic, wherein said bicyclic, heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —CON(R')(R'), —$(CH_2)_2OR'$, —$(CH_2)OR'$, $CH_2CN$, —N(R')(R'), —NR'C(O)OR', —NR'C(O)R', —$(CH_2)_2N(R')(R')$, —$(CH_2)N(R')(R')$ optionally substituted phenyl or phenoxy, or optionally substituted $C_3$-$C_7$ heterocyclic, wherein said heterocyclic has up to 3 heteroatoms selected from O, S, or N.

In one embodiment, the present invention provides compounds of Formula VA-1F, wherein k is 1 and $R^1$ is halo.

In one embodiment, the present invention provides compounds of Formula VA-1F, wherein k is 1 and $R^1$ is $C_1$-$C_4$ alkyl.

In one embodiment, the present invention provides compounds of Formula VA-1F, wherein k is 1 and $R^1$ is Me.

In one embodiment, the present invention provides compounds of Formula VA-1F, wherein k is 1 and $R^1$ is —$CF_3$.

In one embodiment, the present invention provides compounds of Formula VA-1F, wherein k is 1 and $R^1$ is —$OCF_3$.

In one embodiment, the present invention provides compounds of Formula VA-1F, wherein k is 1 and $R^1$ is —$OCH_3$.

In one embodiment, the present invention provides compounds of Formula VA-1F, wherein k is 1 and $R^1$ is —F.

In one embodiment, the present invention provides compounds of Formula VA-1F, wherein k is 1 and $R^1$ is —$SO_2Me$.

In one embodiment, the present invention provides compounds of Formula VA-1B, wherein k is 2 and each $R^1$ is independently $C_1$-$C_4$ alkyl, or halo.

In some embodiments of Formula VA-1F, $WR^{W4}$ is a substituted $C_1$-$C_6$ straight or branched aliphatic, $C_3$-$C_7$ heterocyclic, 3-12 membered cycloaliphatic, or 3-12 membered bicyclic.

In some embodiments of Formula VA-1F, $WR^{W2}$ is —C≡$CCH_2N(R')(R')$, —$(CH_2)_3N(R')(R')$, —$(CH_2)_2N(R')(R')$, —$(CH_2)N(R')(R')$ or —N(R')(R').

In one embodiment, the present invention provides compounds of Formula VA-1F, wherein k is 0.

According to one embodiment of Formula IVD, the following compound of Formula VA-1G is provided:

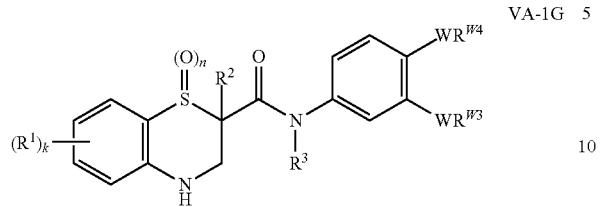

VA-1G wherein $WR^{W3}$ is selected from hydrogen, halo, —OH, —OCF$_3$, NH$_2$, CN, CHF$_2$, NHR', N(R')$_2$, —NHC(O)R', —NHC(O)OR', NHSO$_2$R', —OR', CH$_2$OH, CH$_2$N(R')$_2$, C(O)OR', C(O)N(R')$_2$, SO$_2$NHR', SO$_2$N(R')$_2$, OSO$_2$N(R')$_2$, OSO$_2$CF$_3$, C$_1$-C$_6$ straight or branched aliphatic, 3-12 membered cycloaliphatic, or CH$_2$NHC(O)OR' and $WR^{W4}$ is independently selected from hydrogen, CN, CF$_3$, OCF$_3$, —SO$_2$R', —OC$_1$-C$_3$ aliphatic, halo, C$_1$-C$_6$ straight or branched aliphatic, 3-12 membered cycloaliphatic, phenyl, C$_5$-C$_{10}$ heteroaryl or C$_3$-C$_7$ heterocyclic, wherein said heteroaryl or heterocyclic has up to 3 heteroatoms selected from O, S, or N, wherein said $WR^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, optionally substituted phenyl or phenoxy, —N(R')(R'), —NR'C(O)OR', —NR'C(O)R', —(CH$_2$)$_2$N(R')(R'), or —(CH$_2$)N(R')(R').

In one embodiment, the present invention provides compounds of Formula VA-1G, wherein k is 0.

In one embodiment, the present invention provides compounds of Formula VA-1G, wherein k is 1 and R$^1$ is halo.

In one embodiment, the present invention provides compounds of Formula VA-1G, wherein k is 1 and R$^1$ is C$_1$-C$_4$ alkyl.

In one embodiment, the present invention provides compounds of Formula VA-1G, wherein k is 1 and R$^1$ is Me.

In one embodiment, the present invention provides compounds of Formula VA-1G, wherein k is 1 and R$^1$ is —CF$_3$.

In one embodiment, the present invention provides compounds of Formula VA-1G, wherein k is 1 and R$^1$ is —OCF$_3$.

In one embodiment, the present invention provides compounds of Formula VA-1G, wherein k is 1 and R$^1$ is —OCH$_3$.

In one embodiment, the present invention provides compounds of Formula VA-1G, wherein k is 1 and R$^1$ is —F.

In one embodiment, the present invention provides compounds of Formula VA-1G, wherein k is 1 and R$^1$ is —SO$_2$Me.

In one embodiment, the present invention provides compounds of Formula VA-1G, wherein k is 2 and each R$^1$ is independently C$_1$-C$_4$ alkyl, or halo.

In some embodiments of Formula VA-1G, $WR^{W4}$ is a substituted C$_1$-C$_6$ straight or branched aliphatic, C$_3$-C$_7$ heterocyclic, 3-12 membered cycloaliphatic, or 3-12 membered bicyclic.

In some embodiments of Formula VA-1G, $WR^{W2}$ is —C≡CCH$_2$N(R')(R'), —(CH$_2$)$_3$N(R')(R'), —(CH$_2$)$_2$N(R')(R'), —(CH$_2$)N(R')(R') or —N(R')(R').

According to one embodiment of Formula IVD, the following compound of Formula VA-1H is provided:

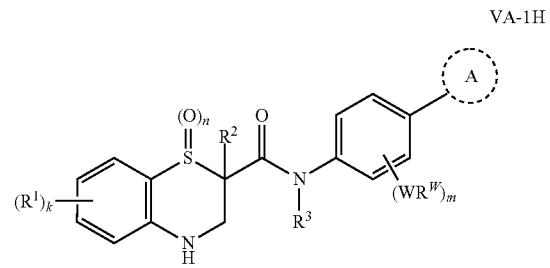

VA-1H ring A is a 5-7 membered monocyclic or bicyclic, heterocyclic or heteroaryl ring optionally substituted with up to p occurrences of -Q-R$^Q$, Q is W;

R$^Q$ is R$^W$; and m is 0-4;

n is 0, 1 or 2;

p is 0-4;

and R$^1$, k, W, and R$^W$ are as defined above.

In one embodiment, the present invention provides compounds of Formula VA-1H, wherein k is 0.

In one embodiment, the present invention provides compounds of Formula VA-1H, wherein k is 1 and R$^1$ is halo.

In one embodiment, the present invention provides compounds of Formula VA-1H, wherein k is 1 and R$^1$ is C$_1$-C$_4$ alkyl.

In one embodiment, the present invention provides compounds of Formula VA-1H, wherein k is 1 and R$^1$ is Me.

In one embodiment, the present invention provides compounds of Formula VA-1H, wherein k is 1 and R$^1$ is —CF$_3$.

In one embodiment, the present invention provides compounds of Formula VA-1H, wherein k is 1 and R$^1$ is —OCF$_3$.

In one embodiment, the present invention provides compounds of Formula VA-1H, wherein k is 1 and R$^1$ is —OCH$_3$.

In one embodiment, the present invention provides compounds of Formula VA-1H, wherein k is 1 and R$^1$ is —F.

In one embodiment, the present invention provides compounds of Formula VA-1H, wherein k is 1 and R$^1$ is —SO$_2$Me.

In one embodiment, the present invention provides compounds of Formula VA-1H, wherein k is 2 and each R$^1$ is independently C$_1$-C$_4$ alkyl, or halo.

In another embodiment, ring A is a 5-7 membered monocyclic, heterocyclic ring having up to 2 heteroatoms selected from O, S, or N, optionally substituted with up to p occurrences of -Q-R$^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring A is a 5-6 membered monocyclic, heteroaryl ring having up to 3 heteroatoms selected from O, S, or N, optionally substituted with up to p occurrences of -Q-R$^Q$. Exemplary such rings include benzimidazol-2-yl, 5-methyl-furan-2-yl, 2,5-dimethyl-pyrrol-1-yl, pyridine-4-yl, 1,2,4-oxadiazol-3-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl, 1,2,4-oxadiazol-5-yl.

In another embodiment, the present invention provides compounds of Formula VA-2:

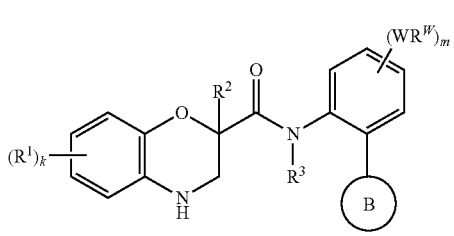

wherein:
ring B is a 5-7 membered monocyclic or bicyclic, heterocyclic or heteroaryl ring optionally substituted with up to p occurrences of -Q-$R^Q$;
Q is W;
$R^Q$ is $R^W$;
m is 0-4;
n is 0, 1 or 2;
p is 0-4; and
$R^1$, k, W, and $R^W$ are as defined above.

In one embodiment, m is 0-2. Or, m is 0. Or m is 1.
In one embodiment, p is 0-2. Or, p is 0. Or, p is 1.

In another embodiment, ring B is a 5-7 membered monocyclic, heterocyclic ring having up to 2 heteroatoms selected from O, S, or N, optionally substituted with up to p occurrences of -Q-$R^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring B is a 5-6 membered monocyclic, heteroaryl ring having up to 3 heteroatoms selected from O, S, or N, optionally substituted with up to p occurrences of -Q-$R^Q$. Exemplary such rings include benzimidazol-2-yl, 5-methyl-furan-2-yl, 2,5-dimethyl-pyrrol-1-yl, pyridine-4-yl, 1,2,4-oxadiazol-3-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl, 1,2,4-oxadiazol-5-yl.

In another embodiment, the present invention provides compounds of Formula VA-3:

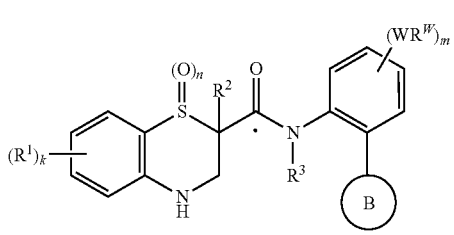

wherein:
ring B is a 5-7 membered monocyclic or bicyclic, heterocyclic or heteroaryl ring optionally substituted with up to p occurrences of -Q-$R^Q$;
Q is W;
$R^Q$ is $R^W$;
m is 0-4;
n is 0, 1 or 2;
p is 0-4; and
$R^1$, k, W, and $R^W$ are as defined above.

In one embodiment, m is 0-2. Or, m is 0. Or m is 1.
In one embodiment, p is 0-2. Or, p is 0. Or, p is 1.

In another embodiment, ring B is a 5-7 membered monocyclic, heterocyclic ring having up to 2 heteroatoms selected from O, S, or N, optionally substituted with up to p occurrences of -Q-$R^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring B is a 5-6 membered monocyclic, heteroaryl ring having up to 3 heteroatoms selected from O, S, or N, optionally substituted with up to p occurrences of -Q-$R^Q$. Exemplary such rings include benzimidazol-2-yl, 5-methyl-furan-2-yl, 2,5-dimethyl-pyrrol-1-yl, pyridine-4-yl, 1,2,4-oxadiazol-3-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl, 1,2,4-oxadiazol-5-yl.

In another embodiment, the present invention provides compounds of Formula VB-1:

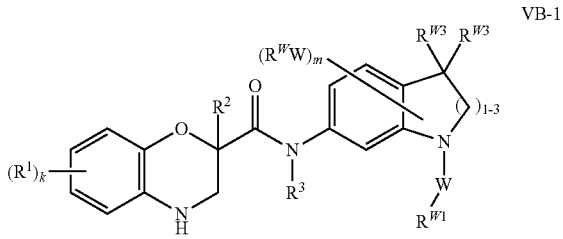

wherein:
$R^{W1}$ is hydrogen or $C_1$-$C_6$ aliphatic;
each of $R^{W3}$ is hydrogen or $C_1$-$C_6$ aliphatic; or both $R^{W3}$ taken together form a $C_3$-$C_6$ cycloalkyl or heterocyclic ring having up to two heteroatoms selected from O, S, or NR', wherein said ring is optionally substituted with up to two $WR^W$ substituents;
m is 0-4; and
k, $R^1$, W, and $R^W$ are as defined above.

In one embodiment, $WR^{W1}$ is hydrogen, $C_1$-$C_6$ aliphatic, $C(O)C_1$-$C_6$ aliphatic, or $C(O)OC_1$-$C_6$ aliphatic.

In another embodiment, each $R^{W3}$ is hydrogen, $C_1$-$C_4$ alkyl. Or, both $R^{W3}$ taken together form a $C_3$-$C_6$ cycloaliphatic ring or 5-7 membered heterocyclic ring having up to two heteroatoms selected from O, S, or N, wherein said cycloaliphatic or heterocyclic ring is optionally substituted with up to three substitutents selected from $WR^{W1}$. Exemplary such rings include cyclopropyl, cyclopentyl, optionally substituted piperidyl, etc.

In another embodiment, the present invention provides compounds of Formula VB-2:

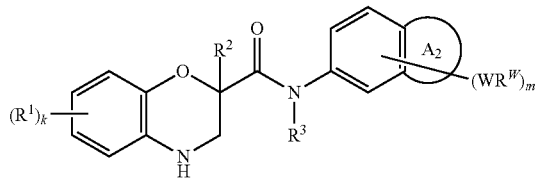

wherein:

ring $A_2$ is a phenyl or a 5-6 membered heteroaryl ring, wherein ring $A_2$ and the phenyl ring fused thereto together have up 4 substituents independently selected from $WR^W$;

m is 0-4; and

W, $R^W$, k, and $R^1$ are as defined above.

In one embodiment, ring $A_2$ is an optionally substituted 5-membered ring selected from pyrrolyl, furanyl, thienyl, pyrazolyl, imidazolyl, thiazolyl, oxazolyl, thiadiazolyl, oxadiazolyl, or triazolyl.

In one embodiment, ring $A_2$ is an optionally substituted 5-membered ring selected from pyrrolyl, pyrazolyl, thiadiazolyl, imidazolyl, oxazolyl, or triazolyl. Exemplary such rings include:

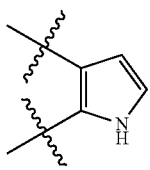
aa

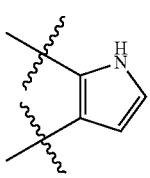
bb

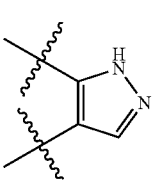
cc

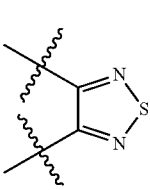
dd

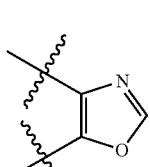
ee

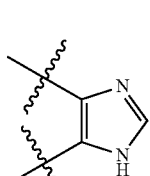
ff

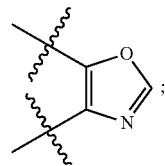
gg wherein said ring is optionally substituted as set forth above.

In another embodiment, ring $A_2$ is an optionally substituted 6-membered ring. Exemplary such rings include pyridyl, pyrazinyl, or triazinyl. In another embodiment, said ring is an optionally pyridyl.

In one embodiment, ring $A_2$ is phenyl.

In another embodiment, ring $A_2$ is pyrrolyl, pyrazolyl, pyridyl, or thiadiazolyl.

Exemplary W in Formula VB-2 includes a bond, C(O), C(O)O or $C_1$-$C_6$ alkylene.

Exemplary $R^W$ in Formula VB-2 include cyano, halo, $C_1$-$C_6$ aliphatic, $C_3$-$C_6$ cycloaliphatic, aryl, 5-7 membered heterocyclic ring having up to two heteroatoms selected from O, S, or N, wherein said aliphatic, phenyl, and heterocyclic are independently and optionally substituted with up to three substituents selected from $C_1$-$C_6$ alkyl, O—$C_1$-$C_6$ alkyl, halo, cyano, OH, or $CF_3$, wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is $C_1$-$C_4$ alkyl.

In one embodiment, the present invention provides compounds of Formula VB-3:

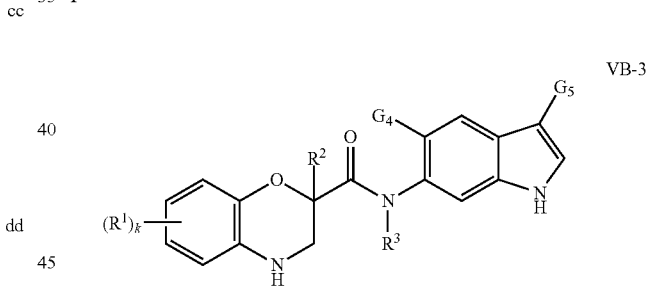

VB-3 wherein:

$G_4$ is hydrogen, halo, CN, $CF_3$, $CHF_2$, $CH_2F$, optionally substituted $C_1$-$C_6$ aliphatic, aryl-$C_1$-$C_6$ alkyl, or a phenyl, wherein $G_4$ is optionally substituted with up to 4 $WR^W$ substituents; wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—;

$G_5$ is hydrogen, an optionally substituted $C_1$-$C_6$ aliphatic, $CF_3$, or CN;

wherein said indole ring system is further optionally substituted with up to 3 substituents independently selected from $WR^W$.

In one embodiment, $G_4$ is hydrogen. Or, $G_5$ is hydrogen.

In another embodiment, $G_4$ is hydrogen, and $G_5$ is $C_1$-$C_6$aliphatic, $CF_3$, or CN, wherein said aliphatic is optionally substituted with $C_1$-$C_6$ alkyl, halo, cyano, or $CF_3$, and wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C$_1$-C$_4$ alkyl.

In another embodiment, G$_4$ is hydrogen, and G$_5$ is cyano, CF$_3$, methyl, ethyl, propyl, isopropyl, butyl, sec-butyl, t-butyl, cyanomethyl, methoxyethyl, CH$_2$C(O)OMe, (CH$_2$)$_2$—NHC(O)O-tert-butyl, or cyclopentyl.

In another embodiment, G$_5$ is hydrogen, and G$_4$ is halo, C$_1$-C$_6$ aliphatic or phenyl, wherein said aliphatic or phenyl is optionally substituted with C$_1$-C$_6$ alkyl, halo, cyano, or CF$_3$, wherein up to two methylene units of said C$_1$-C$_6$ aliphatic or C$_1$-C$_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C$_1$-C$_4$ alkyl.

In another embodiment, G$_5$ is hydrogen, and G$_4$ is halo, CF$_3$, ethoxycarbonyl, t-butyl, 2-methoxyphenyl, 2-ethoxyphenyl, (4-C(O)NH(CH$_2$)$_2$—NMe$_2$)-phenyl, 2-methoxy-4-chloro-phenyl, pyridine-3-yl, 4-isopropylphenyl, 2,6-dimethoxyphenyl, sec-butylaminocarbonyl, ethyl, t-butyl, or piperidin-1-ylcarbonyl.

In another embodiment, G$_4$ and G$_5$ are both hydrogen, and the nitrogen ring atom of said indole ring is substituted with C$_1$-C$_6$ aliphatic, C(O)(C$_1$-C$_6$ aliphatic), or benzyl, wherein said aliphatic or benzyl is optionally substituted with C$_1$-C$_6$ alkyl, halo, cyano, or CF$_3$, wherein up to two methylene units of said C$_1$-C$_6$ aliphatic or C$_1$-C$_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, G$_4$ and G$_5$ are both hydrogen, and the nitrogen ring atom of said indole ring is substituted with acyl, benzyl, C(O)CH$_2$N(Me)C(O)CH$_2$NHMe, or ethoxycarbonyl.

In another embodiment, the present invention provides compounds of Formula VB-4:

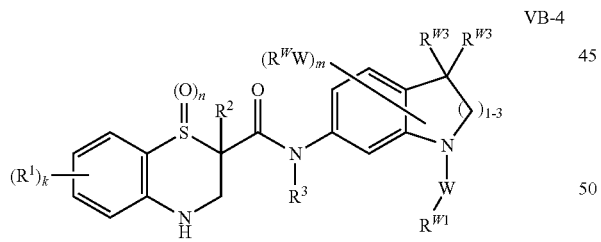

VB-4 wherein:
n is 0, 1 or 2;
R$^{W1}$ is hydrogen or C$_1$-C$_6$ aliphatic;
each of R$^{W3}$ is hydrogen or C$_1$-C$_6$ aliphatic; or
both R$^{W3}$ taken together form a C$_3$-C$_6$ cycloalkyl or heterocyclic ring having up to two heteroatoms selected from O, S, or NR', wherein said ring is optionally substituted with up to two WR$^W$ substituents;
m is 0-4; and
k, R$^1$, W, and R$^W$ are as defined above.

In one embodiment, WR$^{W1}$ is hydrogen, C$_1$-C$_6$ aliphatic, C(O)C$_1$-C$_6$ aliphatic, or C(O)OC$_1$-C$_6$ aliphatic.

In another embodiment, each R$^{W3}$ is hydrogen, C$_1$-C$_4$ alkyl. Or, both R$^{W3}$ taken together form a C$_3$-C$_6$ cycloaliphatic ring or 5-7 membered heterocyclic ring having up to two heteroatoms selected from O, S, or N, wherein said cycloaliphatic or heterocyclic ring is optionally substituted with up to three substitutents selected from WR$^{W1}$. Exemplary such rings include cyclopropyl, cyclopentyl, optionally substituted piperidyl, etc.

In another embodiment, the present invention provides compounds of Formula VB-5:

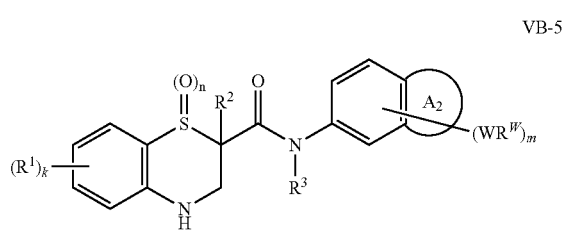

VB-5 wherein:
ring A$_2$ is a phenyl or a 5-6 membered heteroaryl ring, wherein ring A$_2$ and the phenyl ring fused thereto together have up 4 substituents independently selected from WR$^W$;
m is 0-4;
n is 0, 1 or 2; and
W, R$^W$, k, and R$^1$ are as defined above.

In one embodiment, ring A$_2$ is an optionally substituted 5-membered ring selected from pyrrolyl, furanyl, thienyl, pyrazolyl, imidazolyl, thiazolyl, oxazolyl, thiadiazolyl, oxadiazolyl, or triazolyl.

In one embodiment, ring A$_2$ is an optionally substituted 5-membered ring selected from pyrrolyl, pyrazolyl, thiadiazolyl, imidazolyl, oxazolyl, or triazolyl. Exemplary such rings include:

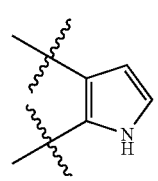

aa

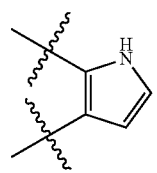

bb

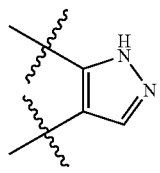

cc

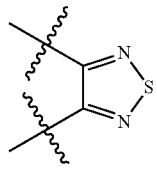

dd

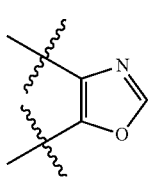

ee

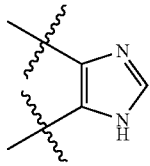

ff

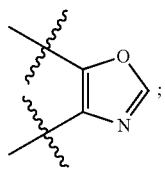

gg wherein said ring is optionally substituted as set forth above.

In another embodiment, ring $A_2$ is an optionally substituted 6-membered ring. Exemplary such rings include pyridyl, pyrazinyl, or triazinyl. In another embodiment, said ring is an optionally pyridyl.

In one embodiment, ring $A_2$ is phenyl.

In another embodiment, ring $A_2$ is pyrrolyl, pyrazolyl, pyridyl, or thiadiazolyl.

Exemplary W in Formula VB-5 includes a bond, C(O), C(O)O or $C_1$-$C_6$ alkylene.

Exemplary $R^W$ in Formula VB-5 include cyano, halo, $C_1$-$C_6$ aliphatic, $C_3$-$C_6$ cycloaliphatic, aryl, 5-7 membered heterocyclic ring having up to two heteroatoms selected from O, S, or N, wherein said aliphatic, phenyl, and heterocyclic are independently and optionally substituted with up to three substituents selected from $C_1$-$C_6$ alkyl, O—$C_1$-$C_6$ alkyl, halo, cyano, OH, or $CF_3$, wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is $C_1$-$C_4$ alkyl.

In one embodiment, the present invention provides compounds of Formula VB-6:

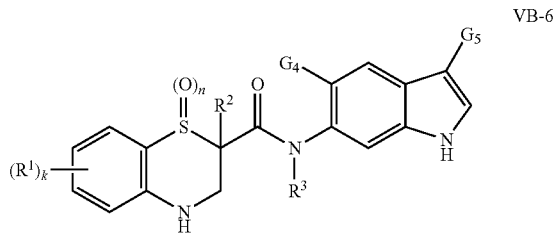

VB-6 wherein:

n is 0, 1 or 2;

$G_4$ is hydrogen, halo, CN, $CF_3$, $CHF_2$, $CH_2F$, optionally substituted $C_1$-$C_6$ aliphatic, aryl-$C_1$-$C_6$ alkyl, or a phenyl, wherein $G_4$ is optionally substituted with up to 4 $WR^W$ substituents; wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—;

$G_5$ is hydrogen, an optionally substituted $C_1$-$C_6$ aliphatic, $CF_3$, or CN;

wherein said indole ring system is further optionally substituted with up to 3 substituents independently selected from $WR^W$.

In one embodiment, $G_4$ is hydrogen. Or, $G_5$ is hydrogen.

In another embodiment, $G_4$ is hydrogen, and $G_5$ is $C_1$-$C_6$ aliphatic, $CF_3$, or CN, wherein said aliphatic is optionally substituted with $C_1$-$C_6$ alkyl, halo, cyano, or $CF_3$, and wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is $C_1$-$C_4$ alkyl.

In another embodiment, $G_4$ is hydrogen, and $G_5$ is cyano, $CF_3$, methyl, ethyl, propyl, isopropyl, butyl, sec-butyl, t-butyl, cyanomethyl, methoxyethyl, $CH_2C(O)OMe$, $(CH_2)_2$—NHC(O)O-tert-butyl, or cyclopentyl.

In another embodiment, $G_5$ is hydrogen, and $G_4$ is halo, $C_1$-$C_6$ aliphatic or phenyl, wherein said aliphatic or phenyl is optionally substituted with $C_1$-$C_6$ alkyl, halo, cyano, or $CF_3$, wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is $C_1$-$C_4$ alkyl.

In another embodiment, $G_5$ is hydrogen, and $G_4$ is halo, $CF_3$, ethoxycarbonyl, t-butyl, 2-methoxyphenyl, 2-ethoxyphenyl, (4-C(O)NH(CH$_2$)$_2$—NMe$_2$)-phenyl, 2-methoxy-4-chloro-phenyl, pyridine-3-yl, 4-isopropylphenyl, 2,6-dimethoxyphenyl, sec-butylaminocarbonyl, ethyl, t-butyl, or piperidin-1-ylcarbonyl.

In another embodiment, $G_4$ and $G_5$ are both hydrogen, and the nitrogen ring atom of said indole ring is substituted with $C_1$-$C_6$ aliphatic, C(O)($C_1$-$C_6$ aliphatic), or benzyl, wherein said aliphatic or benzyl is optionally substituted with $C_1$-$C_6$ alkyl, halo, cyano, or $CF_3$, wherein up to two methylene units of said $C_1$-$C_6$ aliphatic or $C_1$-$C_6$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SO$_2$NR'—, NR'SO$_2$—, or —NR'SO$_2$NR'—. In another embodiment, R' above is C1-C4 alkyl.

In another embodiment, $G_4$ and $G_5$ are both hydrogen, and the nitrogen ring atom of said indole ring is substituted with acyl, benzyl, C(O)CH$_2$N(Me)C(O)CH$_2$NHMe, or ethoxycarbonyl.

In some embodiments of Formulae IA, IB, IIA, IIB, IIIA, IIIA-1, IIIA-2, IIIA-3, IIIB, IIIC, IIID, IIIE, IIIF, IIIF-1, IIIF-2, IIIF-3, MG, IIIH, IIIJ, IIIK, IVA, IVB, IVC, IVD, IVE, IVF, VA-1A, VA-1B, VA-1C, VA-1D, VA-1E, VA-1F, VA-1G, VA-1H, VA-2, VA-3, VB-1, VB-2, VB-3, VB-4, VB-5 or VB-6, $R^2$ is hydrogen.

In some embodiments of Formulae IA, IB, IIA, IIB, IIIA, IIIA-1, IIIA-2, IIIA-3, IIIB, IIIC, IIID, IIIE, IIIF, IIIF-1, IIIF-2, IIIF-3, IIIG, IIIH, IIIJ, IIIK, IVA, IVB, IVC, IVD, IVE, IVF, VA-1A, VA-1B, VA-1C, VA-1D, VA-1E, VA-1F, VA-1G, VA-1H, VA-2, VA-3, VB-1, VB-2, VB-3, VB-4, VB-5 or VB-6, $R^3$ is hydrogen.

In further embodiments of Formula IA, IB, IIA, IIB, IIIA, IIIA-1, IIIA-2, IIIA-3, IIIB, IIIC, IIID, IIIE, IIIF, IIIF-1, IIIF-2, IIIF-3, IIIG, IIIH, IIIJ, IIIK, IVA, IVB, IVC, IVD, IVE, IVF, VA-1A, VA-1B, VA-1C, VA-1D, VA-1E, VA-1F, VA-1G, VA-1H, VA-2, VA-3, VB-1, VB-2, VB-3, VB-4, VB-5 or VB-6, $R^2$ and $R^3$ are hydrogen.
Representative compounds of the present invention are set forth below in Table 1 below.
TABLE 1
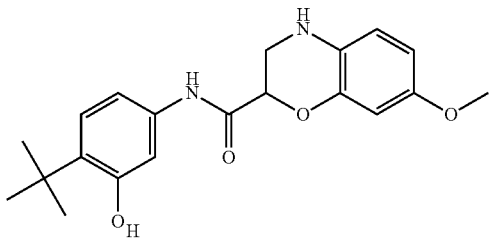
1
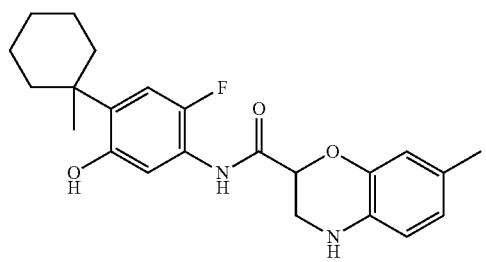 [SMILES: Cc1ccc2c(c1)OC(C(=O)Nc1cc(O)c(C3(C)CCCCC3)cc1F)CN2]
2
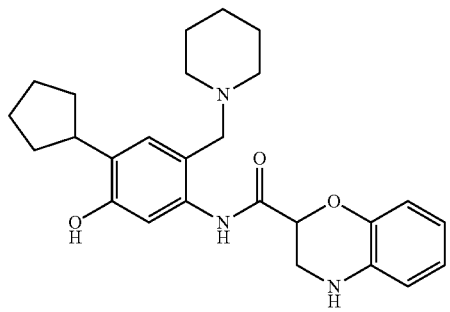 [SMILES: O=C(Nc1cc(O)c(C2CCCC2)cc1CN1CCCCC1)C1CNc2ccccc2O1]
3
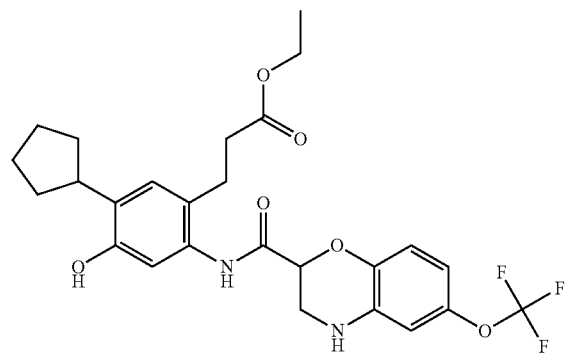 [SMILES: CCOC(=O)CCc1cc(C2CCCC2)c(O)cc1NC(=O)C1CNc2cc(OC(F)(F)F)ccc2O1]
4
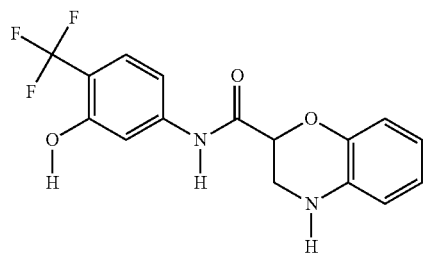 [SMILES: O=C(Nc1ccc(C(F)(F)F)c(O)c1)C1CNc2ccccc2O1]
5

TABLE 1-continued
| | |
|---|---|
| 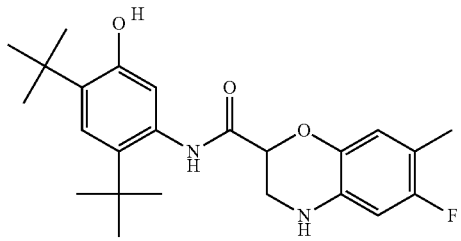 | 6 |
| 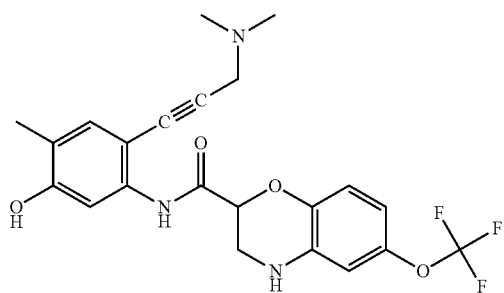 [SMILES: Cc1cc(C#CCN(C)C)c(NC(=O)C2CNc3cc(OC(F)(F)F)ccc3O2)cc1O] | 7 |
| 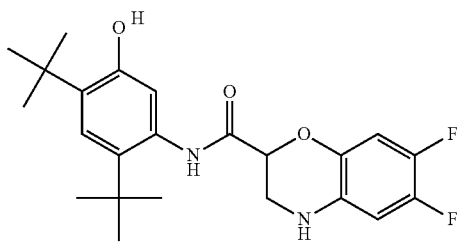 | 8 |
| 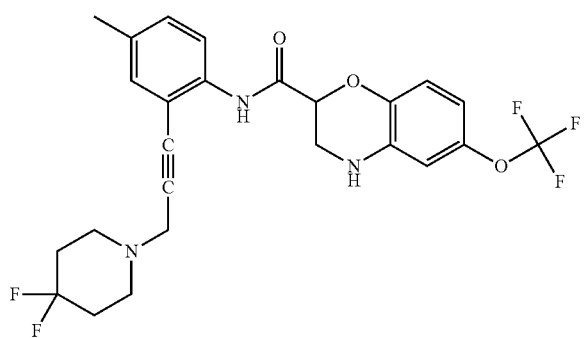 [SMILES: Cc1ccc(NC(=O)C2CNc3cc(OC(F)(F)F)ccc3O2)c(C#CCN2CCC(F)(F)CC2)c1] | 9 |
| 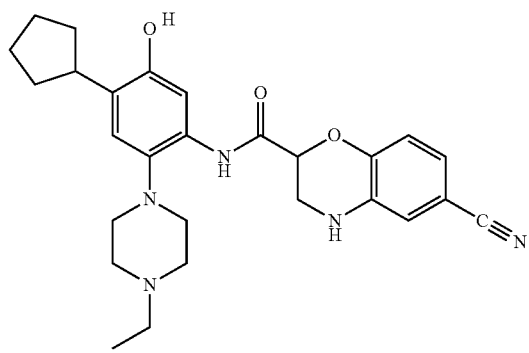 | 10 |

TABLE 1-continued
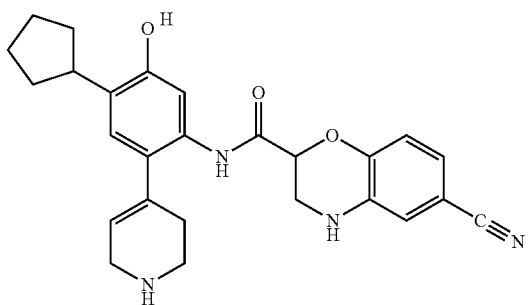
11
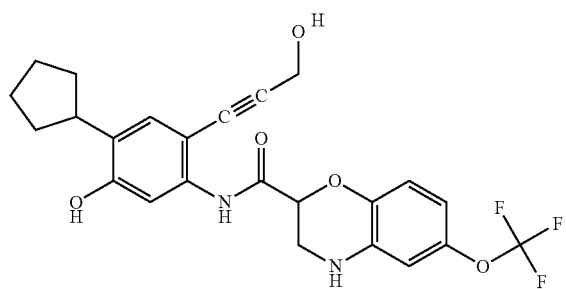
12
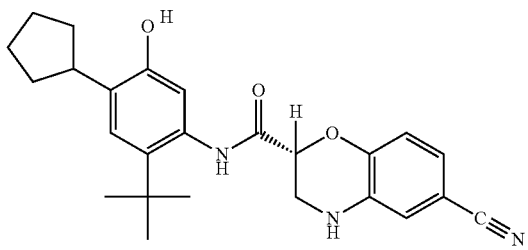
13
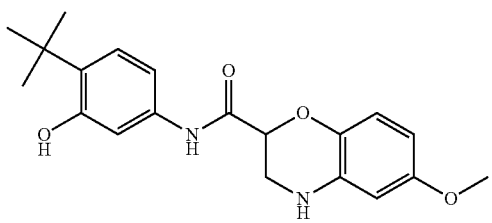 [SMILES: COc1ccc2c(c1)NCC(C(=O)Nc1ccc(C(C)(C)C)c(O)c1)O2]
14
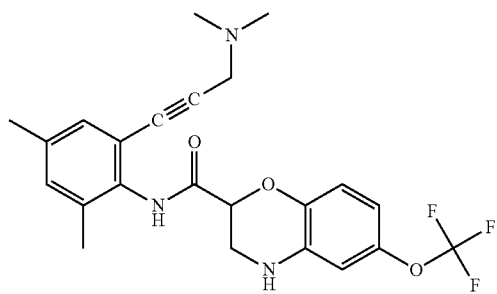 [SMILES: Cc1cc(C)c(NC(=O)C2CNc3cc(OC(F)(F)F)ccc3O2)c(C#CCN(C)C)c1]
15

TABLE 1-continued
| | |
|---|---|
| 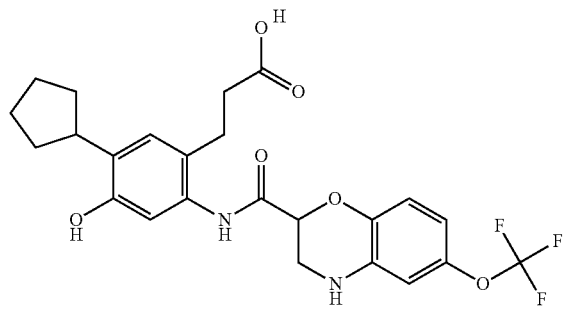 | 16 |
| 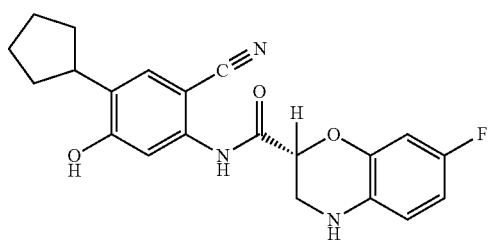 [SMILES: N#Cc1cc(C2CCCC2)c(O)cc1NC(=O)[C@H]1CNc2ccc(F)cc2O1] | 17 |
| 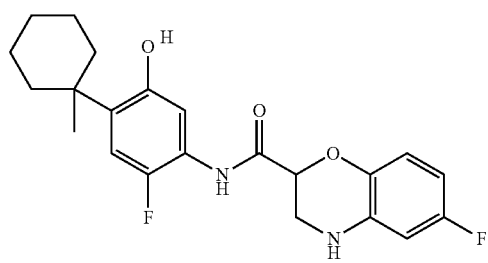 | 18 |
| 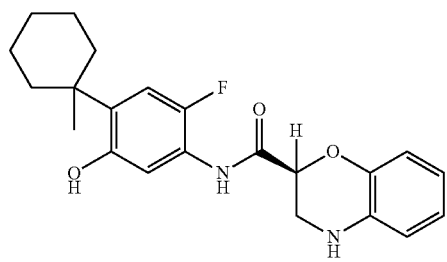 [SMILES: CC1(c2cc(F)c(NC(=O)[C@@H]3CNc4ccccc4O3)cc2O)CCCCC1] | 19 |
| 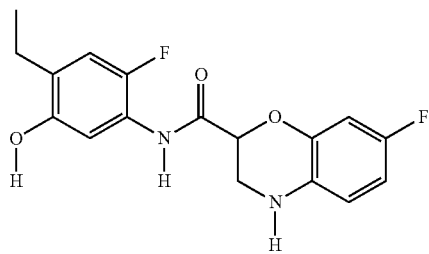 [SMILES: CCc1cc(F)c(NC(=O)C2CNc3ccc(F)cc3O2)cc1O] | 20 |
| 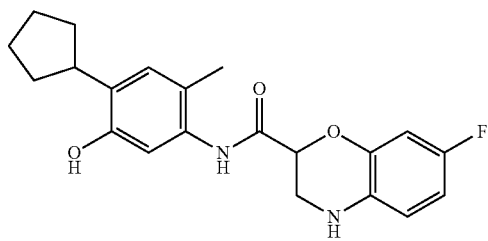 [SMILES: Cc1cc(C2CCCC2)c(O)cc1NC(=O)C1CNc2ccc(F)cc2O1] | 21 |

TABLE 1-continued
| | |
|---|---|
| 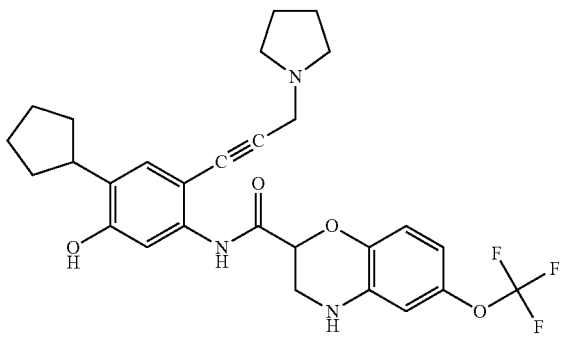 [SMILES: O=C(Nc1cc(O)c(C2CCCC2)cc1C#CCN1CCCC1)C1CNc2cc(OC(F)(F)F)ccc2O1] | 22 |
| 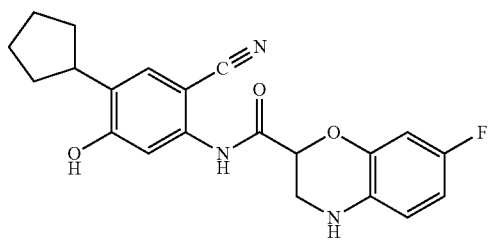 [SMILES: N#Cc1cc(C2CCCC2)c(O)cc1NC(=O)C1CNc2ccc(F)cc2O1] | 23 |
| 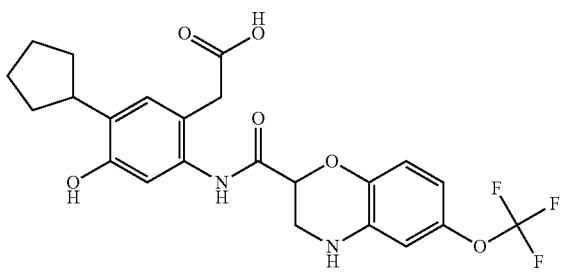 [SMILES: O=C(O)Cc1cc(C2CCCC2)c(O)cc1NC(=O)C1CNc2cc(OC(F)(F)F)ccc2O1] | 24 |
| 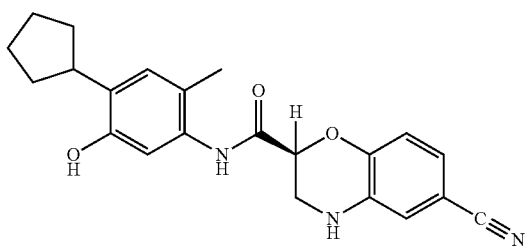 [SMILES: Cc1cc(C2CCCC2)c(O)cc1NC(=O)[C@@H]1CNc2cc(C#N)ccc2O1] | 25 |
| 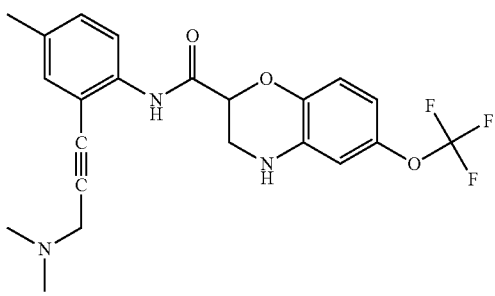 | 26 |
| 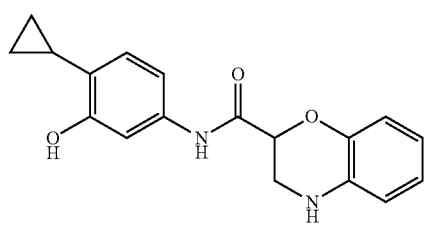 [SMILES: O=C(Nc1ccc(C2CC2)c(O)c1)C1CNc2ccccc2O1] | 27 |

TABLE 1-continued
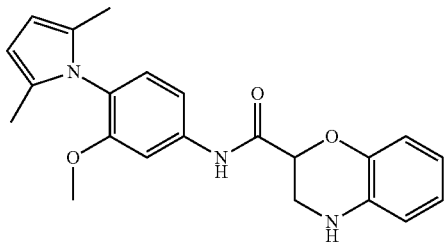 [SMILES: COc1cc(NC(=O)C2CNc3ccccc3O2)ccc1-n1c(C)ccc1C] 28
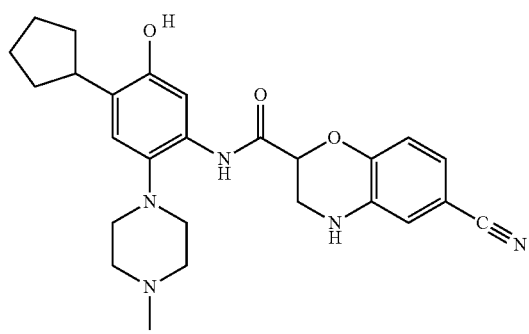 29
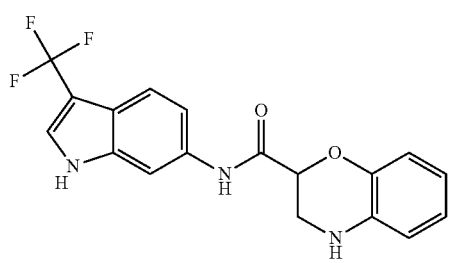 30
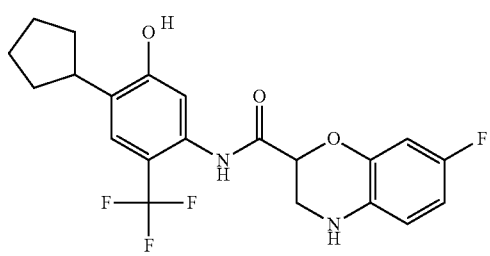 31
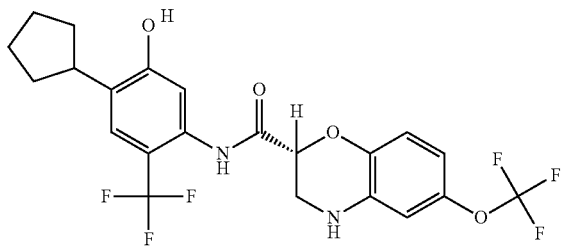 32
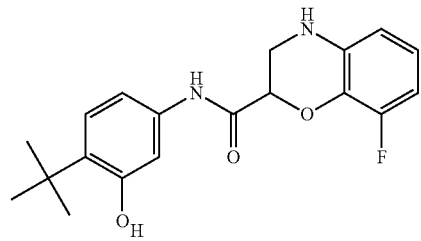 33

TABLE 1-continued
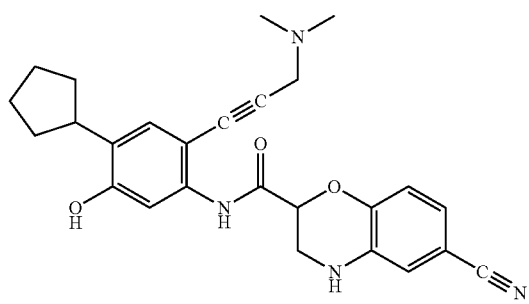 [SMILES: CN(C)CC#Cc1cc(C2CCCC2)c(O)cc1NC(=O)C1CNc2cc(C#N)ccc2O1]
34
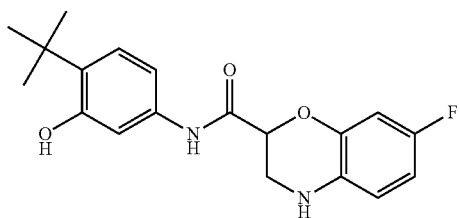 [SMILES: CC(C)(C)c1ccc(NC(=O)C2CNc3ccc(F)cc3O2)cc1O]
35
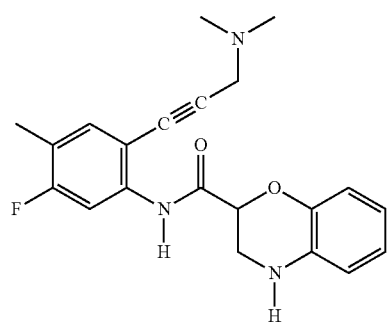 [SMILES: Cc1cc(C#CCN(C)C)c(NC(=O)C2CNc3ccccc3O2)cc1F]
36
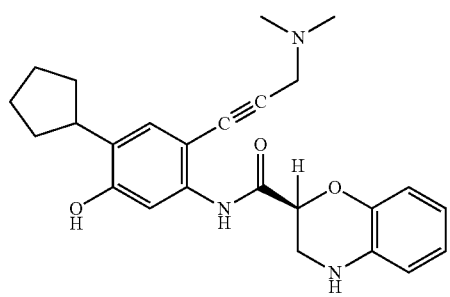 [SMILES: CN(C)CC#Cc1cc(C2CCCC2)c(O)cc1NC(=O)[C@@H]1CNc2ccccc2O1]
37
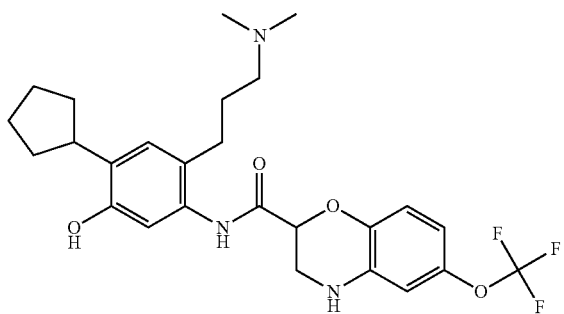 [SMILES: CN(C)CCCc1cc(C2CCCC2)c(O)cc1NC(=O)C1CNc2cc(OC(F)(F)F)ccc2O1]
38

TABLE 1-continued
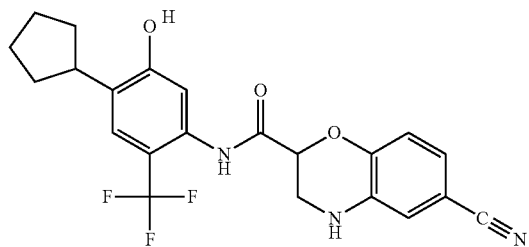 39
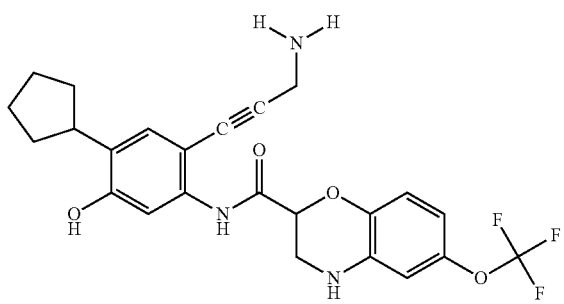 [SMILES: NCC#Cc1cc(C2CCCC2)c(O)cc1NC(=O)C1CNc2cc(OC(F)(F)F)ccc2O1] 40
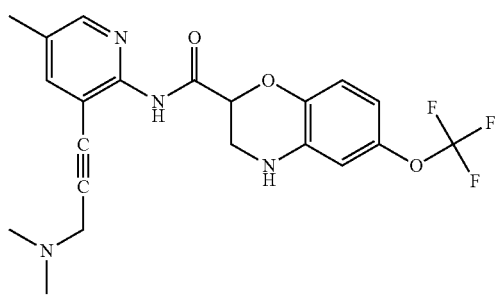 [SMILES: Cc1cnc(NC(=O)C2CNc3cc(OC(F)(F)F)ccc3O2)c(C#CCN(C)C)c1] 41
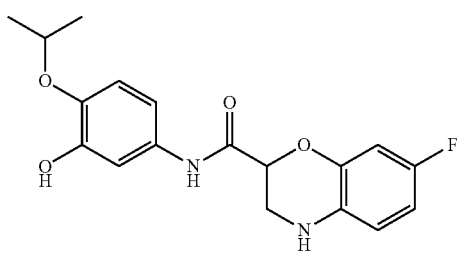 [SMILES: CC(C)Oc1ccc(NC(=O)C2CNc3ccc(F)cc3O2)cc1O] 42
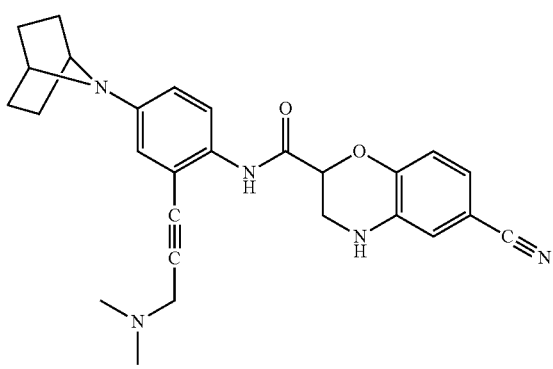 [SMILES: CN(C)CC#Cc1cc(N2C3CCC2CC3)ccc1NC(=O)C1CNc2cc(C#N)ccc2O1] 43

TABLE 1-continued
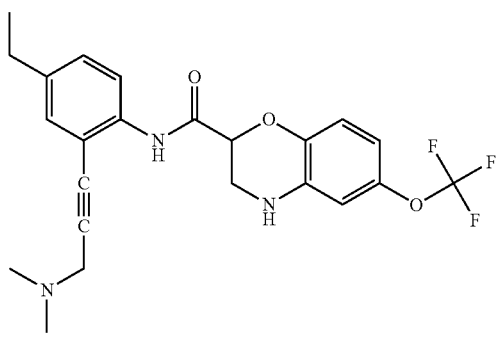 [SMILES: CCc1ccc(NC(=O)C2CNc3cc(OC(F)(F)F)ccc3O2)c(C#CCN(C)C)c1]
44
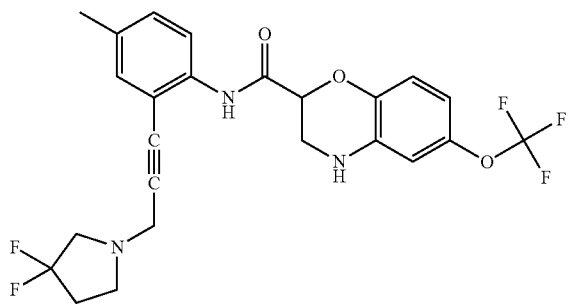 [SMILES: Cc1ccc(NC(=O)C2CNc3cc(OC(F)(F)F)ccc3O2)c(C#CCN2CCC(F)(F)C2)c1]
45
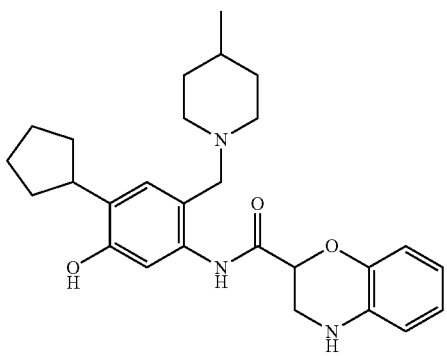 [SMILES: CC1CCN(Cc2cc(C3CCCC3)c(O)cc2NC(=O)C2CNc3ccccc3O2)CC1]
46
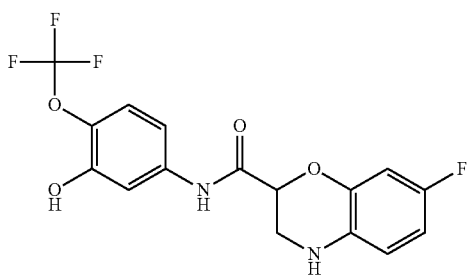 [SMILES: O=C(Nc1ccc(OC(F)(F)F)c(O)c1)C1CNc2ccc(F)cc2O1]
47
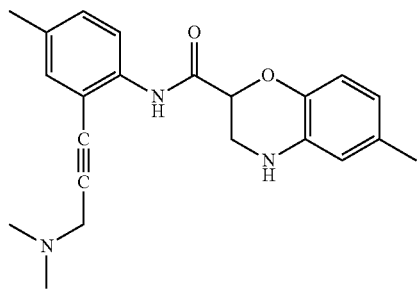
48

TABLE 1-continued
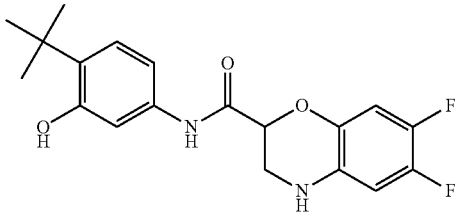 [SMILES: CC(C)(C)c1ccc(NC(=O)C2CNc3cc(F)c(F)cc3O2)cc1O] 49
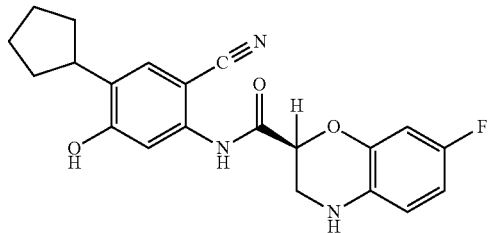 [SMILES: N#Cc1cc(C2CCCC2)c(O)cc1NC(=O)[C@@H]1CNc2ccc(F)cc2O1] 50
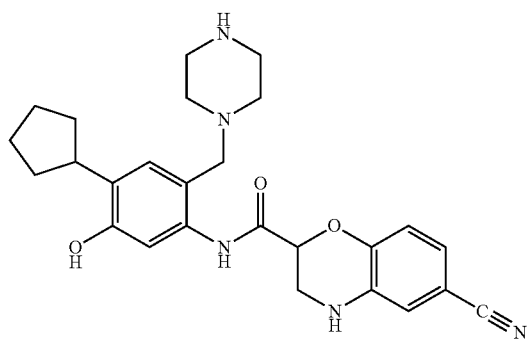 [SMILES: N#Cc1ccc2c(c1)NCC(C(=O)Nc1cc(O)c(C3CCCC3)cc1CN1CCNCC1)O2] 51
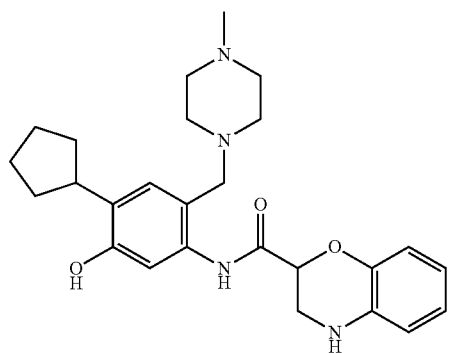 [SMILES: CN1CCN(Cc2cc(C3CCCC3)c(O)cc2NC(=O)C2CNc3ccccc3O2)CC1] 52
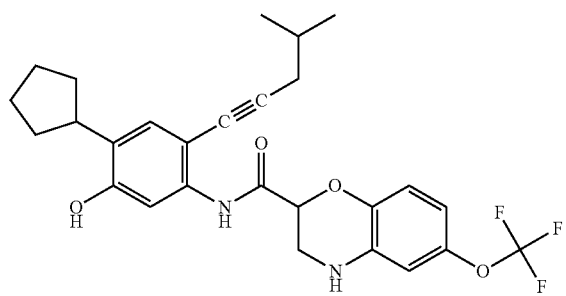 [SMILES: CC(C)CC#Cc1cc(C2CCCC2)c(O)cc1NC(=O)C1CNc2cc(OC(F)(F)F)ccc2O1] 53

TABLE 1-continued
| | |
|---|---|
| 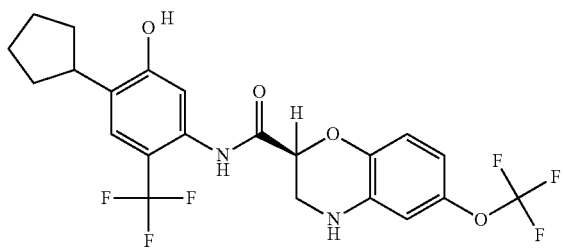 | 54 |
| 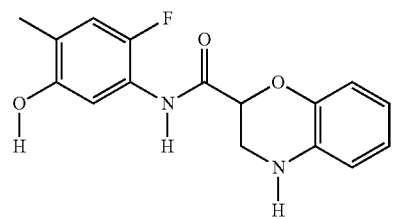 [SMILES: Cc1cc(F)c(NC(=O)C2CNc3ccccc3O2)cc1O] | 55 |
| 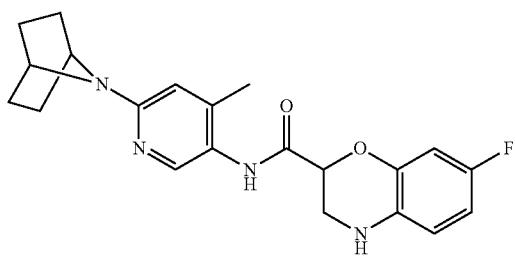 [SMILES: Cc1cc(N2C3CCC2CC3)ncc1NC(=O)C1CNc2ccc(F)cc2O1] | 56 |
| 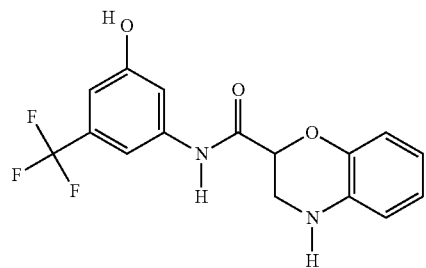 | 57 |
| 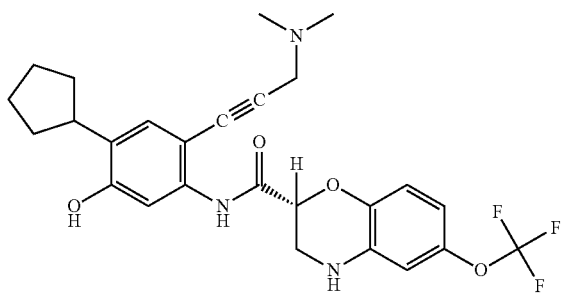 [SMILES: CN(C)CC#Cc1cc(C2CCCC2)c(O)cc1NC(=O)[C@H]1CNc2cc(OC(F)(F)F)ccc2O1] | 58 |
| 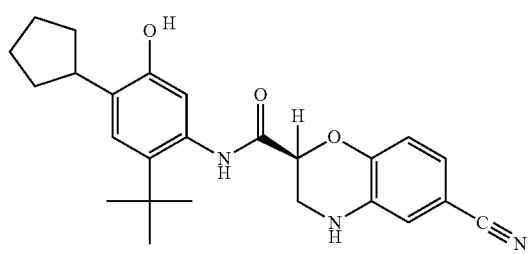 | 59 |

TABLE 1-continued
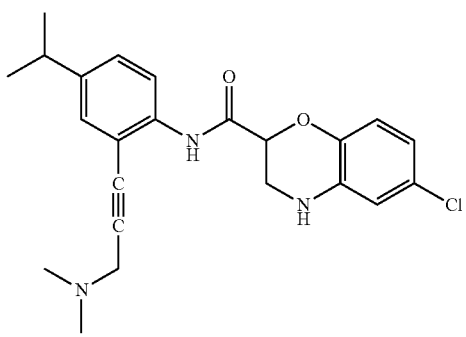 [SMILES: CC(C)c1ccc(NC(=O)C2CNc3cc(Cl)ccc3O2)c(C#CCN(C)C)c1]
60
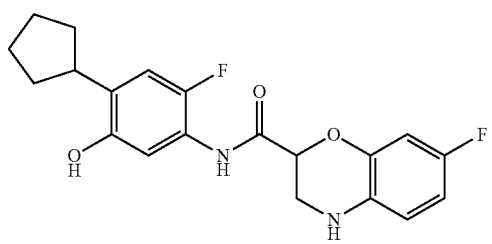 [SMILES: O=C(Nc1cc(O)c(C2CCCC2)cc1F)C1CNc2ccc(F)cc2O1]
61
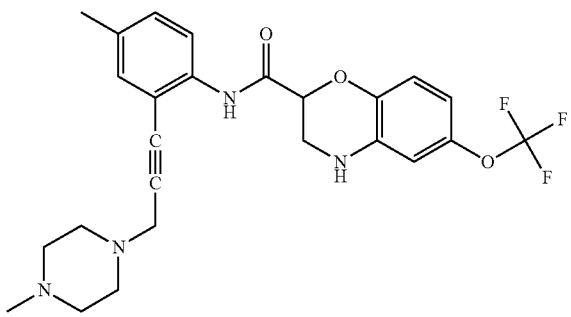 [SMILES: Cc1ccc(NC(=O)C2CNc3cc(OC(F)(F)F)ccc3O2)c(C#CCN2CCN(C)CC2)c1]
62
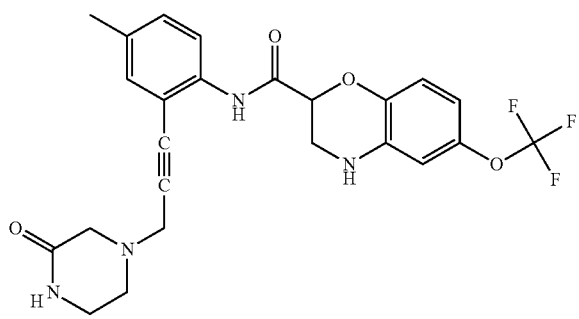
63
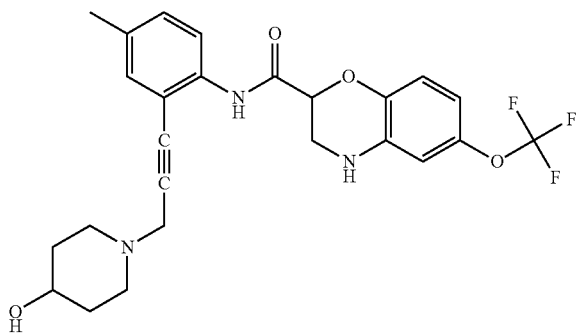 [SMILES: Cc1ccc(NC(=O)C2CNc3cc(OC(F)(F)F)ccc3O2)c(C#CCN2CCC(O)CC2)c1]
64

TABLE 1-continued
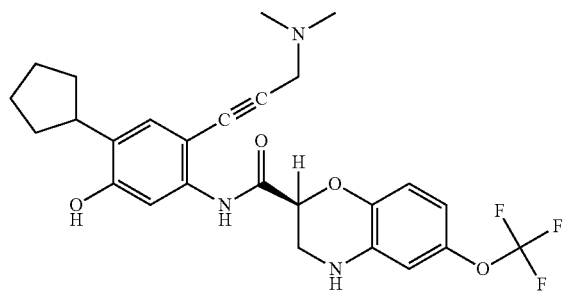 [SMILES: CN(C)CC#Cc1cc(C2CCCC2)c(O)cc1NC(=O)[C@@H]1CNc2cc(OC(F)(F)F)ccc2O1] 65
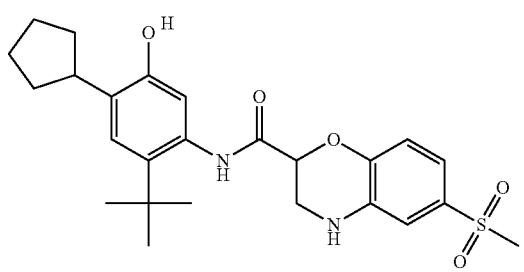 66
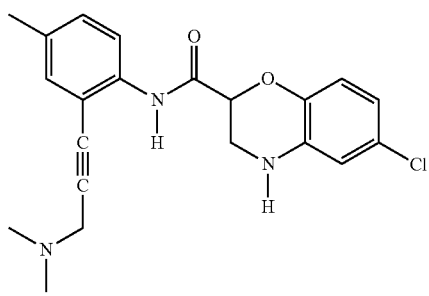 [SMILES: Cc1ccc(NC(=O)C2CNc3cc(Cl)ccc3O2)c(C#CCN(C)C)c1] 67
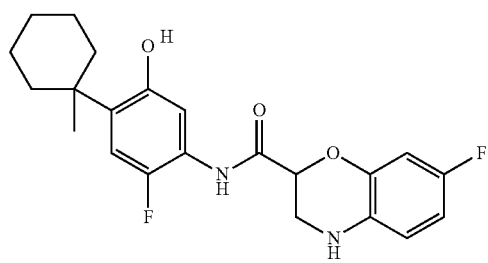 68
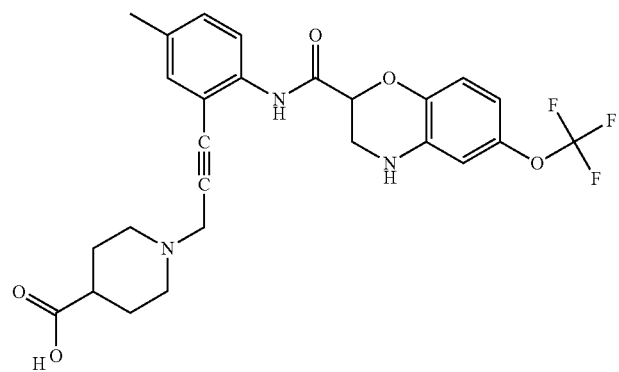 69

TABLE 1-continued
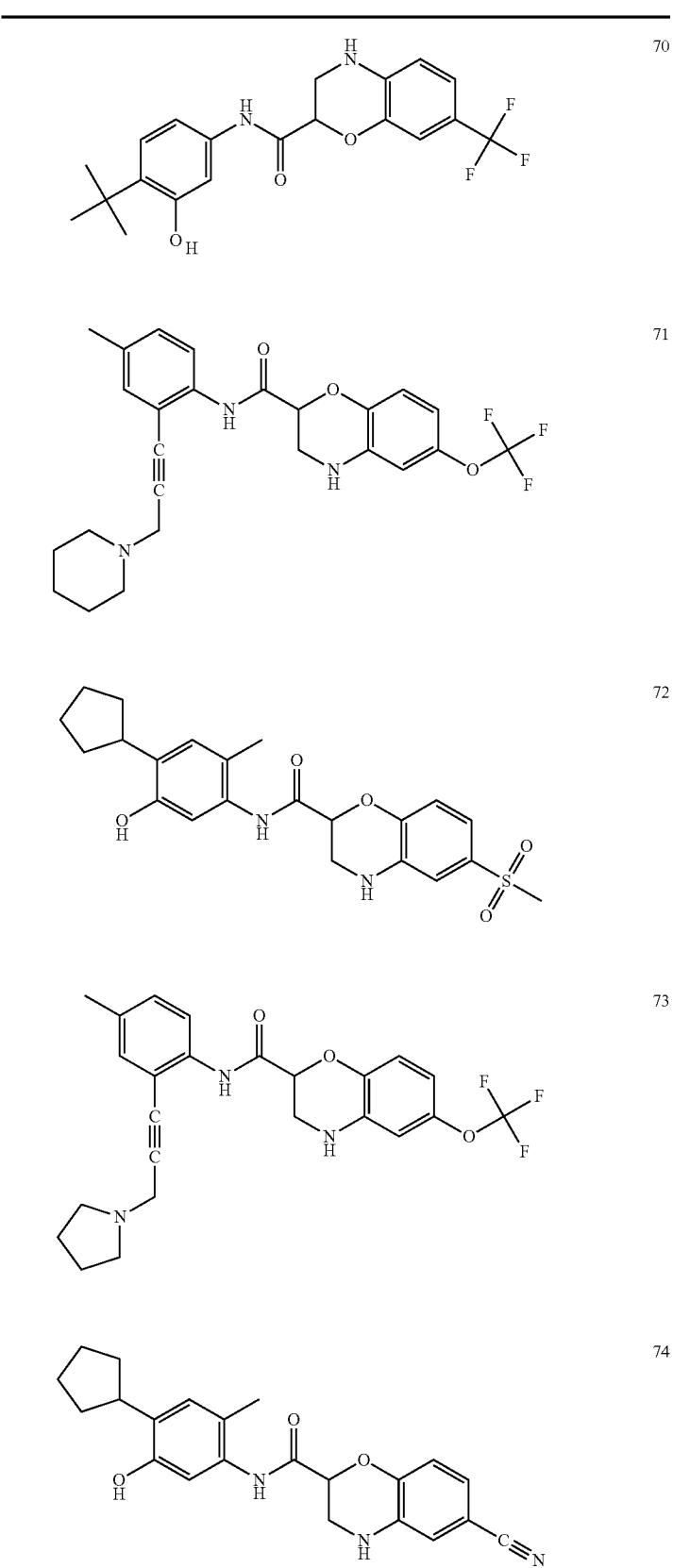

TABLE 1-continued
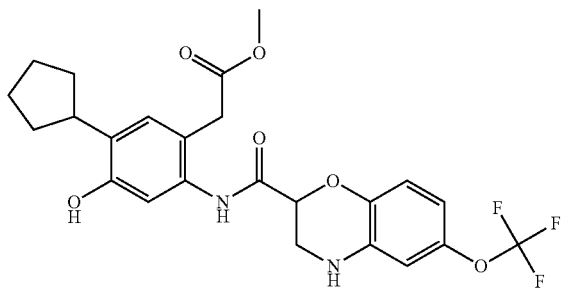 [SMILES: COC(=O)Cc1cc(C2CCCC2)c(O)cc1NC(=O)C1CNc2cc(OC(F)(F)F)ccc2O1]
75
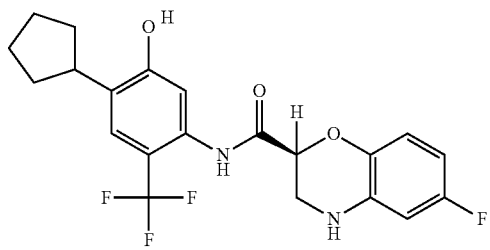
76
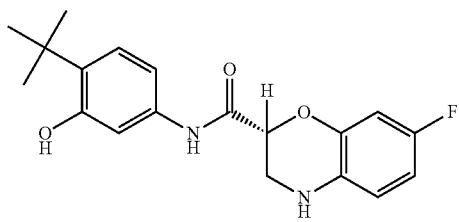 [SMILES: CC(C)(C)c1ccc(NC(=O)[C@H]2CNc3ccc(F)cc3O2)cc1O]
77
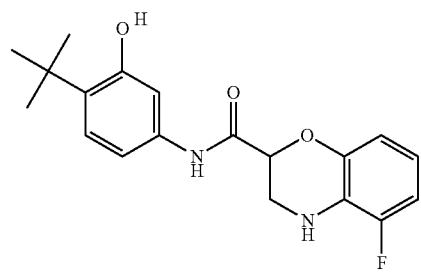
78
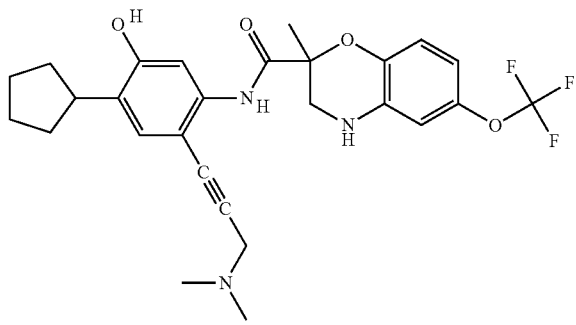
79
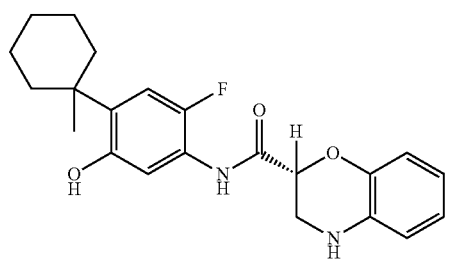 [SMILES: CC1(c2cc(F)c(NC(=O)[C@H]3CNc4ccccc4O3)cc2O)CCCCC1]
80

TABLE 1-continued
| | |
|---|---|
| 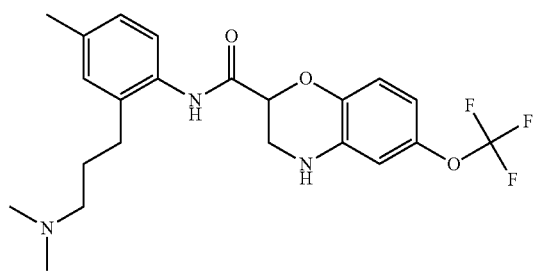 [SMILES: Cc1ccc(NC(=O)C2CNc3cc(OC(F)(F)F)ccc3O2)c(CCCN(C)C)c1] | 81 |
| 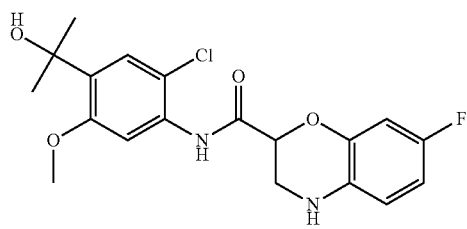 [SMILES: COc1cc(NC(=O)C2CNc3ccc(F)cc3O2)c(Cl)cc1C(C)(C)O] | 82 |
| 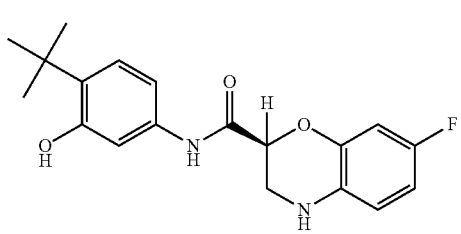 [SMILES: CC(C)(C)c1ccc(NC(=O)[C@@H]2CNc3ccc(F)cc3O2)cc1O] | 83 |
| 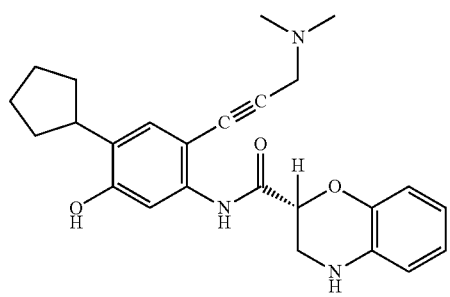 [SMILES: CN(C)CC#Cc1cc(C2CCCC2)c(O)cc1NC(=O)[C@H]1CNc2ccccc2O1] | 84 |
| 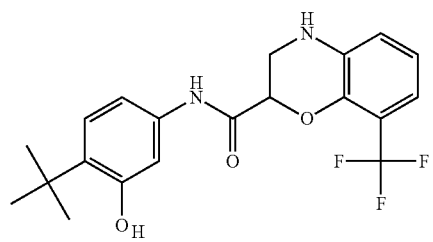 | 85 |
| 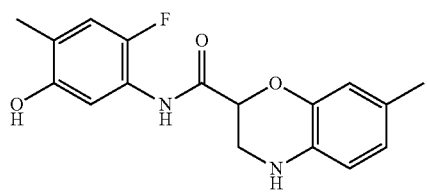 | 86 |

TABLE 1-continued
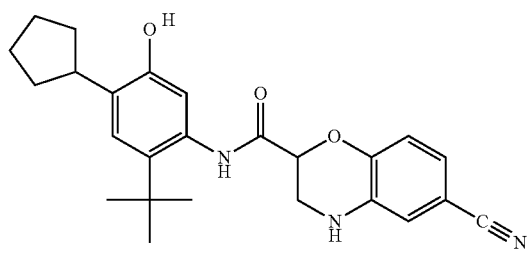
87
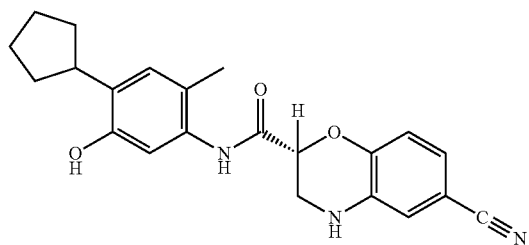 [SMILES: Cc1cc(C2CCCC2)c(O)cc1NC(=O)[C@H]1CNc2cc(C#N)ccc2O1]
88
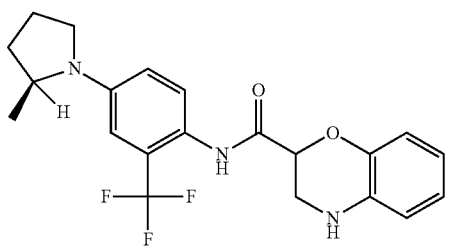 [SMILES: C[C@H]1CCCN1c1ccc(NC(=O)C2CNc3ccccc3O2)c(C(F)(F)F)c1]
89
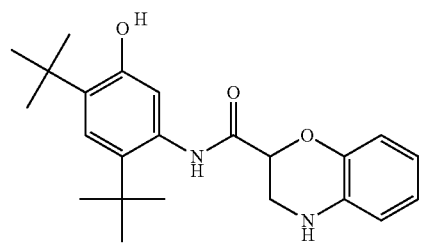
90
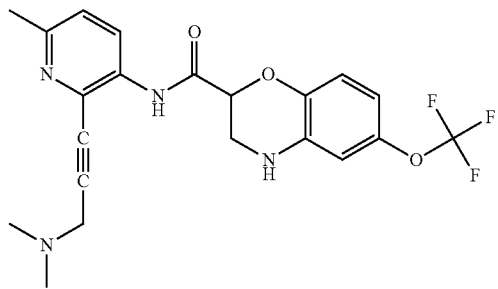 [SMILES: Cc1ccc(NC(=O)C2CNc3cc(OC(F)(F)F)ccc3O2)c(C#CCN(C)C)n1]
91
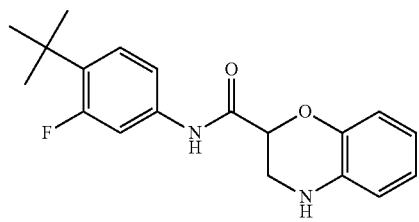 [SMILES: CC(C)(C)c1ccc(NC(=O)C2CNc3ccccc3O2)cc1F]
92

TABLE 1-continued
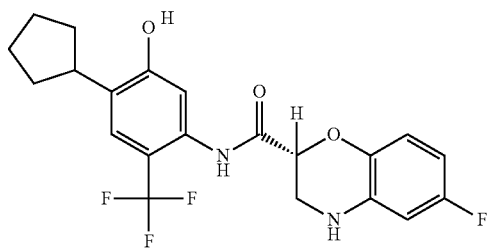
93
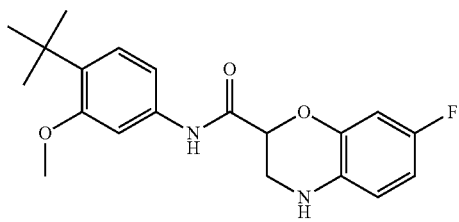 [SMILES: COc1cc(NC(=O)C2CNc3ccc(F)cc3O2)ccc1C(C)(C)C]
94
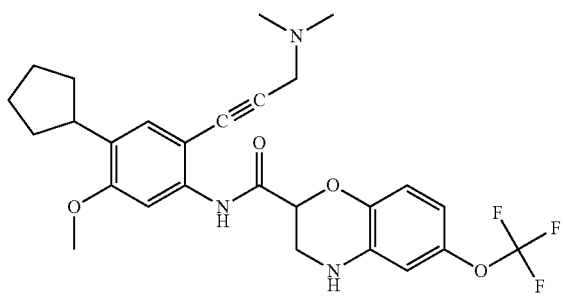 [SMILES: COc1cc(NC(=O)C2CNc3cc(OC(F)(F)F)ccc3O2)c(C#CCN(C)C)cc1C1CCCC1]
95
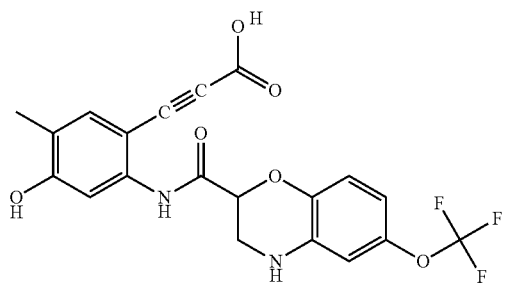
96
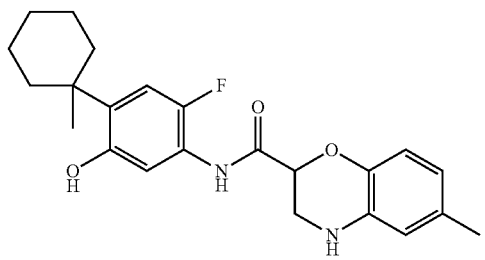 [SMILES: Cc1ccc2c(c1)NCC(C(=O)Nc1cc(O)c(C3(C)CCCCC3)cc1F)O2]
97
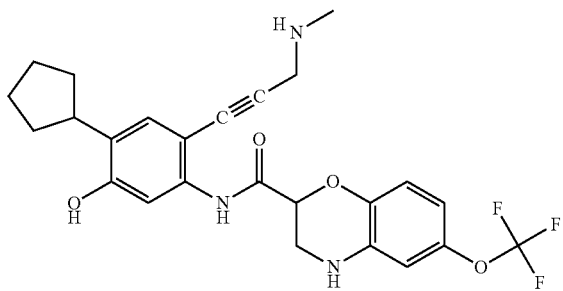
98

TABLE 1-continued
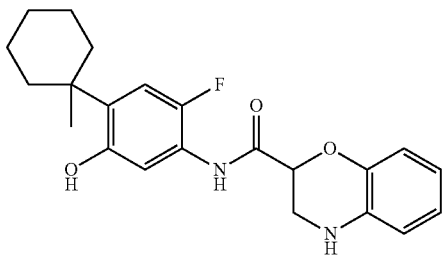 [SMILES: CC1(c2cc(F)c(NC(=O)C3CNc4ccccc4O3)cc2O)CCCCC1]
99
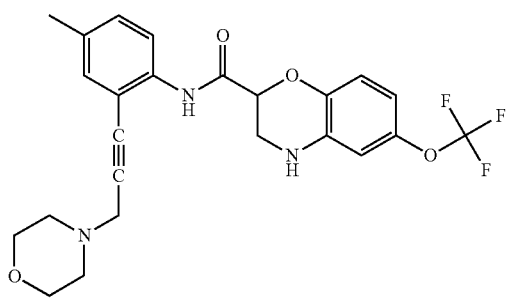 [SMILES: Cc1ccc(NC(=O)C2CNc3cc(OC(F)(F)F)ccc3O2)c(C#CCN2CCOCC2)c1]
100
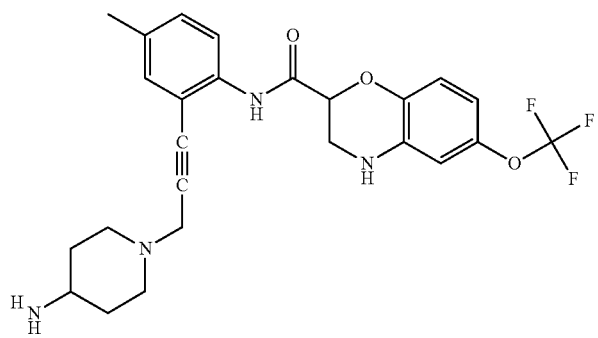
101
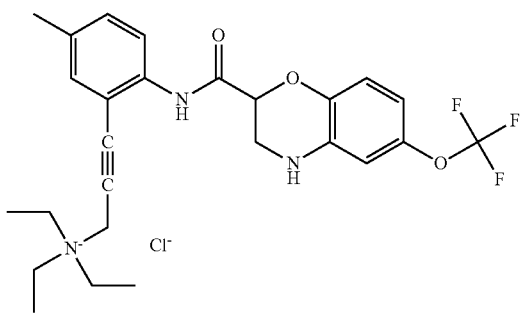
102
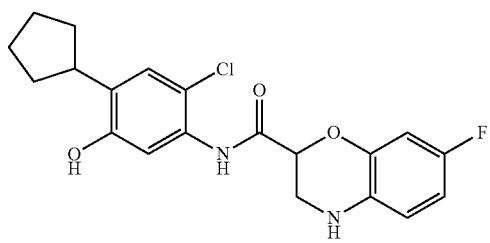
103

TABLE 1-continued
| | |
|---|---|
| 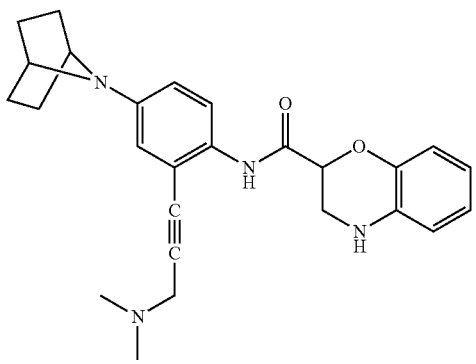 [SMILES: CN(C)CC#Cc1cc(N2C3CCC2CC3)ccc1NC(=O)C1CNc2ccccc2O1] | 104 |
| 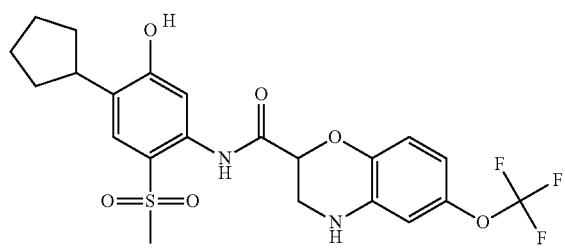 | 105 |
| 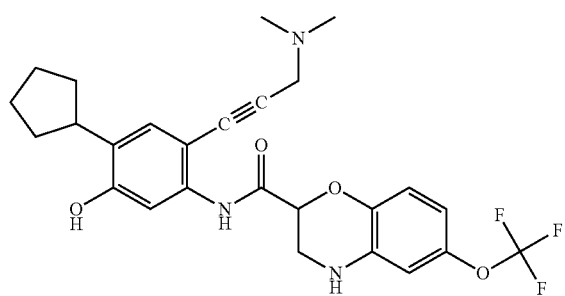 [SMILES: CN(C)CC#Cc1cc(C2CCCC2)c(O)cc1NC(=O)C1CNc2cc(OC(F)(F)F)ccc2O1] | 106 |
| 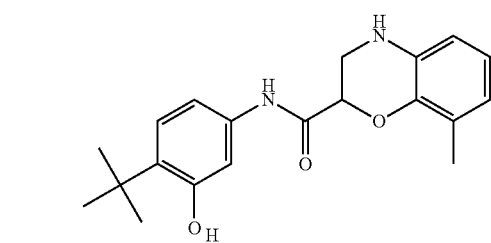 | 107 |
| 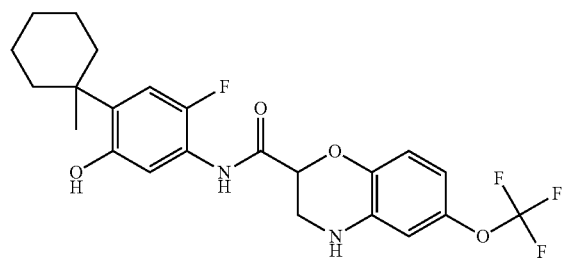 [SMILES: CC1(c2cc(F)c(NC(=O)C3CNc4cc(OC(F)(F)F)ccc4O3)cc2O)CCCCC1] | 108 |
| 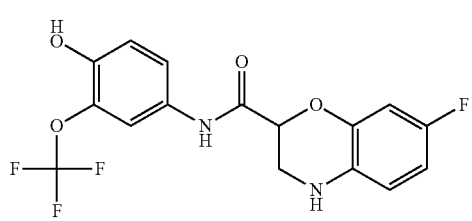 [SMILES: O=C(Nc1ccc(O)c(OC(F)(F)F)c1)C1CNc2ccc(F)cc2O1] | 109 |

TABLE 1-continued
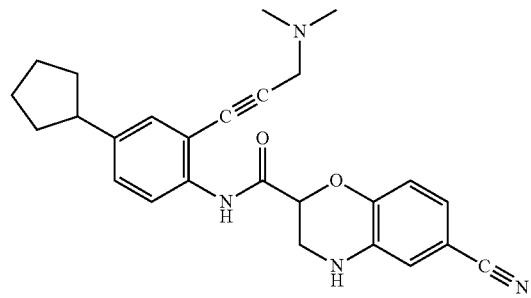 [SMILES: CN(C)CC#Cc1cc(C2CCCC2)ccc1NC(=O)C1CNc2cc(C#N)ccc2O1]
110
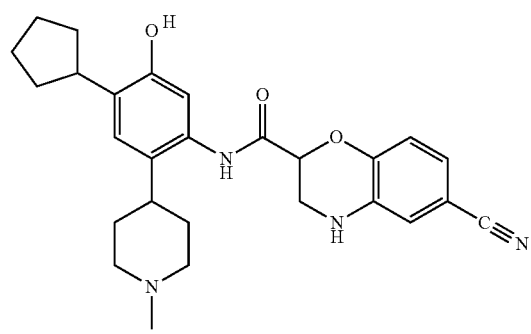
111
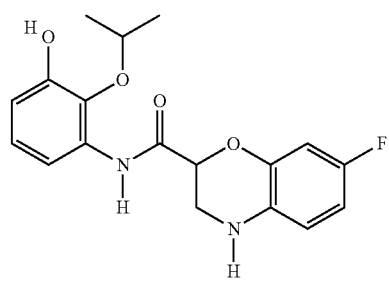
112
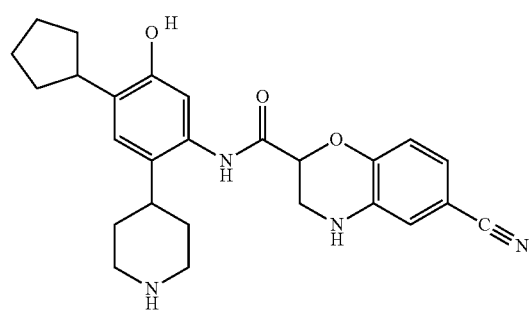
113
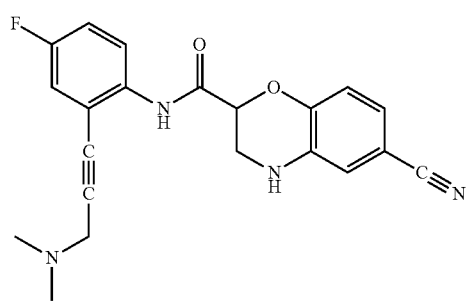 [SMILES: CN(C)CC#Cc1cc(F)ccc1NC(=O)C1CNc2cc(C#N)ccc2O1]
114

TABLE 1-continued
| | |
|---|---|
| 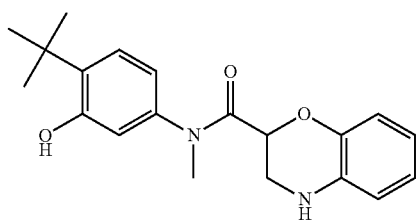 [SMILES: CN(C(=O)C1CNc2ccccc2O1)c1ccc(C(C)(C)C)c(O)c1] | 115 |
| 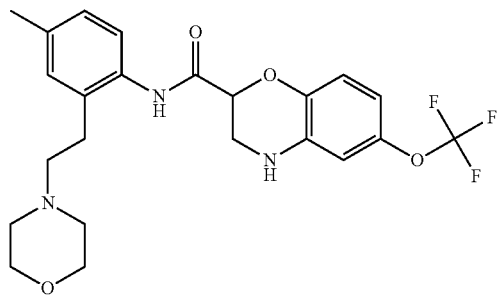 [SMILES: Cc1ccc(NC(=O)C2CNc3cc(OC(F)(F)F)ccc3O2)c(CCN2CCOCC2)c1] | 116 |
| 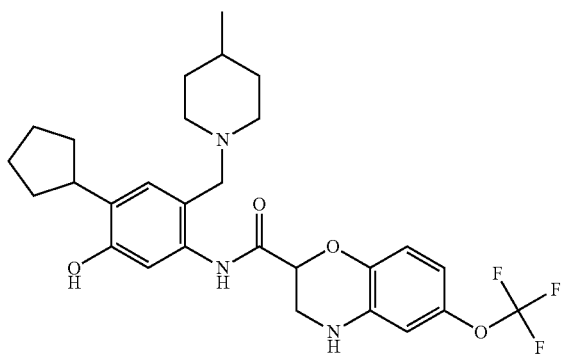 [SMILES: CC1CCN(Cc2cc(C3CCCC3)c(O)cc2NC(=O)C2CNc3cc(OC(F)(F)F)ccc3O2)CC1] | 117 |
| 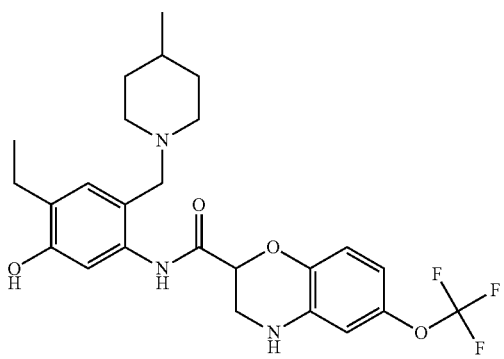 [SMILES: CCc1cc(CN2CCC(C)CC2)c(NC(=O)C2CNc3cc(OC(F)(F)F)ccc3O2)cc1O] | 118 |
| 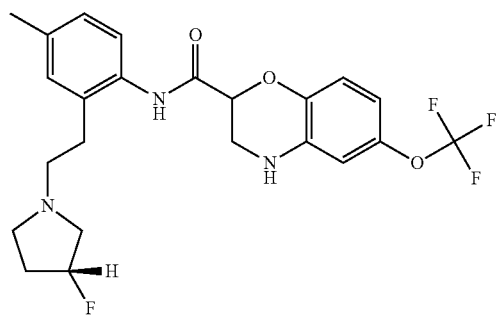 [SMILES: Cc1ccc(NC(=O)C2CNc3cc(OC(F)(F)F)ccc3O2)c(CCN2CC[C@@H](F)C2)c1] | 119 |

TABLE 1-continued
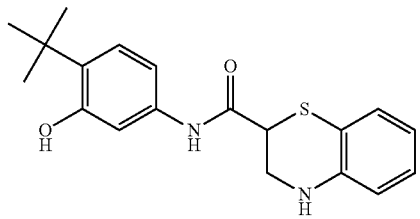 [SMILES: CC(C)(C)c1ccc(NC(=O)C2CNc3ccccc3S2)cc1O]
120
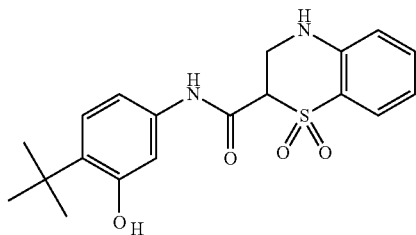
121
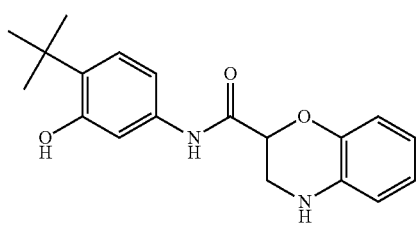
122
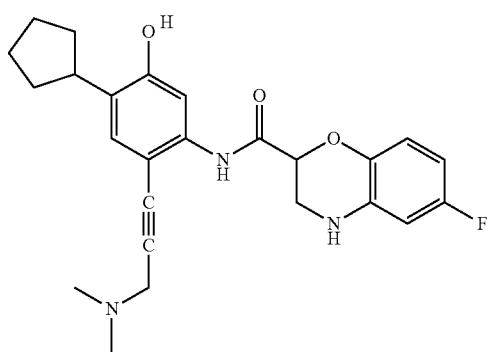
123
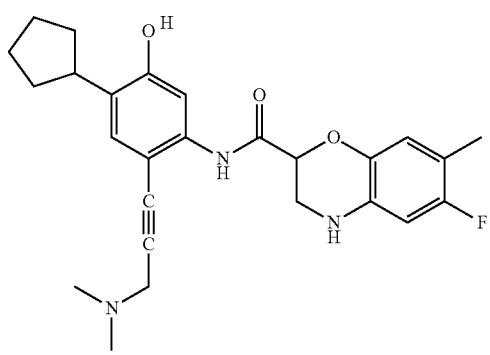
124
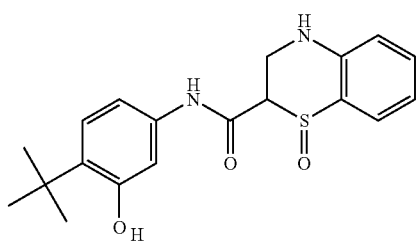
125

TABLE 1-continued

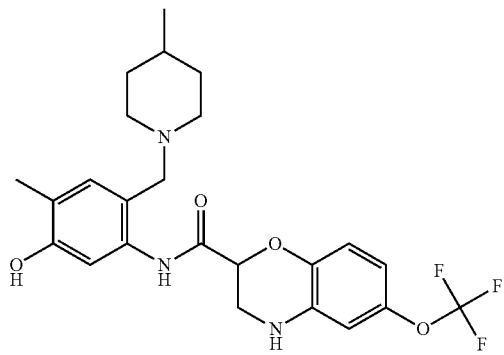 [SMILES: Cc1cc(CN2CCC(C)CC2)c(NC(=O)C2CNc3cc(OC(F)(F)F)ccc3O2)cc1O]

126

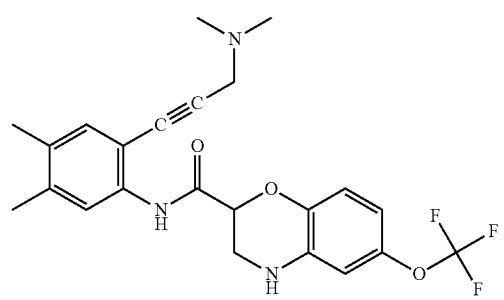 [SMILES: Cc1cc(C#CCN(C)C)c(NC(=O)C2CNc3cc(OC(F)(F)F)ccc3O2)cc1C]

127

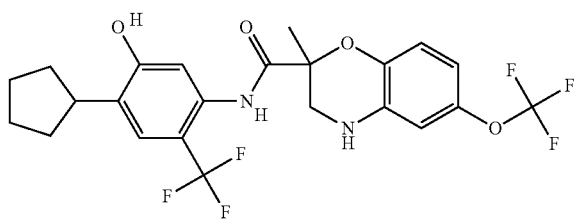

128

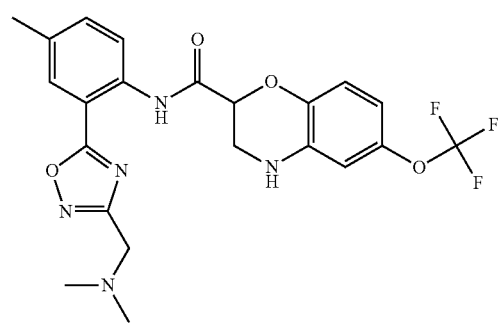 [SMILES: Cc1ccc(NC(=O)C2CNc3cc(OC(F)(F)F)ccc3O2)c(-c2nc(CN(C)C)no2)c1]

129

4. General Synthetic Schemes

Compounds of the present invention are readily prepared by methods known in the art. Illustrated in the Examples hereinbelow are exemplary methods for the preparation of compounds of the present invention.

5. Uses, Formulation and Administration

Pharmaceutically Acceptable Compositions

In one aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating, or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising a compound of Formula I to a subject, preferably a mammal, in need thereof.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In certain embodiments, the present invention provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gasgtro-esophageal reflux disease, gastrointestinal malignancies, inflammatory bowel disease, constipation, diabetes, arthritis, osteoporosis, and osteopenia.

In certain embodiments, the present invention provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of a composition comprising a compound of the present invention.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of the diseases, disorders or conditions as recited above.

The compounds and compositions, according to the method of the present invention, may be administered using any amount and any route of administration effective for treating or lessening the severity of one or more of the diseases, disorders or conditions as recited above.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl$^-$ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient," as used herein, means an animal, preferably a mammal, and most preferably a human.

The pharmaceutically acceptable compositions of this invention can be administered to humans and other animals orally, rectally, parenterally, intracisternally; intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pill's, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as a modulator of CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, a bronchodialator, an anti-biotic, an anti-infective agent, an anti-inflammatory agent, a CFTR modulator other than a compound of the present invention, or a nutritional agent. In a further embodiment, the additional agent is a CFTR modulator other than a compound of the present invention.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent reduces the activity of the epithelial sodium channel blocker (ENaC) either directly by blocking the channel or indirectly by modulation of proteases that lead to an increase in ENaC activity (e.g., seine proteases, channel-activating proteases). Exemplary such agents include camostat (a trypsin-like protease inhibitor), QAU145, 552-02, GS-9411, INO-4995, Aerolytic, and amiloride. Additional agents that reduce the activity of the epithelial sodium channel blocker (ENaC) can be found, for example in PCT Publication No. WO2009/074575, the entire contents of which are incorporated herein in their entirety.

Amongst other diseases described herein, combinations of CFTR modulators, such as compounds of Formula I, and agents that reduce the activity of ENaC are use for treating Liddle's syndrome, an inflammatory or allergic condition including cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as compounds of Formula I, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants," an established patient category of major medical concern and now often identified as incipient or early-phase asthmatics. (For convenience this particular asthmatic condition is referred to as "wheezy-infant syndrome.") Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping." "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of CFTR modulators, such as compounds of Formula I, and agents that reduce the activity of ENaC are useful for the treatment of bronchitis of whatever type or genesis including, e.g., acute, arachidic, catarrhal, croupus, chronic or phthinoid bronchitis.

In another embodiment, the additional agent is a CFTR modulator other than a compound of Formula I, i.e., an agent that has the effect of modulating CFTR activity. Exemplary such agents include ataluren ("PTC124®," 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of Formula I or a composition comprising said compound. The term "biological sample," as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with a compound of Formula I. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of Formula I.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells." *Biophys J* 69(4): 1272-80, and Gonzalez, J. E. and R. Y. Tsien (1997); "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of CFTR or a fragment thereof in a biological sample in vitro or in vivo comprising (i) a composition comprising a compound of Formula I or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of a composition of Formula I. In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

General Synthetic Schemes

Compounds of the present invention are readily prepared by methods known in the art. Illustrated below are exemplary methods for the preparation of compounds of the present invention.

The schemes below illustrate the synthesis compounds of Formula I of the present invention.

Scheme 1

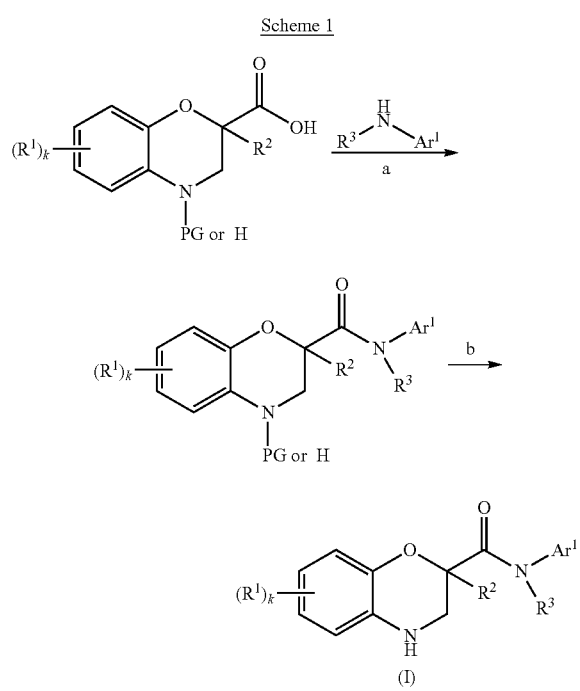

a) HATU, Et₃N, DMF, or propyl phosphonic acid cyclic anhydride (T3P®), pyridine, 2-methyltetrahydrofuran; b) Removal of amine protecting group if present.
PG = protecting group.

Scheme 2

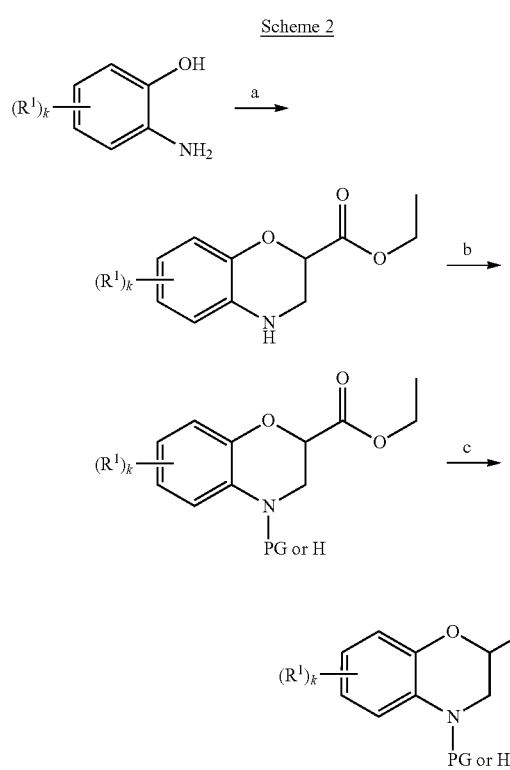

a) Ethyl 2,3-dibromopropanoate, K₂CO₃, acetone heat; b) Optional amine protection, e.g. carbamate protection (Cbz, Fmoc, Boc, etc) or benzyl protection (Bn, PMB, etc);
c) NaOH, MeOH or water; heat;

Intermediate 1

Synthesis of 7-methyl-3,4-dihydro-2H-benzo[b][1,4]oxazine-2-carboxylic acid

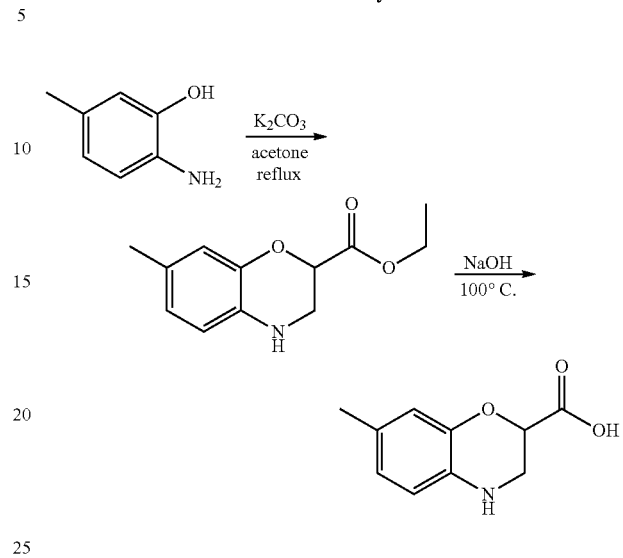

To a solution of 2-amino-5-methylphenol (10 g, 81.3 mmol) in acetone (150 mL) was added K₂CO₃ (24.5 g, 243.9 mmol) and ethyl 2,3-dibromopropanoate (23.3 g, 89.4 mmol). The mixture was heated at reflux for 16 h. The filtrate was concentrated in vacuo to give an oil. Purification by silica gel chromatography (hexane/ethyl acetate gradient) provided ethyl 7-methyl-3,4-dihydro-2H-benzo[b][1,4]oxazine-2-carboxylate (8.5 g, 47.3% yield). ¹H NMR (400 MHz, CDCl₃) δ 6.76 (d, J=0.8 Hz, 1H), 6.60 (dd, J=1.2, 8.0 Hz, 1H), 6.19 (d, J=8.0 Hz, 1H), 4.78 (t, J=3.6 Hz, 1H), 4.29-4.21 (m, 2H), 3.59-3.52 (m, 2H), 2.23 (s, 3H), 1.28 (t, J=7 Hz, 3H).

To the suspension of ethyl 7-methyl-3,4-dihydro-2H-benzo[b][1,4]oxazine-2-carboxylate (8.5 g, 38.5 mmol) in water (60 mL) was added NaOH (3.8 g, 96.1 mmol). The suspension was stirred at 100° C. for 30 min under N₂ atmosphere. The reaction was cooled to room temperature and acidified to pH 2 with conc. HCl. The resulting precipitate was filtered, washed with water and dried to obtain 7-methyl-3,4-dihydro-2H-benzo[b][1,4]oxazine-2-carboxylic acid (5.1 g, 68.7%). ¹H NMR (400 MHz, DMSO-d₆) δ 6.51 (s, 1H), 6.46-6.41 (m, 2H), 5.60 (br s, 1H), 4.73 (t, J=3.6 Hz, 1H), 3.33-3.31 (m, 2H), 2.10 (s, 3H).

Intermediate 2

Synthesis of 6-cyano-4-(ethoxycarbonyl)-3,4-dihydro-2H-benzo[b][1,4]oxazine-2-carboxylic acid

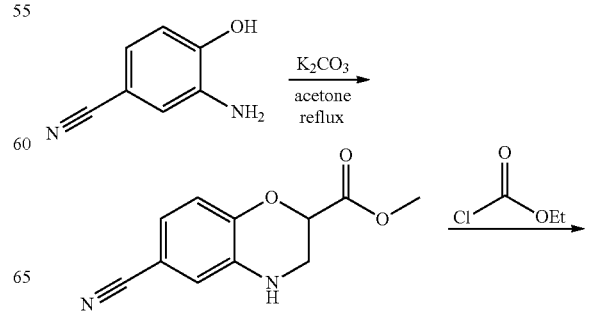

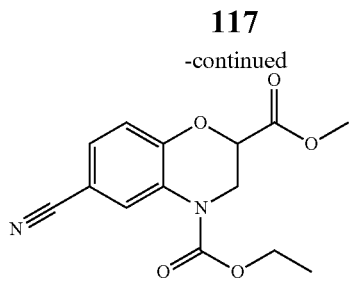

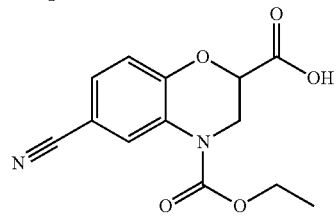

3-Amino-4-hydroxy-benzonitrile (180 mg, 1.34 mmol) was dissolved in acetone (1.4 mL). To the solution was added $K_2CO_3$ (555 mg, 4.02 mmol) and ethyl 2, 3-dibromopropanoate (380 mg, 1.46 mmol). The mixture was heated to reflux for 16 h. After cooling to room temperature the reaction mixture was filtered and concentrated in vacuo to give an oil. The oil was dissolved in methanol and was purified by silica gel chromatography (0-10% dichloromethane/hexanes) to afford methyl 6-cyano-3,4-dihydro-2H-1,4-benzoxazine-2-carboxylate (148 mg, 0.68 mmol). The methyl ester was isolated as methanol was used for loading the compound on silica resulting in transesterification. $^1$H NMR (400.0 MHz, DMSO-$d_6$) δ 6.98 (dd, J=2.0, 8.2 Hz, 1H), 6.93-6.90 (m, 2H), 6.34 (s, 1H), 5.13 (t, J=3.3 Hz, 1H), 3.66 (s, 3H), 3.50-3.41 (m, 2H).

A mixture of methyl 6-cyano-3,4-dihydro-2H-1,4-benzoxazine-2-carboxylate (629 mg, 2.88 mmol) and $K_2CO_3$ (1195 mg, 8.65 mmol) in dichloromethane (30 mL) was cooled at 0° C. and ethyl chloroformate (0.76 mL, 7.8 mmol) was added. The mixture was heated at reflux temperature for 30 h. The reaction was cooled and extracted with dichloromethane (3×20 mL), dried over $Na_2SO_4$ and concentrated. The product 4-ethyl 2-methyl 6-cyano-2H-benzo[b][1,4]oxazine-2,4(3H)-dicarboxylate was obtained as a yellow oil (670 mg, 80% yield) after purification by silica gel column chromatography (0-25% ethyl acetate/hexanes). $^1$H NMR (400.0 MHz, DMSO-$d_6$) δ 8.11 (s, 1H), 7.53 (dd, J=2.0, 8.5 Hz, 1H), 7.18 (d, J=8.5 Hz, 1H), 5.36 (t, J=3.3 Hz, 1H), 4.39 (dd, J=3.5, 14.1 Hz, 1H), 4.27-4.15 (m, 2H), 3.76 (dd, J=3.2, 14.1 Hz, 1H), 3.71-3.67 (m, 3H), 1.25 (t, J=7.1 Hz, 3H).

To a solution of 4-ethyl 2-methyl 6-cyano-2H-benzo[b][1,4]oxazine-2,4(3H)-dicarboxylate (665 mg, 2.29 mmol) in ethanol (12.5 mL) was added NaOH (2.3 mL of 1 M, 2.30 mmol). The mixture was stirred at room temperature for 10 min. A solution of 1 N HCl was slowly added until the pH was acidic. After removing the ethanol, the aqueous layer was extracted with dichloromethane (3×20 mL), dried over $Na_2SO_4$ and concentrated in vacuo to provide 6-cyano-4-ethoxycarbonyl-2,3-dihydro-1,4-benzoxazine-2-carboxylic acid (590 mg, 2.14 mmol). $^1$H NMR (400.0 MHz; DMSO-$d_6$) δ 13.57 (s, 1H), 8.12 (s, 1H), 7.50 (dd, J=2.0, 8.5 Hz, 1H), 7.15 (d, J=8.5 Hz, 1H), 5.20 (s, 1H), 4.44-4.40 (m, 1H), 4.20 (dd, J=7.2, 8.0 Hz, 2H), 3.72 (dd, J=3.3, 14.0 Hz, 1H), 1.25 (t, J=7.1 Hz, 3H).

Scheme 3

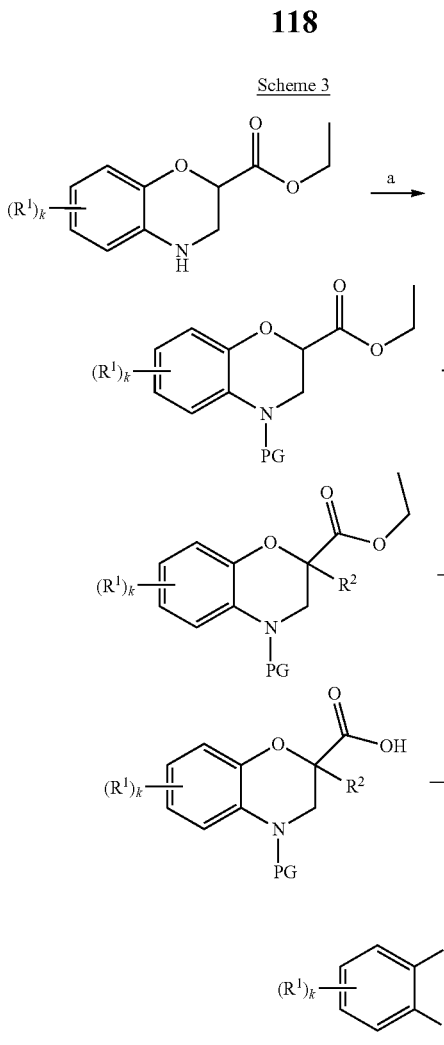

a) Protection of NH, e.g. carbamate protection (Boc, Cbz, Fmoc, etc) or benzyl protection (Bn, PMB, etc); b) LDA, THF, -50° C. followed by alkylating agent $R^2X$; c) NaOH, MeOH; d) Optional NH deprotection prior to amide coupling (e.g. Pd(OH)$_2$, H$_2$, 90 bar, 100° C. for PMB removal).

Intermediate 3

Synthesis of 2-methyl-6-(trifluoromethoxy)-3,4-dihydro-2H-benzo[b][1,4]oxazine-2-carboxylic acid

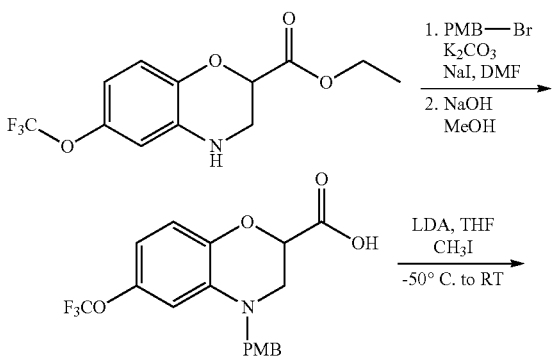

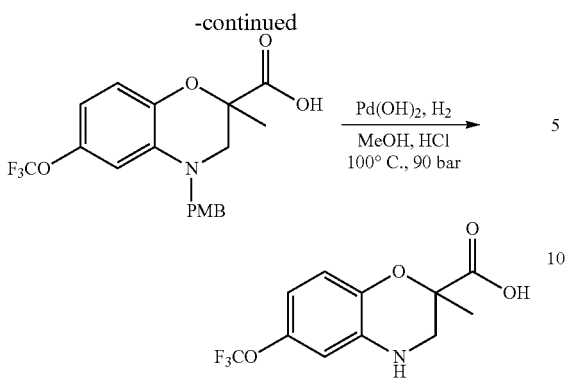

Ethyl 6-(trifluoromethoxy)-3,4-dihydro-2H-1,4-benzoxazine-2-carboxylate (775 mg, 2.66 mmol) was dissolved in DMF (4 mL) containing K$_2$CO$_3$ (1103 mg, 7.98 mmol), sodium iodide (80 mg, 0.53 mmol). 1-(Bromomethyl)-4-methoxy-benzene (1070 mg, 776 μL, 5.32 mmol) was added slowly to the above reaction mixture. The mixture was heated at 60° C. for 6 h. After evaporation of the solvent, the residue was treated with water and extracted with dichloromethane. The organic extracts were dried over Na$_2$SO$_4$ and evaporated in vacuo. The residue was chromatographed over a silica gel column (0-25% ethyl acetate/hexanes) to provide 4-(4-methoxybenzyl)-6-(trifluoromethoxy)-3,4-dihydro-2H-benzo[b][1,4]oxazine-2-carboxylic acid (639 mg, 1.553 mmol, 58.37%) as a white solid. LC/MS m/z 412.4 [M+H]$^+$. $^1$H NMR (400.0 MHz, DMSO-d$_6$) δ 7.18 (d, J=8.5 Hz, 2H), 6.88 (d, J=8.6, 2H), 6.86 (d, J=8.6 Hz, 1H), 6.68 (d, J=2.1 Hz, 1H), 6.54 (d, J=8.7 Hz, 1H), 5.09 (t, J=3.3 Hz, 1H), 4.45 (d, J=15.4 Hz, 1H), 4.29 (d, J=15.3 Hz, 1H), 4.16-4.05 (m, 2H), 3.73 (s, 3H), 3.52-3.42 (m, 2H), 1.13 (t, J=7.1 Hz, 3H).

To a solution of ethyl 4-(4-methoxybenzyl)-6-(trifluoromethoxy)-3,4-dihydro-2H-benzo[b][1,4]oxazine-2-carboxylic acid (330 mg, 0.80 mmol) in methanol (5 mL) was added NaOH (1.6 mL of 5 M, 8.02 mmol). The reaction was stirred for 1 h at room temperature, and then quenched with HCl (1.6 mL of 6 M, 9.6 mmol) to form a white precipitate. The solid was filtered, washed with water and dried under vacuum to provide 4-[(4-methoxyphenyl)methyl]-6-(trifluoromethoxy)-2,3-dihydro-1,4-benzoxine-2-carboxylic acid as a white solid (290 mg, 94% yield). LC/MS m/z 384.2 [M+H]$^+$.

To a solution of 4[(4-methoxyphenyl)methyl]-6-(trifluoromethoxy)-2,3-dihydro-1,4-benzoxazine-2-carboxylic acid (290 mg, 0.76 mmol) in tetrahydrofuran (7 mL), under N$_2$ atmosphere and cooled to −50° C., was added LDA (1.5 mL of 2 M, 3.03 mmol). The mixture was stirred for 2 h at −50° C. then treated with iodomethane (430 mg, 188 μL, 3.03 mmol). The mixture was allowed to warm to room temperature and stirred for 16 h. 30 mL water was added and the solution acidified to ~pH 3 with 1 N HCl. The solution was extracted with ethyl acetate (3×10 mL) and the organic layer washed with brine, dried over Na$_2$SO$_4$, filtered and dried down to provide 4-[(4-methoxyphenyl)methyl]-2-methyl-6-(trifluoromethoxy)-3H-1,4-benzoxazine-2-carboxylic acid as an orange oil (300 mg, quantitative yield). LC/MS m/z 398.0 [M+H]$^+$. $^1$H NMR (400.0 MHz, DMSO-d$_6$) δ 13.11 (s, 1H), 7.21 (d, J=8.6 Hz, 2H), 6.88 (d, J=8.6 Hz, 2H), 6.80 (d, J=8.6 Hz, 1H), 6.60 (d, J=2.4 Hz, 1H), 6.51 (d, J=8.7 Hz, 1H), 4.45 (d, J=15.7 Hz, 1H), 4.30 (d, J=15.7 Hz, 1H), 3.73 (s, 3H), 3.67 (d, J=11.8 Hz, 1H), 3.15 (d, J=11.8 Hz, 1H), 1.48 (s, 3H).

4-[(4-methoxyphenyl)methyl]-2-methyl-6-(trifluoromethoxy)-3H-1,4-benzoxazine-2-carboxylic acid (300 mg, 0.7550 mmol) was dissolved in methanol (50 mL) and 2 M HCl (2 mL), and treated with Pd(OH)$_2$ under H$_2$ (90 bar) at 100° C. (H-Cube, ThalesNano). The product solution was dried down to a brown residue. The residue was redissolved in acetonitrile, filtered and concentrated in vacuo to provide 2-methyl-6-(trifluoromethoxy)-3,4-dihydro-1,4-benzoxazine-2-carboxylic acid hydrochloride (200 mg, 85% yield) as a brown solid. LC/MS m/z 278.3 [M+H]$^+$.

Intermediate 4

Synthesis of 3-(trifluoromethyl)-1H-indol-6-amine

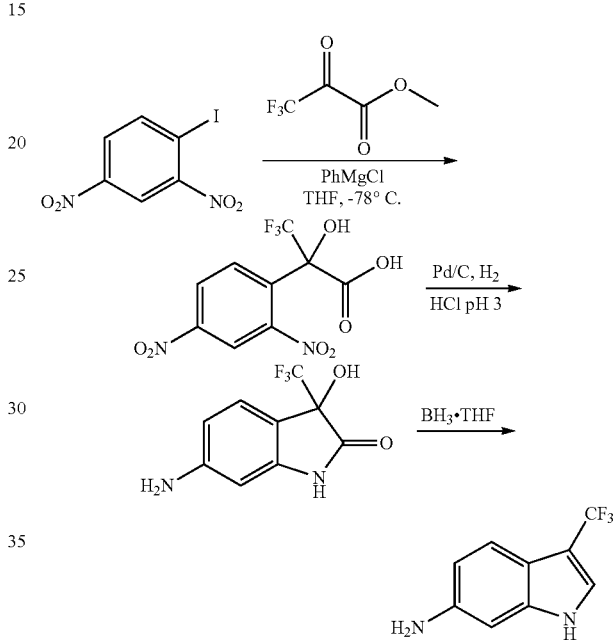

To a solution of 1,4-dinitroiodobenzene (2.12 g, 7.21 mmol) in tetrahydrofuran (11.0 mL) at −78° C. under N$_2$ atmosphere was added phenylmagnesium chloride (2M in THF) (4.0 mL, 8.0 mmol, 1.1 eq) dropwise. The dark red solution was stirred for 30 min at −78° C. then methyltrifluoropyruvate (0.75 mL, 8.65 mmol) was added dropwise. The reaction mixture was stirred for 30 min at −78° C. and for 2 h at room temperature. The reaction was cooled down to −10° C. and quenched by addition of 1 M HCl (6 mL). The mixture was diluted with water (10 mL) and dichloromethane (30 mL). The organic phase was separated and the aqueous phase was extracted with dichloromethane (3×30 mL). The organic phases were combined, dried over Na$_2$SO$_4$, filtered, and concentrated. Purification by silica gel chromatography (0.5-30% ethyl acetate/hexanes) to provided methyl 2-(2,4-dinitrophenyl)-3,3,3-trifluoro-2-hydroxypropanoate (1.34 g, 60%)

To a solution of methyl 2-(2,4-dinitrophenyl)-3,3,3-trifluoro-2-hydroxypropanoate (1.3 g, 4.01 mmol) in ethyl acetate (18 mL) was added pH3HCl (5.2 mL) followed by 10% Pd/C (350 mg) in ethyl acetate (3 mL). The mixture was stirred overnight under an atmosphere of H$_2$. The reaction mixture was filtered through a pad of Celite and the filtrate was concentrated in vacuo. The crude residue obtained was partitioned between, dichloromethane (25 mL) and aqueous saturated NaHCO$_3$ (15 mL). The organic phase was separated and the aqueous phase was extracted dichloromethane (2×25 mL). The organic phases were combined, dried over $Na_2SO_4$, filtered, and concentrated. Purification by silica gel chromatography (50-100% ethyl acetate/hexanes) provided 6-amino-3-hydroxy-3-(trifluoromethyl)indolin-2-one (921 mg, 99%) To a solution of 6-amino-3-hydroxy-3-(trifluoromethyl)indolin-2-one (58 mg, 0.25 mmol) in THF (0.5 mL) at 0° C. was added $BH_3$THF complex (1 M in THF, 1 mL, 0.95 mmol) dropwise. The mixture was stirred for 5 min at 0° C. then for 3 h at room temperature. The reaction was quenched by adding very carefully 6M HCl (3.5 mL) until no more gas release was observed. The mixture was then stirred at 80° C. for 2 h. The solvent was removed under reduce pressure and the solid residue obtained was dissolved in DMF (3 mL), filtered and purified by reverse phase HPLC (10-99% $CH_3CN/H_2O$) to provide 3-(trifluoromethyl)-1H-indol-6-amine (30 mg, 54%, TFA salt).

Intermediate 5

Synthesis of 5-amino-2-ethyl-4-fluorophenyl methyl carbonate

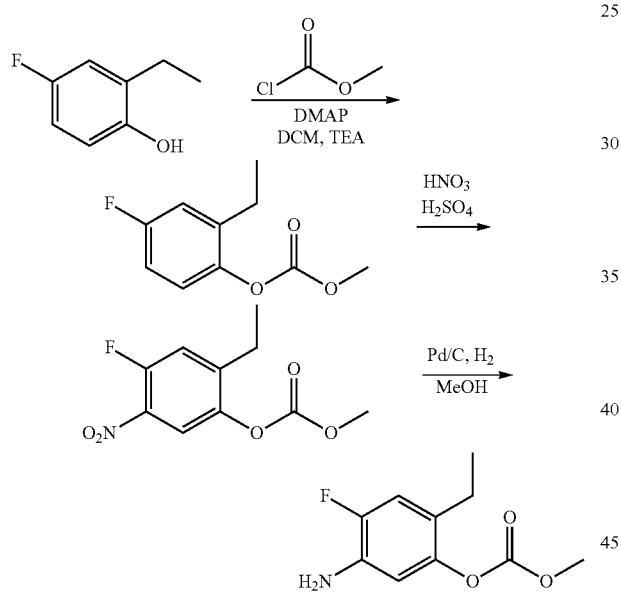

2-Ethyl-4-fluorophenol (2 g, 14.27 mmol) and DMAP (87 mg, 0.71 mmol) was dissolved in dichloromethane (10 mL) and triethylamine (4 mL, 28.5 mmol), cooled to 0° C., then treated with methyl chloroformate (2.02 g, 1.65 mL, 21.40 mmol) and allowed to warm to room temperature over 2 h. The reaction was quenched with water, the layers separated, and the aqueous layer was extracted with dichloromethane. The combined organic extracts were dried over $Na_2SO_4$, filtered and concentrated. Purification by silica gel chromatography (20% ethyl acetate/hexane) provided 2-ethyl-4-fluorophenyl methyl carbonate (2.4 g, 85% yield). $^1$H NMR (400.0 MHz, DMSO-$d_6$) δ 7.26-7.17 (m, 2H), 7.12-7.07 (m, 1H), 5.76 (s, 1H), 3.83 (d, J=4.3 Hz, 2H), 2.54-2.48 (m, 2H), 1.12 (t, J=7.6 Hz, 3H).

2-Ethyl-4-fluorophenyl methyl carbonate (2.4 g, 12.11 mmol) was added dropwise to $H_2SO_4$ (7.2 mL) to generate a yellow homogeneous solution. The solution was then cooled to 0° C. and $KNO_3$ (1.469 g, 14.53 mmol) was added portionwise maintaining the internal temperature below 5° C. The reaction was stirred for 2 h and then poured on ice water. The aqueous layer was extracted with dichloromethane (3×10 mL), dried over $Na_2SO_4$, filtered and concentrated. Purification by silica gel chromatography (10% ethyl acetate/hexane) provided 2-ethyl-4-fluoro-5-nitrophenyl methyl carbonate (1.7 g, 58% yield). $^1$H NMR (400.0 MHz, DMSO-$d_6$) δ 8.20 (d, J=6.8 Hz, 1H), 7.64 (d, J=12.1 Hz, 2H), 3.88 (s, 3H), 2.62 (q, J=7.5 Hz, 1H), 1.15 (t, J=7.5 Hz, 3H).

To a flask charged with 10% Pd/C (170 mg) under inert atmosphere was added a solution of 2-ethyl-4-fluoro-5-nitrophenyl methyl carbonate (1.7 g, 6.99 mmol) in methanol (17 mL). The mixture was stirred overnight under an atmosphere of $H_2$. The reaction was filtered and concentrated in vacuo to provide 5-amino-2-ethyl-4-fluorophenyl methyl carbonate (1.400 g, 6.57 mmol). $^1$H NMR (400.0 MHz, DMSO-$d_6$) δ 6.92 (d, J=12.0 Hz, 1H), 6.52 (d, J=8.1 Hz, 1H), 5.16 (s, 2H), 3.81 (s, 3H), 2.33 (q, J=7.5 Hz, 2H), 1.05 (t, J=7.5 Hz, 3H).

Intermediate 6

Synthesis of 5-amino-4-chloro-2-cyclopentylphenyl methyl carbonate

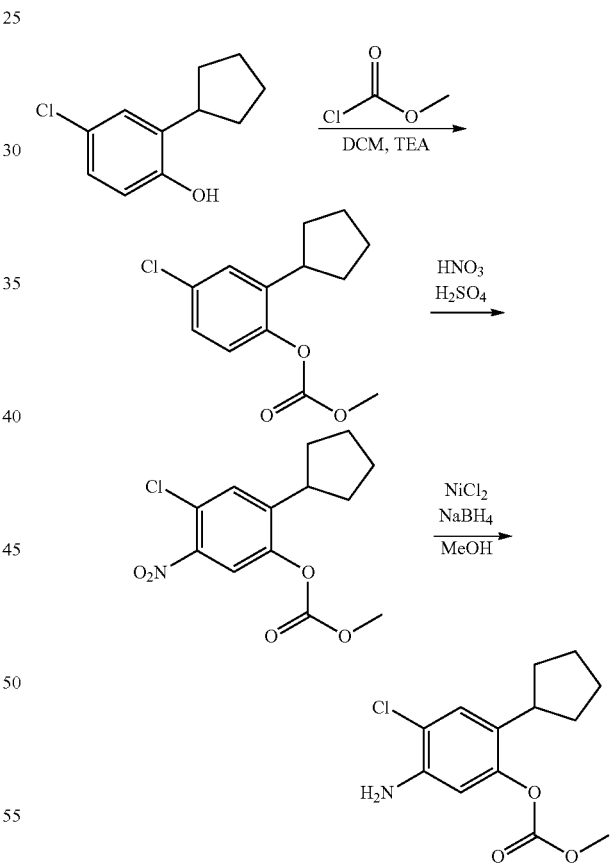

4-Chloro-2-cyclopentylphenol (2.366 g, 7.94 mmol) was dissolved in dichloromethane (20 mL) and triethylamine (2.2 mL, 15.9 mmol). The solution was cooled to 0° C. and treated with methyl chloroformate (920 μL, 11.91 mmol) and allowed to warm to room temperature over 16 h. The reaction was quenched with 3 mL saturated $NaHCO_3$, washed with 50% saturated $NaHCO_3$ (1×50 mL) and brine (1×50 mL), then dried over $Na_2SO_4$. Filtration, followed by concentration in vacuo yielded an oil that was purified by silica gel chromatography (20% ethyl acetate/hexane) to yield 4-chloro-2-cyclopentylphenyl methyl carbonate as a colorless oil. $^1$H NMR (400.0 MHz, DMSO-$d_6$) δ 7.31-7.28 (m, 1H), 7.20-7.13 (m, 1H), 7.06 (d, J=8.6 Hz, 1H), 3.93 (d, J=3.1 Hz, 3H), 3.18-3.09 (m, 1H), 2.08-2.01 (m, 2H), 1.87-1.78 (m, 2H), 1.75-1.65 (m, 2H), 1.61-1.51 (m, 2H).

4-Chloro-2-cyclopentylphenyl methyl carbonate (1.0 g, 3.93 mmol) was added portion wise to H$_2$SO$_4$ (2.9 mL, 54.1 mmol) to generate a colorless homogeneous solution. The solution was then cooled to 0° C. and KNO$_3$ (476 mg, 4.71 mmol) was added portion-wise maintaining the internal temperature below 5° C. The reaction was stirred for 2 h and then poured on ice water. The aqueous layer was extracted with dichloromethane (3×10 mL), dried over Na$_2$SO$_4$, filtered and concentrated. Purification by silica gel chromatography (10% EtOAc/hexane) provided 4-chloro-2-cyclopentyl-5-nitrophenyl methyl carbonate (1021 mg, 87% yield). $^1$H NMR (400.0 MHz, DMSO-$d_6$) δ 7.74 (s, 1H), 7.39 (s, 1H), 5.23 (s, 1H), 3.92-3.88 (m, 3H), 3.13-3.06 (m, 2H), 2.04-1.96 (m, 2H), 1.81-1.62 (m, 2H), 1.53-1.44 (m, 2H).

To a solution of 4-chloro-2-cyclopentyl-5-nitrophenyl methyl carbonate (870 mg, 2.90 mmol) and NiCl$_2$ (376 mg, 2.90 mmol) in methanol (10 mL) at 0° C. was added NaBH$_4$ (330 mg, 8.71 mmol) portion-wise. After 10 min the reaction was quenched with NaHCO$_3$ and diluted with ethyl acetate. The reaction mixture was filtered through a pad of Celite and the layers were separated. The aqueous layer was re-extracted with ethyl acetate (3×100 mL) and the combined organic extracts dried over MgSO$_4$. The solution was filtered and concentrated in vacuo to provide 5-amino-4-chloro-2-cyclopentylphenyl methyl carbonate which was used for the next step without further purification (400 mg, 51% yield). $^1$H NMR (400.0 MHz, DMSO-$d_6$) δ 7.11 (s, 1H), 6.57 (d, J=11.4 Hz, 1H), 5.38 (s, 1H), 3.85-3.80 (m, 3H), 2.89-2.80 (m, 2H), 1.88-1.81 (m, 2H), 1.75-1.56 (m, 2H), 1.52 (s, 2H), 1.46-1.37 (m, 2H).

Intermediate 7

Synthesis of 2-amino-5-cyclopentyl-4-hydroxybenzonitrile

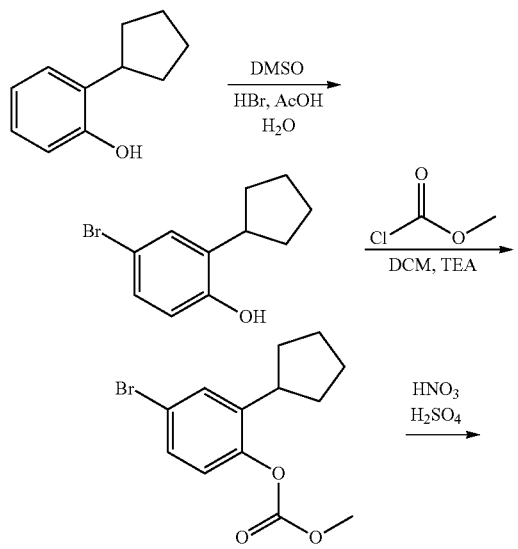

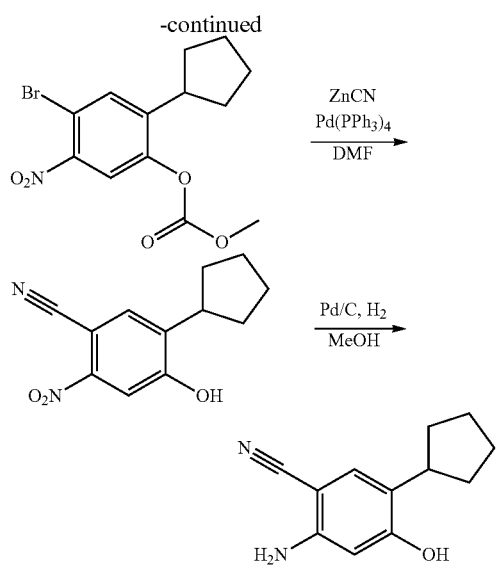

To a stirring solution of 2-cyclopentyl phenol (7.9 g, 48.7 mmol) in acetic acid (32 mL) and water (16 mL) was added HBr (33% in AcOH, 50.45 mL, 292.2 mmol) followed by the dropwise addition of DMSO (34.8 g, 31.6 mL, 445.0 mmol) over 10 min. The reaction was quenched with saturated aqueous NaHCO$_3$ and concentrated in vacuo to remove gasses. The residue was brought up in ether (200 mL), washed with water (2×100 mL) and brine (100 mL) then dried over Na$_2$SO$_4$. The solution was filtered and concentrated in vacuo to produce an oil which was purified by silica gel chromatography (0-10% ethyl acetate/hexane) to provide 4-bromo-2-cyclopentylphenol (10.5 g, 89% yield) as a colorless oil. $^1$H NMR (400.0 MHz, DMSO-$d_6$) δ 9.59 (s, 1H), 7.20 (d, J=2.5 Hz, 1H), 7.13 (dd, J=2.5, 8.5 Hz, 1H), 6.73 (d, J=8.5 Hz, 1H), 3.21-3.13 (m, 1H), 1.95-1.88 (m, 2H), 1.77-1.69 (m, 2H), 1.65-1.44 (m, 4H).

4-Bromo-2-cyclopentylphenol (10.0 g, 41.47 mmol) and DMAP (253 mg, 2.07 mmol) was dissolved in dichloromethane (50 mL) and triethylamine (11.6 mL, 82.94 mmol), cooled to 0° C. and treated with methyl chloroformate (4.8 mL, 62.20 mmol). The reaction was allowed to warm to room temperature over 2 h. The reaction was quenched with water, the layers separated, and the aqueous layer re-extracted with dichloromethane. The combined organic extracts were dried over Na$_2$SO$_4$, filtered and concentrated in vacuo to yield an oil that was purified by silica gel chromatography (20% ethyl acetate/hexane) to yield 4-bromo-2-cyclopentylphenyl methyl carbonate (10.5 g, 85% yield). $^1$H NMR (400.0 MHz, DMSO-$d_6$) δ 7.52 (d, J=2.4 Hz, 1H), 7.44 (dd, J=2.4, 8.6 Hz, 1H), 7.22-7.17 (m, 1H), 3.84 (s, 3H), 3.07-2.98 (m, 1H), 1.95-1.88 (m, 2H), 1.79-1.71 (m, 2H), 1.66-1.46 (m, 4H).

Concentrated H$_2$SO$_4$ (115 mL) was added to 4-bromo-2-cyclopentylphenyl methyl carbonate (26.09 g, 87.21 mmol) and the mixture stirred and cooled to −10° C. KNO$_3$ (13.22 g, 130.80 mmol) was then added in portions with continuous stirring. The reaction was stirred at −10° C. for 1 h then quenched with ice resulting in precipitation of an off-white solid. The solid was filtered, washed with water and dried to provide the product. The water phase was extracted with dichloromethane (3×10 mL) and the combined organic extracts dried over Na$_2$SO$_4$. Purification by silica gel chromatography (5-20% ethyl acetate/hexane) provided additional 4-bromo-2-cyclopentyl-5-nitrophenyl methyl carbonate (combined 21.72 g, 72% yield). $^1$H NMR (400.0 MHz, DMSO-d$_6$) δ 8.12 (s, 1H), 7.88 (s, 1H), 3.88 (d, J=5.7 Hz, 3H), 3.13 (dd, J=9.4, 17.2 Hz, 1H), 1.96-1.92 (m, 2H), 1.80-1.75 (m, 2H), 1.68-1.54 (m, 4H).

To a microwave vial charged with 4-bromo-2-cyclopentyl-5-nitrophenyl methyl carbonate (102 mg, 0.29 mmol), zinc cyanide (35 mg, 0.30 mmol) and Pd(PPh$_3$)$_4$ (21 mg, 0.02 mmol) under an N$_2$ atmosphere was added DMF (500 µL). The reaction was heated under microwave irradiation at 130° C. for 30 min. The reaction was quenched with saturated aqueous Na$_2$CO$_3$ and extracted with ethyl acetate (3×10 mL). The combined organic extracts were dried over Na$_2$SO$_4$, filtered and concentrated in vacuo to yield a brown oil. Purification by silica gel chromatography (0-15% ethyl acetate/hexanes) afforded 5-cyclopentyl-4-hydroxy-2-nitrobenzonitrile as a light yellow solid (40 mg, 58% yield). $^1$H NMR (400.0 MHz, DMSO-d$_6$) δ 11.62 (s, 1H), 7.84 (s, 1H), 7.70 (s, 1H), 3.29-3.24 (m, 1H), 1.99-1.93 (m, 2H), 1.78-1.76 (m, 2H), 1.66-1.57 (m, 4H).

A flask containing 10% Pd/C (4 mg) was evacuated and placed under a N$_2$ atmosphere and suspended in ethanol (2 mL). To this was added 5-cyclopentyl-4-hydroxy-2-nitrobenzonitrile (42 mg, 0.18 mmol) as a solution in ethanol (1.5 mL). The reaction was stirred under H$_2$ atmosphere for 2 h, then filtered and concentrated in vacuo to provide 2-amino-5-cyclopentyl-4-hydroxybenzonitrile as a yellow oil (36 mg, quantitative yield). LC/MS m/z 203.1 [M+H]$^+$.

Intermediate 8

Synthesis of 5-amino-4-bromo-2-cyclopentylphenyl methyl carbonate

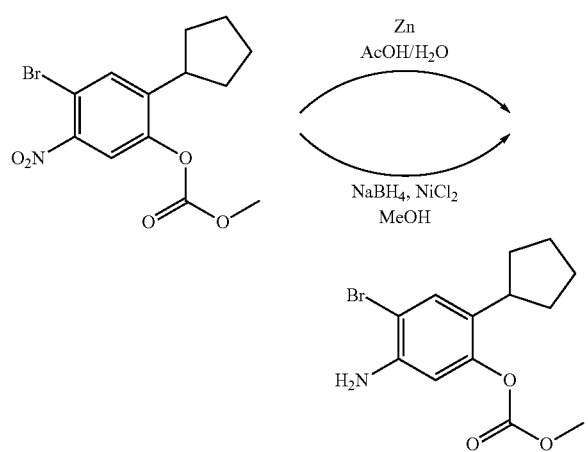

4-bromo-2-cyclopentyl-5-nitrophenyl methyl carbonate (211 mg, 0.61 mmol) was dissolved in a mixture of glacial acetic acid (3 mL) and water (1 mL). Additional acetic acid (1 mL) was added to facilitate stirring. Zn dust (401 mg, 6.13 mmol) was added at room temperature and the reaction stirred for 10 min. The reaction was diluted with acetonitrile (5 mL) and methanol (5 mL) and filtered. The solution was diluted with ethyl acetate, washed with 50% saturated aqueous NaHCO$_3$ (2×20 mL) and brine, dried over Na$_2$SO$_4$, filtered, and dried down to provide 5-amino-4-bromo-2-cyclopentylphenyl methyl carbonate as a light orange solid (189 mg, 98% yield). LC/MS m/z 315.0 [M+H]$^+$.

Alternative Procedure:

To a solution of 4-bromo-2-cyclopentyl-5-nitrophenyl methyl carbonate (100 mg, 0.29 mmol) and NiCl$_2$ (49 mg, 0.38 mmol) in methanol (1.0 mL) was added NaBH$_4$ (14 mg, 0.38 mmol) portion-wise at 0° C. The reaction was stirred for 5 min then quenched with NaHCO$_3$ and diluted with ethyl acetate. The reaction mixture was filtered through a pad of Celite and the layers separated. The aqueous layer was re-extracted with ethyl acetate and the combined organic extracts were dried over Na$_2$SO$_4$, filtered and concentrated. Silica gel chromatography (10% ethyl acetate/hexane) provided 5-amino-4-bromo-2-cyclopentylphenyl methyl carbonate (49 mg, 54% yield).

Intermediate 9

Synthesis of 5-amino-2-cyclopentyl-4-methylphenol

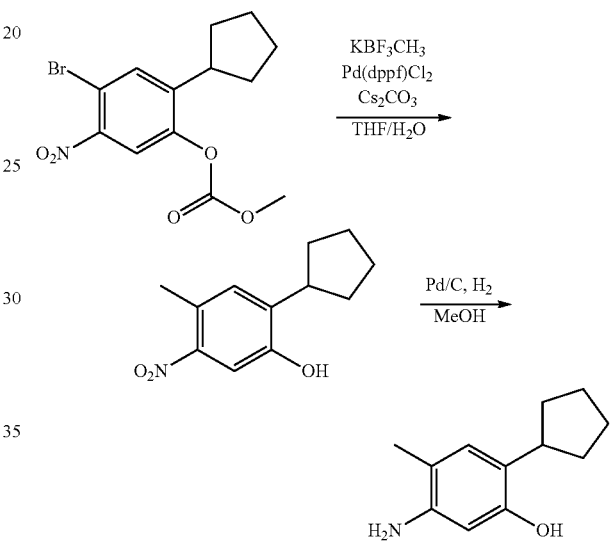

To a microwave tube charged with 4-bromo-2-cyclopentyl-5-nitrophenyl methyl carbonate (500 mg, 1.45 mmol), Pd(dppf)Cl$_2$ (96 mg, 0.13 mmol), potassium trifluoro-methyl-boron (177 mg, 1.45 mmol) and cesium carbonate (1420 mg, 4.36 mmol) was added tetrahydrofuran (2.5 mL) and water (1.25 mL). The reaction heated at 110° C. for 35 min under microwave irradiation. The reaction was partitioned between ethyl acetate and water. The organic layer was separated, dried over Na$_2$SO$_4$, filtered and concentrated in vacuo to yield a brown oil. Purification by silica gel chromatography (0-6% ethyl acetate/hexanes) provided 2-cyclopentyl-4-methyl-5-nitrophenol (167 mg, 52% yield). $^1$H NMR (400.0 MHz, DMSO-d$_6$) δ 10.08 (s, 1H), 7.43-7.38 (m, 1H), 7.22 (s, 1H), 3.28-3.21 (m, 1H), 2.43 (s, 3H), 1.96-1.91 (m, 2H), 1.80-1.51 (m, 6H).

A flask charged with 10% Pd/C (16 mg) was evacuated and placed under a N$_2$ atmosphere. To this was added 2-cyclopentyl-4-methyl-5-nitro-phenol (160 mg, 0.72 mmol) as a solution in methanol (3 mL). The reaction mixture was stirred under H$_2$ atmosphere for 4 h, then filtered and concentrated in vacuo to provide 5-amino-2-cyclopentyl-4-methylphenol a light tan solid (130 mg, 94% yield). $^1$H NMR (400.0 MHz, DMSO-d$_6$) δ 8.47 (s, 1H), 6.60 (s, 1H), 6.08 (s, 1H), 4.44 (s, 2H), 3.02 (dd, J=2.4, 17.2 Hz, 1H), 1.91 (s, 3H), 1.84-1.77 (m, 2H), 1.71-1.66 (m, 2H), 1.58-1.54 (m, 2H), 1.44-1.39 (m, 2H).

Intermediate 10

Synthesis of 5-amino-4-tert-butyl-2-cyclopentylphenyl methyl carbonate

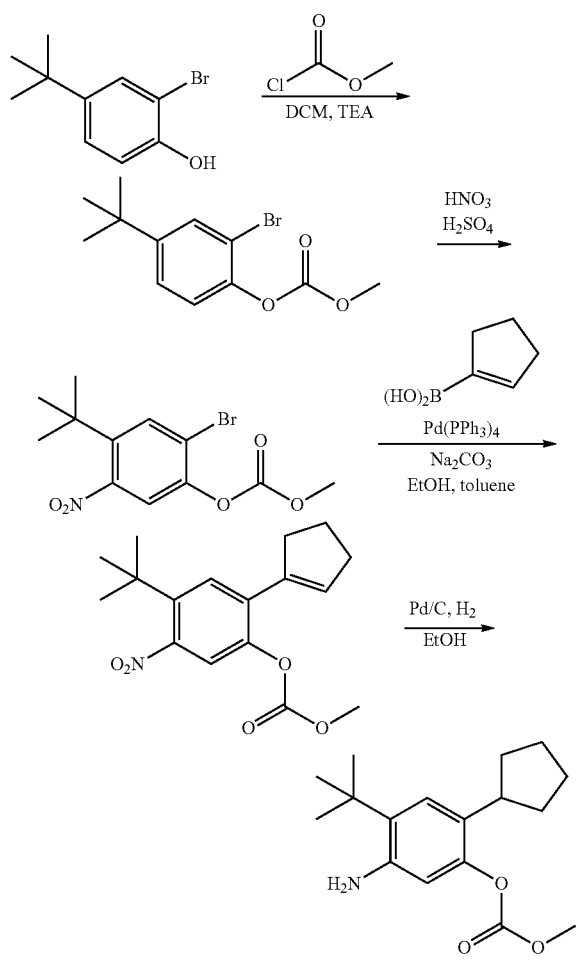

2-Bromo-4-tert-butyl phenol (15.0 g, 65.5 mmol) and DMAP (400 mg, 3.3 mmol) was dissolved in dichloromethane (75 mL) and triethylamine (18.25 mL, 130.9 mmol), cooled to 0° C., then treated with methyl chloroformate (7.6 mL, 98.2 mmol) and allowed to warm to room temperature over 2 h. The reaction was quenched with water and the layers separated. The aqueous layer was extracted with dichloromethane and the combined organic extracts dried over $Na_2SO_4$. The solution was filtered and concentrated in vacuo to yield an oil that was purified by silica gel chromatography (20% ethyl acetate/hexane) to yield 2-bromo-4-tert-butylphenyl methyl carbonate (17 g, 90% yield). $^1$H NMR (400.0 MHz, DMSO-$d_6$) δ 7.67 (d, J=2.3 Hz, 1H), 7.47 (dd, J=2.3, 8.5 Hz, 1H), 7.33 (d, J=8.5 Hz, 1H), 3.86 (s, 3H), 1.29-1.26 (m, 9H).

2-Bromo-4-tert-butylphenyl methyl carbonate (5.0 g, 17.4 mmol) was added portion-wise to $H_2SO_4$ (9.3 mL, 174.1 mmol) to generate a colorless homogeneous solution. This solution was then cooled to 0° C. and treated with $KNO_3$ (2.1 g, 20.9 mmol) portion-wise maintaining the internal temperature below 5° C. The reaction was stirred for 2 h and then poured on ice water. The aqueous layer was extracted with dichloromethane (3×10 mL). The combined organic extracts was dried over $Na_2SO_4$, filtered and concentrated. Purification by silica gel chromatography (10% ethyl acetate/hexane) provided 2-bromo-4-tert-butyl-5-nitrophenyl methyl carbonate (4.4 g, 76% yield). $^1$H NMR (400.0 MHz, DMSO-$d_6$) δ 7.97 (s, 1H), 7.92 (s, 1H), 3.90 (s, 3H), 1.34 (d, J=5.4 Hz, 9H).

A microwave tube was charged with 2-bromo-4-tert-butyl-5-nitrophenyl methyl carbonate (200 mg, 0.60 mmol), 1-cyclopentenylboronic acid (91 mg, 0.81 mmol), $Pd(PPh_3)_4$ (69 mg, 0.06 mmol), 2 M $Na_2CO_3$ (1.5 mL), ethanol (1.5 mL) and toluene (3 mL) under inert atmosphere and was heated under microwave irradiation at 80° C. for 4 h. The reaction was extracted with ethyl acetate then washed with saturated $NaHCO_3$ and brine. The organic layer was dried over $Na_2SO_4$, filtered and concentrated. Purification by silica gel chromatography (0-30% ethyl acetate/hexanes) provided 4-tert-butyl-2-cyclopentenyl-5-nitrophenyl methyl carbonate (76 mg, 40% yield). $^1$H NMR (400.0 MHz, DMSO-$d_6$) δ 7.69 (s, 1H), 7.57 (s, 1H), 6.28 (t, J=1.9 Hz, 1H), 3.86 (d, J=12.5 Hz, 3H), 2.69 (td, J=7.5, 3.2 Hz, 2H), 1.93 (dd, J=7.6, 15.0 Hz, 2H), 1.36-1.33 (m, 11H).

To a flask charged with 10% Pd/C (132 mg) under inert atmosphere was added a solution of 4-tert-butyl-2-cyclopentenyl-5-nitrophenyl methyl carbonate (660 mg, 2.07 mmol) in ethanol (20 mL). The reaction was stirred under $H_2$ atmosphere for 3 h, then filtered and dried down to provide 5-amino-4-tert-butyl-2-cyclopentylphenyl methyl carbonate as an off-white crystalline solid (556 mg, 92% yield). $^1$H NMR (400.0 MHz, DMSO-$d_6$) δ 6.97 (s, 1H), 6.38 (s, 1H), 4.81 (s, 2H), 3.80 (s, 3H), 2.84 (m, 1H), 1.87-1.80 (m, 2H), 1.72-1.66 (m, 2H), 1.62-1.56 (m, 2H), 1.47-1.39 (m, 2H), 1.32 (s, 9H).

Intermediate 11

Synthesis of 5-amino-2-cyclopentyl-4-fluorophenyl methyl carbonate

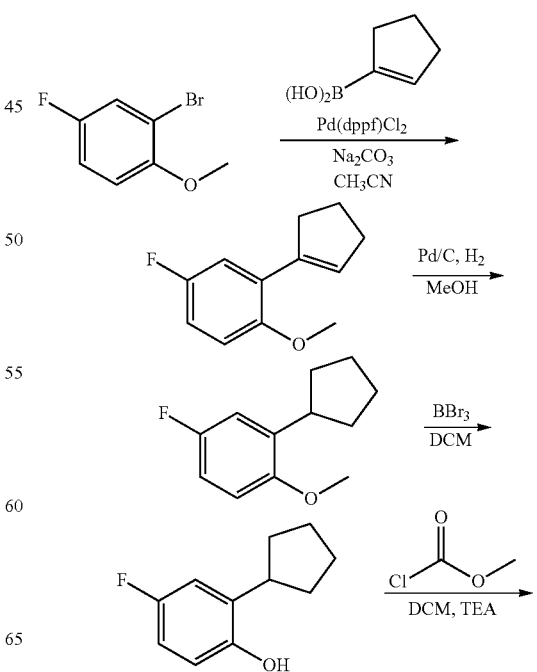

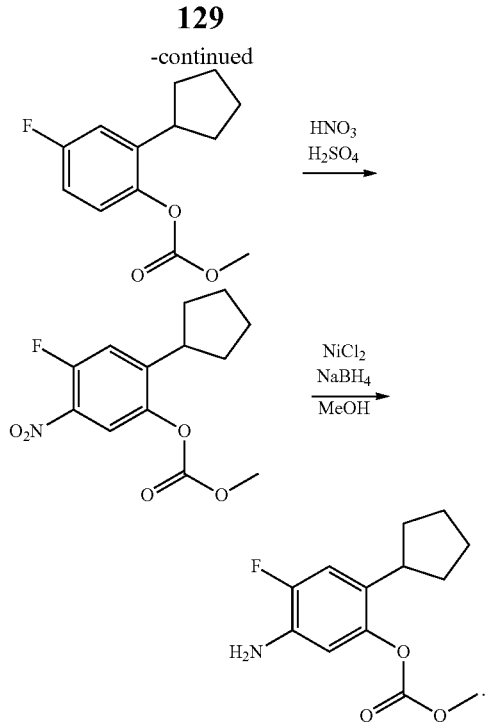

A microwave vial was charged with 2-bromo-4-fluoro-1-methoxybenzene (500 mg, 2.44 mmol), 1-cyclopentenylboronic acid (273 mg, 2.44 mmol), and Pd(dppf)Cl$_2$ (199 mg, 0.24 mmol). The solids were dissolved in acetonitrile (7 mL) and 2 M Na$_2$CO$_3$ (5 mL) and the mixture heated under microwave irradiation for 20 min at 110° C. The reaction was diluted with dichloromethane (50 mL) and the layers separated. The organic layer was washed with brine, dried over Na$_2$SO$_4$, filtered and concentrated. Purification by silica gel chromatography (10-30% ethyl acetate/hexane) provided 2-cyclopentenyl-4-fluoro-1-methoxybenzene (231 mg, 49% yield). $^1$H NMR (400.0 MHz, DMSO-d$_6$) δ 7.01 (dd, J=3.1, 10.0 Hz, 1H), 6.92-6.82 (m, 1H), 6.54 (dd, J=2.4, 6.5 Hz, 1H), 6.54 (s, 1H), 3.87 (s, 3H), 2.78-2.73 (m, 2H), 2.62-2.57 (m, 2H), 2.03-1.95 (m, 2H).

To a flask charged with 2-cyclopentenyl-4-fluoro-1-methoxybenzene (1500 mg, 4.68 mmol) and 10% Pd/C (50 mg) under inert atmosphere was added methanol. The reaction was stirred under H$_2$ atmosphere for 16 h, then filtered and concentrated. Purification by silica gel chromatography (0-30% ethyl acetate/hexanes) provided 2-cyclopentyl-4-fluoro-1-methoxybenzene (800 mg, 88% yield). $^1$H NMR (400.0 MHz, DMSO-d$_6$) δ 6.96 (dd, J=3.0, 9.9 Hz, 1H), 6.88-6.76 (m, 2H), 3.83 (s, 3H), 3.35 (q, J=8.5 Hz, 1H), 2.09-2.01 (m, 2H), 1.86-1.66 (m, 4H), 1.59-1.50 (m, 2H).

To a solution of 2-cyclopentyl-4-fluoro-1-methoxybenzene (280 mg, 1.44 mmol) in dichloromethane (10 mL) was added BBr$_3$ (7.2 mL of 1 M, 7.21 mmol). The reaction was refluxed for 16 h, then cooled to 0° C. and slowly quenched with saturated aqueous NaHCO$_3$. The organic layer was separated and washed with water, brine, then dried over MgSO$_4$. The solution was concentrated in vacuo to provide the product as a dark oil, which purified silica gel chromatography (0-90% ethyl acetate/hexanes) to provide 2-cyclopentyl-4-fluorophenol as a dark brown oil (198 mg, 76%). $^1$H NMR (400.0 MHz, DMSO-d$_6$) δ 9.15 (s, 1H), 6.81 (dd, J=2.9, 10.2 Hz, 1H), 6.72-6.63 (m, 2H), 3.15-3.07 (m, 1H), 1.87-1.80 (m, 2H), 1.70-1.35 (m, 6H).

2-Cyclopentyl-4-fluorophenol (1.70 g, 9.43 mmol) was dissolved in dichloromethane (20 mL) and triethylamine (2.6 mL, 18.85 mmol), cooled to 0° C., then treated with methyl chloroformate (1.09 mL, 14.14 mmol) and allowed to warm to room temperature over 16 h. The reaction was quenched with 3 mL saturated NaHCO$_3$, washed with 50% saturated NaHCO$_3$ (1×50 mL) and brine (1×50 mL), then dried over Na$_2$SO$_4$. Filtration followed by concentration yielded 2-cyclopentyl-4-fluorophenyl methyl carbonate as an oil which was used for the next step without purification. $^1$H NMR (400.0 MHz, CDCl$_3$) δ 7.09-7.01 (m, 2H), 6.92-6.87 (m, 1H), 3.92 (s, 3H), 3.13 (dd, J=8.4, 17.2 Hz, 1H), 2.08-2.01 (m, 2H), 1.86-1.66 (m, 4H), 1.59-1.50 (m, 2H). MS (ESI) m/z (M+H$^+$): 239.5.

2-Cyclopentyl-4-fluorophenyl methyl carbonate (2.246 g, 9.43 mmol) was added portion-wise to H$_2$SO$_4$ (6.9 mL, 130.0 mmol) to generate a colorless homogeneous solution. This solution was then cooled to 0° C. and KNO$_3$ (1.143 g, 11.31 mmol) was added portion-wise maintaining the internal temperature below 5° C. The reaction was stirred for 2 h and then poured on ice water. The aqueous layer was extracted with dichloromethane (3×10 mL). The combined organic extracts were dried over Na$_2$SO$_4$, filtered and concentrated. Purification by silica gel chromatography (10% ethyl acetate/hexanes) provided 2-cyclopentyl-4-fluoro-5-nitrophenyl methyl carbonate (2.063 g, 77% yield). $^1$H NMR (400.0 MHz, DMSO-d$_6$) δ 8.19 (d, J=6.9 Hz, 1H), 7.63 (d, J=12.5 Hz, 1H), 3.89 (t, J=5.9 Hz, 3H), 3.18-3.12 (m, 1H), 1.99-1.92 (m, 2H), 1.82-1.74 (m, 2H), 1.69-1.51 (m, 4H). MS (ESI) m/z (M+H$^+$): 284.3.

To a solution of 2-cyclopentyl-4-fluoro-5-nitrophenyl methyl carbonate (2022 mg, 7.14 mmol) and NiCl$_2$ (925 mg, 7.14 mmol) in methanol (10 mL) cooled to 0° C. was added NaBH$_4$ (810 mg, 21.42 mmol) portion-wise. The reaction was stirred for 10 min then quenched with NaHCO$_3$. The mixture was diluted with ethyl acetate and filtered through a pad of Celite. The layers were separated and the aqueous layer was extracted with ethyl acetate (3×100 mL). The combined organic extracts were dried over MgSO$_4$, filtered and concentrated. Purification by silica gel chromatography (10% ethyl acetate/hexanes) provided 5-amino-2-cyclopentyl-4-fluorophenyl methyl carbonate (1232 mg, 68% yield) as brown solid. $^1$H NMR (400.0 MHz, DMSO-d$_6$) δ 6.94 (d, J=12.6 Hz, 1H), 6.50 (d, J=8.2 Hz, 1H), 5.17 (s, 2H), 3.81 (s, 3H), 2.84 (dd, J=8.4, 17.2 Hz, 1H), 1.87-1.80 (m, 2H), 1.75-1.67 (m, 2H), 1.62-1.53 (m, 2H), 1.45-1.36 (m, 2H). MS (ESI) m/z (M+H): 255.1.

Intermediates 12 and 13

Synthesis of 5-amino-2-(trifluoromethoxy) phenyl methyl carbonate and 4-amino-2-(trifluoromethoxy)phenyl methyl carbonate

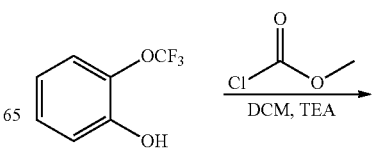

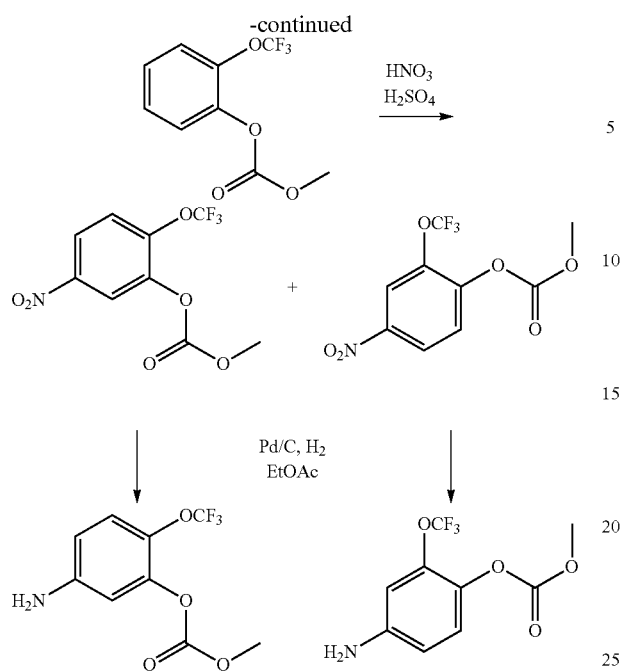

stirred in presence of 10% Pd (27 mg) under H₂ atmosphere for 4 h. The reaction was filtered through a pad of Celite and concentrated in vacuo to provide 4-amino-2-(trifluoromethoxy)phenyl methyl carbonate (45 mg, 72% yield). $^1$H NMR (400.0 MHz, CDCl₃) δ 7.02 (d, J=8.7 Hz, 1H), 6.62-6.60 (m, 1H), 6.56 (dd, J=2.7, 8.7 Hz, 1H), 3.90 (s, 3H), 3.78 (br s, 2H).

Intermediate 14

Synthesis of 5-(benzyloxy)-4-cyclopentyl-2-(trifluoromethyl)aniline

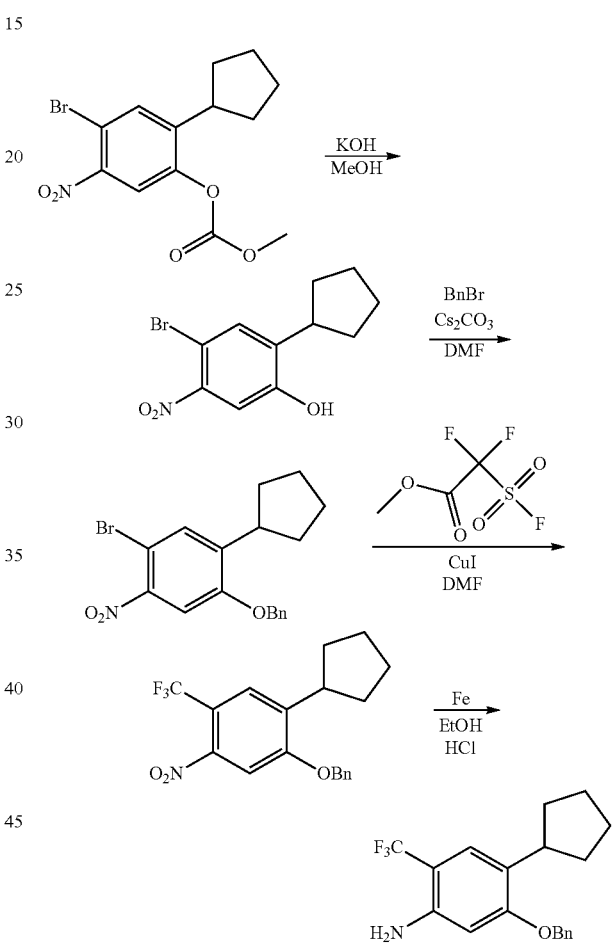

2-(Trifluoromethoxy)phenol (6.0 g, 32.7 mmol) was dissolved in methylene chloride and triethylamine (9.1 mL, 65.4 mmol). The mixture was cooled to 0° C. and methyl chloroformate (2.8 mL, 36.0 mmol) was added dropwise. The mixture was stirred for 2 h at room temperature then quenched with saturated NH₄Cl. The reaction was diluted with water and the aqueous layer extracted with dichloromethane (2×30 mL). The combined extracts were washed with water (100 mL) and brine (100 mL), dried over MgSO₄, filtered and concentrated in vacuo to provide methyl 2-(trifluoromethoxy)phenyl carbonate (7.1 g, 92% yield). $^1$H NMR (400.0 MHz, DMSO-d₆) δ7.36-7.26 (m, 4H), 3.93 (s, 3H).

Methyl 2-(trifluoromethoxy)phenyl carbonate (200 mg, 0.85 mmol) was added portion-wise to H₂SO₄ (600 µL) at 0° C. to generate a colorless homogeneous solution. KNO₃ (103 mg, 1.02 mmol) was added portion-wise maintaining the internal temperature below 5° C. The reaction was stirred for 2 h and then poured on ice water. The aqueous layer was extracted with dichloromethane (3×10 mL). The combined organic extracts were dried over Na₂SO₄, filtered and concentrated. Purification by silica gel chromatography (0-10% ethyl acetate/hexanes) provided the two regioisomers methyl 5-nitro-2-(trifluoromethoxy)phenyl carbonate (Isomer A, 120 mg) and methyl 4-nitro-2-(trifluoromethoxy)phenyl carbonate (Isomer B, 75 mg).

Isomer A: $^1$H NMR (400.0 MHz, CDCl₃) δ 8.24-8.20 (m, 2H), 7.52 (dd, J=1.4, 8.8 Hz, 1H), 3.98 (s, 3H). Isomer B: NMR (400.0 MHz, CDCl₃) δ 8.27-8.24 (m, 2H), 7.54 (dd, J=4.5, 5.2 Hz, 1H), 3.99 (d, J=7.8 Hz, 3H).

A solution of methyl 5-nitro-2-(trifluoromethoxy)phenyl carbonate (120 mg, 0.43 mmol) in ethyl acetate (10 mL) was stirred in presence of 10% Pd/C (45 mg) under H₂ atmosphere for 4 h. The reaction was filtered through a pad of Celite and concentrated in vacuo to provide 5-amino-2-(trifluoromethoxy)phenyl methyl carbonate (90 mg, 84% yield). $^1$H NMR (400.0 MHz, CDCl₃) δ 7.09 (dd, J=1.1, 8.7 Hz, 1H), 6.54 (d, J=2.7 Hz, 1H), 6.51 (dd, J=2.8, 8.7 Hz, 1H), 3.91 (s, 3H), 3.80 (br s, 2H).

A solution of methyl 4-nitro-2-(trifluoromethoxy)phenyl carbonate (70 mg, 0.25 mmol) in ethyl acetate (10 mL) was 4-Bromo-5-nitro-2-cyclopentylphenol (30.0 g, 87.2 mmol) was dissolved in methanol (150 mL) at 50° C. KOH pellets (5.6 g, 174.4 mmol) were added and the brick red solution was stirred at room temperature for 2 h. The reaction was quenched with 1N HCl (170 mL, pH ~7). The reaction was in vacuo to remove methanol, then diluted with water and dichloromethane. The layers were separated and the aqueous layer extracted with dichloromethane. The combined extracts were washed with water, dried over Na₂SO₄, filtered and concentrated in vacuo to provide 4-bromo-2-cyclopentyl-5-nitrophenol as a yellow solid (21.7 g, 87% yield). $^1$H NMR (400.0 MHz, DMSO-d₆) δ 7.52 (s, 1H), 7.39 (s, 1H), 5.32 (s, 1H), 3.28-3.20 (m, 1H), 2.14-2.10 (m, 2H) and 1.87-1.84 (m, 2H), 1.76-1.74 (m, 2H), 1.63-1.59 (m, 2H).

To a solution of 4-bromo-5-nitro-2-cyclopentylphenol (21.7 g, 75.9 mmol) and Cs₂CO₃ (29.7 g, 91.1 mmol) in DMF (190 mL) was added benzylbromide (14.6 g, 10.1 mL, 83.5 mmol) dropwise at room temperature. The reaction was stirred for 16 h. The reaction was diluted with water and extracted with ethyl acetate (3×100 mL). The combined organic extracts were dried over $Na_2SO_4$, filtered and concentrated. Purification by silica gel chromatography (ethyl acetate/hexane gradient) provided 1-(benzyloxy)-4-bromo-2-cyclopentyl-5-nitrobenzene (28.0 g, 98% yield). $^1$H NMR (400.0 MHz, DMSO-$d_6$) δ 7.56 (d, J=10.6 Hz, 2H), 7.51-7.37 (m, 5H), 5.14 (s, 2H), 3.44-3.35 (m, 1H), 2.12-2.05 (m, 2H), 1.86-1.55 (m, 6H).

To a solution of 1-(benzyloxy)-4-bromo-2-cyclopentyl-5-nitrobenzene (5.9 g; 15.7 mmol) and CuI (6.0 g, 31.5 mmol) in DMF (60 mL) at room temperature under inert atmosphere was added methylfluorosulfonyldifluoroacetate (4.0 g, 20.4 mmol) dropwise. The reaction was then heated to 105° C. for 2 h. The reaction was cooled to room temperature, quenched with 50% saturated aqueous $NaHCO_3$ and filtered through a pad of Celite to remove solids. The filtrate was extracted with ethyl acetate, dried over $Na_2SO_4$, filtered and concentrated. Purification by silica gel chromatography (0-10% ethyl acetate/hexane) provided 1-(benzyloxy)-2-cyclopentyl-5-nitro-4-(trifluoromethyl)benzene (5.06 g, 88% yield). $^1$H NMR (400.0 MHz, DMSO-$d_6$) δ 7.64 (s, 1H), 7.49-7.38 (m, 6H), 5.21 (s, 2H), 3.49-3.40 (m, 1H), 2.14-2.07 (m, 2H), 1.87-1.58 (m, 6H).

To a mixture of 1-(benzyloxy)-2-cyclopentyl-5-nitro-4-(trifluoromethyl)benzene (3.0 g, 8.2 mmol) and Fe (2.8 g, 49.3 mmol) in 25% aqueous ethanol (40 mL) was added concentrated HCl (2.1 g, 1.8 mL, 58.7 mmol). The mixture was stirred at 50° C. for 4 h. The reaction was filtered hot and washed with ethanol (2×5 mL). The filtrate was concentrated to ~20 mL volume, resulting in the precipitation of a yellow crystalline solid. The solid was filtered, washed with water and dried to provide 5-(benzyloxy)-4-cyclopentyl-2-(trifluoromethyl)aniline as a yellow-brown crystalline solid (3.0 g, 98% yield). $^1$H NMR (400.0 MHz, CDCl$_3$) δ 7.40-7.35 (m, 5H), 7.25 (d, J=6.7 Hz, 1H), 6.24 (s, 1H), 5.06 (s, 2H), 4.03 (s, 2H), 3.28-3.20 (m, 1H), 1.99-1.95 (m, 2H), 1.74-1.65 (m, 2H), 1.67-1.62 (m, 2H), 1.58-1.54 (m, 2H).

Intermediate 15

Synthesis of methyl 2-(2-amino-5-cyclopentyl-4-hydroxyphenyl)acetate

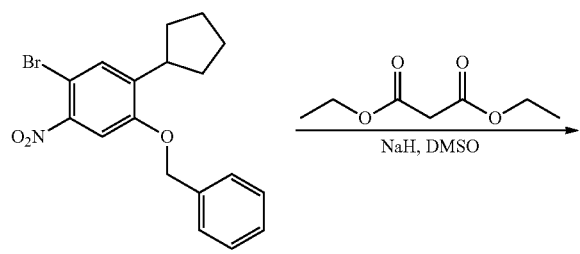

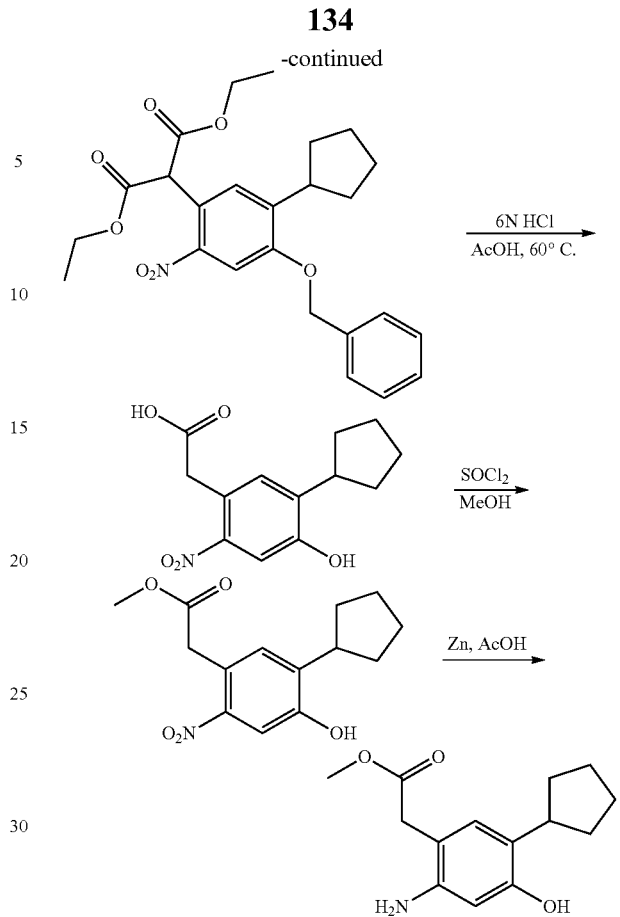

Diethyl malonate (1059 mg, 1.0 mL, 6.6 mmol) was added dropwise to a suspension of NaH (265 mg, 6.6 mmol) in DMSO (3.3 mL). The reaction mixture was warmed to 60° C. for 30 min. A solution of 1-benzyloxy-4-bromo-2-cyclopentyl-5-nitro-benzene (995 mg, 2.6 mmol) in DMSO (3 mL) was added dropwise and the reaction mixture heated at 100° C. for 2 h. The cooled solution was poured into ice water, and the aqueous layer extracted with dichloromethane (3×20 mL). The organic layer was dried down to an orange residue. Purification by silica gel chromatography (0-40% ethyl acetate/hexane) provided diethyl 2-(4-(benzyloxy)-5-cyclopentyl-2-nitrophenyl)malonate as a yellow oil (538 mg, 45% yield). LC/MS m/z 456.2 [M+H]$^+$.

Diethyl 2-(4-benzyloxy-5-cyclopentyl-2-nitro-phenyl)propanedioate (465 mg, 1.0 mmol) was dissolved in acetic acid (2 mL) and heated to 100° C. HCl (1 mL of 6 M, 6.0 mmol) was added dropwise and then the reaction mixture heated at 100° C. for 3 h. The reaction was diluted with water and extracted with ether. The ether was dried over $Na_2SO_4$, filtered, and dried down to a brown oil (270 mg, quantitative yield).

To a solution of 2-(5-cyclopentyl-4-hydroxy-2-nitro-phenyl)acetic acid (270 mg, 1.02 mmol) in methanol was added thionyl chloride (149 μL, 2.04 mmol) dropwise at 25° C. The mixture was stirred at room temperature for 1 h. The reaction was diluted with dichloromethane and washed with 50% saturated $NaHCO_3$ (2×50 mL), brine, dried over $Na_2SO_4$, and concentrated in vacuo to afford methyl 2-(5-cyclopentyl-4-hydroxy-2-nitro-phenyl)acetate as clear brown oil (180 g, 63% yield). LC/MS m/z 280.0 [M+H]$^+$.

Methyl 2-(5-cyclopentyl-4-hydroxy-2-nitro-phenyl)acetate (30 mg, 0.11° mmol) was dissolved in acetic acid (1 mL)

and water (0.5 mL) and treated with Zn dust (7 mg, 0.98 µL, 0.11 mmol) at room temperature. The mixture was stirred for 2 h then diluted with methanol (5 mL) and filtered. The filtrate was diluted with ethyl acetate, washed with 50% saturated NaHCO$_3$ (2×20 mL), water, and brine. The solution was dried over Na$_2$SO$_4$, filtered, and dried down to provide methyl 2-(2-amino-5-cyclopentyl-4-hydroxyphenyl)acetate as an amber colored oil (25 mg, 93% yield). LC/MS m/z 249.8 [M+H]$^+$.

Intermediate 16

Synthesis of 5-amino-2-cyclopentyl-4-(4-ethylpiperazin-1-yl)phenyl methyl carbonate

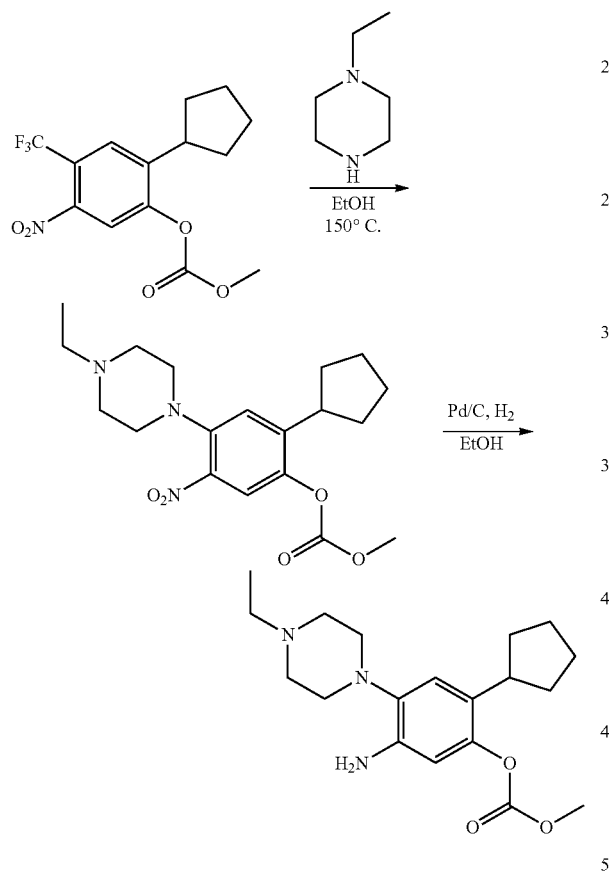

A solution of (4-bromo-2-cyclopentyl-5-nitro-phenyl) methyl carbonate (800 mg, 2.33 mmol) and 1-ethylpiperazine (266 mg, 2.33 mmol) in ethanol (2.4 mL) was heated under microwave irradiation at 150° C. for 6 h, resulting in product formation with loss of the carbonate group. The reaction was concentrated in vacuo and the residue was redissolved in dichloromethane, washed with water, dried over Na$_2$SO$_4$, filtered and reconcentrated. The crude product was dissolved in triethylamine (648 µL, 4.65 mmol) and dichloromethane (2 mL), cooled to 0° C. and methyl chloroformate (180 µL, 2.32 mmol) was added dropwise. The reaction was warmed to room temperature and stirred for 2 h. The reaction was quenched with water and the aqueous layer was extracted with dichloromethane. The combined organics were dried over MgSO$_4$, filtered and concentrated. Purification by silica gel chromatography (0-10% ethyl acetate/hexanes) provided 2-cyclopentyl-4-(4-ethylpiperazin-1-yl)-5-nitrophenyl methyl carbonate (672 mg, 76% yield). $^1$H NMR (400.0 MHz, DMSO-d$_6$) δ 7.66 (d, J=8.6 Hz, 1H), 7.30 (d, J=8.6 Hz, 1H), 3.88 (s, 3H), 3.08-3.06 (m, 1H), 2.88 (s, 4H), 2.34-2.30 (m, 5H), 1.93-1.90 (m, 3H), 1.75-1.72 (m, 2H), 1.65-1.63 (m, 2H), 1.54-1.51 (m, 2H), 1.00 (t, J=7.1 Hz, 3H).

A solution of 2-cyclopentyl-4-(4-ethylpiperazin-1-yl)-5-nitrophenyl methyl carbonate (675 mg, 1.79 mmol) in ethanol (7 mL) treated with 10% Pd/C (68 mg) was stirred under H$_2$ atmosphere for 3 h. The reaction mixture filtered through a plug of silica and washed with methanol. The filtrate was concentrated in vacuo to yield 5-amino-2-cyclopentyl-4-(4-ethylpiperazin-1-yl)phenyl methyl carbonate (500 mg, 80% yield). $^1$H NMR (400.0 MHz, DMSO-d$_6$) δ 6.83 (d, J=8.4 Hz, 1H), 6.57 (d, J=8.4 Hz, 1H), 4.86 (s, 2H), 3.83 (s, 3H), 2.93-2.82 (m, 5H), 2.62 (d, J=9.4 Hz, 2H), 2.36 (q, J=7.2 Hz, 2H), 2.23-2.20 (m, 2H), 1.82-1.81 (m, 2H), 1.69-1.66 (m, 2H), 1.58-1.55 (m, 2H), 1.42-1.39 (m, 2H), 1.01 (t, J=7.1 Hz, 3H).

Intermediate 17

Synthesis of 5-amino-2-cyclopentyl-4-(3-(dimethylamino)prop-1-ynyl)phenol

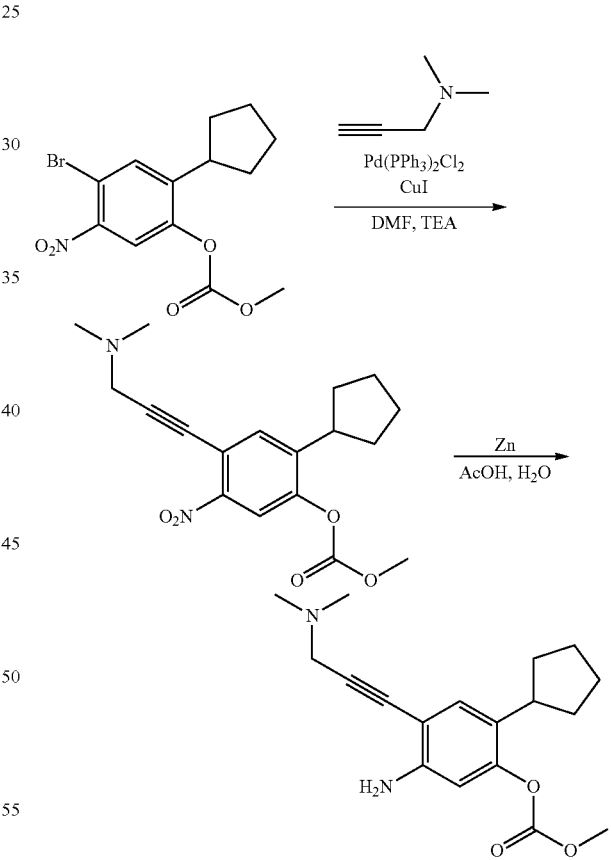

4-Bromo-2-cyclopentyl-5-nitrophenyl methyl carbonate (1000 mg, 2.9 mmol), Pd(PPh$_3$)$_2$Cl$_2$ (102 mg, 0.15 mmol), and CuI (17 mg, 0.087 mmol) were added to a large microwave tube which was flushed with N$_2$ and capped. In a separate flask, DMF (10 mL), triethylamine (10 mL), and N,N-dimethylprop-2-yn-1-amine (725 mg, 929 µL, 8.72 mmol) were added and degassed by N$_2$ bubbling (10 min). The degassed solution was then cannulated into the capped microwave tube under N$_2$ atmosphere and heated under microwave irradiation for 10 min at 100° C. resulting in product formation with partial loss of the carbonate group. The reaction was diluted with ethyl acetate, washed with 50% saturated sodium bicarbonate solution (2×20 mL), water, and brine. The solution was dried over Na$_2$SO$_4$, filtered, and dried down to a red solid. The crude reaction mixture was dissolved in dichloromethane (35 mL) and triethylamine (1.17 g, 1.62 mL, 11.62 mmol) and treated dropwise with methyl chloroformate (549 mg, 449 µL, 5.81 mmol) at room temperature. The reaction was stirred for 10 min then diluted with ethyl acetate, washed with 50% saturated sodium bicarbonate solution (2×20 mL), water, and brine. The solution was dried over Na$_2$SO$_4$, filtered, and dried down to provide 2-cyclopentyl-4-(3-(dimethylamino)prop-1-ynyl)-5-nitrophenyl methyl carbonate as a brown/orange solid. $^1$H NMR (400.0 MHz, DMSO-d$_6$) δ 8.14 (s, 1H), 7.68 (s, 1H), 3.89 (d, J=3.9 Hz, 3H), 3.54 (s, 2H), 3.23 (s, 1H), 3.14 (dd, J=9.3, 17.1 Hz, 1H), 2.25 (d, J=8.2 Hz, 6H), 1.99-1.92 (m, 2H), 1.79-1.73 (m, 2H), 1.69-1.51 (m, 3H).

2-Cyclopentyl-4-(3-(dimethylamino)prop-1-ynyl)-5-nitrophenyl methyl carbonate (800 mg, 2.31 mmol) was dissolved in a mixture of glacial acetic acid (10 mL) and water (2.5 mL). Zn dust (1511 mg, 23.10 mmol) was added at room temperature. The solution was stirred for 10 min then diluted with methanol (5 mL) and filtered. The solution was concentrated and redissolved in ethyl acetate. The ethyl acetate solution was washed with 50% saturated NaHCO$_3$ (2×20 mL) and brine, dried over Na$_2$SO$_4$, filtered, and dried down to a light orange solid. Purification by silica gel chromatography (5-15% methanol/dichloromethane) provided 5-amino-2-cyclopentyl-4-(3-(dimethylamino)prop-1-ynyl)phenyl methyl carbonate as a light orange oil (420 mg, 57% yield). $^1$H NMR (400.0 MHz, DMSO-d$_6$) δ 7.07 (s, 1H), 6.47 (s, 1H), 5.31 (s, 2H), 3.83 (d, J=5.7 Hz, 3H), 3.48 (d, J=4.6 Hz, 2H), 2.86-2.81 (m, 1H), 2.23 (s, 6H), 1.87-1.80 (m, 2H), 1.74-1.66 (m, 2H), 1.62-1.55 (m, 2H), 1.45-1.38 (m, 2H).

Intermediate 18

Synthesis of tert-butyl 4-(2-amino-5-cyclopentyl-4-(methoxycarbonyloxy)phenyl)piperidine-1-carboxylate

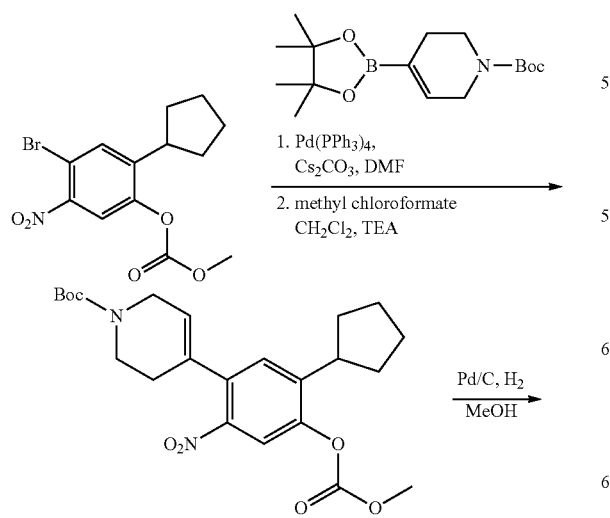

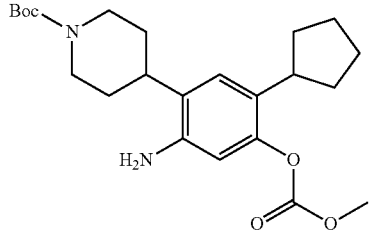

4-Bromo-2-cyclopentyl-5-nitrophenyl methyl carbonate (700 mg, 2.03 mmol), tert-butyl 4-(4,4,5,5-tetramethyl-1,3,2-dioxaborolan-2-yl)-3,6-dihydro-2H-pyridine-1-carboxylate (629 mg, 2.03 mmol), Pd(PPh$_3$)$_4$ (235 mg, 0.20 mmol), and Cs$_2$CO$_3$ (1325 mg, 4.07 mmol) were combined in DMF (10 mL) and heated at 90° C. for 4 h under N$_2$ atmosphere. The reaction was diluted with water and extracted with dichloromethane (3×10 mL). The organic fractions were combined, dried over MgSO$_4$, filtered and concentrated. Purification by silica gel chromatography (0-100% ethyl acetate/hexanes) yielded tert-butyl 4-(5-cyclopentyl-4-hydroxy-2-nitrophenyl)-5,6-dihydropyridine-1(2H)-carboxylate (596 mg, 77% yield). LC/MS m/z 389.4 [M+H]$^+$.

Tert-butyl 4-(5-cyclopentyl-4-hydroxy-2-nitro-phenyl)-3,6-dihydro-2H-pyridine-1-carboxylate (596 mg, 1.53 mmol) was dissolved in dichloromethane (5 mL) and triethylamine (388 mg, 535 µL, 3.84 mmol) then treated dropwise with methyl chloroformate (178 µL, 2.301 mmol). The reaction was stirred for 5 min at room temperature and then concentrated in vacuo to tert-butyl 4-(5-cyclopentyl-4-(methoxycarbonyloxy)-2-nitrophenyl)-5,6-dihydropyridine-1(2H)-carboxylate (680 mg, 99% yield). The material was used without purification. LC/MS m/z 447.4 [M+H]$^+$.

Tert-butyl 4-(5-cyclopentyl-4-methoxycarbonyloxy-2-nitro-phenyl)-3,6-dihydro-2H-pyridine-1-carboxylate (680 mg, 1.52 mmol) in methanol (30 mL) was treated with 10% Pd/C (162 mg) and stirred under H$_2$ for 1 h at room temperature. The reaction was filtered and concentrated in vacuo to provide tert-butyl 4-(2-amino-5-cyclopentyl-4-(methoxycarbonyloxy)phenyl)piperidine-1-carboxylate (520 mg, 82% yield). LC/MS m/z 419.7 [M+H]$^+$.

Intermediate 19

Synthesis of 5-amino-2-cyclopentyl-4-(4-methylpent-1-ynyl)phenyl methyl carbonate

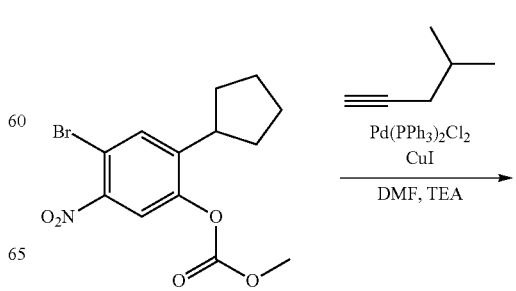

-continued

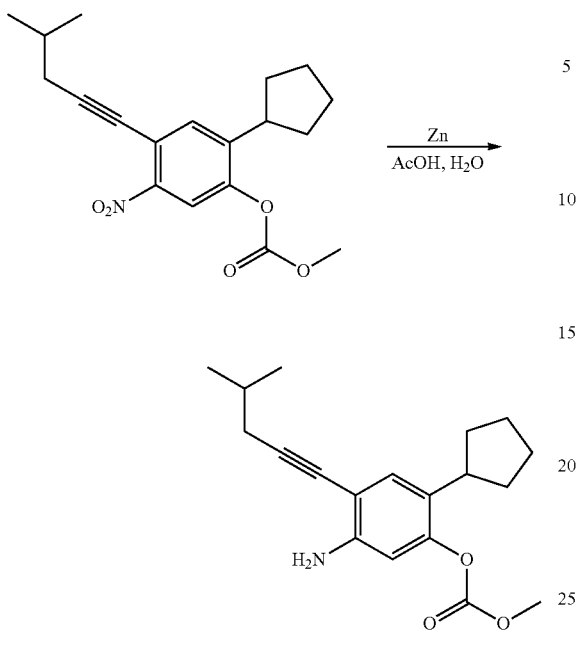

To 4-bromo-2-cyclopentyl-5-nitrophenyl methyl carbonate (100 mg, 0.29 mmol), Pd(PPh$_3$)$_2$Cl$_2$ (4 mg, 0.006 mmol), and CuI (1 mg, 0.006 mmol) was added DMF (600 µL), triethylamine (750 µL), and 4-methylpent-1-yne (72 mg, 103 µL, 0.87 mmol). The reaction mixture was stirred under N$_2$ atmosphere for 20 min, resulting in product formation with partial loss of the carbonate group. The reaction was diluted with ethyl acetate, washed with 50% saturated sodium bicarbonate solution (2×20 mL), water, and brine. The solution was dried over Na$_2$SO$_4$ and filtered through a plug of silica. The filtrate was treated with triethylamine (29 mg, 40 µL, 0.29 mmol) and then dropwise with methyl chloroformate (14 mg, 11 µL, 0.14 mmol). The reaction mixture was stirred for 10 min, and was then dried down, diluted with ethyl acetate, washed with 50% saturated sodium bicarbonate solution (2×20 mL), water, 0.5 M HCl, and brine. The solution was dried over Na$_2$SO$_4$, filtered, and concentrated in vacuo to provide 2-cyclopentyl-4-(4-methylpent-1-ynyl)-5-nitrophenyl methyl carbonate as an orange oil (75 mg, 75% yield). $^1$H NMR (400.0 MHz, DMSO-d$_6$) δ 8.05 (s, 1H), 7.77 (s, 1H), 4.00 (s, 3H), 3.25-3.18 (m, 1H), 2.46 (d, J=6.3 Hz, 2H), 2.00-1.88 (m, 3H), 1.79-1.75 (m, 2H), 1.73-1.55 (m, 4H), 1.06 (d, J=6.6 Hz, 6H).

2-Cyclopentyl-4-(4-methylpent-1-ynyl)-5-nitrophenyl methyl carbonate (75 mg, 0.22 mmol) was dissolved in a mixture of glacial acetic acid (940 µL) and water (235 µL). Zn dust (71 mg, 1.09 mmol) was added at room temperature and the reaction stirred for 10 min. The reaction was diluted with methanol (5 mL), filtered and concentrated. The product was brought up in dichloromethane, washed with 50% saturated NaHCO$_3$, dried over Na$_2$SO$_4$, filtered, and dried down to provide 5-amino-2-cyclopentyl-4-(4-methylpent-1-ynyl) phenyl methyl carbonate as a clear orange oil (68 mg, 99% yield). LC/MS m/z 316.2 [M+H]$^+$.

Intermediate 20

Synthesis of 2-(3-(dimethylamino)prop-1-ynyl)-4-fluoroan

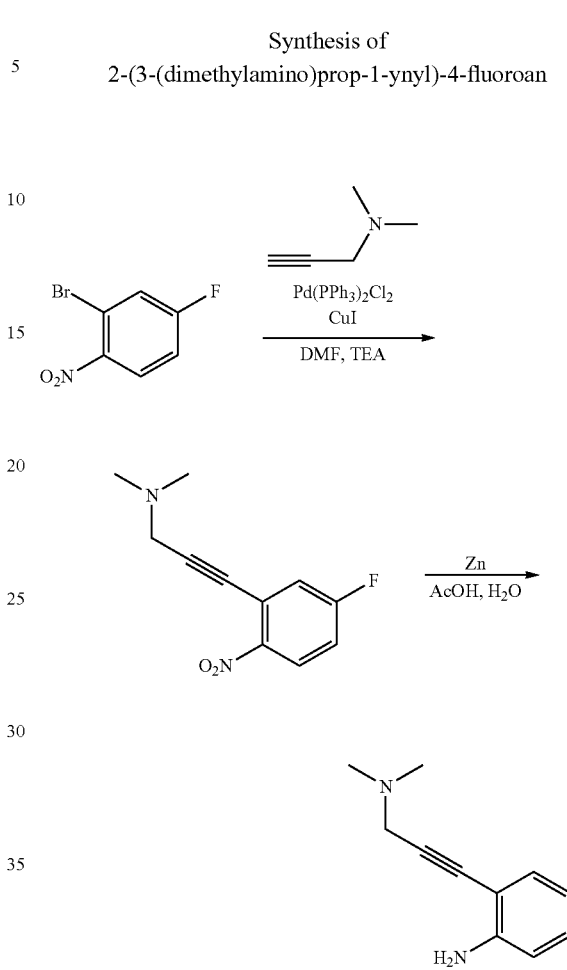

To a flask charged with N,N-dimethylprop-2-yn-1-amine (737 mg, 945 µL, 8.86 mmol), 2-bromo-4-fluoro-1-nitrobenzene (1300 mg, 5.91 mmol), PdCl$_2$(PPh$_3$)$_2$ (415 mg, 0.59 mmol), CuI (169 mg, 0.89 mmol) were added triethylamine (2.47 mL, 17.73 mmol) and DMF (10 mL) under N$_2$ atmosphere. The reaction mixture was heated at 60° C. for 5 h, then poured into water (300 mL) and extracted with ethyl acetate (3×40 mL). The organic fractions were combined, dried over MgSO$_4$, filtered, and concentrated in vacuo. Purification by silica gel chromatography (50-100% ethyl acetate/hexanes) yielded 3-(4-fluoro-2-nitrophenyl)-N,N-dimethylprop-2-yn-1-amine (895 mg, 68% yield). LC/MS m/z 223.0 [M+H]$^+$.

3-(5-fluoro-2-nitrophenyl)-N,N-dimethylprop-2-yn-1-amine (895 mg, 4.03 mmol) and Zn dust (2635 mg, 40.28 mmol) were stirred in water (2 mL) and acetic acid (6 mL) for 20 min at room temperature. The reaction was diluted with methanol (5 mL) and filtered. The mixture was added to water (100 mL) and was extracted with ethyl acetate (3×10 mL). The combined organic extracts were dried over MgSO$_4$, filtered, and concentrated in vacuo to yield 2-(3-(dimethylamino)prop-1-ynyl)-5-fluoroaniline (610 mg, 79% yield) which was used without further purification. LC/MS m/z 193.0 [M+H]$^+$.

Intermediate 21

Synthesis of 5-amino-4-(3-(dimethylamino)prop-1-ynyl)-2-methylphenyl methyl carbonate

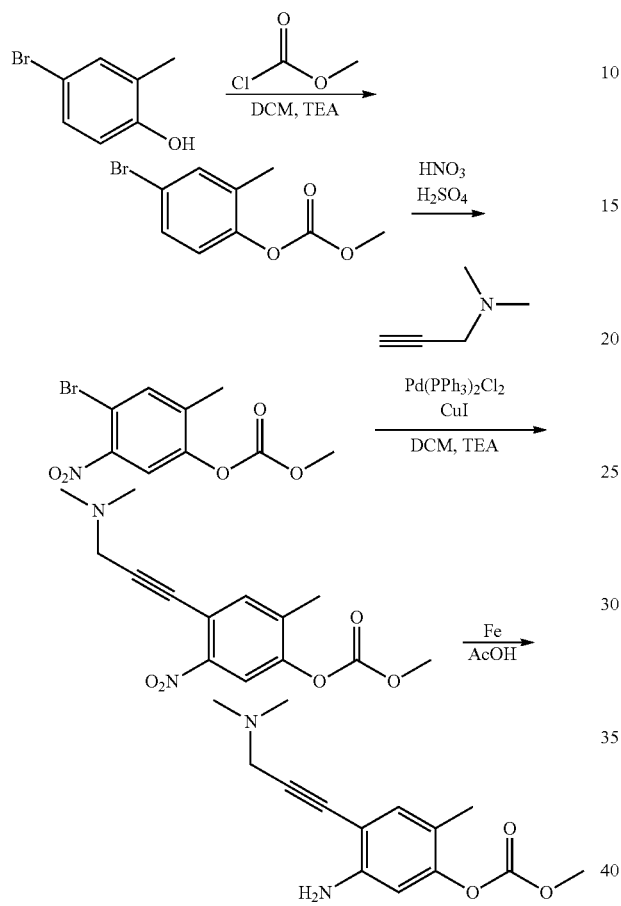

4-Bromo-2-methyl-phenol (3.63 g, 19.41 mmol) was dissolved in dichloromethane (18 mL) and triethylamine (5.41 mL, 38.80 mmol), cooled to 0° C., then treated with methyl chloroformate (2.25 mL, 29.12 mmol) and allowed to warm to room temperature over 2 h. The reaction was quenched with water and the layers separated. The aqueous layer was extracted with dichloromethane and the combined organic extracts was dried over $Na_2SO_4$, filtered, and concentrated in vacuo to yield an oil that was purified by silica gel chromatography (10% ethyl acetate/hexane) to yield 4-bromo-2-methylphenyl methyl carbonate (4.1 g, 86% yield) as a white solid. $^1$H NMR (400.0 MHz, DMSO-$d_6$) δ 7.56 (d, J=2.1 Hz, 1H), 7.44 (dd, J=2.3, 8.6 Hz, 1H), 7.18 (d, J=8.6 Hz, 1H), 3.84 (s, 3H), 2.15 (s, 3H).

4-Bromo-2-methylphenyl methyl carbonate (4.0 g, 16.32 mmol) was added portion-wise to $H_2SO_4$ (12.0 mL) to generate a homogeneous solution. This solution was then cooled to 0° C. internal temperature and $KNO_3$ (2.0 g, 19.6 mmol) was added portion-wise maintaining the internal temperature below 5° C. The reaction was stirred for 2 h and then poured over ice. The aqueous layer was extracted with dichloromethane, washed with saturated $NaHCO_3$ and water, dried over $Na_2SO_4$, and concentrated. Purification by silica gel chromatography (0-5% ethyl acetate/hexanes) provided 4-bromo-2-methyl-5-nitrophenyl methyl carbonate (3.4 g, 71% yield). $^1$H NMR (400.0 MHz, DMSO-$d_6$) δ 8.11 (s, 1H), 7.95 (s, 1H), 3.88 (s, 3H), 2.25 (s, 3H).

To 4-bromo-2-methyl-5-nitrophenyl methyl carbonate (500 mg, 1.72 mmol), $Pd(PPh_3)_2Cl_2$ (30 mg, 0.04 mmol), and CuI (3 mg, 0.02 mmol) were added DMF (5.0 mL), triethylamine (5.0 mL), and N,N-dimethylprop-2-yn-1-amine (717 mg, 919 µL, 8.62 mmol) under nitrogen atmosphere. The reaction mixture was heated under microwave irradiation at 100° C. for 15 min, resulting in product formation with partial loss of the carbonate group. The reaction was quenched with water and the aqueous layer was extracted with ethyl acetate, washed with 50% saturated $NaHCO_3$ (2×20 mL), water, and brine. The solution was dried over $Na_2SO_4$, filtered, and dried down to a red oil. The oil was dissolved in cold (0° C.) dichloromethane (4 mL) and triethylamine (132 µL, 1.71 mmol) then treated dropwise with methyl chloroformate (132 µL, 1.71 mmol). After 5 min the reaction was quenched with water and the aqueous layer extracted with dichloromethane. The organic layer was dried over $MgSO_4$, filtered and concentrated. Purification by silica gel chromatography (0-60% ethyl acetate/hexanes) provided 4-(3-(dimethylamino)prop-1-ynyl)-2-methyl-5-nitrophenyl methyl carbonate (100 mg, 20% yield). LC/MS m/z 293.3 [M+H]$^+$.

To a solution of 4-(3-(dimethylamino)prop-1-ynyl)-2-methyl-5-nitrophenyl methyl carbonate (120 mg; 0.41 mmol) in ethanol (2.7 mL) and glacial acetic acid (1.5 mL) was added Fe (92 mg, 1.64 mmol). The mixture was heated at 60° C. for 1 h and then cooled to room temperature. The mixture was diluted with water and carefully neutralized with solid $Na_2CO_3$. The resulting solution was extracted with ethyl acetate. The combined organic extracts were dried over $MgSO_4$ and concentrated in vacuo. The residue was purified by silica gel chromatography (0-20% ethyl acetate/hexanes) to provide 5-amino-4-(3-(dimethylamino)prop-1-ynyl)-2-methylphenyl methyl carbonate (85 mg, 79% yield). LC/MS m/z 218.3 [M+H]$^+$.

Intermediate 22

Synthesis of ethyl 3-(2-amino-5-cyclopentyl-4-(methoxycarbonyloxy)phenyl)propanoate

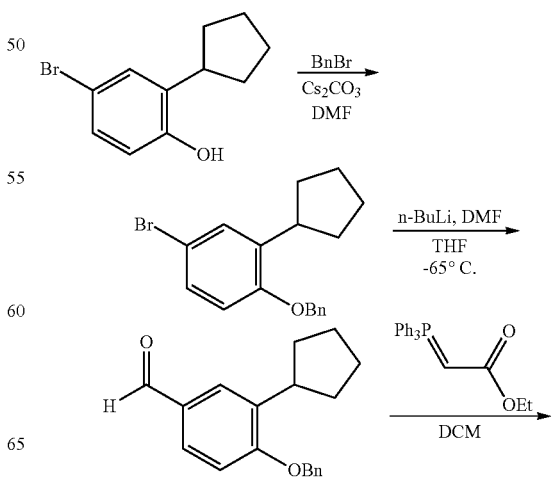

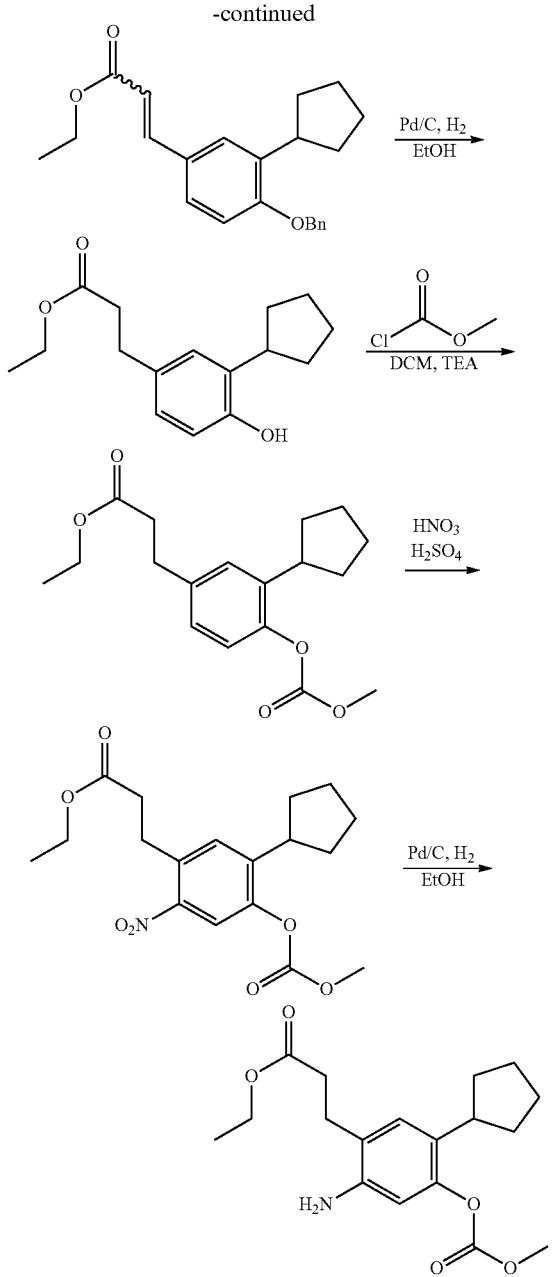

To a solution of 4-bromo-2-cyclopentyl-phenol (2.0 g, 8.29 mmol) and Cs₂CO₃ (3.24 g, 9.95 mmol) in DMF (13.0 mL) was added benzyl bromide (1.6 g, 1.09 mL, 9.12 mmol) dropwise. The reaction was stirred at room temperature under inert atmosphere for 2 h. The reaction was quenched with water and the aqueous layer was extracted with dichloromethane. The organic layer was dried over Na₂SO₄ and concentrated. Purification by silica gel chromatography (5% ethyl acetate/hexane) provided 1-benzyloxy-4-bromo-2-cyclopentyl-benzene (1.8 g, 64% yield). ¹H NMR (400.0 MHz, DMSO-d₆) δ 7.43-7.40 (m, 4H), 7.35-7.28 (m, 3H), 6.99 (d, J=9.4 Hz, 1H), 5.12 (s, 2H), 3.28-3.24 (m, 1H), 1.94-1.92 (m, 2H), 1.70-1.69 (m, 2H), 1.61-1.52 (m, 4H).

A stirred solution of 1-benzyloxy-4-bromo-2-cyclopentyl-benzene (1500 mg, 4.53 mmol) in tetrahydrofuran (13.4 mL) was cooled to −65° C. n-BuLi (3.11 mL of 1.6 M, 4.98 mmol) was added dropwise over several minutes. After 30 min, DMF (497 mg, 526.0 μL, 6.79 mmol) was added dropwise over a period of 10 min. Stirring at −65° C. was maintained for 20 min, and then the reaction was quenched by the addition of HCl (9.06 mL of 1 M, 9.06 mmol). The aqueous and organic layers were separated. The organic layer was washed with saturated NaHCO₃ (10 mL) and water (10 mL), dried over Na₂SO₄, filtered and concentrated. Purification by silica gel chromatography (0-10% ethyl acetate/hexanes) provided 4-benzyloxy-3-cyclopentyl-benzaldehyde (800 mg, 63% yield) white solid. ¹H NMR (400.0 MHz, DMSO-d₆) δ 9.86 (s, 1H), 7.76 (dd, J=2.1, 6.6 Hz, 2H), 7.49-7.29 (m, 5H), 7.26-7.20 (m, 1H), 5.26 (s, 2H), 3.37-3.26 (m, 1H), 2.00-1.90 (m, 2H), 1.73-1.50 (m, 6H).

A mixture of 4-benzyloxy-3-cyclopentyl-benzaldehyde (1.3 g, 4.64 mmol) and ethyl 2-triphenylphosphoranylidene-acetate (1.6 g, 4.64 mmol) in dichloromethane (12 mL) was heated at reflux for 24 h. The reaction was cooled to room temperature and concentrated in vacuo. Purification by silica gel chromatography (0-10% ethyl acetate/hexanes) yielded ethyl 3-(4-benzyloxy-3-cyclopentyl-phenyl)prop-2-enoate (1.2 g, 81% yield). ¹H NMR (400.0 MHz, DMSO-d₆) δ 7.61-7.57 (m, 2H), 7.52 (dd, J=2.1, 8.5 Hz, 1H), 7.46-7.39 (m, 4H), 7.33 (t, J=7.1 Hz, 1H), 7.06 (d, J=8.5 Hz, 1H), 6.49 (d, J=16 Hz, 1H), 5.18 (s, 2H), 4.16 (q, J=7.1 Hz, 2H), 3.32-3.27 (m, 1H), 1.99-1.92 (m, 2H), 1.74-1.67 (m, 2H), 1.65-1.58 (m, 4H), 1.24 (t, J=7 Hz, 3H).

A flask containing 10% Pd/C (120 mg) was evacuated and then purged under a N₂ atmosphere. To this was added a solution of ethyl 3-(4-benzyloxy-3-cyclopentyl-phenyl) prop-2-enoate (1.2 g, 3.42 mmol) in ethanol (15 mL). The reaction was stirred under H₂ atmosphere for 12 h at room temperature. The catalyst was filtered off and the solvent was removed under reduced pressure. Purification by silica gel chromatography (0-30% ethyl acetate/hexanes) afforded ethyl 3-(3-cyclopentyl-4-hydroxy-phenyl)propanoate (857 mg, 96% yield). ¹H NMR (400.0 MHz, DMSO-d₆) δ 9.01 (s, 1H), 6.93 (d, J=2.1 Hz, 1H), 6.79 (dd, J=2.2, 8.1 Hz, 1H), 6.65 (d, J=8.1 Hz, 1H), 4.02 (q, J=7.1 Hz, 2H), 3.21-3.12 (m, 1H), 2.71 (t, J=7.5 Hz, 2H), 2.53-2.50 (m, obscured by DMSO peak, 2H), 1.92-1.85 (m, 2H), 1.78-1.68 (m, 2H), 1.66-1.55 (m, 2H), 1.54-1.45 (m, 2H), 1.15 (t, J=7.1 Hz, 3H).

To a solution of ethyl 3-(3-cyclopentyl-4-hydroxy-phenyl) propanoate (857 mg, 3.27 mmol) and triethylamine (911 μL, 6.53 mmol) in dichloromethane (5 mL) under a N₂ atmosphere at 0° C. was added methyl chloroformate (463 mg, 377 μL, 4.90 mmol) dropwise. After 1 h, the reaction mixture was partitioned between dichloromethane/water, separated and the aqueous layer was extracted once more with dichloromethane. The combined organics were dried over Na₂SO₄, filtered and concentrated. Purification by silica gel chromatography (0-30% ethyl acetate/hexanes) provided ethyl 3-(3-cyclopentyl-4-methoxycarbonyloxy-phenyl)propanoate (920 mg, 88% yield). ¹H NMR (400.0 MHz, DMSO-d₆) δ 7.20 (d, J=1.7 Hz, 1H), 7.09-7.03 (m, 2H), 4.04 (q, J=7.1 Hz, 2H), 3.82 (s, 3H), 3.03-2.96 (m, 1H), 2.83 (t, J=7.6 Hz, 2H), 2.61 (t, J=7.6 Hz, 2H), 1.93-1.86 (m, 2H), 1.77-1.72 (m, 2H), 1.66-1.58 (m, 2H), 1.54-1.47 (m, 2H), 1.15 (t, J=7.1 Hz, 3H).

Ethyl 3-(3-cyclopentyl-4-methoxycarbonyloxy-phenyl) propanoate (920 mg, 2.87 mmol) was dissolved in H₂SO₄ (2.2 mL) and the reaction mixture was cooled to −2° C. internal temperature. KNO₃ (348 mg, 3.45 mmol) was added in portions over 1 h maintain the internal temperature at 0° C. After 1 h at 0° C. the reaction mixture was poured over ice (30 mL) and partitioned between dichloromethane/water and separated. The organic layer was washed twice with a saturated aqueous NaHCO₃, dried over Na₂SO₄, filtered and concentrated. Purification by silica gel chromatography (0-40% ethyl acetate/hexanes) afforded ethyl 3-(5-cyclopentyl-4-methoxycarbonyloxy-2-nitro-phenyl)propanoate (827 mg, 76% yield). ¹H NMR (400.0 MHz, DMSO-d₆) δ 7.96 (s, 1H), 7.53 (s, 1H), 4.04 (q, J=7.1 Hz, 2H), 3.86 (s, 3H), 3.11 (t, J=7.6 Hz, 3H), 2.68 (t, J=7.6 Hz, 2H), 1.99-1.91 (m, 2H), 1.82-1.75 (m, 2H), 1.69-1.61 (m, 2H), 1.58-1.53 (m, 2H), 1.15 (t, J=7.1 Hz, 3H).

A flask containing ethyl 3-(5-cyclopentyl-4-methoxycarbonyloxy-2-nitro-phenyl)propanoate (258 mg, 0.71 mmol) and 10% Pd/C (26 mg) was evacuated and flushed with N₂. Ethanol (3 mL) was added and the reaction stirred for 6 h under H₂ atmosphere. The reaction was filtered and the solvent was removed under reduced pressure to provide ethyl 3-(2-amino-5-cyclopentyl-4-(methoxycarbonyloxy) phenyl)propanoate (175 mg, 74% yield). ¹H NMR (400.0 MHz, DMSO-d₆) δ 6.83 (s, 1H), 6.33 (s, 1H), 4.94 (s, 2H), 4.06-4.01 (m, 2H), 3.79 (s, 3H), 2.88-2.79 (m, 1H), 2.68 (t, J=7.4 Hz, 2H), 2.55-2.50 (m, obscured by DMSO peak, 2H), 1.84-1.77 (m, 2H), 1.72-1.66 (m, 2H), 1.62-1.55 (m, 2H), 1.45-1.36 (m, 2H), 1.17 (td, J=7.1, 3.4 Hz, 3H).

Intermediate 23

Synthesis of 5-amino-2-cyclopropylphenol

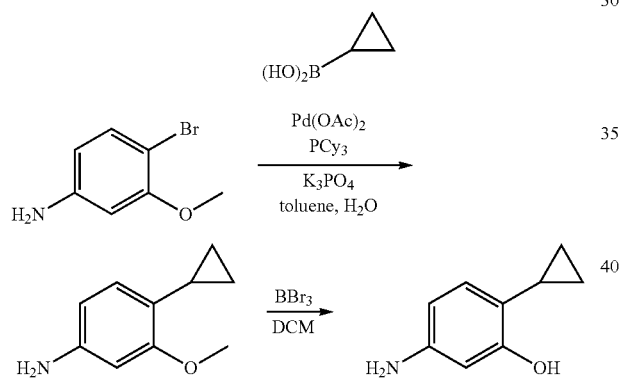

To a stirred solution of 4-bromo-3-methoxyaniline (1 g, 4.98 mmol) in 3:2 toluene/water (10 mL) was added cyclopropylboronic acid (514 mg, 5.98 mmol), Pd(OAc)₂ (56 mg, 0.25 mmol), PCy₃ (140 mg, 0.5 mmol) and K₃PO₄ (3.18 g, 15 mmol) at room temperature. The mixture was stirred at 100° C. for 10 h. The solid was filtered and the filtrate concentrated in vacuo. Purification by silica gel chromatography (2-10% ethyl acetate/hexanes) provided 4-cyclopropyl-3-methoxyaniline (200 mg, 25%) as a brown solid. ¹H NMR (300 MHz, CDCl₃) 6.67 (d, J=7.8 Hz, 1H), 6.24-6.20 (m, 2H), 3.82 (s, 3H), 3.50 (brs, 2H), 2.02-1.95 (m, 1H), 0.85-0.79 (m, 2H), 0.57-0.51 (m, 2H).

A solution of BBr₃ in dichloromethane (4.47 mL of 1 M, 4.47 mmol) was added to a solution of 4-cyclopropyl-3-methoxyaniline (243 mg, 1.49 mmol) in dichloromethane (15 mL) at 0° C. under N₂ atmosphere. The reaction was stirred for 30 min at 0° C. then diluted with dichloromethane (10 mL). The reaction mixture was washed with aqueous NaHCO₃, water and brine. The organic layer was dried over Na₂SO₄, filtered and concentrated in vacuo. The product was purified by HPLC (10-99% CH₃CN 0.05% TFA) to provide 5-amino-2-cyclopropylphenol (115 mg, 52% yield). LC/MS m/z 150.1 [M+H]⁺.

Intermediate 24

Synthesis of 4-tert-butyl-3-methoxyaniline

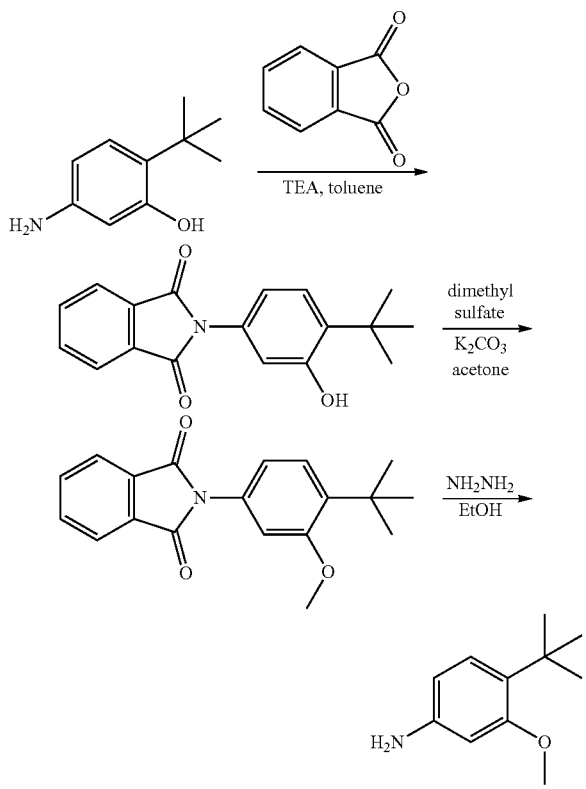

A mixture of 5-amino-2-tert-butyl-phenol (300 mg, 1.82 mmol), isobenzofuran-1,3-dione (283 mg, 1.91 mmol), triethylamine (759 μL, 5.45 mmol) in toluene (5.0 mL) was stirred at 110° C. for 13 h. The reaction mixture was cooled, diluted with ethyl acetate (15 mL), and washed with 10% aqueous NaHCO₃ (10 mL) and water. The organic layer was dried over Na₂SO₄, filtered and concentrated in vacuo to provide 2-(4-tert-butyl-3-hydroxyphenyl)isoindoline-1,3-dione (450 mg, 84% yield) as a light brown solid which was used for next reaction without further purification. ¹H NMR (400.0 MHz, DMSO-d₆) δ 9.72 (s, 1H), 7.96 (m, 2H), 7.90 (m, 2H), 7.25 (d, J=8.3 Hz, 1H), 6.85 (d, J=2.0 Hz, 1H), 6.79 (dd, J=2.1, 8.3 Hz, 1H), 1.38 (s, 9H).

A mixture of 2-(4-tert-butyl-3-hydroxy-phenyl)isoindoline-1,3-dione (450 mg, 1.52 mmol), dimethyl sulfate (385 mg, 288 μL, 3.05 mmol), K₂CO₃ (632 mg, 4.57 mmol) in acetone (10 mL) was stirred at 50° C. for 3 h. The reaction was cooled to room temperature, filtered and washed with acetone (10 mL). The filtrate was concentrated in vacuo and the residue purified by silica gel chromatography (20% ethyl acetate/hexane) to provide 2-(4-tert-butyl-3-methoxyphenyl)isoindoline-1,3-dione (420 mg, 89% yield). ¹H NMR (400.0 MHz, CDCl₃) δ 7.72 (m, 2H), 7.55 (m, 2H), 7.15 (d, J=8.3 Hz, 1H), 6.72 (dd, J=2.1, 8.2 Hz, 1H), 6.68 (d, J=2.0 Hz, 1H), 3.61 (s, 3H), 1.15 (d, J=3.4 Hz, 9H).

A slurry of 2-(4-tert-butyl-3-methoxy-phenyl)isoindoline-1,3-dione (400 mg, 1.29 mmol) and NH$_2$NH$_2$ (207 mg, 203 µL, 6.47 mmol) in ethanol (10 mL) was refluxed for 3 h. The reaction was cooled and concentrated in vacuo. The residue was extracted with water (25 mL) and ethyl acetate (3×10 mL). The combined organic extracts were washed with water, dried over Na$_2$SO$_4$, filtered and concentrated. Purification by silica gel chromatography (25-40% ethyl acetate/hexanes) provided 4-tert-butyl-3-methoxy-aniline (190 mg, 82% yield) as light brown oil. $^1$H NMR (400.0 MHz, CDCl$_3$) δ 6.97 (d, J=8.1 Hz, 1H), 6.17 (m, 2H), 3.71 (d, J=3.3 Hz, 3H), 3.53 (br s, 2H), 1.25 (d, J=3.3 Hz, 9H).

Intermediate 25

Synthesis of 2-bromo-4-cyclopentyl-5-methoxyaniline

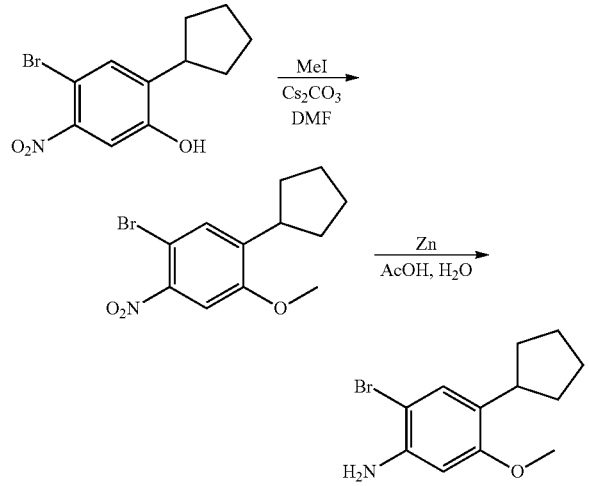

To a solution of 4-bromo-2-cyclopentyl-5-nitro-phenol (310 mg, 1.08 mmol) and Cs$_2$CO$_3$ (529 mg, 1.62 mmol) in DMF (2.0 mL) was added iodomethane (769 mg, 337 µL, 5.42 mmol) dropwise. The reaction was stirred at 50° C. under inert atmosphere for 16 h. The reaction was quenched with water and the aqueous layer was extracted with ethyl acetate. The organic layer was dried over Na$_2$SO$_4$ and concentrated. Purification by silica gel chromatography (0-20% ethyl acetate/hexane) provided 1-bromo-5-cyclopentyl-4-methoxy-2-nitrobenzene as a light yellow oil (288 mg, 89% yield). $^1$H NMR (400.0 MHz, DMSO-d$_6$) 7.65 (d, J=6.6 Hz, 2H), 3.87 (s, 3H), 3.29-3.21 (m, 1H), 1.99-1.91 (m, 3H), 1.81-1.50 (m, 5H).

1-Bromo-5-cyclopentyl-4-methoxy-2-nitrobenzene (100 mg, 0.33 mmol) was dissolved in acetic acid (1 mL) and water (250 µL) and treated with Zn (109 mg, 1.67 mmol) at room temperature and stirred for 1.5 h. The reaction was diluted with ethyl acetate and filtered. The organic layer was washed with 50% saturated NaHCO$_3$ and brine, dried over Na$_2$SO$_4$, filtered, and concentrated in vacuo to provide 2-bromo-4-cyclopentyl-5-methoxyaniline as a clear brown oil (85 mg, 94% yield). LC/MS m/z 270.2 [M+H]$^+$.

Intermediate 26

Synthesis of 2-(4-amino-5-chloro-2-methoxyphenyl)propan-2-ol

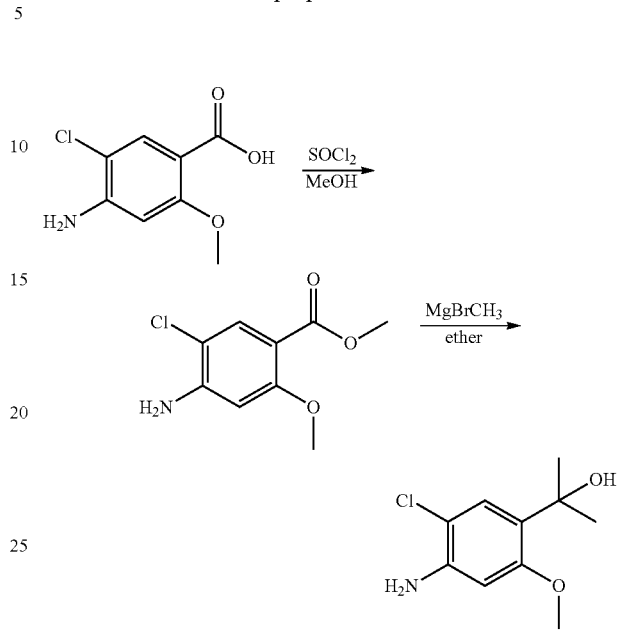

To a solution of 4-amino-5-chloro-2-methoxybenzoic acid (20.0 g, 99.2 mmol) in methanol (250 mL) was added thionyl chloride (7.2 mL, 99.2 mmol). The reaction was refluxed for 16 h then concentrated in vacuo. Purification by silica gel chromatography (0-90% ethyl acetate/hexanes) provided methyl 4-amino-5-chloro-2-methoxybenzoate (21.3 g, quantitative yield). LC/MS m/z 216.3 [M+H]$^+$.

To a solution of methyl 4-amino-5-chloro-2-methoxybenzoate (15.0 g, 69.6 mmol) in diethyl ether (350 mL) was added CH$_3$MgBr (236 g, 229 mL of 1.4 M, 320 mmol) at −78° C. The reaction allowed to warm to room temperature over 24 h. The reaction mixture was quenched with saturated NH$_4$Cl and the mixture filtered through a pad of Celite. The aqueous phase was extracted with ethyl acetate and the organic layer then washed with brine, dried over MgSO$_4$ and concentrated in vacuo. Purification by silica gel chromatography (0-60% ethyl acetate/hexanes) provided 2-(4-amino-5-chloro-2-methoxyphenyl)propan-2-ol as a yellow solid (10.0 g, 67% yield). LC/MS m/z 216.1 [M+H]$^+$. $^1$H NMR (400.0 MHz, CDCl$_3$) δ 7.16 (s, 1H), 6.34 (s, 1H), 4.01 (br s, 2H), 3.88 (s, 1H), 3.84 (s, 3H), 1.55 (s, 6H).

Intermediate 27

Synthesis of 2-bromo-4-ethylaniline

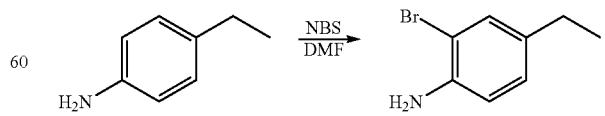

To 4-ethylaniline (1.76 g, 14.52 mmol) and NBS (2.58 g, 14.52 mmol) was added DMF (67 mL) and the reaction mixture was stirred at 0° C. for 10 min. The reaction mixture was purified by silica gel chromatography (0-50% ethyl acetate/hexanes) to provide 2-bromo-4-ethylaniline (2.7 g, 93% yield). LC/MS m/z 201.0 [M+H]+.

Intermediate 28

Synthesis of 2-bromo-4-cyclopentylaniline

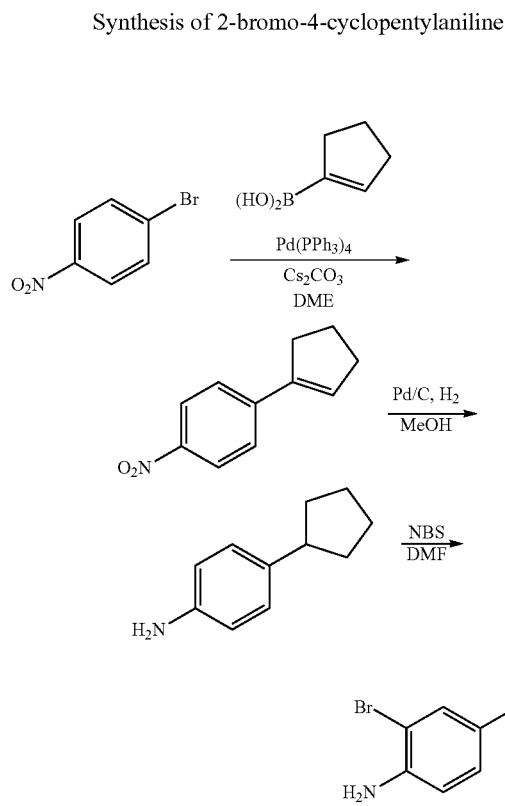

To 1-bromo-4-nitro-benzene (700 mg, 3.46 mmol), 1-cyclopentenylboronic acid (392 mg, 3.50 mmol), Pd(PPh$_3$)$_4$ (200 mg, 0.17 mmol), and Cs$_2$CO$_3$ (2258 g, 6.93 mmol) was added DME (8.4 mL) and ethanol (1.4 mL) and the reaction mixture was heated at 105° C. for 3 h. The reaction was concentrated in vacuo and purified by silica gel chromatography (0-100% ethyl acetate/hexanes) to provide 1-(1-cyclopentenyl)-4-nitro-benzene (545 mg, 83% yield). $^1$H NMR (400.0 MHz, CDCl$_3$) δ 8.19-8.15 (m, 2H), 7.58-7.52 (m, 2H), 6.44-6.42 (m, 1H), 2.77-2.71 (m, 2H), 2.62-2.56 (m, 2H), 2.11-2.03 (m, 2H).

1-(1-Cyclopentenyl)-4-nitro-benzene (225 mg, 1.19 mmol) in methanol (10 mL) and dichloromethane (2.5 mL) was treated with 10% Pd/C (70 mg) and stirred under H$_2$ atmosphere for 1 h at room temperature. The reaction was filtered and concentrated in vacuo to provide 4-cyclopentylaniline (180 mg, 94% yield). $^1$H NMR (400.0 MHz, MeOD) δ 7.01 (d, J=8.2 Hz, 2H), 6.73-6.70 (m, 2H), 2.88 (dd, J=2.3, 17.3 Hz, 1H), 2.00-1.95 (m, 2H), 1.80-1.75 (m, 2H), 1.70-1.64 (m, 2H), 1.56-1.49 (m, 2H).

4-Cyclopentylaniline (210 mg, 1.30 mmol) was dissolved in cold (0° C.) DMF (8 mL) and treated with NBS (232 mg, 1.30 mmol). The reaction was stirred at 0° C. for 5 min and then warmed to room temperature for 1 h. The reaction mixture was poured into water (40 mL) and extracted with ethyl acetate (3×20 mL). The combined organic extracts dried over MgSO$_4$, filtered and concentrated in vacuo. Purification by silica gel chromatography (0-50% ethyl acetate/hexanes) yielded 2-bromo-4-cyclopentylaniline (251 mg, 80% yield). LC/MS m/z 242.0 [M+H]+.

Intermediate 29

Synthesis of (S)-4-(2-methylpyrrolidin-1-yl)-2-(trifluoromethyl)aniline

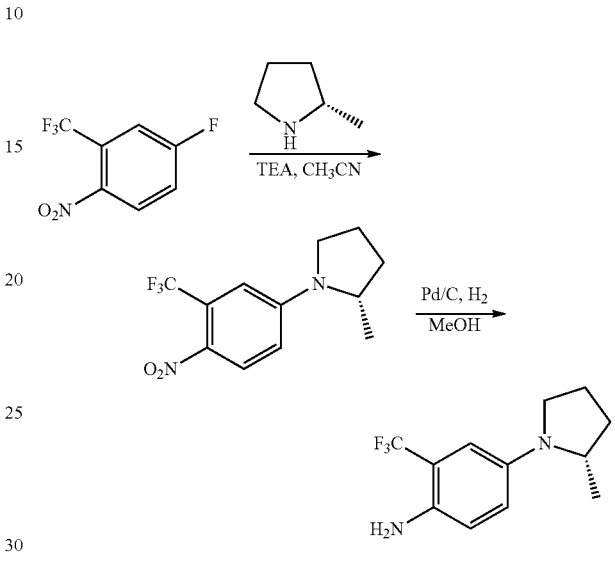

To a solution of (S)-2-methylpyrrolidine tosylate (10.6 g, 41.2 mmol) in acetonitrile (85 mL) was added 4-fluoro-1-nitro-2-(trifluoromethyl)benzene (6.6 g, 31.7 mmol) dropwise and followed by triethylamine (11.0 mL, 79.3 mmol) dropwise. The reaction was heated at 82° C. for 16 h. The reaction was quenched with water and extracted with ethyl acetate. The organic layer was washed with 1N HCl, then dried over Na$_2$SO$_4$ and concentrated in vacuo to yield (S)-2-methyl-1-(4-nitro-3-(trifluoromethyl)phenyl)pyrrolidine (8.7 g, quantitative yield). LC/MS m/z 275.3 [M+H]+.

To a solution of (S)-2-methyl-1-(4-nitro-3-(trifluoromethyl)phenyl)pyrrolidine (12.0 g, 43.68 mmol) in methanol (75 mL) was added 10% Pd/C (1.2 g). The reaction was stirred under H$_2$ atmosphere for 16 h. The mixture was filtered through a pad of Celite and concentrated. Purification by silica gel chromatography (0-100% ethyl acetate/hexanes) provided (S)-4-(2-methylpyrrolidin-1-yl)-2-(trifluoromethyl)aniline as a brown oil (10.5 g, 98% yield). LC/MS m/z 245.1 [M+H]+.

Intermediate 30

Synthesis of 6-(7-azabicyclo[2.2.1]heptan-7-yl)-4-methylpyridin-3-amine

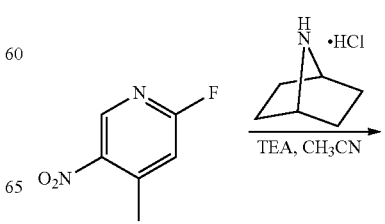

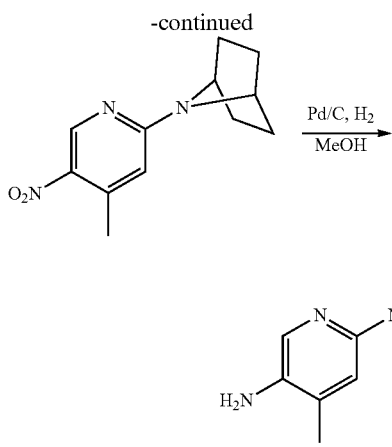

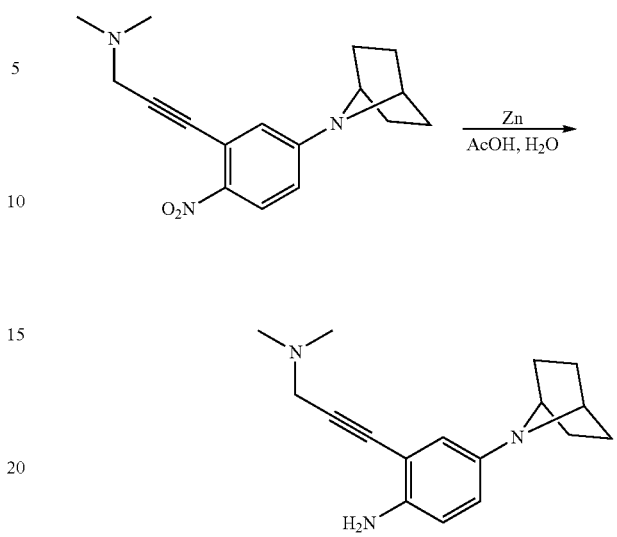

To a solution of 2-fluoro-4-methyl-5-nitropyridine (150 mg, 0.96 mmol) in acetonitrile (5 mL) was added 7-azabicyclo[2.2.1]heptane hydrochloride (153 mg, 1.15 mmol) and triethylamine (335 μL, 2.40 mmol). The reaction was heated at 80° C. for 16 h. The reaction was quenched with water (2 mL) and solvent was evaporated. The residue was dissolved in ethyl acetate (15 mL), washed with 1N HCl (10 mL), dried over MgSO$_4$, filtered and concentrated in vacuo to afford 6-(7-azabicyclo[2.2.1]heptan-7-yl)-4-methylpyridin-3-amine (160 mg, 71% yield) as yellow solid which was used in next step without purification. $^1$H NMR (400.0 MHz, CDCl$_3$) δ 8.96 (s, 1H), 6.37 (s, 1H), 4.59 (s, 2H), 2.59 (d, J=0.4 Hz, 3H), 1.83-1.80 (m, 4H), 1.61-1.54 (m, 4H).

To a solution of 6-(7-azabicyclo[2.2.1]heptan-7-yl)-4-methylpyridin-3-amine (146 mg, 0.63 mmol) in a 1:1 mixture of methanol/ethyl acetate was added 10% Pd/C and stirred under hydrogen atmosphere for 2 h. The reaction was diluted with ethyl acetate (5 mL) and filtered through a pad of Celite. The filtrate was concentrated in vacuo to afford 6-(7-azabicyclo[2.2.1]heptan-7-yl)-4-methylpyridin-3-amine as yellow solid (120 mg, 94% yield). $^1$H NMR (400.0 MHz, CDCl$_3$) δ 7.68 (s, 1H), 6.50 (s, 1H), 4.34-4.31 (m, 2H), 3.20 (s, 2H), 2.14 (s, 3H), 1.78-1.75 (m, 4H), 1.44-1.39 (m, 4H).

Intermediate 31

Synthesis of 4-(7-azabicyclo[2.2.1]heptan-7-yl)-2-(3-(dimethylamino)prop-1-ynyl)aniline

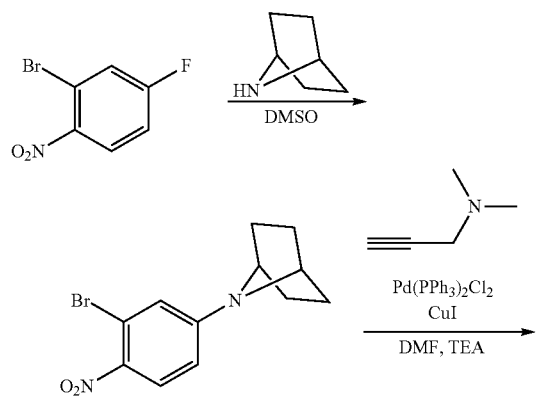

To a solution of 2-bromo-4-fluoro-1-nitro-benzene (250 mg, 1.14 mmol) in DMSO (2 mL) was added 7-azabicyclo[2.2.1]heptane (182 mg, 1.36 mmol) portion-wise. The reaction was stirred at 80° C. for 24 h. The reaction was quenched with water and the aqueous layer was extracted with dichloromethane. The combined organic extracts were washed with 1 N HCl, dried over MgSO$_4$, filtered and concentrated in vacuo to provide 7-(3-bromo-4-nitrophenyl)-7-azabicyclo[2.2.1]heptane (864 mg, 98% yield). LC/MS m/z 298.5 [M+H]$^+$.

To 7-(3-bromo-4-nitro-phenyl)-7-azabicyclo[2.2.1]heptane (500 mg, 1.68 mmol), Pd(PPh$_3$)$_2$Cl$_2$ (59 mg, 0.08 mmol), and CuI (10 mg, 0.05 mmol) were added DMF (5 mL), triethylamine (5 mL), and N,N-dimethylprop-2-yn-1-amine (420 mg, 538 μL, 5.05 mmol) under N$_2$ atmosphere. The reaction was heated under microwave irradiation for 10 min at 100° C. The reaction mixture was diluted with ethyl acetate, washed with 50% saturated NaHCO$_3$ (2×20 mL), water, and brine. The organic layer was dried over Na$_2$SO$_4$, filtered, and concentrated in vacuo to a red solid. Purification by silica gel chromatography (0-50% dichloromethane/ethyl acetate) provided 3-[5-(7-Azabicyclo[2.2.1]heptan-7-yl)-2-nitro-phenyl]-N,N-dimethyl-prop-2-yn-1-amine (400 mg, 79% yield). LC/MS m/z 300.5 [M+H]$^+$.

3-[5-(7-Azabicyclo[2.2.1]heptan-7-yl)-2-nitro-phenyl]-N,N-dimethyl-prop-2-yn-1-amine (75 mg, 0.25 mmol) was dissolved in a mixture of glacial acetic acid (940 μL) and water (230 μL). Zn dust (164 mg, 2.51 mmol) was added at room temperature. The solution was stirred for 10 min. The reaction was diluted with methanol (5 mL), filtered and concentrated. The residue was dissolved in ethyl acetate, washed with 50% saturated NaHCO$_3$ (2×20 mL) and brine, dried over Na$_2$SO$_4$, filtered, and dried down to a light orange solid. Purification by silica gel chromatography (5-15% methanol/dichloromethane) provided 4-(7-azabicyclo[2.2.1]heptan-7-yl)-2-(3-(dimethylamino)prop-1-ynyl)aniline as a light orange oil (20 mg, 30% yield). LC/MS m/z 270.5 [M+H]$^+$.

Intermediate 32

Synthesis of 2-(3-((dimethylamino)methyl)-1,2,4-oxadiazol-5-yl)-4-methylaniline

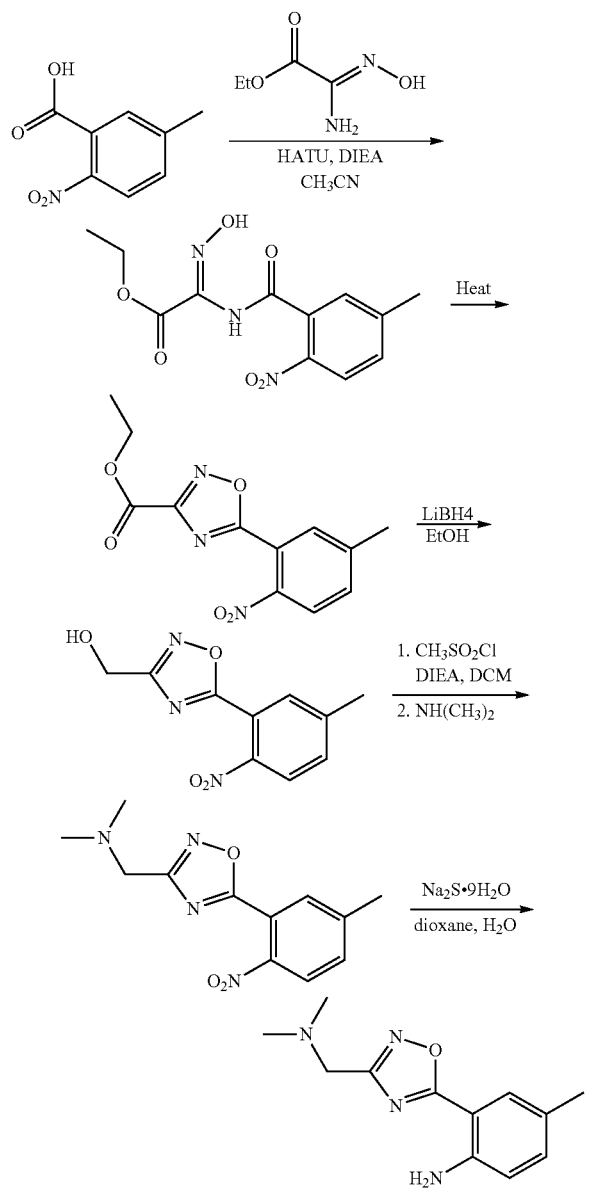

To 5-methyl-2-nitro-benzoic acid (100 mg, 0.55 mmol), ethyl 2-(hydroxyamino)-2-imino-acetate (73 mg, 0.55 mmol), and HATU (210 mg, 0.55 mmol) were added acetonitrile (4 mL) and DIEA (96 µL, 0.55 mmol). The reaction was stirred at room temperature for 25 min resulting in a thick white precipitate. The solid was filtered, washed with water then dried to yield ethyl 2-(hydroxyimino)-2-(5-methyl-2-nitrobenzamido)acetate as a white solid (150 mg, 92% yield). LC/MS m/z 296.1 [M+H]$^+$. $^1$H NMR (400.0 MHz, DMSO-do) δ 8.05 (d, J=8.3 Hz, 1H), 7.74 (d, J=0.9 Hz, 1H), 7.61 (d, J=8.4 Hz, 1H), 7.16 (br s, 2H), 4.28 (q, J=7.1 Hz, 2H), 2.47 (s, 3H), 1.28 (t, J=7.1 Hz, 3H).

Ethyl 2-(hydroxyimino)-2-(5-methyl-2-nitrobenzamido)acetate (72 mg, 0.55 mmol) was heated gently until melted and the heat continued for approximately 3 min to provide ethyl 5-(5-methyl-2-nitrophenyl)-1,2,4-oxadiazole-3-carboxylate (60 mg, 89% yield). LC/MS m/z 278.2 [M+H]$^+$. $^1$H NMR (400.0 MHz, DMSO-d$_6$) δ 8.21 (d, J=8.4 Hz, 1H), 7.94 (d, J=1.2 Hz, 1H), 7.82 (d, J=8.4 Hz, 1H), 4.46 (q, J=7.1 Hz, 2H), 2.52 (s, 3H), 1.36 (t, J=7.1 Hz, 3H).

Ethyl 5-(5-methyl-2-nitro-phenyl)-1,2,4-oxadiazole-3-carboxylate (60 mg, 0.22 mmol) was dissolved in ethanol (3 mL) and treated with lithium borohydride (9 mg, 0.43 mmol) at room temperature. The mixture was stirred for 1 h, then quenched with saturated NH$_4$Cl and extracted into dichloromethane. The organic layer was washed with brine, dried over Na$_2$SO$_4$, filtered and concentrated in vacuo to provide (5-(5-methyl-2-nitrophenyl)-1,2,4-oxadiazol-3-yl)methanol (35 mg, 69% yield). LC/MS m/z 236.0 [M+H]$^+$.

(5-(5-Methyl-2-nitrophenyl)-1,2,4-oxadiazol-3-yl)methanol (25 mg, 0.11 mmol) was dissolved in dichloromethane (1 mL) and DIEA (56 µL, 0.32 mmol) at 0° C. Methanesulfonyl chloride (11 µL, 0.14 mmol) in dichloromethane (0.3 mL) was added and the reaction was stirred for 20 min at 0° C. to provide the mesylate intermediate. LC/MS m/z 313.9 [M+H]$^+$. Dimethylamine (1.59 mL of 2 M, 3.19 mmol) was added to the above mesylate solution at 0° C. and the reaction was allowed to warm to room temperature. The reaction was diluted with dichloromethane, washed with 50% saturated NaHCO$_3$ and brine, filtered and concentrated in vacuo to provide N,N-dimethyl-1-(5-(5-methyl-2-nitrophenyl)-1,2,4-oxadiazol-3-yl)methanamine (25 mg, 90% yield). LC/MS m/z 263.0 [M+H]$^+$.

To a solution of N,N-dimethyl-1-(5-(5-methyl-2-nitrophenyl)-1,2,4-oxadiazol-3-yl)methanamine (38 mg, 0.15 mmol) in dioxane (1 mL) at 80° C. was added a hot solution (80° C.) of sodium disulfide nonahydrate (70 mg, 0.29 mmol) in water (1 mL). The reaction was heated at 80° C. for 30 min resulting in clean conversion to the desired product. The reaction was diluted with dichloromethane then washed with 50% saturated NaHCO$_3$ (2×20 mL) and brine. The solution was dried over Na$_2$SO$_4$, filtered and dried down to provide 2-(3-((dimethylamino)methyl)-1,2,4-oxadiazol-5-yl)-4-methylaniline as a light orange oil (29 mg, 86% yield). LC/MS m/z 233.2 [M+H]$^+$.

Intermediate 33

Synthesis of 4-tert-butyl-3-fluoroaniline

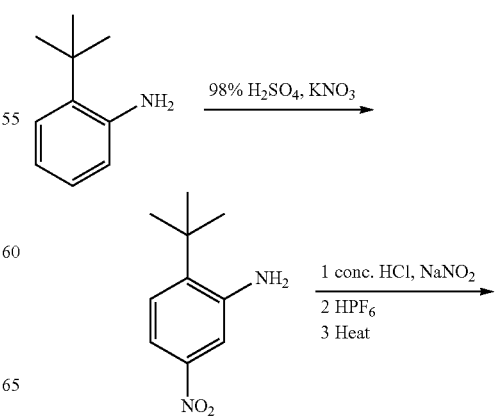

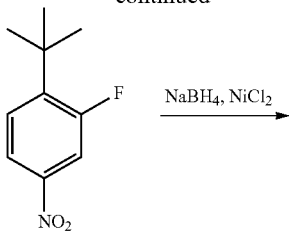

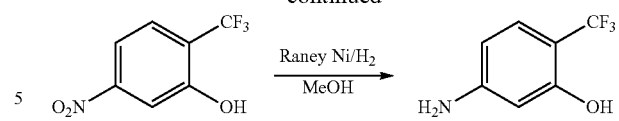

To $KNO_3$ (7.5 g, 73.8 mmol) in conc.$H_2SO_4$ (50 mL) was slowly added to a mixture of 2-tert-butylaniline (11.0 g, 73.8 mmol) in conc.$H_2SO_4$ (50 mL) at −10° C. The mixture was stirred at −10° C. for 1 hour and poured into ice-water. The mixture was extracted with EtOAc (150 mL×3). The combined organics were washed with brine, dried over anhydrous $Na_2SO_4$, and purified by chromatography on silica gel to obtain 2-tert-butyl-5-nitroaniline (9.0 g, 63%). $^1$H NMR (400 MHz, $CDCl_3$) δ 7.53 (dd, J=2.8, 8.8 Hz, 1H), 7.46 (d, J=2.8 Hz, 1H), 7.34 (d, J=8.8 Hz, 1H), 4.12 (br s, 2H), 1.44 (s, 9H).

To a stirred solution of 2-tert-butyl-5-nitroaniline (5.0 g, 25.8 mmol) in $H_2O$ (20 mL) was added conc.HCl (10 mL). After a solution was observed, the mixture was cooled to 0° C. followed by the slow addition of $NaNO_2$ (1.78 g, 25.8 mmol) in $H_2O$ (10 mL). The reaction mixture was stirred at 0° C. for another 0.5 hours. Then $HPF_6$ solution (40 mL) was added in two batches. The precipitate obtained by filtration was then heated under infrared light about 130-150° C. while grey solid slowly burned to dark viscous oil. The reaction process was monitored by TLC. The obtained dark oil was purified by chromatography on silica gel to afford 1-tert-butyl-2-fluoro-4-nitrobenzene (600 mg, 12.0% yield). $^1$H NMR (400 MHz, $CDCl_3$) δ 7.96 (dd, J=2.4, 8.8 Hz, 1H), 7.87 (dd, J=2.4, 12.0 Hz, 1H), 7.48 (t, J=8.0 Hz, 1H), 1.43 (s, 9H).

$NaBH_4$ (289 mg, 7.6 mmol) was added to a solution of 1-tert-butyl-2-fluoro-4-nitrobenzene (750 mg, 3.8 mmol) and $NiCl_2.6H_2O$ (2.6 g, 11.4 mmol) in MeOH (15 mL) at −15° C. After addition, the mixture was stirred for 2 minutes and water was added to quench the reaction. The mixture was extracted with ethyl acetate (50 mL×3). The combined organic layers were dried over anhydrous $Na_2SO_4$ and evaporated in vacuo to afford 4-tert-butyl-3-fluoroaniline (470 mg, 74%). $^1$H NMR (400 MHz, $CDCl_3$) δ 7.08-7.02 (m, 1H), 6.42-6.34 (m, 2H), 1.32 (s, 9H). MS (ESI) m/z: 168.2 [M+H]$^+$.

Intermediate 34

Synthesis of 5-amino-2-(trifluoromethyl)phenol

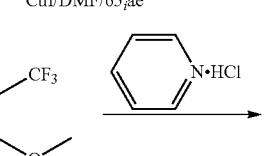

A mixture of 1-bromo-2-methoxy-4-nitro-benzene (20 g, 86 mmol), $FSO_2CF_2CO_2$ (100 g, 0.52 mol) and CuI (65 g, 340 mmol) in dry DMF (200 mL) was stirred at 75° C. under an atmosphere of $N_2$ overnight. The solvent was evaporated off under reduced pressure. EtOAc was added to the residue and the solid was removed by filtration. The filtrate was washed with water (100 mL×2), brine (100 mL), dried over anhydrous $Na_2SO_4$ and purified by silica gel column chromatography (petroleum as eluant) to afford 2-methoxy-4-nitro-1-(trifluoromethyl)benzene and starting material as a 1:1 mixture (16 g). The mixture was taken onto the next step without further purification. $^1$H-NMR (300 MHz, $CDCl_3$) δ 7.90-7.86 (m, 1H), 7.85 (s, 1H), 7.77-7.69 (m, 4H), 4.02 (s, 3H), 4.00 (s, 3H).

To a mixture of 2-methoxy-4-nitro-1-(trifluoromethyl) benzene and 1-bromo-2-methoxy-4-nitro-benzene (16 g, crude) was added pyridine hydrochloride (100 g, 860 mmol) and the reaction mixture was stirred at 210° C. for 40 min. Then the mixture was poured into ice-water and extracted with EtOAc (80 mL×3). The combined organic layers were washed with water (100 mL×2) and brine (50 mL), dried over anhydrous $Na_2SO_4$ and purified by silica gel column chromatography (5% EtOAc in petroleum as eluant) to afford 5-nitro-2-(trifluoromethyl)phenol and 2-bromo-5-nitrophenol (10 g, crude). 1H-NMR (300 MHz, $CDCl_3$) δ 7.86-7.80 (m, 3H), 7.72-7.63 (m, 3H).

To a solution of 5-nitro-2-(trifluoromethyl)phenol and 2-bromo-5-nitrophenol (10 g, crude) in MeOH (60 mL) was added Raney Ni (2 g) under an atmosphere of nitrogen. The mixture was stirred under hydrogen atmosphere (1 atm) at r. t. for 4 h. The catalyst was filtered off through the celite pad and the filtrate was evaporated under vacuum. The crude product was purified by preparative HPLC to obtain 5-amino-2-(trifluoromethyl)phenol (1.7 g, 11% yield for 3 steps). 1H-NMR (400 MHz, DMSO-d6) δ 9.79 (s, 1H), 7.04 (d, J=8.8 Hz, 1H), 6.10 (s, 1H), 6.01 (d, J=8.4 Hz, 1H), 5.58 (br s, 2H).

Intermediate 35

Synthesis of 5-amino-2-tert-butylphenol

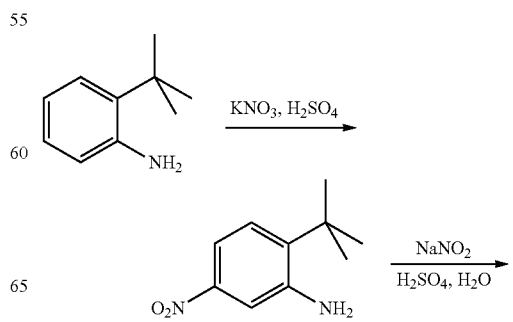

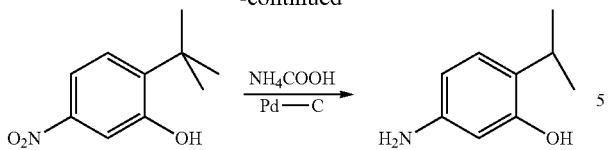

2-tert-Butyl-5-nitroaniline: To a cooled solution of sulfuric acid (90%, 50 mL) was added dropwise 2-tert-butyl-phenylamine (4.5 g, 30 mmol) at 0° C. Potassium nitrate (4.5 g, 45 mmol) was added in portions at 0° C. The reaction mixture was stirred at 0-5° C. for 5 min, poured into ice-water and then extracted with EtOAc three times. The combined organic layers were washed with brine and dried over $Na_2SO_4$. After removal of solvent, the residue was purified by recrystallization using 70% EtOH—$H_2O$ to give 2-tert-butyl-5-nitroaniline (3.7 g, 64%). $^1$H NMR (400 MHz, $CDCl_3$) δ 7.56 (dd, J=8.7, 2.4 Hz, 1H), 7.48 (d, J=2.4 Hz, 1H), 7.36 (d, J=8.7 Hz, 1H), 4.17 (s, 2H), 1.46 (s, 9H); HPLC ret. time 3.27 min, 10-99% $CH_3CN$, 5 min run; ESI-MS 195.3 m/z ($MH^+$).

2-tert-Butyl-5-nitrophenol: To a mixture of 2-tert-butyl-5-nitroaniline (1.94 g, 10 mmol) in 40 mL of 15% $H_2SO_4$ was added dropwise a solution of $NaNO_2$ (763 mg, 11.0 mmol) in water (3 mL) at 0° C. The resulting mixture was stirred at 0-5° C. for 5 min. Excess $NaNO_2$ was neutralized with urea, then 5 mL of $H_2SO_4$—$H_2O$ (v/v 1:2) was added and the mixture was refluxed for 5 min. Three additional 5 mL aliquots of $H_2SO_4$—$H_2O$ (v/v 1:2) were added while heating at reflux. The reaction mixture was cooled to room temperature and extracted with EtOAc twice. The combined organic layers were washed with brine and dried over $MgSO_4$. After removal of solvent, the residue was purified by column chromatography (0-10% EtOAc-Hexane) to give 2-tert-butyl-5-nitrophenol (1.2 g, 62%). $^1$H NMR (400 MHz, $CDCl_3$) δ 7.76 (dd, J=8.6, 2.2 Hz, 1H), 7.58 (d, J=2.1 Hz, 1H), 7.43 (d, J=8.6 Hz, 1H), 5.41 (s, 1H), 1.45 (s, 9H); HPLC ret. time 3.46 min, 10-99% $CH_3CN$, 5 min run.

2-tert-Butyl-5-aminophenol: To a refluxing solution of 2-tert-butyl-5-nitrophenol (C-1-a) (196 mg, 1.0 mmol) in EtOH (10 mL) was added ammonium formate (200 mg, 3.1 mmol), followed by 140 mg of 10% Pd—C. The reaction mixture was refluxed for additional 30 min, cooled to room temperature and filtered through a plug of Celite. The filtrate was concentrated to dryness and purified by column chromatography (20-30% EtOAc-Hexane) to give 2-tert-butyl-5-aminophenol (C-1) (144 mg, 87%). $^1$H NMR (400 MHz, DMSO-$d_6$) δ 8.76 (s, 1H), 6.74 (d, J=8.3 Hz, 1H), 6.04 (d, J=2.3 Hz, 1H), 5.93 (dd, J=8.2, 2.3 Hz, 1H), 4.67 (s, 2H), 1.26 (s, 9H); HPLC ret. time 2.26 min, 10-99% $CH_3CN$, 5 min run; ESI-MS 166.1 m/z ($MH^+$).

Intermediate 36

Synthesis of 5-Amino-4-fluoro-2-(1-methylcyclohexyl)phenol

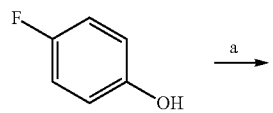

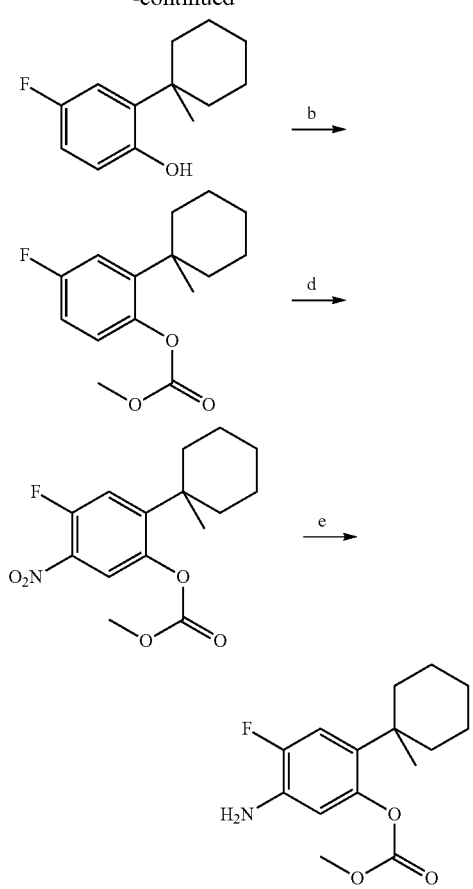

a) 1-methylcyclohexanol, $H_2SO_4$; b) $MeCO_2Cl$, TEA, DMAP; c) $KNO_3$, $H_2SO_4$; d) piperidine, $CH_2Cl_2$; d) $H_2$, Pd-C, MeOH.

Preparation of 5-amino-4-fluoro-2-(1-methylcyclohexyl)phenyl methyl carbonate Step 1: 4-fluoro-2-(1-methylcyclohexyl)phenol

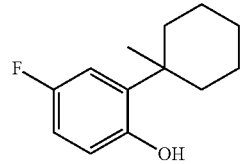

4-Fluorophenol (41.8 g, 373 mmol) and 1-methylcyclohexanol (63.8 g, 560 mmol) dissolved in 600 mL of dried $CH_2Cl_2$, were treated with concentrated sulfuric acid (98%, 22.3 mL, 418 mmol). The mixture was stirred at room temperature for 50 hours. The reaction mixture was then extracted by $CH_2Cl_2$ (250 mL×3). The organic layer was washed with saturated a.q $NaHCO_3$., dried over $MgSO_4$, and evaporated under vacuum. The residue was purified by column chromatography on silica gel to give 4-fluoro-2-(1-methylcyclohexyl)phenol as a dark green oil—47.6 g. $^1$H NMR (400 MHz, $CDCl_3$) δ 7.00 (dd, J=3.2, 11.2 Hz, 1H), 6.76-6.71 (m, 1H), 6.62-6.59 (m, 1H), 5.27 (brs, 1H), 2.13-2.07 (m, 2H), 1.70-1.37 (m, 8H), 1.32 (s, 3H).

Preparation of 4-fluoro-2-(1-methylcyclohexyl)phenyl methyl carbonate

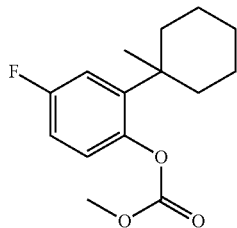 [SMILES: COC(=O)Oc1ccc(F)cc1C1(C)CCCCC1]

To a solution of 4-fluoro-2-(1-methylcyclohexyl)phenol (23.5 g, 113 mmol), TEA (31 mL, 226 mmol) and DMAP (700 mg, 5.7 mmol) in $CH_2Cl_2$(250 mL) was added methyl chloroformate dropwise at 0° C. The mixture was allowed to warm to room temperature and stirred for 2 hours. The reaction mixture was poured onto crushed ice and extracted with $CH_2Cl_2$(100 mL×3). The organic layer was washed with brine, dried over $MgSO_4$, evaporated under vacuum. The crude product was purified by chromatography on silica gel diluted with (hexane:ethyl acetate=100:1) to give 4-fluoro-2-(1-methylcyclohexyl)phenyl methyl carbonate as red brown oil (43.9 g, 72.1% yield). $^1$H NMR (400 MHz, $CDCl_3$) δ 7.10 (dd, J=3.2, 11.2 Hz, 1H), 7.05-7.02 (m, 1H), 6.93-6.88 (m, 1H), 3.91 (s, 3H), 2.02-1.96 (m, 2H), 1.66-1.36 (m, 8H), 1.23 (s, 3H).

Preparation of: 4-fluoro-2-(1-methylcyclohexyl)-5-nitrophenyl methyl carbonate

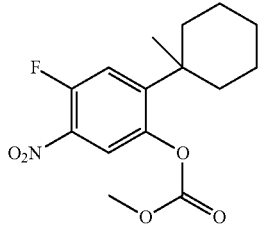 [SMILES: COC(=O)Oc1cc(N)c(F)cc1C1(C)CCCCC1]

To a solution of 4-fluoro-2-(1-methylcyclohexyl)phenyl methyl carbonate (21.5 g, 81 mmol) in 10 mL of concentrated sulfuric acid was added drop-wise to ice cold mixture of concentrated sulfuric acid (120 mL) and $KNO_3$ (8.2 g, 81 mmol) at 0° C. After addition, the reaction mixture was stirred for 15 min while warming to ambient temperature, poured onto crushed ice, extracted with ethyl acetate (120 mL×3). The organic layer was washed with brine, dried over $MgSO_4$, and evaporated under vacuum. The residue was purified by chromatography on silica gel (hexane:ethyl acetate=100:1) to give 4-fluoro-2-(1-methylcyclohexyl)-5-nitrophenyl methyl carbonate as a yellow oil (40.8 g, 81% yield). $^1$H NMR (400 MHz, $CDCl_3$) δ 7.90 (d, J=6.8 Hz, 1H), 7.34 (d, J=13.2 Hz, 1H), 3.97 (s, 1H), 2.02-1.96 (m, 2H), 1.73-1.45 (m, 8H), 1.39 (s, 3H).

Preparation of 5-amino-4-fluoro-2-(1-methylcyclohexyl)phenyl methyl carbonate

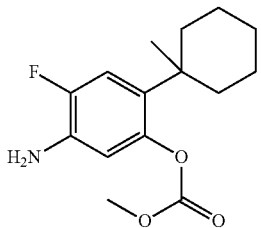

To a solution of 4-fluoro-2-(1-methylcyclohexyl)-5-nitrophenyl methyl carbonate 24.1 g, 77.5 mmol) in 220 mL of $CH_3OH$ was added Pd/C 10%, 9.6 g, then ammonium formate (26.7 g, 445 mmol) was portion-wise added to the above reaction mixture at room temperature until starting material is consumed. The mixture was filtrated and the filtrate was evaporated under vacuum. The residue was purified by column chromatography on silica gel diluted with hexane:ethyl acetate=50:1 to give 5-amino-4-fluoro-2-(1-methylcyclohexyl)phenyl methyl carbonate as a red brown oil (17.9 g, 82% yield). $^1$H NMR (400 MHz, $CDCl_3$) δ 6.99 (d, J=13.6 Hz, 1H), 6.51 (d, J=8.4 Hz, 1H), 3.89 (s, 3H), 3.43 (brs, 2H), 1.96-1.91 (m, 2H), 1.58-1.38 (m, 8H), 1.18 (s, 3H): MS m/z: 281.9 [M+H]

Intermediate 37

Synthesis of 5-amino-2,4-di-tert-butylphenol

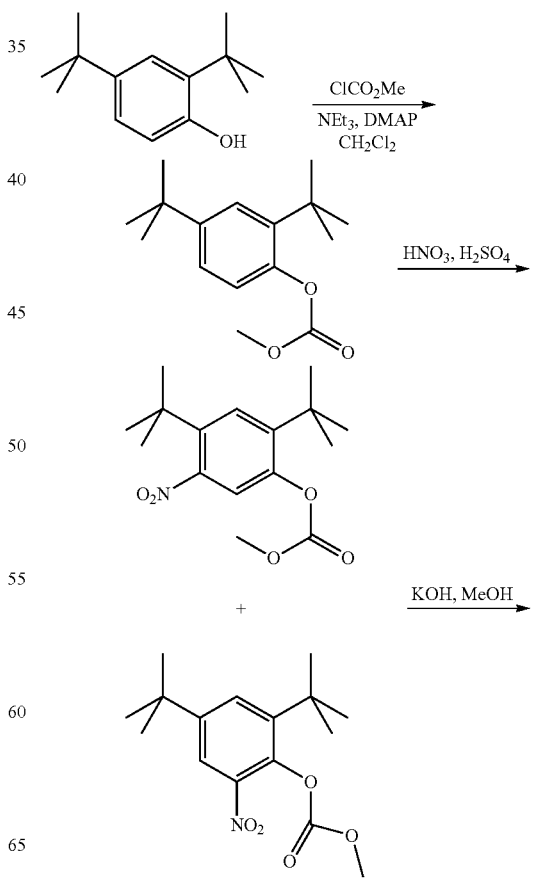

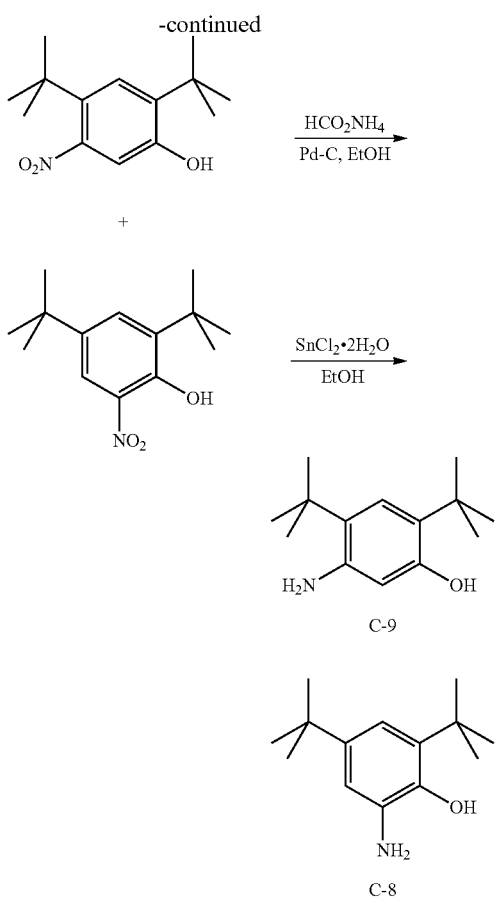

Carbonic acid 2,4-di-tert-butyl-phenyl ester methyl ester: Methyl chloroformate (58 mL, 750 mmol) was added dropwise to a solution of 2,4-di-tert-butyl-phenol (103.2 g, 500 mmol), Et₃N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d₆) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Carbonic acid 2,4-di-tert-butyl-5-nitro-phenyl ester methyl ester and Carbonic acid 2,4-di-tert-butyl-6-nitro-phenyl ester methyl ester: To a stirring mixture of carbonic acid 2,4-di-tert-butyl-phenyl ester methyl ester (4.76 g, 18 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO₄), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

2,4-Di-tert-butyl-5-nitro-phenol and 2,4-Di-tert-butyl-6-nitro-phenol: The mixture of carbonic acid 2,4-di-tert-butyl-5-nitro-phenyl ester methyl ester and carbonic acid 2,4-di-tert-butyl-6-nitro-phenyl ester methyl ester (4.2 g, 12.9 mmol) was dissolved in MeOH (65 mL) and KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO₄), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d₆) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl₃) δ 11.48 (s, 1H), 7.98 (d, J=2.5 Hz, 1H), 7.66 (d, J=2.4 Hz, 1H), 1.47 (s, 9H), 1.34 (s, 9H).

C-9; 5-Amino-2,4-di-tert-butyl-phenol: To a refluxing solution of 2,4-di-tert-butyl-5-nitro-phenol (1.86 g, 7.4 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d₆) δ 8.64 (s, 1H, OH), 6.84 (s, 1H), 6.08 (s, 1H), 4.39 (s, 2H, NH₂), 1.27 (m, 18H); HPLC ret. time 2.72 min, 10-99% CH₃CN, 5 min run; ESI-MS 222.4 m/z (MH⁺).

C-8; 6-Amino-2,4-di-tert-butyl-phenol: A solution of 2,4-di-tert-butyl-6-nitro-phenol (27 mg, 0.11 mmol) and SnCl₂·2H₂O (121 mg, 0.54 mmol) in EtOH (1.0 mL) was heated in microwave oven at 100° C. for 30 min. The mixture was diluted with EtOAc and water, basified with sat. NaHCO₃ and filtered through Celite. The organic layer was separated and dried over Na₂SO₄. Solvent was removed by evaporation to provide 6-amino-2,4-di-tert-butyl-phenol (C-8), which was used without further purification. HPLC ret. time 2.74 min, 10-99% CH₃CN, 5 min run; ESI-MS 222.5 m/z (MH⁺).

Intermediate 38

Synthesis of 2-(3-((dimethylamino)methyl)-1,2,4-oxadiazol-5-yl)-4-methylaniline

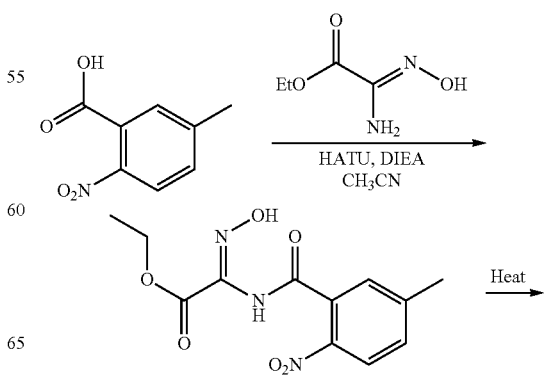

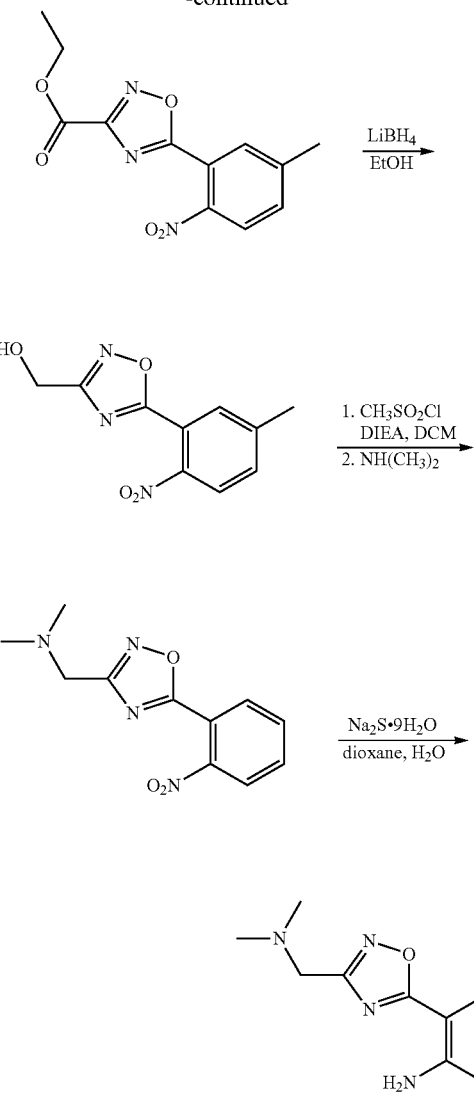

To a solution of 5-methyl-2-nitro-benzoic acid (100 mg, 0.55 mmol) and HATU (210 mg, 0.55 mmol) in acetonitrile (4 mL) and DIEA (96 µL, 0.55 mmol) was added ethyl 2-(hydroxyamino)-2-imino-acetate (73 mg, 0.55 mmol). The reaction was stirred at room temperature for 25 min resulting in a thick white precipitate. The solid was filtered, washed with water and dried to yield ethyl 2-(hydroxyimino)-2-(5-methyl-2-nitrobenzamido)acetate as a white solid (150 mg, 92% yield). LC/MS m/z 296.1 [M+H]+. 1H NMR (400.0 MHz, DMSO-d6) δ 8.05 (d, J=8.3 Hz, 1H), 7.74 (d, J=0.9 Hz, 1H), 7.61 (d, J=8.4 Hz, 1H), 7.16 (br s, 2H), 4.28 (q, J=7.1 Hz, 2H), 2.47 (s, 3H), 1.28 (t, J=7.1 Hz, 3H).

Neat ethyl 2-(hydroxyimino)-2-(5-methyl-2-nitrobenzamido)acetate (72 mg, 0.55 mmol) was heated in a vial until melted and the melt maintained for approximately 3 min until the material was converted to ethyl 5-(5-methyl-2-nitrophenyl)-1,2,4-oxadiazole-3-carboxylate, which formed a white solid upon cooling (60 mg, 89% yield). LC/MS m/z 278.2 [M+H]+. 1H NMR (400.0 MHz, DMSO-d6) δ 8.21 (d, J=8.4 Hz, 1H), 7.94 (d, J=1.2 Hz, 1H), 7.82 (d, J=8.4 Hz, 1H), 4.46 (q, J=7.1 Hz, 2H), 2.52 (s, 3H), 1.36 (t, J=7.1 Hz, 3H).

Ethyl 5-(5-methyl-2-nitro-phenyl)-1,2,4-oxadiazole-3-carboxylate (60 mg, 0.22 mmol) was dissolved in ethanol (3 mL) and treated with lithium borohydride (9 mg, 0.4 mmol) at room temperature. The mixture was stirred for 1 h then quenched with saturated ammonium chloride and extracted into dichloromethane. The organic layer was washed with brine, dried over Na2SO4, filtered and concentrated in vacuo to provide (5-(5-methyl-2-nitrophenyl)-1,2,4-oxadiazol-3-yl)methanol (35 mg, 69% yield). LC/MS m/z 236.0 [M+H]+.

To a solution of [5-(5-methyl-2-nitro-phenyl)-1,2,4-oxadiazol-3-yl]methanol (25 mg, 0.11 mmol) in cold (0° C.) dichloromethane (1 mL) and DIEA (56 µL, 0.32 mmol) was added a solution of mesyl chloride (11 µL, 0.14 mmol) in dichloromethane (0.3 mL). The reaction was stirred for 20 min at 0° C. to form the mesylate intermediate (LC/MS m/z 313.9 [M+H]+). Dimethylamine (1.6 mL of 2 M solution, 3.2 mmol) was added and the reaction allowed to come to room temperature. The reaction was diluted with dichloromethane, washed with 50% saturated sodium bicarbonate solution and brine, dried over Na2SO4, filtered and concentrated to provide N,N-dimethyl-1-[5-(5-methyl-2-nitro-phenyl)-1,2,4-oxadiazol-3-yl]methanamine (25 mg, 90% yield). LC/MS m/z 263.0 [M+H]+.

To a solution of N,N-dimethyl-1-[5-(5-methyl-2-nitrophenyl)-1,2,4-oxadiazol-3-yl]methanamine (38 mg, 0.15 mmol) in dioxane (1 mL) at 80° C. was added a hot solution (80° C.) of disodium sulfur dihydride anion nonahydrate (70 mg, 0.29 mmol) in water (1 mL). The reaction was heated at 80° C. for 30 min then cooled to room temperature. The reaction was diluted with dichloromethane, washed with 50% saturated sodium bicarbonate solution (2×20 mL), and brine. The solution was dried over Na2SO4, filtered, and concentrated in vacuo to provide 2-(3-((dimethylamino)methyl)-1,2,4-oxadiazol-5-yl)-4-methylaniline (29 mg, 86% yield). LC/MS m/z 233.2 [M+H]+.

Intermediate 39

Synthesis of 4-methyl-2-(2-morpholinoethyl)aniline

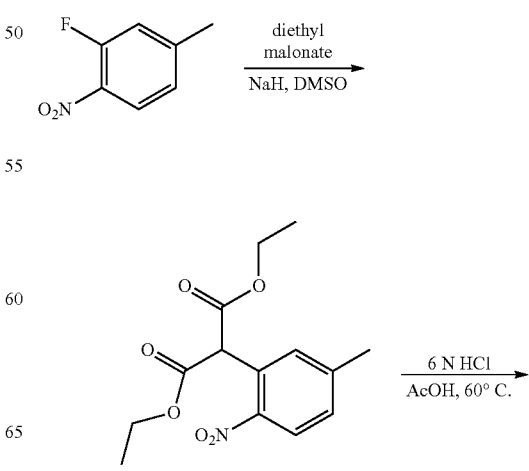

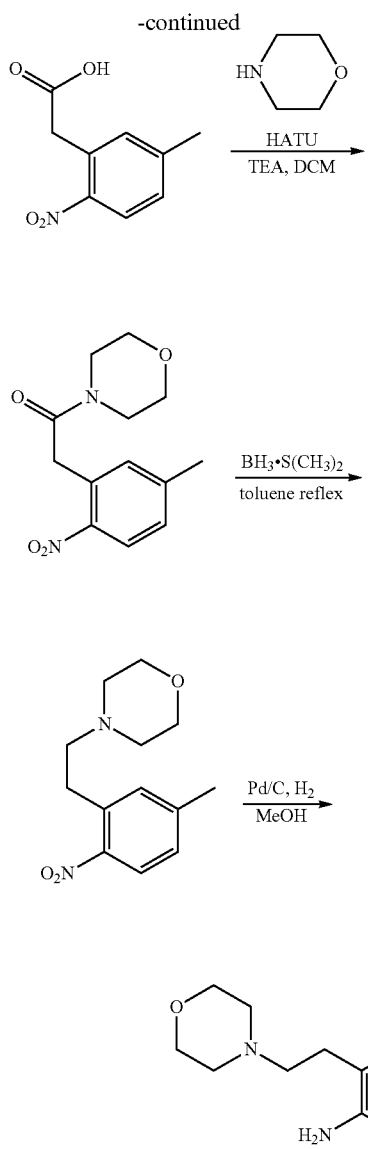

To a suspension of NaH (3.22 g, 80.6 mmol) in DMSO (20 mL) was added diethyl malonate (12.9 g, 12.2 mL, 80.6 mmol) dropwise. The reaction mixture was heated at 60° C. for 30 min. A solution of 2-fluoro-4-methyl-1-nitro-benzene (5.00 g, 32.2 mmol) in DMSO (6 mL) was added and the reaction mixture heated at 60° C. for 2 h. The reaction was quenched with saturated ammonium chloride (20 mL), acidified (pH~1) with 1N HCl and extracted into ether. The product was dried over $Na_2SO_4$, filtered, and concentrated in vacuo. Silica gel chromatography (0-60% ethyl acetate/hexane) provided diethyl 2-(5-methyl-2-nitrophenyl)malonate as a yellow solid (9.50 g, 99% yield). LC/MS m/z 296.2 [M+H]+. $^1$H NMR (400.0 MHz, DMSO-$d_6$) δ 8.05 (d, J=8.4 Hz, 1H), 7.46 (dd, J=1.2, 8.4 Hz, 1H), 7.30 (d, J=1.2 Hz, 1H), 5.36 (s, 1H), 4.22-4.14 (q, 1H), 2.43 (s, 3H), 1.18 (t, J=7.1 Hz, 6H).

Diethyl 2-(5-methyl-2-nitro-phenyl)propanedioate (9.50 g, 32.2 mmol) was suspended in glacial acetic acid (40 mL) and warmed until it had dissolved. Hydrochloric acid (40 mL of 6 M solution, 240.0 mmol) was added dropwise and the solution heated at reflux for 24 h. After cooling to room temperature the reaction was diluted with water and extracted with ether. The ether was dried over $Na_2SO_4$, filtered, and concentrated in vacuo to afford a light orange solid. The solid was dissolved in minimal $CH_3CN$ and added dropwise to stirring 0.05 N HCl (300 mL) resulting in a beige precipitate. The suspension was cooled in an ice bath, filtered, and washed with water to obtain 2-(5-methyl-2-nitro-phenyl)acetic acid as a beige crystalline solid (5.30 g, 84% yield). LC/MS m/z 391.4 [M+H]+. $^1$H NMR (400.0 MHz, DMSO-$d_6$) δ 12.51 (s, 1H), 8.01 (d, J=8.9 Hz, 1H), 7.36 (m, 2H), 3.95 (s, 2H), 2.40 (s, 3H).

2-(5-Methyl-2-nitro-phenyl)acetic acid (250 mg, 1.28 mmol) and HATU (443 mg, 1.17 mmol) were suspended in dichloromethane (5 mL) and treated with triethylamine (162 µL, 1.17 mmol) and morpholine (112 µL, 1.28 mmol). The solution was heated at 40° C. for 10 min. The reaction was washed with 1 N HCl and saturated sodium bicarbonate solution, dried over $Na_2SO_4$, filtered and concentrated in vacuo. Silica gel chromatography (1-10% methanol/dichloromethane) provided 2-(5-methyl-2-nitro-phenyl)-1-morpholino-ethanone as a white solid (267 mg, 87% yield). LC/MS m/z 265.0 [M+H]+. $^1$H NMR (400.0 MHz, DMSO-$d_6$) S 7.97 (d, J=8.3 Hz, 1H), 7.33 (dd, J=1.3, 8.3 Hz, 1H), 7.27 (s, 1H), 4.10 (s, 2H), 3.66-3.64 (m, 2H), 3.59-3.54 (m, 4H), 3.43-3.41 (m, 2H), 2.39 (s, 3H).

2-(5-Methyl-2-nitro-phenyl)-1-morpholino-ethanone (267 mg, 1.01 mmol) was dissolved in toluene (10 mL) and treated with borane dimethylsulfide (983 mg, 1.23 mL, 11.7 mmol) and heated at reflux for 2 h. The reaction was concentrated in vacuo then resuspended in 2 N HCl (8 mL) and heated at reflux for 30 min. The reaction was diluted with 1N HCl and washed with ethyl acetate. The solution was basified (5 N NaOH) and the product extracted into dichloromethane (3×20 mL). The combined organic layers were washed with brine, dried over $Na_2SO_4$, filtered and concentrated in vacuo to provide 4-[2-(5-methyl-2-nitro-phenyl)ethyl]morpholine as an oil (200 mg, 79% yield). LC/MS m/z 251.2 [M+H]+.

4-[2-(5-Methyl-2-nitro-phenyl)ethyl]morpholine (150 mg, 0.599 mmol) and Pd (10%, wet) (128 mg, 0.0599 mmol) were brought up in methanol (5 mL) under $H_2$ atmosphere and stirred vigorously for 1 h at 40° C. The reaction was filtered and concentrated in vacuo to provide 4-methyl-2-(2-morpholinoethyl)aniline (110 mg, 0.499 mmol, 83%) as an amber oil. LC/MS m/z 221.2 [M+H]+. $^1$H NMR (400.0 MHz, DMSO-$d_6$) δ 6.72-6.68 (m, 2H), 6.51 (d, J=7.9 Hz, 1H), 4.64 (s, 2H), 3.58 (t, J=4.6 Hz, 4H), 2.57-2.53 (m, 2H), 2.44-2.40 (m, 6H), 2.11 (s, 3H).

Intermediate 40

Synthesis of (S)-2-(2-(3-fluoropyrrolidin-1-yl)ethyl)-4-methylaniline (S)-2-(2-(3-fluoropyrrolidin-1-yl)ethyl)-4-methylaniline was synthesized using the same synthetic route as 4-methyl-2-(2-morpholinoethyl)aniline above with the substitution of (S)-3-fluoropyrrolidine for morpholine. LC/MS m/z 253.0 [M+H]+.

Scheme 3

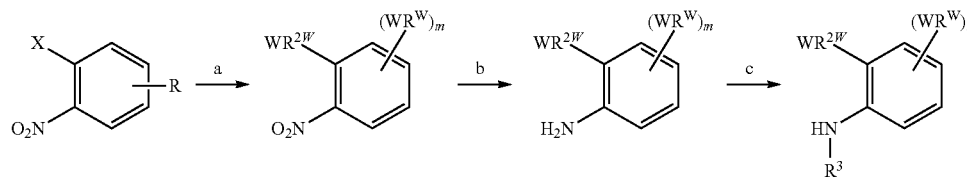

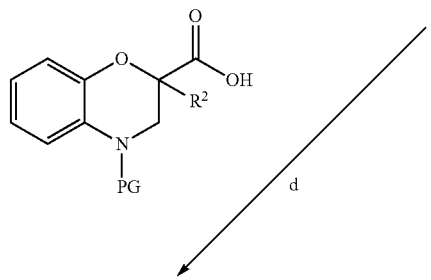

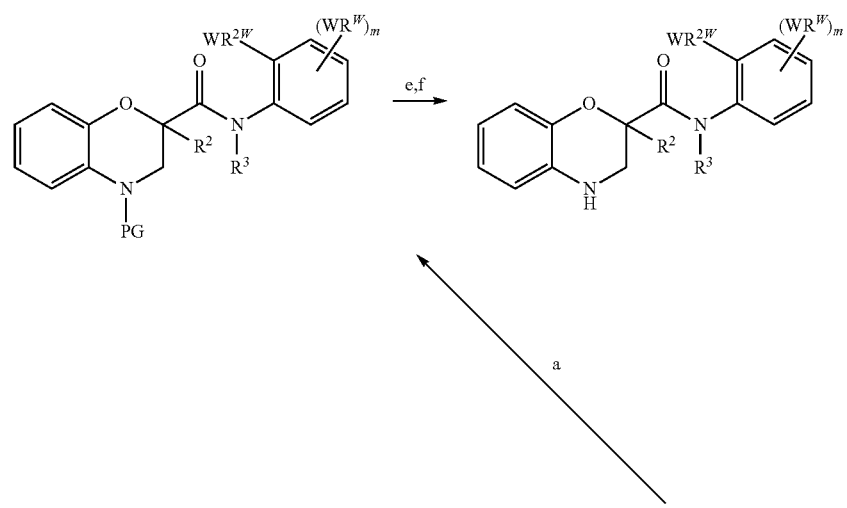

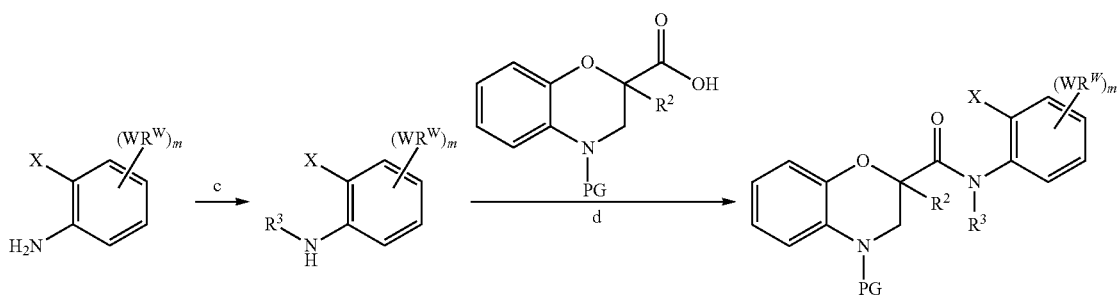

a) metal-mediated coupling reaction (Suzuki, Sonogashira, etc) or $S_NAr$ chemistry; b) nitro reduction to amine; c) alkylation via RX and base or reductive amination; d) amide bond formation; e) deprotection of benzoxazine nitrogen if necessary; f) deprotection if $WR^W$ = protected phenol. If $WR^{2W}$ contains a secondary cyclic or primary/secondary acyclic amine, it may be deprotected if necessary and further elaborated through alkylations, acylations, etc. If $WR^{2W}$ consists of an ester or carboxylic acid, it may be deprotected if necessary and further elaborated through amide bond formation, formation of heterocycles, etc. If $WR^{2W}$ consists of a hydroxyalkyl, it may be deprotected if necessary and further elaborated through conversion to the corresponding mesylate (or tosylate, chloride, etc.) and displacement with a nucleophile.

Example 1

Preparation of N-(4-cyclopentyl-5-hydroxy-2-(3-(methylamino)prop-1-ynyl)phenyl)-6-(trifluoromethoxy)-3,4-dihydro-2H-benzo[b][1,4]oxazine-2-carboxamide (Compound 98, Table 1)

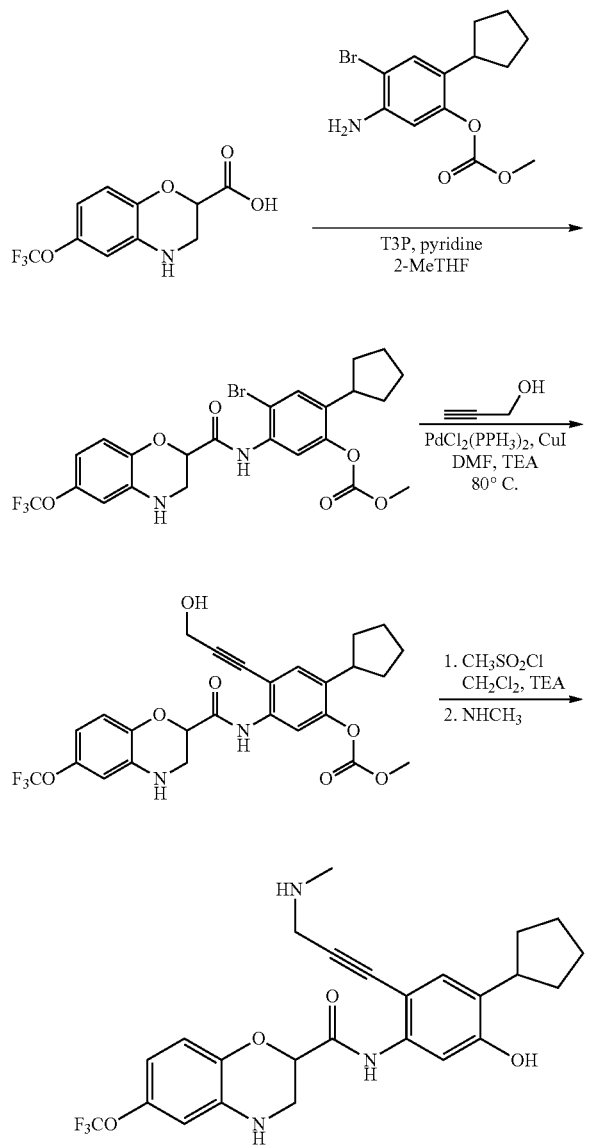

6-(Trifluoromethoxy)-3,4-dihydro-2H-1,4-benzoxazine-2-carboxylic acid (490 mg, 1.86 mmol) and (5-amino-4-bromo-2-cyclopentyl-phenyl) methyl carbonate (585 mg, 1.86 mmol) were dissolved in 2-methyltetrahydrofuran (13 mL). Pyridine (376 µL, 4.65 mmol) and T3P (2960 mg, 2.8 mL of 50% w/w solution, 4.66 mmol) were added and the reaction was stirred for 1 h at room temperature. Purification by silica gel chromatography (10-75% ethyl acetate/hexanes) yielded 4-bromo-2-cyclopentyl-5-(6-(trifluoromethoxy)-3,4-dihydro-2H-benzo[b][1,4]oxazine-2-carboxamido)phenyl methyl carbonate (802 mg, 77% yield). LC/MS m/z 560.2 [M+H]$^+$.

4-Bromo-2-cyclopentyl-5-(6-(trifluoromethoxy)-3,4-dihydro-2H-benzo[b][1,4]oxazine-2-carboxamido)phenyl methyl carbonate (812 mg, 1.45 mmol), triethylamine (2.0 mL, 14.52 mmol), prop-2-yn-1-ol (326 mg, 338 µL, 5.81 mmol), PdCl$_2$(PPh$_3$)$_2$ (204 mg, 0.29 mmol), and CuI (69 mg, 0.36 mmol) were combined in DMF (6 mL) and heated at 80° C. for 1 h. The mixture was added to 300 mL of saturated aqueous NaHCO$_3$ and then extracted with dichloromethane (3×70 mL). The organic fractions were combined, dried over MgSO$_4$, and concentrated in vacuo. Purification by silica gel chromatography (0-100% ethyl acetate/hexanes) yielded 2-cyclopentyl-4-(3-hydroxyprop-1-ynyl)-5-(6-(trifluoromethoxy)-3,4-dihydro-2H-benzo[b][1,4]oxazine-2-carboxamido)phenyl methyl carbonate (410 mg, 53% yield). LC/MS m/z 535.4 [M+H]$^+$.

2-Cyclopentyl-4-(3-hydroxyprop-1-ynyl)-5-(6-(trifluoromethoxy)-3,4-dihydro-2H-benzo[b][1,4]oxazine-2-carboxamido)phenyl methyl carbonate (20 mg, 0.037 mmol) was dissolved in dichloromethane (1 mL) and triethylamine (20 µL, 0.14 mmol) and cooled to 0° C. Methanesulfonyl chloride (4.3 mg, 2.9 µL, 0.04 mmol) in 1 mL of dichloromethane was slowly added to the reaction. Conversion to the mesylate was complete after 10 min. MeNH$_2$ (100 µL of 2 M in THF, 0.20 mmol) was then added and the reaction stirred at room temperature for 10 h. The solution was concentrated in vacuo and purified by HPLC (10-99% CH$_3$CN/0.035% TFA) to provide N-(4-cyclopentyl-5-hydroxy-2-(3-(methylamino)prop-1-ynyl)phenyl)-6-(trifluoromethoxy)-3,4-dihydro-2H-benzo[b][1,4]oxazine-2-carboxamide (21 mg, 97% yield). LC/MS m/z 490.4 [M+H]$^+$. $^1$H NMR (400.0 MHz, MeOD) δ 7.65 (s, 1H), 7.28 (s, 1H), 6.97 (d, J=8.7 Hz, 1H), 6.60 (s, 1H), 6.54 (dd, J=1.8, 8.7 Hz, 1H), 4.78 (dd, J=3.0, 7.0 Hz, 1H), 4.14 (dd, J=16.6, 27.1 Hz, 2H), 3.67 (dd, J=3.0, 12.1 Hz, 1H), 3.49-3.44 (m, 1H), 3.24 (m, 1H), 2.79 (s, 3H), 2.05-1.92 (m, 2H), 1.81-1.77 (m, 2H), 1.71-1.68 (m, 2H), 1.54-1.51 (m, 2H).

Example 2

Preparation of N-(4-methyl-2-(3-morpholinoprop-1-ynyl)phenyl)-6-(trifluoromethoxy)-3,4-dihydro-2H-benzo[b][1,4]oxazine-2-carboxamide (Compound 100, Table 1)

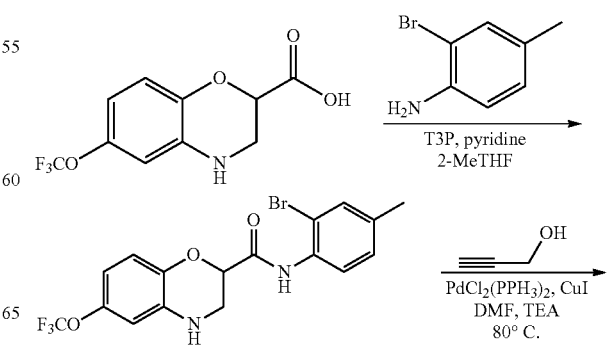

-continued

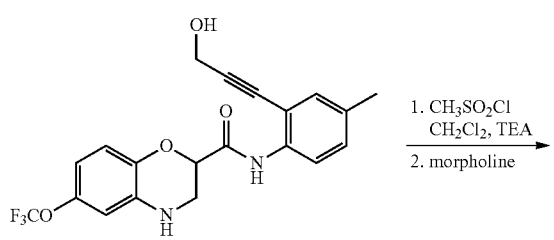

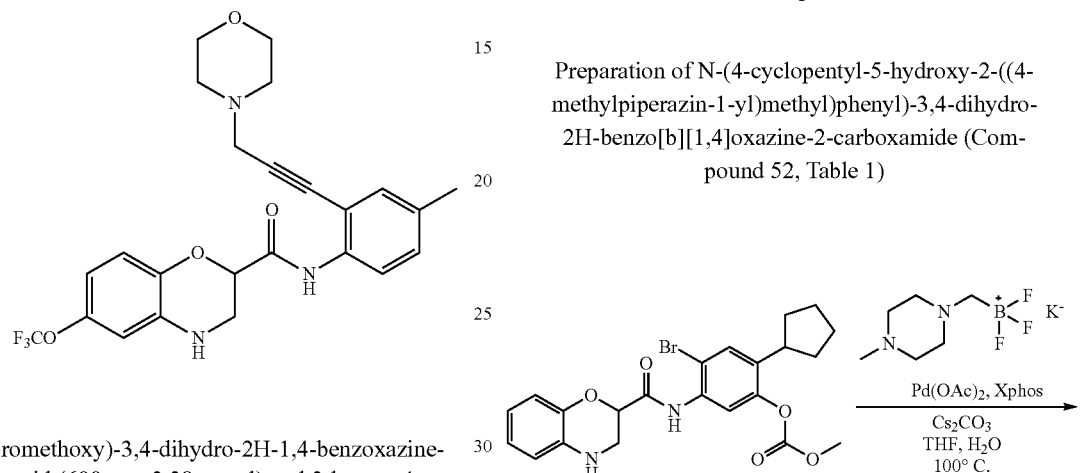

6-(Trifluoromethoxy)-3,4-dihydro-2H-1,4-benzoxazine-2-carboxylic acid (600 mg, 2.28 mmol) and 2-bromo-4-methyl-aniline (424 mg, 286 µL, 2.28 mmol) were dissolved in 2-methyltetrahydrofuran (7 mL) and pyridine (461 µL, 5.70 mmol). T3P (2902 mg, 2.7 mL of 50% w/w solution, 4.56 mmol) was added and the reaction was stirred for 30 min at room temperature. Purification by silica gel chromatography (10-100% ethyl acetate/hexanes) provided N-(2-bromo-4-methylphenyl)-6-(trifluoromethoxy)-3,4-dihydro-2H-benzo[b][1,4]oxazine-2-carboxamide (743 mg, 76% yield). LC/MS m/z 432.4 [M+H]+.

Prop-2-yn-1-ol (195 mg, 202 µL, 3.48 mmol), N-(2-bromo-4-methyl-phenyl)-6-(trifluoromethoxy)-3,4-dihydro-2H-1,4-benzoxazine-2-carboxamide (300 mg, 0.69 mmol), PdCl2(PPh3)2 (122 mg, 0.17 mmol), CuI (19.88 mg, 0.10 mmol), and triethylamine (970 µL, 6.96 mmol) were combined in DMF (5 mL) and heated at 75° C. for 18 h. Purification by silica gel chromatography (0-50% ethyl acetate/hexanes) provided N-(2-(3-hydroxyprop-1-ynyl)-4-methylphenyl)-6-(trifluoromethoxy)-3,4-dihydro-2H-benzo[b][1,4]oxazine-2-carboxamide (204 mg, 72% yield). LC/MS m/z 407.4 [M+H]+.

N-[2-(3-hydroxyprop-1-ynyl)-4-methyl-phenyl]-6-(trifluoromethoxy)-3,4-dihydro-2H-1,4-benzoxazine-2-carboxamide (390 mg, 0.96 mmol) was dissolved in dichloromethane (4 mL) and DIEA (248 mg, 334 µL, 1.92 mmol). The mixture was cooled to 0° C. and treated dropwise with a solution of methanesulfonyl chloride (110 mg, 74 µL, 0.96 mmol) in dichloromethane (1 mL). The mixture was stirred for 10 min at 0° C. Conversion to the mesylate intermediate was complete after ~10 min and the product used for the next reaction without isolation.

To 3-(5-methyl-2-(6-(trifluoromethoxy)-3,4-dihydro-2H-benzo[b][1,4]oxazine-2-carboxamido)phenyl)prop-2-ynyl methanesulfonate (20 mg, 0.04 mmol) in dichloromethane (1 mL) and DIEA (0.1 mmol) was added morpholine (36 µL, 0.4 mmol). The mixture was stirred for 10 hrs at room temperature. The mixture was concentrated in vacuo and then taken up in methanol. Purification via HPLC (10-99% CH3CN/5 mM HCl) provided N-(4-methyl-2-(3-morpholinoprop-1-ynyl)phenyl)-6-(trifluoromethoxy)-3,4-dihydro-2H-benzo[b][1,4]oxazine-2-carboxamide bis-hydrochloride (5 mg, 22% yield). LC/MS m/z 476.5 [M+H]+.

Example 3

Preparation of N-(4-cyclopentyl-5-hydroxy-2-((4-methylpiperazin-1-yl)methyl)phenyl)-3,4-dihydro-2H-benzo[b][1,4]oxazine-2-carboxamide (Compound 52, Table 1)

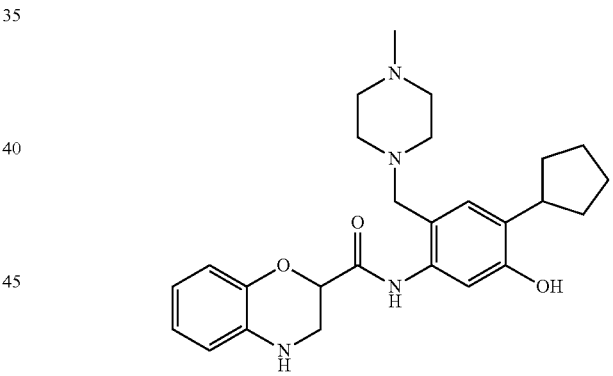

To (4-methylpiperazin-1-yl)methyl-(trifluoro)borane (10 mg, 0.053 mmol), Pd(OAc)2, (0.3 mg, 0.0016 mmol), X-Phos (1.5 mg, 0.003 mmol), and Cs2CO3 (51 mg, 0.15 mmol) was added dropwise 4-bromo-2-cyclopentyl-5-(3,4-dihydro-2H-benzo[b][1,4]oxazine-2-carboxamido)phenyl methyl carbonate (25 mg, 0.053 mmol) in THF/water (10:1, 600 µL) under N2 atmosphere. The reaction was heated under microwave irradiation at 100° C. for 45 min. The reaction was cooled to room temperature and treated with 1 M NaOH. After 10 min the mixture was filtered and purified by HPLC (10-99% CH3CN/0.05% TFA) to provide N-(4-cyclopentyl-5-hydroxy-2-((4-methylpiperazin-1-yl)methyl)phenyl)-3,4-dihydro-2H-benzo[b][1,4]oxazine-2-carboxamide trifluoroacetate (1.6 mg, 14% yield). LC/MS m/z 451.5 [M+H]+.

Example 4

Preparation of 6-cyano-N-(4-cyclopentyl-5-hydroxy-2-(piperazin-1-ylmethyl)phenyl)-3,4-dihydro-2H-benzo[b][1,4]oxazine-2-carboxamide (Compound 51, Table 1)

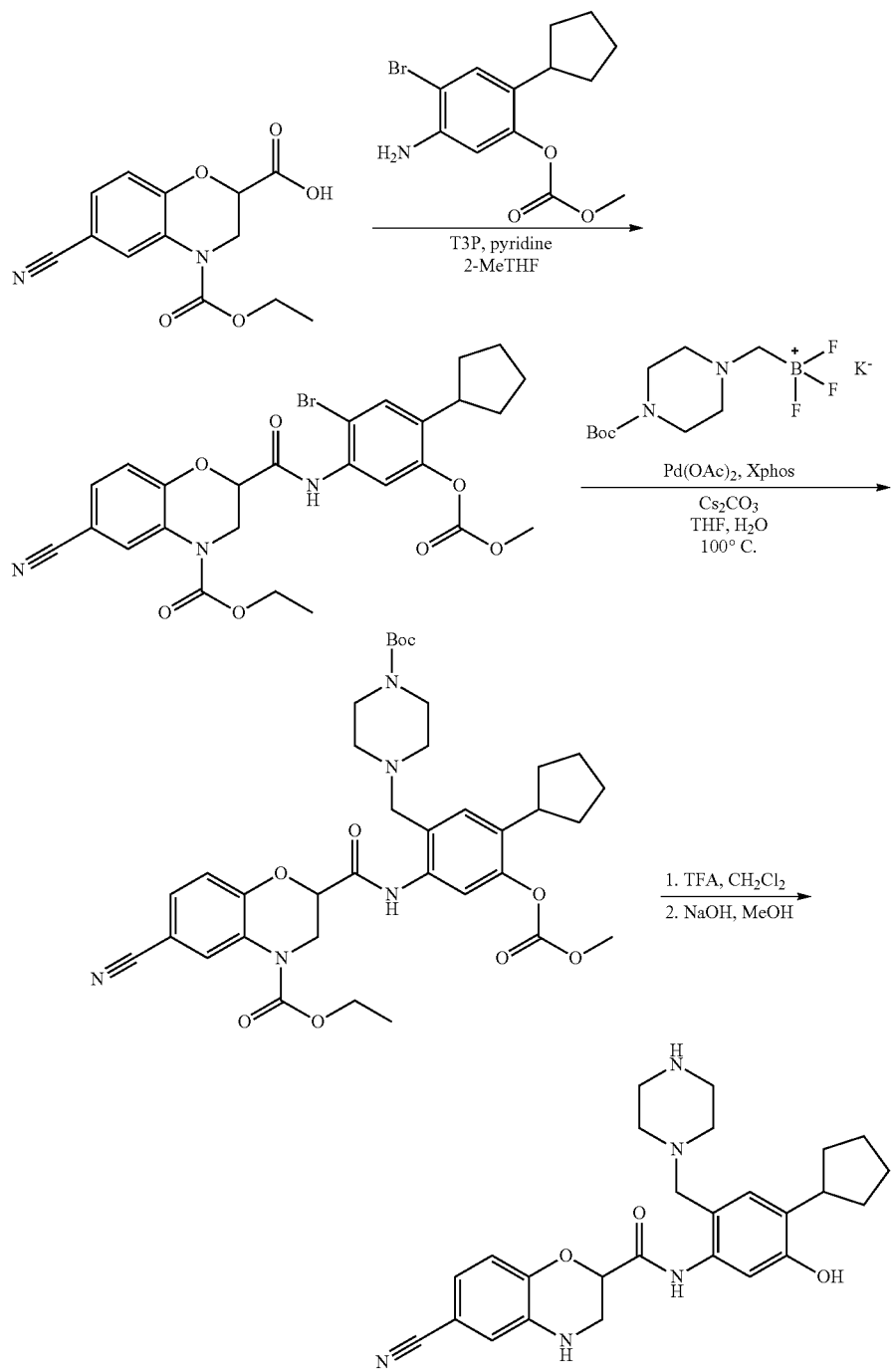

To a solution of 6-cyano-4-ethoxycarbonyl-2,3-dihydro-1,4-benzoxazine-2-carboxylic acid (552 mg, 2.0 mmol) and (5-amino-4-bromo-2-cyclopentyl-phenyl) methyl carbonate (691 mg, 2.20 mmol) in 2-methyltetrahydrofuran (7 mL) at room temperature was added pyridine (404 μL, 5.0 mmol) followed by the addition of T3P (3181 mg, 2.98 mL of 50% w/w solution, 5.0 mmol). The reaction was stirred at room temperature for 1 h. The reaction mixture was diluted with ethyl acetate then quenched with a saturated aqueous solution of NaHCO₃ (4 mL) and stirred for 15 min. The layers were separated, and the aqueous layer was extracted once more with ethyl acetate. The combined organic extracts were filtered to give a white solid. The remaining filtrate was dried over $Na_2SO_4$, filtered and concentrated in vacuo to obtain a creamy solid. The combined solids were triturated with hexane (5×5 mL) and washed with ethyl acetate (1 mL) and dichloromethane (1 mL) to provide ethyl 2-(2-bromo-4-cyclopentyl-5-(methoxycarbonyloxy)phenylcarbamoyl)-6-cyano-2H-benzo[b][1,4]oxazine-4(3H)-carboxylate as a white solid (403 mg, 99% yield). LC/MS m/z 573.1 [M+H]+.

A mixture of ethyl 2-(2-bromo-4-cyclopentyl-5-(methoxycarbonyloxy)phenylcarbamoyl)-6-cyano-2H-benzo[b][1,4]oxazine-4(3H)-carboxylate (53.0 mg, 0.092 mmol), Pd(OAc)$_2$ (0.6 mg, 0.003 mmol), X-Phos (2.6 mg, 0.006 mmol), tert-butyl 4-(trifluoromethylboranylmethyl)piperazine-1-carboxylate (25.0 mg, 0.09 mmol) and Cs$_2$CO$_3$ (90 mg, 0.28 mmol) in THF/water (10:1, 400 µL) under N$_2$ atmosphere was heated under microwave irradiation at 100° C. for 1 h. The reaction was filtered and purified by HPLC (10-99% CH$_3$CN/water) to provide ethyl 2-(2-((4-(tert-butoxycarbonyl)piperazin-1-yl)methyl)-4-cyclopentyl-5-(methoxycarbonyloxy)phenylcarbamoyl)-6-cyano-2H-benzo[b][1,4]oxazine-4(3H)-carboxylate (15.0 mg, 24% yield). LC/MS m/z 692.5 [M+H]+.

To a solution of ethyl 2-(2-((4-(tert-butoxycarbonyl)piperazin-1-yl)methyl)-4-cyclopentyl-5-(methoxycarbonyloxy) phenylcarbamoyl)-6-cyano-2H-benzo[b][1,4]oxazine-4 (3H)-carboxylate (15 mg, 0.022 mmol) in dichloromethane (500 µL) was added TFA (3 µL, 0.04 mmol) and the reaction was stirred overnight at room temperature. The reaction was quenched with aqueous NaHCO$_3$ and the layers separated. The aqueous layer was extracted with dichloromethane, dried over MgSO$_4$, filtered and concentrated. The crude product was dissolved in methanol and 1 M NaOH and the reaction was heated at reflux for 5 min. The reaction was quenched with 1 M HCl and the aqueous layer was extracted with dichloromethane. The organic layer was dried over MgSO$_4$, filtered and concentrated. Purification by HPLC (10-99% CH$_3$CN/0.05% TFA) provided 6-cyano-N-[4-cyclopentyl-5-hydroxy-2-(piperazin-1-ylmethyl)phenyl]-3,4-dihydro-2H-1,4-benzoxazine-2-carboxamide (3 mg, 24% yield). LC/MS m/z 462.5 [M+H]+.

Example 5

Preparation of 6-cyano-N-(4-cyclopentyl-5-hydroxy-2-(1-methylpiperidin-4-yl)phenyl)-3,4-dihydro-2H-benzo[b][1,4]oxazine-2-carboxamide (Compound 111, Table 1)

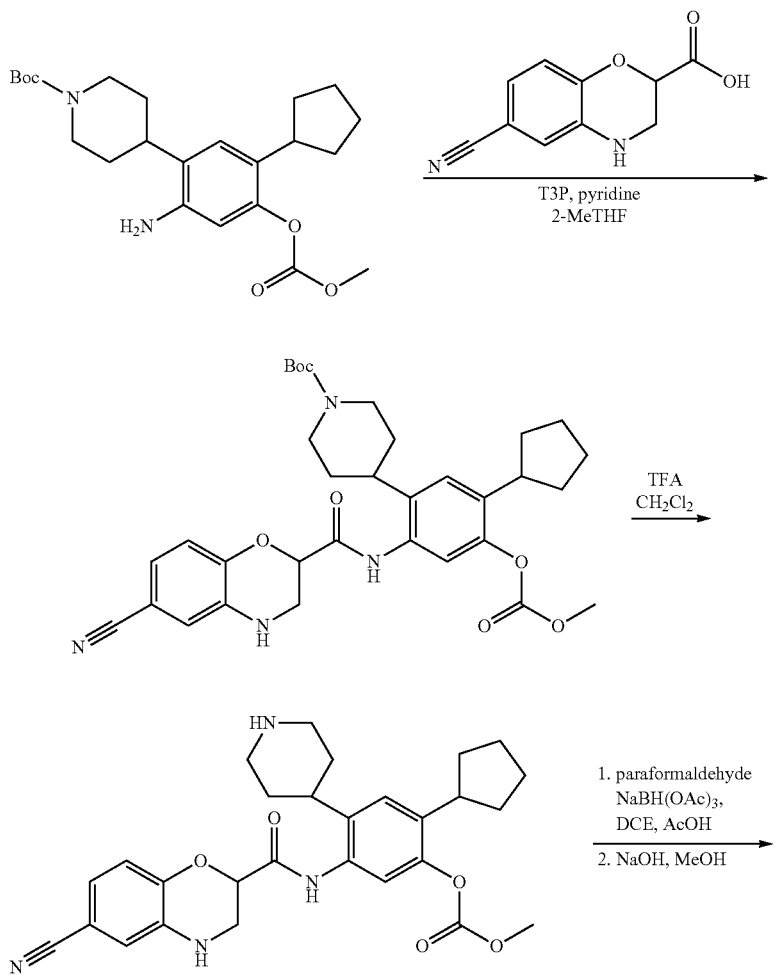

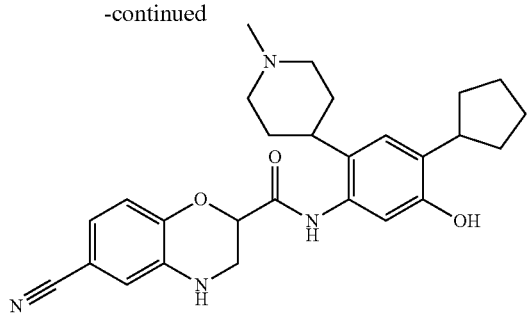

6-Cyano-3,4-dihydro-2H-1,4-benzoxazine-2-carboxylic acid (146 mg, 0.72 mmol), tert-butyl 4-(2-amino-5-cyclopentyl-4-methoxycarbonyloxy-phenyl)piperidine-1-carboxylate (300 mg, 0.72 mmol), T3P (570 mg, 533 µL of 50% w/w solution, 1.79 mmol) were dissolved in pyridine (142 mg, 145 µL, 1.79 mmol) and dichloromethane (10 mL) and stirred for 30 min at room temperature. Purification by silica gel chromatography (10-75% ethyl acetate/hexanes) provided tert-butyl-4-[2-[(6-cyano-3,4-dihydro-2H-1,4-benzoxazine-2-carbonyl)amino]-5-cyclopentyl-4-methoxycarbonyloxy-phenyl]piperidine-1-carboxylate (333 mg, 77% yield). LC/MS m/z 605.6 [M+H]$^+$.

Tert-butyl 4-[2-[(6-cyano-3,4-dihydro-2H-1,4-benzoxazine-2-carbonyl)amino]-5-cyclopentyl-4-methoxycarbonyloxy-phenyl]piperidine-1-carboxylate (100 mg, 0.17 mmol) was taken up in dichloromethane (3 mL) and TFA (1 mL, 13 mmol) and allowed to stir for 10 min at room temperature. The mixture was concentrated in vacuo and the residue was dissolved in 1,2-dichloroethane (2 mL). Paraformaldehyde (5 mg, 0.17 mmol) and acetic acid (9 µL, 0.17 mmol) were added and the mixture was heated at 60° C. for 10 min. Sodium triacetoxyborohydride (105 mg, 0.50 mmol) was added and the reaction was stirred for an additional 10 min. The mixture was added to saturated aqueous NaHCO$_3$ (50 mL) and was extracted with ethyl acetate (3×10 mL). The combined organic extracts were dried over MgSO$_4$, filtered and concentrated in vacuo. The residue was dissolved in methanol (3 mL) and treated with solid KOH (93 mg, 1.65 mmol). The reaction was stirred for 20 min at room temperature, poured into 1 N HCl (50 mL) and was extracted with ethyl acetate (3×10 mL). The combined organic extracts were dried over MgSO$_4$, filtered and concentrated in vacuo. HPLC purification (10-99% CH$_3$CN/0.05% HCl) provided 6-cyano-N-(4-cyclopentyl-5-hydroxy-2-(1-methylpiperidin-4-yl)phenyl)-3,4-dihydro-2H-benzo[b][1,4]oxazine-2-carboxamide (6 mg, 7% yield). LC/MS m/z 461.4 [M+H]$^+$. $^1$H NMR (400.0 MHz, MeOD) δ 7.09 (d, J=1.8 Hz, 3H), 7.02 (s, 1H), 6.63 (d, J=1.6 Hz, 1H), 5.11 (dd, J=3.2, 4.6 Hz, 1H), 3.64 (dd, J=4.7, 12.0 Hz, 1H), 3.49-3.38 (m, 3H), 3.26 (q, obscured by solvent peak, J=9.2 Hz, 1H), 2.95 (s, 3H), 2.74-2.64 (m, 3H), 1.98-1.93 (m, 2H), 1.84-1.58 (m, 10H).

Example 6

6-cyano-N-(4-cyclopentyl-5-hydroxy-2-(1,2,3,6-tetrahydropyridin-4-yl)phenyl)-3,4-dihydro-2H-benzo[b][1,4]oxazine-2-carboxamide (Compound 11, Table 1)

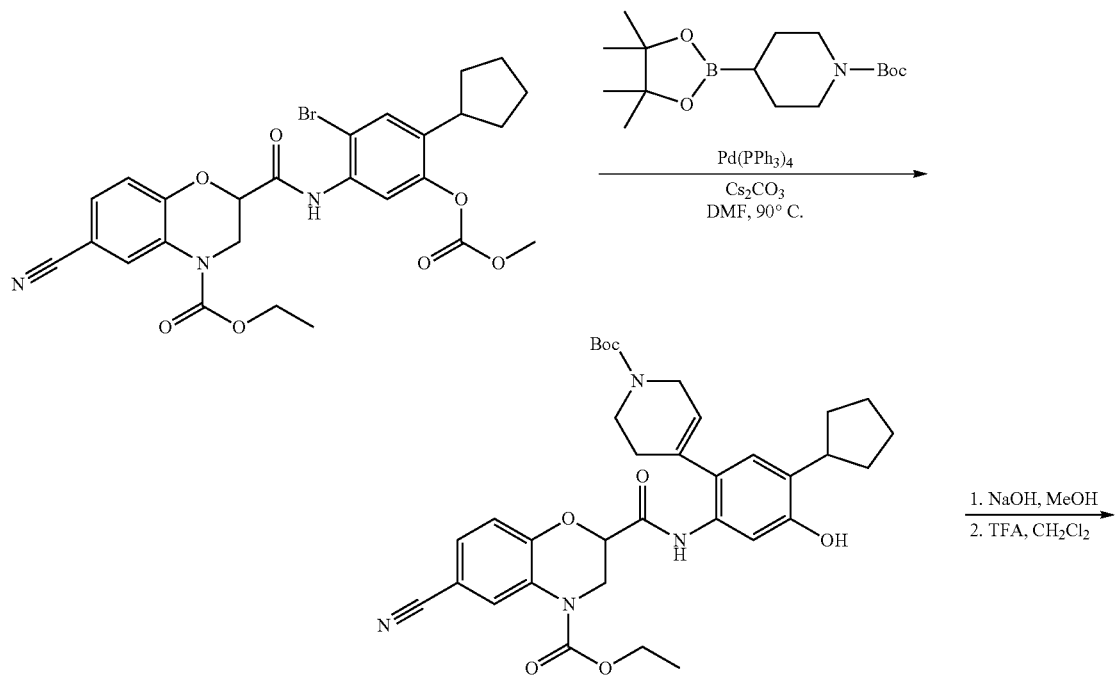

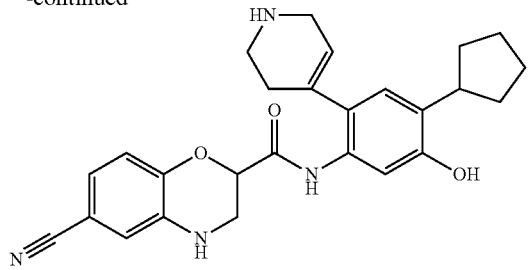

Ethyl 2-(2-bromo-4-cyclopentyl-5-(methoxycarbonyloxy)phenylcarbamoyl)-6-cyano-2H-benzo[b][1,4]oxazine-4(3H)-carboxylate (166 mg, 0.29 mmol), tert-butyl 4-(4,4,5,5-tetramethyl-1,3,2-dioxaborolan-2-yl)-3,6-dihydro-2H-pyridine-1-carboxylate (90 mg, 0.29 mmol), Pd(PPh$_3$)$_4$ (34 mg, 0.03 mmol), and Cs$_2$CO$_3$ (189 mg, 0.58 mmol) were combined in DMF (4 mL) and heated at 90° C. for 4 h. The reaction was quenched with water (50 mL) and extracted with dichloromethane (3×10 mL). The combined organic extracts were dried over MgSO$_4$, filtered and concentrated in vacuo. Purification by silica gel chromatography (0-100% ethyl acetate/hexanes) yielded ethyl 2-(2-(1-(tert-butoxycarbonyl)-1,2,3,6-tetrahydropyridin-4-yl)-4-cyclopentyl-5-hydroxyphenylcarbamoyl)-6-cyano-2H-benzo[b][1,4]oxazine-4(3H)-carboxylate (100 mg, 56% yield). LC/MS m/z 617.4 [M+H]$^+$.

Ethyl 2-(2-(1-(tert-butoxycarbonyl)-1,2,3,6-tetrahydropyridin-4-yl)-4-cyclopentyl-5-(methoxycarbonyloxy)phenylcarbamoyl)-6-cyano-2H-benzo[b][1,4]oxazine-4(3H)-carboxylate (50 mg, 0.08 mmol) and NaOH (162 mg, 4.05 mmol) were dissolved in 5:1 methanol/water (3.6 mL) and heated at 60° C. for 2 h. The mixture was added to 1 N HCl (25 mL) and extracted with ethyl acetate (3×10 mL). The combined organic extracts were dried over MgSO$_4$, filtered, and concentrated in vacuo. Removal of the Boc protecting group was achieved by dissolving the compound in dichloromethane (3.0 mL) and TFA (3.0 mL) and stirring for 10 min before being concentrated in vacuo. HPLC purification (10-99% CH$_3$CN/0.05% TFA) provided 6-cyano-N-(4-cyclopentyl-5-hydroxy-2-(1,2,3,6-tetrahydropyridin-4-yl)phenyl)-3,4-dihydro-2H-benzo[b][1,4]oxazine-2-carboxamide (7 mg, 19% yield). LC/MS m/z 562.2 [M+H]$^+$. $^1$H NMR (400.0 MHz, MeOD) δ 9.56 (s, 1H), 9.15 (s, 1H), 7.16 (s, 1H), 7.01 (m, 3H), 6.90 (s, 1H), 6.45 (s, 1H), 5.56 (s, 1H), 4.89 (q, J=3.0 Hz, 1H), 3.61 (s, 2H), 3.56-3.53 (m, 1H), 3.44-3.39 (m, 1H), 3.33 (m, obscured by H$_2$O peak, 1H), 3.23-3.16 (m, 3H), 2.44 (s, 2H), 1.93 (m, 1.97-1.90, 2H), 1.78-1.71 (m, 2H), 1.65-1.62 (m, 2H), 1.56-1.45 (m, 2H).

Example 7

Preparation of 2-cyclopentyl-4-(3-(dimethylamino)prop-1-ynyl)-5-(6-(trifluoromethoxy)-3,4-dihydro-2H-benzo[b][1,4]oxazine-2-carboxamido)phenyl methyl carbonate and N-(4-cyclopentyl-2-(3-(dimethylamino)propyl)-5-hydroxyphenyl)-6-(trifluoromethoxy)-3,4-dihydro-2H-benzo[b][1,4]oxazine-2-carboxamide (Compounds 106 and 38, Table 1)

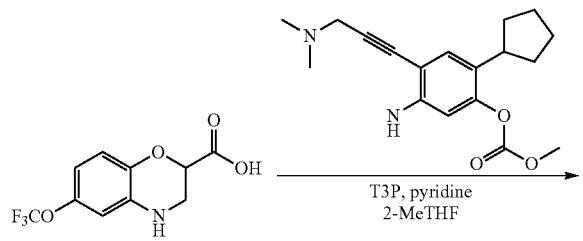

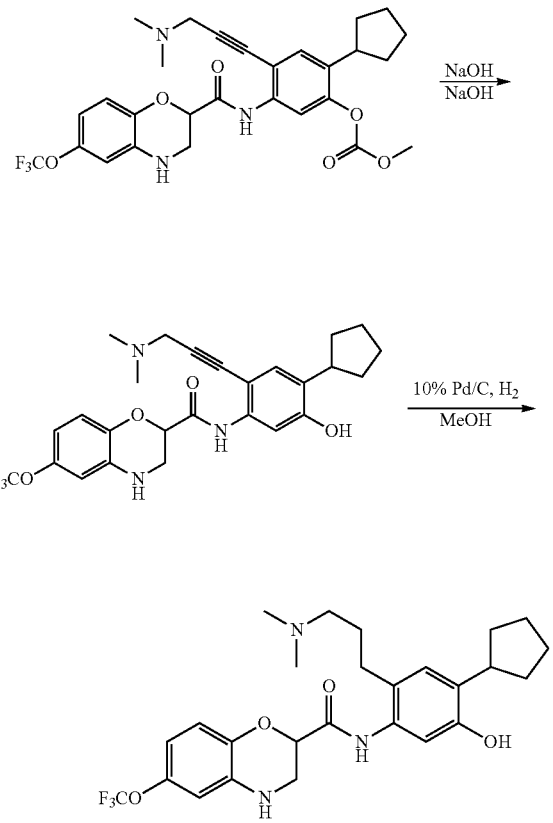

5-Amino-2-cyclopentyl-4-(3-(dimethylamino)prop-1-ynyl)phenyl methyl carbonate (150 mg, 0.47 mmol) was dissolved in 2-methyltetrahydrofuran (3 mL) and T3P (754 mg, 705 µL of 50% w/w, 1.18 mmol). 6-(Trifluoromethoxy)-3,4-dihydro-2H-1,4-benzoxazine-2-carboxylic acid (125 mg, 0.47 mmol) was added portion-wise over 30 min. After 3 h the reaction was diluted with ethyl acetate, washed with 10% saturated NaHCO$_3$ (2×20 mL) and brine. The solution was dried over Na$_2$SO$_4$, filtered, and dried down to an orange solid. Purification by silica gel chromatography (1% methanol/dichloromethane) provided 2-cyclopentyl-4-(3-(dimethylamino)prop-1-ynyl)-5-(6-(trifluoromethoxy)-3,4-dihydro-2H-benzo[b][1,4]oxazine-2-carboxamido)phenyl methyl carbonate as a colorless oil. LC/MS m/z 562.2 [M+H]$^+$. The oil was dissolved in methanol (3 mL) and treated with NaOH (0.5 mL of 5 M, 2.4 mmol) and stirred for 5 min. Water (5 mL) and saturated NaHCO₃ (2 mL) were added until a white precipitate formed. The product was extracted into ethyl acetate, washed with brine, dried over Na₂SO₄, filtered and concentrated in vacuo to provide N-(4-cyclopentyl-2-(3-(dimethylamino)prop-1-ynyl)-5-hydroxyphenyl)-6-(trifluoromethoxy)-3,4-dihydro-2H-benzo[b][1,4]oxazine-2-carboxamide as a off-white solid (90 mg, 34% yield). LC/MS m/z 504.2 [M+H]⁺. ¹H NMR (400.0 MHz, DMSO-d₆) δ 10.72 (s, 1H), 10.16 (s, 1H), 9.25 (s, 1H), 7.53 (s, 1H), 7.25 (s, 1H), 6.95 (d, J=8.7 Hz, 1H), 6.60 (d, J=2.0 Hz, 1H), 6.52-6.49 (m, 1H), 4.91 (dd, J=3.0, 6.3 Hz, 1H), 4.32 (t, J=3.8 Hz, 2H), 3.54 (dd, J=3.0, 12.2 Hz, 1H), 3.42 (dd, J=6.3, 12.3 Hz, 1H), 3.14 (quin, J=8.4 Hz, 1H), 2.85 (d, J=4.4 Hz, 6H), 1.91 (m, 2H), 1.72 (m, 2H), 1.63-1.60 (m, 2H), 1.48 (m, 2H).

N-(4-cyclopentyl-2-(3-(dimethylamino)prop-1-ynyl)-5-hydroxyphenyl)-6-(trifluoromethoxy)-3,4-dihydro-2H-benzo[b][1,4]oxazine-2-carboxamide (17 mg, 0.03 mmol) was dissolved in methanol (3 mL) and treated with 10% Pd/C (3 mg). The reaction was stirred under H₂ atmosphere for 30 min. The reaction filtered, treated with 1 mL 1 N HCl and concentrated in vacuo to provide N-(4-cyclopentyl-2-(3-(dimethylamino)propyl)-5-hydroxyphenyl)-6-(trifluoromethoxy)-3,4-dihydro-2H-benzo[b][1,4]oxazine-2-carboxamide bis-hydrochloride as an off-white solid (15 mg, 85% yield). LC/MS m/z 508.2 [M+H]⁺. ¹H NMR (400.0 MHz, DMSO-d₆) δ 9.67 (s, 1H), 9.31 (s, 1H), 9.27 (s, 1H), 6.95 (s, 1H), 6.91 (d, J=8.7 Hz, 1H), 6.78 (s, 1H), 6.61 (m, 1H), 6.50 (d, J=8.0 Hz, 1H), 4.86 (dd, J=3.3, 5.4 Hz, 1H), 3.53-3.49 (d, obscured by H₂O peak, 2H), 3.14 (q, J=7.7 Hz, 1H), 2.91-2.87 (m, 2H), 2.71-2.67 (m, 6H), 2.36-2.32 (m, 2H), 1.90 (s, 2H), 1.73 (d, J=4.3 Hz, 4H), 1.61 (d, J=5.1 Hz, 2H), 1.57-1.52 (m, 2H).

Example 8

Preparation of N-(4-(7-azabicyclo[2.2.1]heptan-7-yl)-2-(3-(dimethylamino)prop-1-ynyl)phenyl)-6-cyano-3,4-dihydro-2H-benzo[b][1,4]oxazine-2-carboxamide (Compound 43, Table 1)

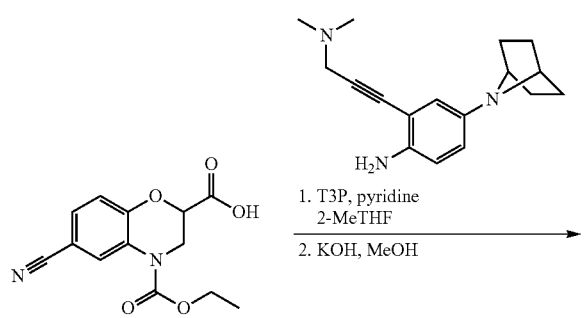

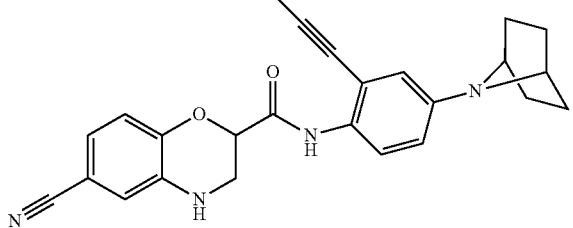

To a solution of 6-cyano-4-ethoxycarbonyl-2,3-dihydro-1,4-benzoxazine-2-carboxylic acid (30 mg, 0.11 mmol) and 4-(7-azabicyclo[2.2.1]heptan-7-yl)-2-(3-dimethylamino-prop-1-ynyl)aniline (29 mg, 0.11 mmol) in 2-methyltetrahydrofuran (300 µL) was added pyridine (35 µL, 0.43 mmol) followed by T3P (173 µl, of 50% w/w, 0.27 mmol) at 0° C. The reaction was warmed to room temperature and stirred for 1 h. The reaction was diluted with ethyl acetate (10 mL) and washed with aqueous 10% NaHCO₃ (2×5 mL) and brine (10 mL). The organic phase was dried over MgSO₄, filtered and concentrated. Purification by silica gel chromatography (0-20% ethyl acetate/hexanes) provided ethyl 2-(4-(7-azabicyclo[2.2.1]heptan-7-yl)-2-(3-(dimethylamino)prop-1-ynyl)phenylcarbamoyl)-6-cyano-2H-benzo[b][1,4]oxazine-4(3H)-carboxylate (35 mg, 61% yield). LC/MS m/z 528.5 [M+H]⁺. ¹H NMR (400.0 MHz, DMSO-d₆) δ 9.35 (s, 1H), 8.16 (s, 1H), 7.56 (dd, J=2.0, 8.5 Hz, 1H), 7.50 (d, J=8.7 Hz, 1H), 7.25 (d, J=8.5 Hz, 1H), 6.96-6.92 (m, 2H), 5.17 (t, J=4.5 Hz, 1H), 4.23 (s, 2H), 4.20 (q, J=7.1 Hz, 2H), 4.10 (d, J=4.4 Hz, 2H), 3.44 (d, J=2.2 Hz, 2H), 2.23 (s, 6H), 1.62 (d, J=7.0 Hz, 4H), 1.38 (d, J=6.8 Hz, 4H), 1.24 (t, J=7.1 Hz, 3H).

To a solution of ethyl 2-(4-(7-azabicyclo[2.2.1]heptan-7-yl)-2-(3-(dimethylamino)prop-1-ynyl)phenylcarbamoyl)-6-cyano-2H-benzo[b][1,4]oxazine-4(3H)-carboxylate (35 mg, 0.06 mmol) in methanol (350 µL) at 0° C. was added solid KOH (75 mg, 1.33 mmol). The reaction was heated to 60° C. Once the reaction was complete, the reaction mixture was cooled to room temperature and purified by HPLC (10-99% CH₃CN/0.05% TFA) to provide N-(4-(7-azabicyclo[2.2.1]heptan-7-yl)-2-(3-(dimethylamino)prop-1-ynyl)phenyl)-6-cyano-3,4-dihydro-2H-benzo[b][1,4]oxazine-2-carboxamide trifluoroacetate (4 mg, 10% yield). LC/MS m/z 456.7 [M+H]⁺.

Example 9

Preparation of N-(4-tert-butyl-3-hydroxyphenyl)-N-methyl-3,4-dihydro-2H-benzo[b][1,4]oxazine-2-carboxamide hydrochloride (Compound 115, Table 1)

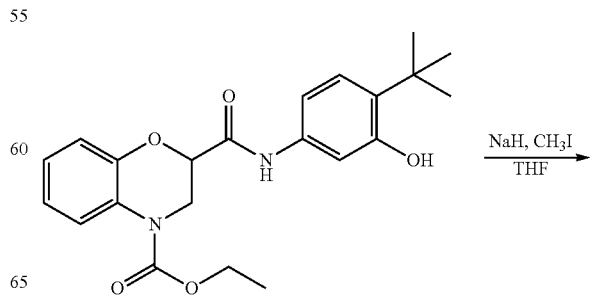

Example 10

Preparation of N-(4-tert-butyl-3-hydroxy-phenyl)-3,4-dihydro-2H-1,4-benzothiazine-2-carboxamide, N-(4-tert-butyl-3-hydroxy-phenyl)-1-oxo-3,4-dihydro-2H-benzo[b][1,4]thiazine-2-carboxamide, and N-(4-tert-butyl-3-hydroxy-phenyl)-1,1-dioxo-3,4-dihydro-2H-benzo[b][1,4]thiazine-2-carboxamide (Compounds 120, 125, and 121, Table 1)

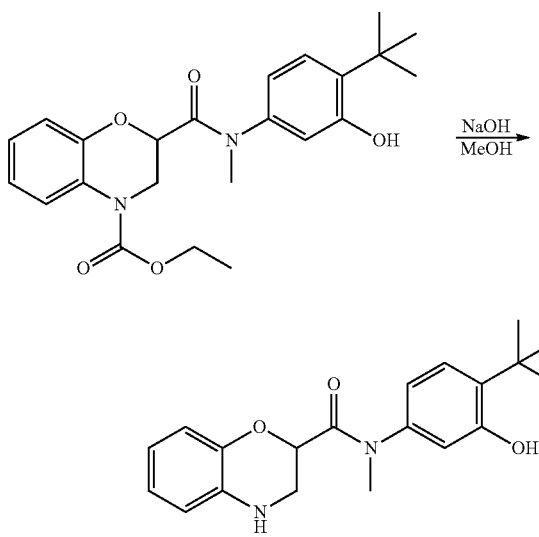

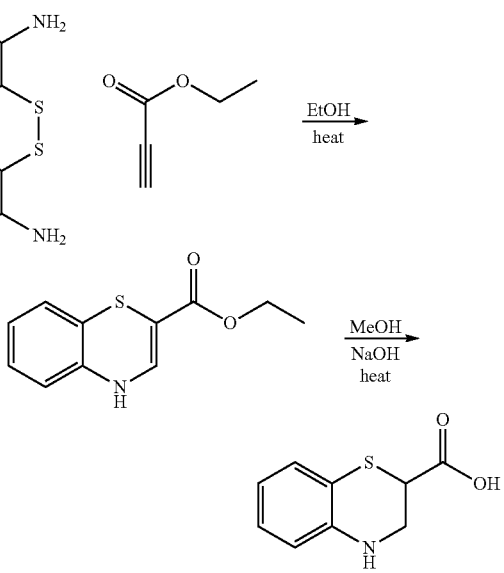

To a solution of ethyl 2-(4-tert-butyl-3-hydroxyphenylcarbamoyl)-2H-benzo[b][1,4]oxazine-4(3H)-carboxylate (50 mg, 0.13 mmol) in THF at 0° C. was added NaH (10 mg, 0.25 mmol) and the mixture stirred for 10 min. Methyl iodide (23 mg, 10 µL, 0.16 mmol) was added and mixture was stirred for 1 h at room temperature. HPLC purification (20-99% MeOH/water) provided ethyl 2-((4-tert-butyl-3-hydroxyphenyl)(methyl)carbamoyl)-2H-benzo[b][1,4]oxazine-4(3H)-carboxylate (18 mg, 32% yield). LC/MS m/z 413.0 [M+H]+. $^1$H NMR (400.0 MHz, DMSO-$d_6$) δ 9.85 (s, 1H), 7.57 (d, J=6.9 Hz, 1H), 7.24 (d, J=8.4 Hz, 1H), 7.00 (t, J=7.1 Hz, 1H), 6.88-6.79 (m, 4H), 4.79 (br s, 1H), 4.21-4.11 (m, 2H), 4.02-3.98 (m, 1H), 3.65 (d, J=13.4 Hz, 1H), 3.10 (s, 3H), 1.35 (s, 9H), 1.24 (t, J=7.1 Hz, 3H).

To a mixture of ethyl 2-((4-tert-butyl-3-hydroxyphenyl)(methyl)carbamoyl)-2H-benzo[b][1,4]oxazine-4(3H)-carboxylate (18 mg, 0.044 mmol) in methanol (900 µL) was added NaOH (11 mg, 0.27 mmol) and the reaction heated to reflux for 4 h. HPLC purification (20-99% MeOH/5 mM HCl) provided N-(4-tert-butyl-3-hydroxyphenyl)-N-methyl-3,4-dihydro-2H-benzo[b][1,4]oxazine-2-carboxamide hydrochloride (6 mg, 34% yield). LC/MS m/z 341.4 [M+H]+. $^1$H NMR (400.0 MHz, DMSO-$d_6$) δ 9.80 (s, 1H), 7.18 (d, J=8.7 Hz, 1H), 6.76 (d, J=1.4 Hz, 2H), 6.66 (m, 2H), 6.52-6.48 (m, 2H), 4.36 (d, J=6.2 Hz, 1H), 4.07 (br s, 2H), 3.32 (d, J=11.4 Hz, 1H), 3.21 (m, 4H), 1.33 (s, 9H).

2-(2-Aminophenyl)disulfanylaniline (1.0 g, 4.0 mmol) and ethyl prop-2-ynoate (790 mg, 816 µL, 8.05 mmol) were combined in a microwave tube and heated at 150° C. for 30 min. The reaction was concentrated in vacuo. Silica gel chromatography (10-35% ethyl acetate/hexane) provided ethyl 4H-1,4-benzothiazine-2-carboxylate as an orange solid (200 mg, 23% yield). LC/MS m/z 222.0 [M+H]+. $^1$H NMR (400.0 MHz, CDCl$_3$) δ 7.11 (d, J=6.6 Hz, 1H), 6.86-6.82 (m, 1H), 6.79-6.74 (m, 2H), 6.27 (d, J=7.9 Hz, 1H), 5.68 (br d, J=4.2 Hz, 1H), 4.19 (q, J=7.2 Hz, 2H), 1.28 (t, J=7.1 Hz, 3H)

Ethyl 4H-1,4-benzothiazine-2-carboxylate (200 mg, 0.904 mmol) was dissolved in methanol (5 mL) and treated with NaOH (181 µL of 5 M, 0.904 mmol). The reaction was heated at reflux for 40 min, resulting in complete consumption of starting material. The reaction was acidified with 1 N HCl and the product extracted into ether. The ether layer was dried over Na$_2$SO$_4$, filtered and concentrated in vacuo to provide a residue that was taken directly to the next amide coupling step to provide the 3,4-dihydro-2H-benzo[b][1,4]thiazine-2-carboxyamide product.

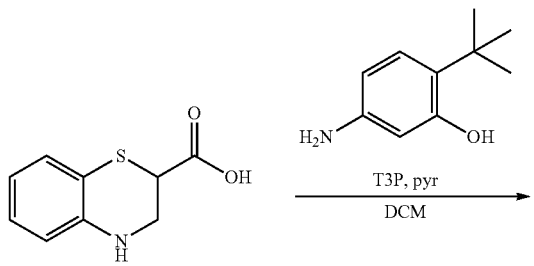

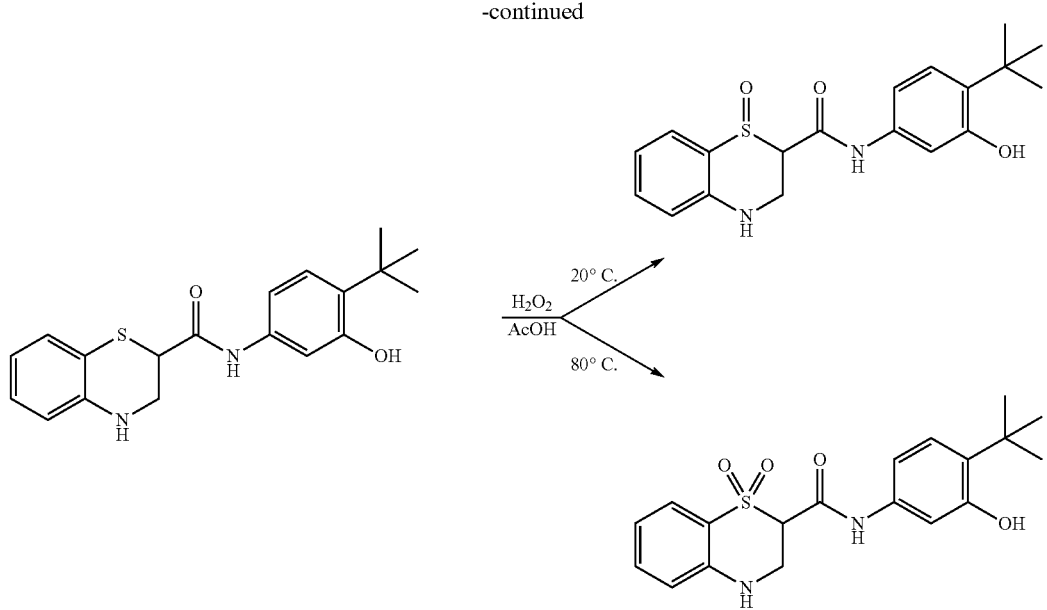

A solution of 3,4-dihydro-2H-1,4-benzothiazine-2-carboxylic acid (80 mg, 0.41 mmol) and 5-amino-2-tert-butyl-phenol (67 mg, 0.41 mmol) in dichloromethane (3 mL) was treated with propane phosphonic acid anhydride (610 µl, of 50% w/w in ethyl acetate, 1.02 mmol) and pyridine (99 µL, 1.2 mmol) and stirred for 30 min at room temperature. The reaction was washed with water, dried over $Na_2SO_4$, and concentrated in vacuo. HPLC purification (20-99% $CH_3CN$/0.05% TFA) provided N-(4-tert-butyl-3-hydroxy-phenyl)-3,4-dihydro-2H-1,4-benzothiazine-2-carboxamide (51 mg, 36% yield). LC/MS m/z 343.2 [M+H]+. $^1$H NMR (400.0 MHz, DMSO-$d_6$) δ 10.07 (s, 1H), 9.38 (s, 1H), 7.20 (d, J=2.0 Hz, 1H), 7.03 (d, J=8.4 Hz, 1H), 6.93 (dd, J=1.1, 7.7 Hz, 1H), 6.88-6.83 (m, 2H), 6.58 (d, J=7.5 Hz, 1H), 6.51-6.47 (t, J=7.5, 1H), 3.92 (dd, J=3.0, 8.0 Hz, 1H), 3.72 (dd, J=3.0, 12.3 Hz, 1H), 3.53 (dd, J=8.1, 12.3 Hz, 1H), 1.31 (s, 9H).

A solution of N-(4-tert-butyl-3-hydroxy-phenyl)-3,4-dihydro-2H-1,4-benzothiazine-2-carboxamide (20 mg, 0.058 mmol) in acetic acid (500 µL) was treated with hydrogen peroxide (12 µL of aq. 30% w/w, 0.12 mmol) and stirred at room temperature for 2 h. The reaction was diluted with DMF and purified by HPLC (10-99% $CH_3CN$/5 mM HCl) to provide N-(4-tert-butyl-3-hydroxy-phenyl)-1-oxo-3,4-dihydro-2H-benzo[b][1,4]thiazine-2-carboxamide (8 mg, 38% yield). LC/MS m/z 359.2 [M+H]+.

A solution of N-(4-tert-butyl-3-hydroxy-phenyl)-3,4-dihydro-2H-1,4-benzothiazine-2-carboxamide (20 mg, 0.058 mmol) in acetic acid (500 µL) treated with hydrogen peroxide (30 µL of aq. 30% w/w, 0.29 mmol) and stirred at 80° C. for 3 h. HPLC purification (10-99% $CH_3CN$/5 mM HCl) provided N-(4-tert-butyl-3-hydroxy-phenyl)-1,1-dioxo-3,4-dihydro-2H-benzo[b][1,4]thiazine-2-carboxamide (4 mg, 18% yield). LC/MS m/z 375.0 [M+H]+.

Analytical data for the compounds of Table 1 is shown below:

TABLE 2

| Compound No. | LC/MS M + 1 | LC/RT min | NMR |
|---|---|---|---|
| 1 | 357.00 | 1.64 | — |
| 2 | 399.20 | 2.20 | — |
| 3 | 436.50 | 1.18 | — |
| 4 | 523.20 | 1.95 | — |
| 5 | 339.10 | 1.57 | — |
| 6 | 415.40 | 2.26 | $^1$H NMR (400.0 MHz, DMSO-$d_6$) δ 9.26 (s, 1H), 8.87 (s, 1H), 7.12 (s, 1H), 6.87 (s, 1H), 6.70 (d, J = 7.5 Hz, 1H), 6.39 (d, J = 11.0 Hz, 1H), 6.01 (s, 1H), 4.73 (dd, J = 2.9, 6.3 Hz, 1H), 3.45 (s, 2H), 2.07-2.05 (m, 3H), 1.33 (s, 9H), 1.22 (s, 9H). |
| 7 | 450.50 | 1.10 | — |
| 8 | 419.40 | 2.19 | $^1$H NMR (400.0 MHz, DMSO-$d_6$) δ 9.28 (s, 1H), 8.99 (s, 1H), 7.12 (s, 1H), 6.92 (dd, J = 7.8, 11.5 Hz, 1H), 6.74 (s, 1H), 6.61 (dd, J = 8.1, 12.2 Hz, 1H), 4.82 (dd, J = 3.3, 5.5 Hz, 1H), 3.48-3.38 (m, 3H), 1.33 (s, 9H), 1.19 (s, 9H). |
| 9 | 510.40 | 4.15 | — |
| 10 | 476.50 | 1.37 | $^1$H NMR (400.0 MHz, DMSO-$d_6$) δ 10.20 (s, 1H), 9.60 (s, 1H), 8.67 (s, 1H), 7.74 (s, 1H), 7.13 (s, 1H), 7.07-7.03 (m, 3H), 6.54 (s, 1H), |

TABLE 2-continued

| Compound No. | LC/MS M + 1 | LC/RT min | NMR |
|---|---|---|---|
| | | | 4.97-4.95 (m, 1H), 3.79-3.73 (m, 1H), 3.53-3.49 (m, 4H), 3.28-3.24 (m, 2H), 3.15-3.12 (m, 2H), 3.05-2.96 (m, 2H), 2.78-2.76 (m, 1H), 2.67-2.62 (m, 2H), 1.94-1.92 (m, 2H); 1.75-1.72 (m, 2H), 1.63-1.60 (m, 2H), 1.29 (t, J = 7.2 Hz, 3H). |
| 11 | 445.40 | 2.64 | $^1$H NMR (400.0 MHz, MeOD) δ 9.56 (s, 1H), 9.15 (s, 1H), 7.16 (s, 1H), 7.01 (m, 3H), 6.90 (s, 1H), 6.45 (s, 1H), 5.56 (s, 1H), 4.89 (q, J = 3.0 Hz, 1H), 3.61 (s, 2H), 3.56-3.53 (m, 1H), 3.44-3.39 (m, 1H), 3.33 (m, obscured by H$_2$O peak, 1H), 3.23-3.16 (m, 3H), 2.44 (s, 2H), 1.93 (m, 1.97-1.90, 2H), 1.78-1.71 (m, 2H), 1.65-1.62 (m, 2H), 1.56-1.45 (m, 2H). |
| 12 | 477.30 | 6.23 | $^1$H NMR (400.0 MHz, MeOD) δ 7.85 (s, 1H), 7.19 (s, 1H), 7.05 (d, J = 8.7 Hz, 1H), 6.58 (d, J = 2.0 Hz, 1H), 6.51 (dd, J = 1.8, 8.8 Hz, 2H), 4.76 (dd, J = 3.0, 7.2 Hz, 1H), 4.46 (s, 2H), 3.68 (dd, J = 3.0, 12.1 Hz, 1H), 3.44 (dd, J = 7.2, 12.1 Hz, 1H), 3.22 (dd, J = 1.7, 16.9 Hz, 1H), 1.98-1.96 (m, 2H), 1.81-1.77 (m, 2H), 1.69-1.67 (m, 2H), 1.56-1.50 (m, 2H). |
| 13 | 420.50 | 1.98 | $^1$H NMR (400.0 MHz, DMSO-d$_6$) δ 9.18 (s, 1H), 9.06 (s, 1H), 7.06 (s, 1H), 6.98 (d, J = 3.5 Hz, 2H), 6.68 (s, 1H), 6.44 (s, 1H), 4.92 (dd, J = 3.2, 5.5 Hz, 1H), 3.51-3.46 (m, 3H), 3.17-3.15 (m, 1H), 1.91-1.87 (m, 2H), 1.73-1.71 (m, 2H), 1.63-1.55 (m, 4H), 1.18 (s, 9H). |
| 14 | 357.00 | 1.76 | $^1$H NMR (400.0 MHz, DMSO-d$_6$) δ 9.67 (s, 1H), 9.37 (s, 1H), 7.27 (d, J = 2.1 Hz, 1H), 7.03 (d, J = 8.5 Hz, 1H), 6.89 (dd, J = 2.1, 8.5 Hz, 1H), 6.75 (d, J = 8.7 Hz, 1H), 6.19 (d, J = 2.9 Hz, 1H), 6.11 (dd, J = 2.9, 8.7 Hz, 1H), 4.58-4.55 (m, 2H), 3.62 (s, 3H), 3.47 (dd, J = 2.9, 12.0 Hz, 1H), 3.31 (dd, J = 7.2, 12.0 Hz, 1H), 1.32 (s, 9H). |
| 15 | 448.40 | 3.77 | — |
| 16 | 495.10 | 1.59 | $^1$H NMR (400.0 MHz, DMSO-d$_6$) δ 12.16 (s, 1H), 9.41 (s, 1H), 9.18 (s, 1H), 6.94-6.87 (m, 3H), 6.57 (d, J = 2.2 Hz, 1H), 6.47 (d, J = 9.0 Hz, 1H), 6.34 (s, 1H), 4.80 (q, J = 3.1 Hz, 1H), 3.51 (dd, J = 2.9, 12.2 Hz, 1H), 3.41 (dd, J = 6.0, 10.0 Hz, 1H), 3.16-3.12 (m, 1H), 2.37-2.33 (m, 2H), 1.85-1.83 (m, 2H), 1.74-1.70 (m, 2H), 1.64-1.58 (m, 2H), 1.54-1.50 (m, 4H). |
| 17 | 382.50 | 1.89 | $^1$H NMR (400.0 MHz, DMSO-d$_6$) δ 9.82 (s, 1H), 7.47 (s, 1H), 7.20 (s, 1H), 6.69 (dd, J = 1.9, 9.4 Hz, 1H), 6.62-6.59 (m, 2H), 5.84 (s; 1H), 4.84 (dd, J = 3.3, 6.5 Hz, 1H), 3.49-3.46 (m, 2H), 3.37-3.32 (m, 1H), 1.95-1.90 (m, 3H), 1.76-1.72 (m, 2H), 1.62-1.45 (m, 4H). |
| 18 | 403.20 | 2.16 | — |
| 19 | 385.20 | 2.12 | $^1$H NMR (400.0 MHz, DMSO-d$_6$) δ 9.39 (s, 2H), 7.37 (d, J = 7.3 Hz, 1H), 6.96 (s, 1H), 6.93 (s, 1H), 6.83 (d, J = 7.1 Hz, 1H), 6.72 (t, J = 7.4 Hz, 1 H), 6.62 (dd, J = 1.6, 7.8 Hz, 1H), 6.55 (t, 7.8 Hz, 1H), 5.91 (s, 1H), 4.79 (dd, J = 2.9, 6.5 Hz, 1H), 3.50-3.46 (m, 1H), 2.08-2.00 (m, 2H), 1.61-1.55 (m, 3H), 1.54-1.48 (m, 2H), 1.40-1.35 (m, 3H), 1.23 (s, 3H). |
| 20 | 335.30 | 1.69 | $^1$H NMR (400.0 MHz, DMSO-d$_6$) δ 9.46 (s, 1H), 9.34 (s, 1H), 7.29 (d, J = 6.9 Hz, 1H), 6.95 (d, J = 11.4 Hz, 1H), 6.72 (dd, J = 2.3, 9.9 Hz, 1H), 6.61-6.58 (m, 2H), 5.81 (s, 1H), 4.82 (dd, J = 2.9, 6.2 Hz, 1H), 3.45 (d, J = 12.0 Hz, 1H), 3.34 (d, J = 9.9 Hz, 1H), 2.51-2.45 (m, 2H), 1.10 (t, J = 7.5 Hz, 3H). |
| 21 | 371.00 | 1.78 | $^1$H NMR (400.0 MHz, DMSO-d$_6$) δ 9.11 (s, 1H), 9.06 (s, 1H), 6.95 (s, 1H), 6.90 (s, 1H), 6.73 (dd, J = 1.9, 9.6 Hz, 1H), 6.60-6.52 (m, 2H), 5.81 (s, 1H), 4.81 (dd, J = 3.2, 5.6 Hz, 1H), 3.46-3.34 (m, 2H), 3.16-3.11 (m, 1H), 1.96 (s, 3H), 1.90-1.85 (m, 2H), 1.74-1.69 (m, 2H), 1.64-1.58 (m, 2H), 1.48-1.52 (m, 2H). |
| 22 | 530.50 | 4.50 | $^1$H NMR (400.0 MHz, MeOD) δ 7.56 (s, 1H), 7.29 (s, 1H), 6.97 (d, J = 8.7 Hz, 1H), 6.61 (d, |

TABLE 2-continued

| Compound No. | LC/MS M + 1 | LC/RT min | NMR |
|---|---|---|---|
| | | | J = 2.1 Hz, 1H), 6.55 (d, J = 8.8 Hz, 1H), 4.77 (q, J = 3.0, 7.2 Hz, 1H), 4.36 (q, J = 16.5 Hz, 2H), 3.68 (dd, J = 3.0, 12.1 Hz, 2H), 3.49-3.42 (m, 3H), 3.23 (dd, J = 7.5, 16.8 Hz, 2H), 2.02-1.99 (m, 6H), 1.81-1.67 (m, 4H), 1.59-1.52 (m, 2H). |
| 23 | 382.30 | 1.90 | $^1$H NMR (400.0 MHz, DMSO-d$_6$) δ 10.70 (br s, 1H), 9.83 (s, 1H), 7.48 (s, 1H), 7.21 (s, 1H), 6.69 (dd, J = 2.3, 9.8 Hz, 1H), 6.63-6.56 (m, 2H), 5.84 (s, 1H), 4.84 (dd, J = 3.0, 6.3 Hz, 1H), 3.48 (dt, J = 12.1, 3.8 Hz, 1H), 3.37 (dd, J = 2.6, 6.5 Hz, 1H), 3.20-3.10 (m, 1H), 1.95-1.88 (m, 2H), 1.74-1.70 (m, 2H), 1.65-1.49 (m, 4H). |
| 24 | 481.20 | 1.67 | — |
| 25 | 378.10 | 1.72 | — |
| 26 | 434.50 | 3.47 | — |
| 27 | 311.30 | 1.50 | $^1$H NMR (400.0 MHz, DMSO-d$_6$) δ 9.70 (s, 1H), 9.36 (s, 1H), 7.27 (d, J = 2.0 Hz, 1H), 6.90 (dd, J = 2.0, 8.3 Hz, 1H), 6.83 (dd, J = 1.2, 7.9 Hz, 1H), 6.72-6.65 (m, 1H), 6.60 (dd, J = 1.5, 7.9 Hz, 1H), 6.57-6.55 (m, 2H), 4.62 (dd, J = 2.8, 7.1 Hz, 1H), 3.48 (dt, J = 12.0, 3.8 Hz, 1H), 3.34-3.29 (m, 1H), 3.17 (d, J = 5.3 Hz, 1H), 2.03-1.96 (m, 1H), 0.83-0.79 (m, 2H), 0.56-0.52 (m, 2H). |
| 28 | 378.20 | 1.78 | — |
| 29 | 462.50 | 1.33 | $^1$H NMR (400.0 MHz, DMSO-d$_6$) δ 10.39 (s, 1H), 9.60 (s, 1H), 8.68 (s, 1H), 7.73 (s, 1H), 7.15 (s, 1H), 7.06-7.01 (m, 3H), 6.54 (s, 1H), 4.96 (q, J = 3.1 Hz, 1H), 3.80-3.72 (m, 1H), 3.54-3.52 (m, 2H), 3.45-3.43 (m, 2H), 3.27-3.23 (m, 2H), 3.05-2.94 (m, 2H), 2.83-2.79 (m, 4H), 1.94-1.91 (m, 2H), 1.76-1.73 (m, 2H), 1.63-1.60 (m, 2H), 1.43-1.41 (m, 2H). |
| 30 | 362.30 | 1.73 | $^1$H NMR (400.0 MHz, DMSO-d$_6$) δ 11.83 (d, J = 2.4 Hz, 1H), 9.99 (s, 1H), 8.12 (d, J = 1.5 Hz, 1H), 7.90 (q, J = 1.4 Hz, 1H), 7.52 (d, J = 8.4 Hz, 1H), 7.33 (dd, J = 1.8, 8.7 Hz, 1H), 6.87 (dd, J = 1.4, 7.9 Hz, 1H), 6.72 (t, J = 7.9 Hz, 1H), 6.61 (dd, J = 1.4, 7.9 Hz, 1H), 6.57 (t, J = 1.6, 7.9 Hz, 1H), 5.86 (br s, 1H), 4.70 (dd, J = 2.8, 7.1 Hz, 1H), 3.54 (dd, J = 2.8, 12.0 Hz, 1H), 2.55 (s, 1H). |
| 31 | 425.10 | 2.15 | $^1$H NMR (400.0 MHz, DMSO-d$_6$) δ 10.39 (s, 1H), 9.25 (s, 1H), 7.35 (s, 1H), 6.69 (dd, J = 2.2, 9.8 Hz, 1H), 6.64-6.56 (m, 3H), 4.85 (q, J = 3.0 Hz, 1H), 3.44 (dd, J = 3.0, 12.1 Hz, 1H), 3.34 (q, J = 6.1 Hz, 1H), 3.25-3.15 (m, 2H), 1.99-1.90 (m, 2H), 1.78-1.73 (m, 2H), 1.69-1.52 (m, 4H). |
| 32 | 491.30 | 2.34 | $^1$H NMR (400.0 MHz, DMSO-d$_6$) δ 10.38 (s, 1H), 9.25 (s, 1H), 7.35 (s, 1H), 7.23 (s, 1H), 6.87 (d, J = 8.7 Hz, 1H), 6.58 (d, J = 2.0 Hz, 1H), 6.49 (dd, J = 2.0, 8.7 Hz, 2H), 6.37 (s, 1H), 4.85 (q, J = 3.0 Hz, 1H), 3.51 (dd, J = 2.8, 9.4 Hz, 1H), 3.40-3.35 (m, 1H), 3.20 (dd, J = 9.4, 17.0 Hz, 1H), 1.94 (d, J = 5.4 Hz, 1H), 1.78-1.74 (m, 2H), 1.69-1.52 (m, 4H). |
| 33 | 345.10 | 1.88 | $^1$H NMR (400.0 MHz, DMSO-d$_6$) δ 9.85 (s, 1H), 9.39 (s, 1H), 7.24 (d, J = 2.1 Hz, 1H), 7.05 (d, J = 8.5 Hz, 1H), 6.89 (dd, J = 2.1, 8.4 Hz, 1H), 6.66 (td, J = 8.1, 4.6 Hz, 1H), 6.48-6.40 (m, 2H), 6.18 (br s, 1H), 4.69 (dd, J = 2.8, 6.6 Hz, 1H), 3.53 (dd, J = 2.8, 12.4 Hz, 1H), 3.42-3.36 (m, 1H), 1.32 (s, 9H). |
| 34 | 445.00 | 1.33 | $^1$H NMR (400.0 MHz, DMSO-d$_6$) δ 9.94 (s, 1H), 9.04 (s, 1H), 7.76 (s, 1H), 7.15 (s, 1H), 7.08-6.99 (m, 3H), 6.49 (s, 1H), 4.97 (q, J = 3.1 Hz, 1H), 3.57-3.52 (m, 1H), 3.47-3.44 (m, 3H), 3.13-3.10 (m, 1H), 2.23 (s, 6H), 1.89-1.86 (m, 2H), 1.73-1.69 (m, 2H), 1.61-1.58 (m, 2H), 1.50-1.46 (m, 2H). |
| 35 | 345.30 | 1.82 | $^1$H NMR (400.0 MHz, DMSO-d$_6$) δ 9.75 (s, 1H), 9.38 (s, 1H), 7.25 (d, J = 2.1 Hz, 1H), 7.04 (d, J = 8.5 Hz, 1H), 6.89 (dd, J = 2.1, 8.5 Hz, 1H), 6.73 (dd, J = 2.5, 10.0 Hz, 1H), 6.59-6.56 (m, 2H), 4.81 (br s, 1H), 4.70 (dd, J = 2.9, 6.6 |

TABLE 2-continued

| Compound No. | LC/MS M + 1 | LC/RT min | NMR |
|---|---|---|---|
| | | | Hz, 1H), 3.44 (d, J = 2.9 Hz, 1H), 3.33 (d, J = 6.5 Hz, 1H), 1.31 (s, 9H). |
| 36 | 368.20 | 1.06 | $^1$H NMR (400.0 MHz, DMSO-d$_6$) δ 9.20 (s, 1H), 8.05 (d, J = 12.0 Hz, 1H), 7.45 (d, J = 8.4 Hz, 1H), 6.91-6.89 (m, 1H), 6.75 (dd, J = 1.3, 15.1 Hz, 1H), 6.64-6.57 (m, 2H), 5.97 (s, 1H), 4.89 (dd, J = 3.2, 6.0 Hz, 1H), 3.55-3.39 (m, 4H), 2.25 (s, 3H), 2.18-2.15 (m, 6H). |
| 37 | 420.20 | 1.27 | — |
| 38 | 508.20 | 0.76 | $^1$H NMR (400.0 MHz, DMSO-d$_6$) δ 9.67 (s, 1H), 9.31 (s, 1H), 9.27 (s, 1H), 6.95 (s, 1H), 6.91 (d, J = 8.7 Hz, 1H), 6.78 (s, 1H), 6.61 (m, 1H), 6.50 (d, J = 8.0 Hz, 1H), 4.86 (dd, J = 3.3, 5.4 Hz, 1H), 3.53-3.49 (m, obscured by H$_2$O peak, 2H), 3.14 (quin, J = 7.7 Hz, 1H), 2.91-2.87 (m, 2H), 2.71-2.67 (d, 6H), 2.36-2.32 (m, 2H), 1.90 (m, 2H), 1.73 (d, J = 4.3 Hz, 4H), 1.61 (d, J = 5.1 Hz, 2H), 1.57-1.52 (m, 2H). |
| 39 | 432.70 | 2.04 | — |
| 40 | 476.30 | 4.09 | — |
| 41 | 435.50 | 1.33 | — |
| 42 | 347.30 | 1.40 | $^1$H NMR (400.0 MHz, DMSO-d$_6$) δ 8.11 (s, 1H), 7.48 (d, J = 2.3 Hz, 1H), 6.87 (d, J = 8.5 Hz, 1H), 6.78-6.72 (m, 2H), 6.63-6.56 (m, 2H), 5.61 (s, 1H), 4.74-4.72 (m, 1H), 4.63 (qn, J = 6.1 Hz, 1H), 3.76-3.72 (m, 2H), 3.51-3.47 (m, 1H), 1.39 (s, 6H). |
| 43 | 456.70 | 0.97 | $^1$H NMR (400.0 MHz, DMSO-d$_6$) δ 9.35 (s, 1H), 8.16 (s, 1H), 7.56 (dd, J = 2.0, 8.5 Hz, 1H), 7.50 (d, J = 8.7 Hz, 1H), 7.25 (d, J = 8.5 Hz, 1H), 6.96-6.92 (m, 2H), 5.17 (t, J = 4.5 Hz, 1H), 4.23 (s, 2H), 4.20 (q, J = 7.1 Hz, 2H), 4.10 (d, J = 4.4 Hz, 2H), 3.44 (d, J = 2.2 Hz, 2H), 2.23 (s, 6H), 1.62 (d, J = 7.0 Hz, 4H), 1.38 (d, J = 6.8 Hz, 4H), 1.24 (t, J = 7.1 Hz, 3H). |
| 44 | 448.40 | 3.33 | $^1$H NMR (400.0 MHz, MeOD) δ 7.80 (d, J = 8.4 Hz, 1H), 7.43 (d, J = 1.9 Hz, 1H), 7.33 (dd, J = 2.0, 8.4 Hz, 1H), 6.96 (d, J = 8.7 Hz, 1H), 6.60 (d, J = 2.1 Hz, 1H), 6.53 (dd, J = 1.8, 8.7 Hz, 1H), 4.79 (dd, J = 3.0, 7.2 Hz, 1H), 4.34 (q, J = 16.5 Hz, 2H), 3.68 (dd, J = 3.0, 12.1 Hz, 1H), 3.47 (dd, J = 7.1, 12.1 Hz, 1H), 3.08 (s, 6H), 2.64 (q, J = 7.6 Hz, 2H), 1.23 (t, J = 7.6 Hz, 3H). |
| 45 | 496.40 | 5.42 | — |
| 46 | 450.20 | 1.14 | — |
| 47 | 373.20 | 1.46 | $^1$H NMR (400.0 MHz, DMSO-d$_6$) δ 10.22 (s, 1H), 10.00 (s, 1H), 7.51 (d, J = 2.2 Hz, 1H), 7.19 (d, J = 8.6 Hz, 1H), 7.05 (dd, J = 2.3, 8.8 Hz, 1H), 6.74-6.71 (m, 1H), 6.61-6.54 (m, 2H), 5.80 (s, 1H), 4.74 (dd, J = 2.8, 6.2 Hz, 1H), 3.48-3.45 (m, 1H), 3.34 (d, J = 11.7 Hz, 1H). |
| 48 | 364.30 | 1.32 | $^1$H NMR (400.0 MHz, DMSO-d$_6$) δ 9.12 (s, 1H), 8.11 (d, J = 8.4 Hz, 1H), 7.29 (d, J = 1.5 Hz, 1H), 7.20 (d, J = 8.5 Hz, 1H), 6.77 (d, J = 8.1 Hz, 1H), 6.43-6.37 (m, 2H), 5.86 (s, 2H), 4.80 (q, J = 3.0 Hz, 1H), 3.53 (d, J = 10.4 Hz, 2H), 3.47-3.45 (m, 1H), 2.25-2.24 (m, 9H), 2.13 (s, 3H). |
| 49 | 363.50 | 1.90 | — |
| 50 | 382.50 | 1.89 | $^1$H NMR (400.0 MHz, DMSO-d$_6$) δ 10.66 (s, 1H), 9.84 (s, 1H), 7.48 (s, 1H), 7.21 (s, 1H), 6.69 (dd, J = 2.4, 9.8 Hz, 1H), 6.63-6.58 (m, 2H), 5.84 (s, 1H), 4.84 (dd, J = 2.9, 6.3 Hz, 1H), 3.48 (dt, J = 12.1, 3.8 Hz, 1H), 3.37 (dd, J = 2.6, 6.3 Hz, 1H), 3.17-3.13 (m, 1H), 1.91-1.88 (m, 2H), 1.76-1.73 (m, 2H), 1.65-1.51 (m, 4H). |
| 51 | 462.50 | 1.14 | — |
| 52 | 451.50 | 1.07 | — |
| 53 | 503.40 | 2.70 | $^1$H NMR (400.0 MHz, DMSO-d$_6$) δ 9.86 (s, 1H), 9.00 (s, 1H), 7.83 (s, 1H), 7.10 (s, 1H), 6.88 (d, J = 8.7 Hz, 1H), 6.61 (d, J = 2.0 Hz, 1H), 6.53 (d, J = 8.4 Hz, 1H), 6.41 (s, 1H), 4.87 (dd, J = 3.1, 6.4 Hz, 1H), 3.55-3.52 (m, 1H), 3.42-3.38 (m, 1H), 3.13-3.11 (m, 1H), 237 |

TABLE 2-continued

| Compound No. | LC/MS M + 1 | LC/RT min | NMR |
|---|---|---|---|
| | | | (d, J = 6.6 Hz, 2H), 1.90-1.82 (m, 3H), 1.73-1.70 (m, 2H), 1.61-1.58 (m, 2H), 1.50-1.43 (m, 2H), 0.97 (d, J = 6.6 Hz, 6H). |
| 54 | 491.30 | 2.34 | ¹H NMR (400.0 MHz, DMSO-d₆) δ 10.38 (s, 1H), 9.25 (s, 1H), 7.35 (s, 1H), 7.22 (s, 1H), 6.87 (d, J = 8.7 Hz, 1H), 6.58 (d, J = 2.0 Hz, 1H), 6.49 (dd, J = 2.1, 8.6 Hz, 1H), 6.36 (s, 1H), 4.85 (q, J = 3.0 Hz, 1H), 3.50 (dd, J = 2.8, 9.5 Hz, 1H), 3.41-3.35 (m, 1H), 3.20 (dd, J = 9.4, 17.0 Hz, 1H), 1.99-1.93 (m, 2H), 1.78-1.74 (m, 2H), 1.66-1.52 (m, 4H). |
| 55 | 303.30 | 1.42 | ¹H NMR (400.0 MHz, DMSO-d₆) δ 9.36 (s, 2H), 7.33 (d, J = 7.0 Hz, 1H), 6.96 (d, J = 11.3 Hz, 1H), 6.82 (d, J = 7.0 Hz, 1H), 6.71 (s, H), 6.71 (dd, J = 1.3, 15.1 Hz, 1H), 6.62 (dd, J = 1.5, 8 Hz, 1H), 6.53 (dd, J = 1.3, 15.1 Hz, 1H), 5.90 (s, 1H), 4.77 (dd, J = 2.9, 6.6 Hz, 1H), 3.50-3.47 (m, 1H), 3.37-3.33 (m, 1H), 2.07 (s, 3H). |
| 56 | 383.20 | 1.00 | ¹H NMR (400.0 MHz, DMSO-d₆) δ 9.76 (s, 1H), 8.02 (d, J = 7.4 Hz, 1H), 7.37 (s, 1H), 6.73 (dd, J = 2.7, 9.9 Hz, 1H), 6.67-6.58 (m, 2H), 4.94 (dd, J = 3.5, 5.3 Hz, 1H), 3.50-3.42 (m, 2H), 2.21 (s, 3H), 2.17 (s, 3H), 1.77-1.73 (m, 4H), 1.57-1.54 (m, 4H). |
| 57 | 339.30 | 1.55 | ¹H NMR (400.0 MHz, DMSO-d₆) δ 10.17 (s, 1H), 10.13 (s, 1H), 7.52 (s, 1H), 7.47 (s, 1H), 6.85 (dd, J = 1.4, 7.9 Hz, 1H), 6.76-6.69 (m; 1H), 6.72-6.69 (m, 2H), 6.61-6.53 (m, 1H), 5.90 (s, 1H), 4.70 (dd, J = 2.9, 6.7 Hz, 1H), 3.50 (dd, J = 2.6, 12.0 Hz, 1H), 3.34-3.32 (m, 1H). |
| 58 | 504.40 | 1.47 | ¹H NMR (400.0 MHz, DMSO-d₆) δ 9.95 (s, 1H), 9.04 (s, 1H), 7.83 (s, 1H), 7.15 (s, 1H), 6.97 (d, J = 8.7 Hz, 1H), 6.60 (d, J = 2.0 Hz, 1H), 6.53 (d, J = 8.3 Hz, 1H), 6.40 (s, 1H), 4.87 (q, J = 3.2 Hz, 1H), 3.52-3.48 (m, 2H), 3.27 (s, 2H), 3.14-3.12 (m, 1H), 2.23 (s, 6H), 1.90-1.87 (m, 2H), 1.61-1.49 (m, 4H), 0.90-0.86 (m, 2H). |
| 59 | 420.50 | 1.98 | ¹H NMR (400.0 MHz, DMSO-d₆) δ 9.18 (s, 1H), 9.07 (s, 1H), 7.06 (s, 1H), 6.98 (s, 2H), 6.68 (s, 1H), 6.44 (s, 1H), 4.92 (s, 1H), 3.51-3.46 (m, 3H), 3.17-3.15 (m, 1H), 1.90-1.88 (m, 2H), 1.70 (s, 2H), 1.61-1.55 (m, 4H), 1.18 (s, 9H). |
| 60 | 412.00 | 1.22 | — |
| 61 | 375.30 | 1.91 | ¹H NMR (400.0 MHz, DMSO-d₆) δ 9.47 (s, 1H), 9.35 (s, 1H), 7.29 (d, J = 7.0 Hz, 1H), 6.97 (d, J = 12.0 Hz, 1H), 6.71 (d, J = 2.4 Hz, 1H), 6.61-6.59 (m, 2H), 5.81 (s, 1H), 4.83 (q, J = 3.2 Hz, 1H), 3.46-3.36 (m, 2H), 3.19-3.10 (m, 1H), 1.91-1.89 (m, 2H), 1.76-1.71 (m, 2H), 1.67-1.58 (m, 2H), 1.55-1.51 (m, 2H). |
| 62 | 489.50 | 3.73 | — |
| 63 | 489.40 | 3.80 | — |
| 64 | 490.50 | 3.28 | — |
| 65 | 504.20 | 1.53 | ¹H NMR (400.0 MHz, DMSO-d₆) δ 9.95 (s, 1H), 9.04 (s, 1H), 7.82 (s, 1H), 7.15 (s, 1H), 6.97 (d, J = 8.7 Hz, 1H), 6.60 (d, J = 2.2 Hz, 1H), 6.54-6.51 (m, 1H), 6.40 (s, 1H), 4.87 (q, J = 3.2 Hz, 1H), 3.55-3.48 (m, 4H), 3.14-3.12 (m, 1H), 2.23 (s, 6H), 1.90-1.87 (m, 2H), 1.61-1.58 (m, 2H), 1.48-1.46 (m, 2H), 0.88-0.86 (m, 2H). |
| 66 | 473.10 | 1.83 | — |
| 67 | 384.30 | 1.37 | ¹H NMR (400.0 MHz, DMSO-d₆) δ 9.15 (s, 1H), 8.04 (d, J = 8.4 Hz, 1H), 7.30 (s, 1H), 7.20 (dd, J = 1.4, 8.4 Hz, 1H), 6.90 (d, J = 8.5 Hz, 1H), 6.65 (d, J = 2.5 Hz, 1H), 6.58 (dd, J = 2.5, 8.5 Hz, 1H), 6.29 (s, 1H), 4.85 (q, J = 3.1 Hz, 1H), 3.53-3.47 (m, 3H), 3.42-3.40 (m, 1H), 2.25 (s, 3H), 2.24 (s, 6H). |
| 68 | 403.20 | 2.10 | ¹H NMR (400.0 MHz, DMSO-d₆) δ 9.49 (s, 1H), 9.38 (s, 1H), 7.33 (d, J = 7.3 Hz, 1H), 6.95 (d, J = 13.4 Hz, 1H), 6.73 (dd, J = 2.1, 9.7 Hz, 1H), 6.62-6.55 (m, 2H), 5.81 (s, 1H), 4.84 (q, J = 3.0 Hz, 1H), 3.48-3.43 (m, 1H), 3.36-3.34 |

TABLE 2-continued

| Compound No. | LC/MS M + 1 | LC/RT min | NMR |
|---|---|---|---|
| | | | (m, 1H), 2.11-2.06 (m, 2H), 1.60-1.56 (m, 2H), 1.54-1.51 (m, 2H), 1.38-1.32 (m, 4H), 1.23 (s, 3H). |
| 69 | 518.60 | 3.04 | — |
| 70 | 395.00 | 2.03 | $^1$H NMR (400.0 MHz, DMSO-$d_6$) δ 9.80 (s, 1H), 9.38 (s, H), 7.21 (d, J = 2.2 Hz, 1H), 7.11 (d, J = 2.1 Hz, 1H), 7.04 (d, J = 8.5 Hz, 2H), 6.90-6.87 (m, 1H), 6.72-6.68 (m, 2H), 4.73 (dd, J = 3.4, 5.0 Hz, 1H), 3.58-3.51 (m, 1H), 3.45-3.40 (m, 2H), 1.30 (s, 9H). |
| 71 | 474.50 | 3.97 | — |
| 72 | 431.10 | 1.59 | $^1$H NMR (400.0 MHz, DMSO-$d_6$) δ 9.17 (s, 1H), 9.10 (s, 1H), 7.13 (d, J = 2.0 Hz, 1H), 7.09-7.03 (m, 2H), 6.91 (d, J = 6.5 Hz, 2H), 6.50 (s, 1H), 4.94-4.92 (m, 1H), 3.55-3.48 (m, 2H), 3.13 (q, J = 9.5 Hz, 1H), 3.07 (s, 3H), 1.96 (s, 3H), 1.88-1.85 (m, 2H), 1.74-1.72 (m, 2H), 1.61-1.58 (m, 2H), 1.53-1.49 (m, 2H). |
| 73 | 460.50 | 3.79 | — |
| 74 | 378.50 | 1.83 | $^1$H NMR (400.0 MHz, DMSO-$d_6$) δ 9.18 (s, 1H), 9.10 (s, 1H), 6.95 (s, 1H), 6.90 (s, 1H), 6.42 (s, 2H), 4.92 (dd, J = 3.2, 5.3 Hz, 1H), 3.54-3.43 (m, 2H), 3.15-3.12 (m, 1H), 1.95 (s, 3H), 1.91-1.83 (m, 2H), 1.74 (s, 2H), 1.71-1.68 (m, 2H), 1.61-1.58 (m, 2H), 1.55-1.46 (m, 2H). |
| 75 | 495.40 | 2.01 | $^1$H NMR (400.0 MHz, MeOD) δ 7.03 (d, J = 13.3 Hz, 2H), 6.94 (d, J = 8.7 Hz, 1H), 6.59-6.59 (m, 1H), 6.52-6.50 (m, 1H), 4.83 (dd, J = 3.2, 6.0 Hz, 1H), 3.67 (s, 3H), 3.63-3.52 (m, 2H), 3.29-3.22 (m, 3H), 2.00-1.96 (m, 2H), 1.85-1.78 (m, 2H), 1.73-1.56 (m, 4H), 1.31 (s, H). |
| 76 | 425.20 | 2.13 | $^1$H NMR (400.0 MHz, DMSO-$d_6$) δ 10.34 (s, 1H), 9.21 (s, 1H), 7.35 (s, 1H), 7.27 (s, 1H), 6.79 (dd, J = 5.5, 8.7 Hz, 2H), 6.41 (dd, J = 2.9, 10.4 Hz, 1H), 6.32 (td, J = 8.6, 3.8 Hz, 1H), 6.26 (s, 1H), 4.78 (dd, J = 2.7, 6.0 Hz, 1H), 3.50-3.47 (m, 1H), 3.20 (dd, J = 9.2, 16.9 Hz, 1H), 1.93-1.89 (m, 2H), 1.74-1.67 (m, 2H), 1.56-1.52 (m, 4H). |
| 77 | 345.20 | 1.70 | $^1$H NMR (400.0 MHz, DMSO-$d_6$) δ 9.74 (s, 1H), 9.37 (s, 1H), 7.25 (d, J = 2.1 Hz, 1H), 7.04 (d, J = 8.5 Hz, 1H), 6.88 (dd, J = 2.2, 8.4 Hz, 1H), 6.72 (dd, J = 2.4, 9.9 Hz, 1H), 6.58-6.56 (m, 2H), 5.78 (s, 1H), 4.69 (dd, J = 2.9, 6.6 Hz, 1H), 3.48-3.43 (m, 1H), 1.31 (s, 9H). |
| 78 | 345.10 | 1.74 | — |
| 79 | 518.40 | 1.37 | — |
| 80 | 385.20 | 2.12 | — |
| 81 | 438.40 | 2.77 | $^1$H NMR (400.0 MHz, MeOD) δ 7.16-7.11 (m, 3H), 6.99-6.96 (m, 1H), 6.60 (d, J = 2.6 Hz, 1H), 6.54-6.51 (m, 1H), 4.91 (dd, J = 3.2, 5.1 Hz, 1H), 3.63-3.59 (m, 2H), 2.94-2.90 (m, 2H), 2.79 (s, 6H), 2.51-2.47 (m, 2H), 2.32 (s, 3H), 1.85-1.81 (m, 2H). |
| 82 | 395.10 | 1.67 | $^1$H NMR (400.0 MHz, DMSO-$d_6$) δ 9.36 (s, 1H), 7.59 (s, 2H), 7.25 (s, 1H), 6.80-6.76 (m, 1H), 6.65-6.57 (m, 2H), 4.95-4.91 (m, 2H), 3.77 (s, 3H), 3.50-3.39 (m, 2H), 1.45 (s, 6H). |
| 83 | 345.20 | 1.70 | $^1$H NMR (400.0 MHz, DMSO-$d_6$) δ 9.74 (s, 1H), 9.38 (s, 1H), 7.25 (d, J = 2.1 Hz, 1H), 7.04 (d, J = 8.5 Hz, 1H), 6.88 (dd, J = 2.2, 8.4 Hz, 1H), 6.72 (dd, J = 2.4, 9.9 Hz, 1H), 6.59-6.56 (m, 2H), 6.57 (dd, J = 3.2, 5.7 Hz, 1H), 5.79 (s, 1H), 4.70 (dd, J = 2.8, 6.5 Hz, 1H), 3.44 (s, 1H), 1.31 (s, 9H). |
| 84 | 420.20 | 1.26 | $^1$H NMR (400.0 MHz, MeOD) δ 10.01 (s, 1H), 9.68 (s, 1H), 7.83 (s, 1H), 7.21 (s, 1H), 6.93 (d, J = 8.0 Hz, 1H), 6.81-6.79 (m, 1H), 6.72-6.69 (m, 2H), 4.76 (dd, J = 3.0, 7.0 Hz, 1H), 3.65 (dd, J = 3.0, 12.0 Hz, 1H), 3.55 (q, J = 10.4 Hz, 2H), 3.44 (dd, J = 7.0, 12.0 Hz, 1H), 3.26-3.23 (m, 1H), 2.36 (s, 6H), 1.99-1.94 (m, 2H), 1.81-1.80 (m, 2H), 1.73-1.71 (m, 2H), 1.59-1.55 (m, 2H). |

TABLE 2-continued

| Compound No. | LC/MS M + 1 | LC/RT min | NMR |
|---|---|---|---|
| 85 | 395.00 | 2.07 | ¹H NMR (400.0 MHz, DMSO-d$_6$) δ 9.59 (s, 1H), 9.39 (s, 1H), 7.21 (d, J = 2.2 Hz, 1H), 7.04 (d, J = 8.5 Hz, 1H), 6.84-6.80 (m, 4H), 6.34 (s, 1H), 4.86 (dd, J = 3.4, 5.0 Hz, 1H), 3.56-3.46 (m, 2H), 1.30 (s, 9H). |
| 86 | 317.10 | 1.49 | ¹H NMR (400.0 MHz, DMSO-d$_6$) δ 9.37 (s, 1H), 9.31 (s, 1H), 7.34 (d, J = 7.0 Hz, 1H), 6.97 (d, J = 11.3 Hz, 1H), 6.66 (s, 1H), 6.59-6.52 (m, 2H), 5.67 (s, 1H), 4.74 (dd, J = 2.9, 6.5 Hz, 1H), 3.46-3.42 (m, 1H), 3.33-3.28 (m, 1H), 2.15 (s, 3H), 2.07 (s, 3H). |
| 87 | 420.50 | 2.02 | ¹H NMR (400.0 MHz, DMSO-d$_6$) δ 9.18 (s, 1H), 9.06 (s, 1H), 7.06 (s, 1H), 6.98 (d, J = 3.4 Hz, 2H), 6.68 (s, 2H), 6.44 (s, 1H), 4.92 (dd, J = 3.2, 5.3 Hz, 1H), 3.51-3.49 (m, 2H), 3.16 (d, J = 7.8 Hz, 1H), 1.97-1.89 (m, 2H), 1.69 (s, 2H), 1.61-1.53 (m, 4H), 1.18 (s, 9H), 0.86 (s, 1H). |
| 88 | 378.10 | 1.72 | — |
| 89 | 406.30 | 2.03 | ¹H NMR (400.0 MHz, DMSO-d$_6$) δ 9.26 (s, 1H), 7.30 (d, J = 8.8 Hz, 1H), 6.82-6.79 (m, 2H), 6.73-6.70 (m, 2H), 6.62 (dd, J = 1.5, 7.9 Hz, 1H), 6.55 (t, J = 7.2 Hz, 1H), 4.67 (dd, J = 2.8, 7.3 Hz, 1H), 3.94-3.92 (m, 1H), 3.50 (dd, J = 2.9, 11.9 Hz, 1H), 3.42-3.39 (m, 1H), 3.27 (dd, J = 7.3, 12.0 Hz, 1H), 2.06-2.03 (m, 4H), 1.71-1.67 (m, 1H), 1.25 1.20 (m, 1H), 1.11 (d, J = 6.2 Hz, 3H). |
| 90 | 383.30 | 2.17 | — |
| 91 | 435.10 | 0.95 | — |
| 92 | 329.50 | 2.03 | — |
| 93 | 425.20 | 2.13 | ¹H NMR (400.0 MHz, DMSO-d$_6$) δ 10.34 (s, 1H), 9.21 (s, 1H), 7.35 (s, 1H), 7.27 (s, 1H), 6.79 (dd, J = 5.5, 8.7 Hz, 1H), 6.41 (dd, J = 3.0, 10.4 Hz, 1H), 6.32 (td, J = 8.6, 3.9 Hz, 1H), 6.26 (s, 1H), 4.78 (dd, J = 2.9, 6.3 Hz, 1H), 3.49 (dt, J = 12.1, 3.7 Hz, 1H), 3.37-3.35 (m, 1H), 3.20 (dd, J = 9.4, 17.1 Hz, 1H), 1.94-1.90 (m, 2H), 1.78-1.73 (m, 2H), 1.69-1.61 (m, 2H), 1.56-1.52 (m, 2H). |
| 94 | 359.00 | 2.08 | ¹H NMR (400.0 MHz, DMSO-d$_6$) δ 9.90 (s, 1H), 7.38 (d, J = 1.7 Hz, 1H), 7.18-7.11 (m, 2H), 6.74 (dd, J = 2.5, 9.9 Hz, 1H), 6.63-6.55 (m, 2H), 5.63 (br s, 1H), 4.74 (dd, J = 2.9, 6.5 Hz, 1H), 3.77 (s, 3H), 3.49 (dd, J = 2.9, 12.2 Hz, 1H), 3.34 (dd, J = 6.6, 12.2 Hz, 1H), 1.30 (s, 9H). |
| 95 | 518.40 | 1.53 | ¹H NMR (400.0 MHz, DMSO-d$_6$) δ 9.16 (s, 1H), 7.91 (s, 1H), 7.23 (s, 1H), 6.98 (d, J = 8.7 Hz, 1H), 6.60 (d, J = 2.2 Hz, 1H), 6.54-6.51 (m, 1H), 6.41 (s, 1H), 4.91 (q, J = 3.1 Hz, 1H), 3.79 (s, 3H), 3.57-3.50 (m, 3H), 3.46-3.41 (m, 1H), 3.20-3.14 (m, 1H), 3.16 (s, H), 2.24 (s, 6H), 1.94-1.90 (m, 2H), 1.73-1.70 (m, 2H), 1.62-1.59 (m, 2H), 1.51-1.44 (m, 2H). |
| 96 | 437.30 | 1.70 | — |
| 97 | 399.30 | 2.20 | ¹H NMR (400.0 MHz, DMSO-d$_6$) δ 9.39 (s, 1H), 9.33 (s, 1H), 7.38 (d, J = 7.3 Hz, 1H), 6.96 (s, 1H), 6.92 (s, 1H), 6.71 (d, J = 8.0 Hz, 1H), 6.42 (d, J = 1.4 Hz, 1H), 6.35 (dd, J = 1.6, 8.1 Hz, 1H), 5.83 (s, 1H), 4.74 (dd, J = 2.9, 6.5 Hz, 1H), 3.46 (dt, J = 12.0, 3.7 Hz, 1H), 2.15 (s, 3H), 2.13-2.06 (m, 2H), 1.57 (d, J = 10.1 Hz, 2H), 1.50 (d, J = 8.7 Hz, 2H), 1.42-1.35 (m, 4H), 1.23 (s, 3H). |
| 98 | 490.40 | 4.19 | ¹H NMR (400.0 MHz, MeOD) δ 7.65 (s, 1H), 7.28 (s, 1H), 6.97 (d, J = 8.7 Hz, 1H), 6.60 (s, 1H), 6.54 (dd, J = 1.8, 8.7 Hz, 1H), 4.78 (dd, J = 3.0, 7.0 Hz, 1H), 4.14 (dd, J=16.6, 27.1 Hz, 2H), 3.67 (dd, J = 3.0, 12.1 Hz, 1H), 3.49-3.44 (m, 1H), 3.24 (m, 1H), 2.79 (s, 3H), 2.05-1.92 (m, 2H), 1.81-1.77 (m, 2H), 1.71-1.68 (m, 2H), 1.54-1.51 (m, 2H). |
| 99 | 385.10 | 2.19 | ¹H NMR (400.0 MHz, DMSO-d$_6$) δ 9.40 (s, 2H), 7.37 (d, J = 7.3 Hz, 1H), 6.96 (s, 1H), 6.93 (s, 1H), 6.83 (dd, J = 1.2, 7.9 Hz, 1H), 6.73 (t, J = 8 Hz, 1H), 6.62 (dd, J = 1.5, 7.9 Hz, 1H), 6.56 (t, J = 8 Hz, 1H), 4.79 (dd, J = 2.9, 6.5 Hz, 1H), |

TABLE 2-continued

| Compound No. | LC/MS M + 1 | LC/RT min | NMR |
|---|---|---|---|
|  |  |  | 3.49 (dd, J = 3.0, 12.0 Hz, 1H), 3.38-3.33 (m, 1H), 2.08-2.00 (m, 2H), 1.58-1.50 (m, 2H), 1.48-1.36 (m, 6H), 1.23 (s, 3H). |
| 100 | 476.50 | 3.71 | — |
| 101 | 489.70 | 2.77 | — |
| 102 | 490.50 | 3.86 | — |
| 103 | 391.30 | 2.12 | $^1$H NMR (400.0 MHz, DMSO-$d_6$) δ 9.22 (s, 1H), 7.46 (s, 1H), 7.11 (s, 1H), 6.78-6.75 (m, 1H), 6.64-6.56 (m, 2H), 5.90 (s, 1H), 5.76 (s, 1H), 4.88 (dd, J = 3.1, 5.5 Hz, 1H), 3.46-3.36 (m, 2H), 3.19-3.10 (m, 1H), 1.91-1.89 (m, 2H), 1.76-1.71 (m, 2H), 1.67-1.58 (m, 2H), 1.55-1.51 (m, 2H). |
| 104 | 431.50 | 1.11 | $^1$H NMR (400.0 MHz, DMSO-$d_6$) δ 10.22 (s, 1H), 9.27 (s, 1H), 7.58 (d, J = 8.7 Hz, 1H), 7.07 (dd, J = 2.6, 13.2 Hz, 2H), 6.87-6.85 (m, 1H), 6.74 (dd, J = 1.3, 15.1 Hz, 1H), 6.74 (s, 1H), 6.65-6.55 (m, 2H), 4.75 (dd, J = 2.9, 6.6 Hz, 1H), 4.34 (d, J = 7.2 Hz, 2H), 4.32 (s, 1H), 3.50 (dd, J = 3.0, 12.0 Hz, 1H), 3.36 (dd, J = 6.7, 12.0 Hz, 1H), 2.89 (s, 6H), 1.64 (d, J = 7.4 Hz, 4H), 1.42 (d, J = 6.9 Hz, 4H). |
| 105 | 501.40 | 1.04 | $^1$H NMR (400.0 MHz, DMSO-$d_6$) δ 10.08 (s, 1H), 9.99 (s, 1H), 8.14 (s, 1H), 7.28 (s, 1H), 6.89 (d, J = 8.7 Hz, 1H), 6.58 (s, 1H), 6.55-6.52 (m, 1H), 6.36 (s, 1H), 4.96-4.94 (m, 1H), 3.54-3.45 (m, 2H), 3.29-3.23 (m, 1H), 2.96 (s, 3H), 1.98-1.95 (m, 2H), 1.80-1.72 (m, 2H), 1.68-1.63 (m, 2H), 1.52-1.49 (m, 2H). |
| 106 | 504.20 | 0.77 | — |
| 107 | 341.00 | 1.89 | — |
| 108 | 469.40 | 2.36 | $^1$H NMR (400.0 MHz, DMSO-$d_6$) δ 9.51 (s, 1H), 9.38 (s, 1H), 7.34 (d, J = 7.3 Hz, 1H), 6.93-6.87 (m, 2H), 6.57 (d, J = 2.1 Hz, 1H), 6.47 (dd, J = 2.0, 8.7 Hz, 1H), 6.34 (s, 1H), 4.82 (q, J = 3.1 Hz, 1H), 3.52 (d, J = 12.9 Hz, 1H), 3.38 (d, J = 6.5, 12.4 Hz, 1H), 2.10-2.05 (m, 2H), 1.57-1.55 (m, 2H), 1.50-1.49 (m, 2H), 1.42-1.35 (m, 4H), 1.23 (s, 3H). |
| 109 | 373.20 | 1.50 | — |
| 110 | 429.40 | 4.06 | — |
| 111 | 461.40 | 2.87 | $^1$H NMR (400.0 MHz, MeOD) δ 7.09 (d, J = 1.8 Hz, 3H), 7.02 (s, 1H), 6.63 (d, J = 1.6 Hz, 1H), 5.11 (dd, J = 3.2, 4.6 Hz, 1H), 3.64 (dd, J = 4.7, 12.0 Hz, 1H), 3.49-3.38 (m, 3H), 3.26 (q, obscured by solvent peak, J = 9.2 Hz, 1H), 2.95 (s, 3H), 2.74-2.64 (m, 3H), 1.98-1.93 (m, 2H), 1.84-1.58 (m, 10H). |
| 112 | 347.00 | 1.54 | $^1$H NMR (400.0 MHz, DMSO-$d_6$) δ 9.54 (s, 1H), 8.97 (s, 1H), 7.73 (dd, J = 1.4, 8.2 Hz, 1H), 6.85 (t, J = 8.2 Hz, 1H), 6.78-6.75 (m, 1H), 6.64-6.61 (m, 3H), 5.87 (s, 1H), 4.91 (t, J = 4.2 Hz, 1H), 4.57 (qn, J = 6.1 Hz, 1H), 3.41 (dd, J = 2.6, 4.0 Hz, 2H), 2.08 (s, H), 1.21 (d, J = 6.1 Hz, 3H), 1.02 (d, J = 6.1 Hz, 3H). |
| 113 | 447.40 | 2.40 | $^1$H NMR (400.0 MHz, MeOD) δ 6.99 (d, J = 8.4 Hz, 1H), 6.95-6.91 (m, 2H), 6.91 (s, 1H), 6.55 (s, 1H), 4.92 (dd, J = 3.2, 4.7 Hz, 1H), 3.62-3.57 (m, 1H), 3.49-3.45 (m, 1H), 3.32-3.29 (m, 2H), 3.25-3.16 (m, 1H), 2.78-2.72 (m, 2H), 2.68-2.60 (m, 1H), 1.92-1.81 (m, 2H), 1.72-1.48 (m, 10H). |
| 114 | 379.20 | 2.21 | $^1$H NMR (400.0 MHz, MeOD) δ 7.79 (dd, J = 5.1, 9.0 Hz, 1H), 7.40 (dd, J = 3.0, 8.6 Hz, 1H), 7.31-7.26 (m, 1H), 7.08-7.02 (m, 3H), 4.93 (dd, J = 3.1, 6.7 Hz, 1H), 4.35 (q, J = 16.5 Hz, 2H), 3.71 (dd, J = 3.1, 12.2 Hz, 1H), 3.56-3.52 (m, 1H), 3.03 (s, 6H). |
| 115 | 341.2 | 2.59 | $^1$H NMR (400.0 MHz, DMSO-$d_6$) δ 9.80 (s, 1H), 7.18 (d, J = 8.7 Hz, 1H), 6.76 (d, J = 1.4 Hz, 2H), 6.66 (m, 2H), 6.52-6.48 (m, 2H), 4.36 (d, J = 6.2 Hz, 1H), 4.07 (br s, 2H), 3.32 (d, J = 11.4 Hz, 1H), 3.21 (m, 4H), 1.33 (s, 9H). |
| 116 | 466.2 | 1.32 | $^1$H NMR (400.0 MHz, DMSO-$d_6$) δ 9.46 (s, 1H), 7.23 (d, J = 8.0 Hz, 1H), 7.06 (s, 1H), 7.01 (d, J = 8.1 Hz, 1H), 6.88 (d, J = 8.7 Hz, 1H), 6.58 (d, J = 2.1 Hz, 1H), 6.49 (dd, J = 2.2, 8.6 |

TABLE 2-continued

| Compound No. | LC/MS M + 1 | LC/RT min | NMR |
|---|---|---|---|
| | | | Hz, 1H), 6.36 (s, 1H), 4.79 (dd, J = 3.0, 6.3 Hz, 1H), 3.54 (t, J = 4.5 Hz, 5H), 3.44-3.39 (m, 1H), 2.62-2.58 (m, 2H), 2.39-2.35 (m, 6H), 2.26 (s, 3H). |
| 117 | 534.5 | 1.7 | $^1$H NMR (400.0 MHz, DMSO-d$_6$) δ 10.79 (s, 1H), 9.29 (s, 1H), 7.70 (s, 1H), 6.86 (d, J = 9.9 Hz, 2H), 6.61 (d, J = 1.9 Hz, 1H), 6.49 (d, J = 8.9 Hz, 1H), 6.44 (s, 1H), 4.63 (dd, J = 2.7, 7.8 Hz, 1H), 3.60 (m, 1H), 3.40 (dd, J = 13.1, 25.1 Hz, 2H), 3.35-3.27 (m, 1H), 3.14-3.10 (m, 1H), 2.78 (d, J = 11.1 Hz, 1H), 2.69 (d, J = 11.4 Hz, 1H), 1.87 (m, 4H), 1.72 (m, 2H), 1.59 (m, 2H), 1.50 (m, 4H), 1.31 (br s, 1H), 1.07-1.02 (m, 2H), 0.78 (d, J = 6.4 Hz, 3H). |
| 118 | 494.5 | 1.51 | $^1$H NMR (400.0 MHz, DMSO-d$_6$) δ 10.80 (s, 1H), 9.33 (s, 1H), 7.70 (s, 1H), 6.87-6.84 (m, 2H), 6.61 (d, J = 2.0 Hz, 1H), 6.45 (s, 1H), 4.63 (dd, J = 2.7, 7.9 Hz, 1H), 3.61 (m, 1H), 3.40 (d, J = 10.4 Hz, 2H), 3.35-3.30 (m, 2H), 2.79 (d, J = 11.8 Hz, 1H), 2.70 (d, J = 10.7 Hz, 1H), 2.45 (q, J = 7.5 Hz, 2H), 1.87 (m, 2H), 1.50 (d, J = 11.4 Hz, 2H), 1.30 (br s, 1H), 1.08 (t, J = 7.5 Hz, 3H), 1.10-1.00 (m, 2H), 0.78 (d, J = 6.5 Hz, 3H). |
| 119 | 468.4 | 1.22 | — |
| 120 | 343.2 | 1.77 | $^1$H NMR (400.0 MHz, DMSO-d$_6$) δ 10.07 (s, 1H), 9.38 (s, 1H), 7.20 (d, J = 2.0 Hz, 1H), 7.03 (d, J = 8.4 Hz, 1H), 6.93 (dd, J = 1.1, 7.7 Hz, 1H), 6.88-6.83 (m, 2H), 6.58 (d, J = 7.5 Hz, 1H), 6.51-6.47 (t, J = 7.5 Hz, 1H), 3.92 (dd, J = 3.0, 8.0 Hz, 1H), 3.72 (dd, J = 3.0, 12.3 Hz, 1H), 3.53 (dd, J = 8.1, 12.3 Hz, 1H), 1.31 (s, 9H). |
| 121 | 375 | 1.57 | — |
| 122 | 327 | 1.8 | — |
| 123 | 438.7 | 0.66 | — |
| 124 | 452.4 | 1.24 | — |
| 125 | 359.2 | 1.4 | — |
| 126 | 480.5 | 1.36 | $^1$H NMR (400.0 MHz, DMSO-d$_6$) δ 10.79 (s, 1H), 9.35 (s, 1H), 7.71 (s, 1H), 6.87-6.84 (m, 2H), 6.61 (d, J = 2.1 Hz, 1H), 6.49 (dd, J = 2.2, 8.5 Hz, 1H), 6.45 (s, 1H), 4.63 (dd, J = 2.7, 7.9 Hz, 1H), 3.62-3.59 (m, 1H), 3.38 (d, J = 8.5 Hz, 2H), 3.33-3.30 (m, 1H), 2.78 (d, J = 11.2 Hz, 1H), 2.70 (d, J = 10.4 Hz, 1H), 2.04 (s, 3H), 1.89-1.84 (m, 2H), 1.50 (d, J = 12.3 Hz, 2H), 1.31 (br s, 1H), 1.07-1.02 (m, 2H), 0.78 (d, J = 6.5 Hz, 3H). |
| 127 | 448.3 | 1.53 | $^1$H NMR (400.0 MHz, DMSO-d$_6$) δ 9.22 (s, 1H), 7.83 (s, 1H), 7.28 (s, 1H), 6.94 (d, J = 8.7 Hz, 1H) 6.60 (d, J = 2.0 Hz, 1H), 6.51 (dd, J = 2.2, 8.4 Hz, 1H), 6.39 (s, 1H), 4.86-4.84 (m, 1H), 3.76 (br s, 1H), 3.55 (m, 1H), 3.35 (m, 2H), 2.43 (s, 6H), 2.23 (s, 3H), 2.18 (s, 3H). |
| 128 | 505.4 | 2.38 | $^1$H NMR (400.0 MHz, DMSO-d$_6$) δ 10.34 (s, 1H), 8.97 (s, 1H), 7.31 (s, 1H), 7.23 (s, 1H), 6.89 (d, J = 8.7 Hz, 1H), 6.58 (d, J = 2.0 Hz, 1H), 6.52-6.49 (dd, J = 8.7 Hz, 2.3 Hz, 1H), 4.59 (br s, 2H), 3.62 (d, J = 12.0 Hz, 1H), 3.17 (quin, J = 7.5 Hz, 1H), 3.08 (d, J = 12.0 Hz, 1H), 1.95-1.91 (m, 2H), 1.77-1.71 (m, 2H), 1.64-1.59 (m, 2H), 1.55-1.45 (m, 2H), 1.50 (s, 3H). |
| 129 | 478 | 1.33 | $^1$H NMR (400.0 MHz, DMSO-d$_6$) δ 11.43 (s, 1H), 8.55 (d, J = 8.6 Hz, 1H), 7.96 (d, J = 1.6 Hz, 1H), 7.53 (dd, J = 1.9, 8.7 Hz, 1H), 7.22 (d, J = 8.7 Hz, 1H), 6.60 (d, J = 2.0 Hz, 1H), 6.52 (dd, J = 2.0, 8.6 Hz, 1H), 6.42 (s, 1H), 4.87 (dd, J = 3.0, 7.0 Hz, 1H), 3.70 (d, J = 1.7 Hz, 2H), 3.60 (dt, J = 12.2, 3.8 Hz, 1H), 3.43-3.38 (m, 1H), 2.38 (s, 3H), 2.25 (s, 6H). |

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, CaCl$_2$ 2, MgCl$_2$ 1, HEPES 10, pH 7.4 with NaOH.

Chloride-Free Bath Solution: Chloride Salts in Bath Solution #1 are Substituted with Gluconate Salts.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours. Electrophysiological Assays for assaying ΔF508-CFTR modulation properties of compounds.

1. Ussing Chamber Assay

Ussing chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large concentration gradient across the epithelium. Forskolin (10 µM) and all test compounds were added to the apical side of the cell culture inserts. The efficacy of the putative ΔF508-CFTR potentiators was compared to that of the known potentiator, genistein.

2. Patch-Clamp Recordings

Total Cl current in ΔF508-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 µg/ml amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 µM forskolin and 20 µM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing 2 active channels. The maximum number of simultaneous openings determined the number of active channels during the course of an experiment. To determine the single-channel current amplitude, the data recorded from 120 sec of ΔF508-CFTR activity was filtered "off-line" at Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Compounds of the invention are useful as modulators of ATP binding cassette transporters. Examples of activities and efficacies of the compounds of Formula I are shown below in Table 3. The compound activity is illustrated with "+++" if activity was measured to be less than 5.0 μM, "++" if activity was measured to be from 5 μM to 20.0 μM, "+" if activity was measured to be greater than 20.0 μM, and "−" if no data was available. The efficacy is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with 4-methyl-2-(5-phenyl-1H-pyrazol-3-yl)phenol.

TABLE 3

| Compound No. | Activity, $EC_{50}$ (μm) | % Efficacy |
|---|---|---|
| 1 | ++ | + |
| 2 | +++ | ++ |
| 3 | +++ | ++ |
| 4 | +++ | +++ |
| 5 | ++ | + |
| 6 | +++ | ++ |
| 7 | +++ | ++ |
| 8 | +++ | ++ |
| 9 | +++ | ++ |
| 10 | ++ | + |
| 11 | ++ | ++ |
| 12 | +++ | ++ |
| 13 | +++ | +++ |
| 14 | ++ | + |
| 15 | +++ | ++ |
| 16 | +++ | ++ |
| 17 | +++ | ++ |
| 18 | +++ | ++ |
| 19 | +++ | ++ |
| 20 | +++ | ++ |
| 21 | +++ | ++ |
| 22 | +++ | +++ |
| 23 | +++ | ++ |
| 24 | +++ | +++ |
| 25 | +++ | ++ |
| 26 | +++ | ++ |
| 27 | +++ | ++ |
| 28 | ++ | ++ |
| 29 | ++ | + |
| 30 | ++ | ++ |
| 31 | +++ | ++ |
| 32 | +++ | ++ |
| 33 | +++ | ++ |
| 34 | +++ | ++ |
| 35 | +++ | ++ |
| 36 | ++ | ++ |
| 37 | +++ | ++ |
| 38 | +++ | ++ |
| 39 | +++ | ++ |
| 40 | +++ | ++ |
| 41 | +++ | ++ |
| 42 | ++ | + |
| 43 | +++ | ++ |
| 44 | +++ | +++ |
| 45 | +++ | ++ |
| 46 | +++ | +++ |
| 47 | +++ | ++ |
| 48 | +++ | ++ |
| 49 | +++ | ++ |
| 50 | +++ | ++ |
| 51 | ++ | ++ |
| 52 | +++ | ++ |
| 53 | +++ | ++ |
| 54 | +++ | ++ |
| 55 | +++ | ++ |
| 56 | ++ | ++ |
| 57 | +++ | ++ |
| 58 | +++ | +++ |
| 59 | +++ | ++ |
| 60 | +++ | ++ |
| 61 | +++ | ++ |
| 62 | +++ | ++ |
| 63 | +++ | ++ |
| 64 | +++ | ++ |
| 65 | +++ | +++ |
| 66 | +++ | ++ |
| 67 | +++ | ++ |
| 68 | +++ | ++ |
| 69 | ++ | ++ |
| 70 | +++ | ++ |
| 71 | +++ | ++ |
| 72 | +++ | ++ |
| 73 | +++ | ++ |
| 74 | +++ | ++ |
| 75 | +++ | +++ |
| 76 | +++ | ++ |
| 77 | +++ | ++ |
| 78 | +++ | ++ |
| 79 | +++ | +++ |
| 80 | +++ | ++ |
| 81 | ++ | ++ |
| 82 | +++ | ++ |
| 83 | +++ | ++ |
| 84 | +++ | ++ |
| 85 | +++ | ++ |
| 86 | +++ | ++ |
| 87 | +++ | ++ |
| 88 | +++ | ++ |
| 89 | +++ | ++ |
| 90 | +++ | ++ |
| 91 | +++ | ++ |
| 92 | +++ | ++ |
| 93 | +++ | ++ |

TABLE 3-continued

| Compound No. | Activity, $EC_{50}$ (μm) | % Efficacy |
|---|---|---|
| 94 | +++ | ++ |
| 95 | +++ | +++ |
| 96 | +++ | ++ |
| 97 | +++ | ++ |
| 98 | +++ | ++ |
| 99 | +++ | ++ |
| 100 | +++ | +++ |
| 101 | ++ | + |
| 102 | ++ | ++ |
| 103 | +++ | ++ |
| 104 | ++ | ++ |
| 105 | ++ | +++ |
| 106 | +++ | +++ |
| 107 | +++ | ++ |
| 108 | +++ | ++ |
| 109 | ++ | ++ |
| 110 | +++ | ++ |
| 111 | ++ | + |
| 112 | ++ | ++ |
| 113 | ++ | + |
| 114 | ++ | ++ |
| 115 | +++ | ++ |
| 116 | +++ | ++ |
| 117 | +++ | +++ |
| 118 | +++ | +++ |
| 119 | ++ | ++ |
| 120 | +++ | ++ |
| 121 | +++ | ++ |
| 122 | − | − |
| 123 | +++ | ++ |
| 124 | +++ | ++ |
| 125 | +++ | + |
| 126 | +++ | +++ |
| 127 | +++ | ++ |
| 128 | +++ | ++ |
| 129 | +++ | ++ |

What is claimed is:

1. A method of treating or lessening the severity of a disease in a patient, wherein said disease is selected from cystic fibrosis, hereditary emphysema, COPD, or dry-eye disease, said method comprising the step of administering to said patient an effective amount of a compound of Formula I:

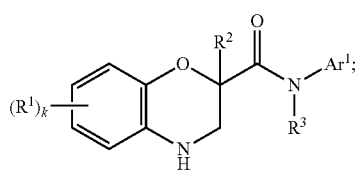

or a pharmaceutically acceptable salt thereof, wherein:

$Ar^1$ is a 5-6 membered aromatic monocyclic ring having 0-4 heteroatoms independently selected from nitrogen, oxygen, or sulfur, wherein said ring is optionally fused to a 5-12 membered monocyclic or bicyclic, aromatic ring, wherein each ring contains 0-4 heteroatoms independently selected from nitrogen, oxygen, or sulfur, wherein $Ar^1$ has m substituents, each independently selected from —$WR^W$;

W is a bond or is an optionally substituted $C_1$-$C_6$ alkylidene chain wherein up to two methylene units of W are optionally and independently replaced by O, —CO—, —CS—, —COCO—, —CONR'—, —CONR'NR'—, —$CO_2$—, —OCO—, —$NR'CO_2$—, —O—, —NR'CONR'—, —C(O)NR'—, —OCONR'—, —NR'NR', —NR'NR'CO—, —NR'CO—, —S—, —SO, —$SO_2$—, —NR'—, —$SO_2NR'$—, $NR'SO_2$—, or —$NR'SO_2NR'$—;

$R^W$ is independently R', halo, $NO_2$, CN, $CF_3$, $OCF_3$, an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or a 7-12 membered saturated, partially unsaturated, or fully unsaturated bicyclic ring system having 0-5 heteroatoms independently selected from nitrogen, oxygen, or sulfur;

m is 0-5;

k is 0-3;

each $R^1$ is independently —X—$R^x$;

X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —$CO_2$—, —OCO—, —$NR'CO_2$—, —O—, —NR'CONR'—, —OCONR'—, —NR'NR', —NR'NR'CO—, —NR'CO—, —S—, —SO, —$SO_2$—, —NR'—, —$SO_2NR'$—, $NR'SO_2$—or —$NR'SO_2NR'$—;

$R^x$ is independently halo, $NO_2$, CN, $CF_3$, $OCF_3$, $OCH_3$, an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or a 7-12 membered saturated, partially unsaturated, or fully unsaturated bicyclic ring system having 0-5 heteroatoms independently selected from nitrogen, oxygen, or sulfur;

$R^2$ is hydrogen, halo, or a $C_1$-$C_6$ aliphatic group optionally substituted with —X—$R^x$;

$R^3$ is hydrogen or a $C_1$-$C_6$ aliphatic group optionally substituted with —X—$R^x$;

R' is independently selected from hydrogen, an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or a 7-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

2. The method according to claim 1, wherein said disease is cystic fibrosis.

3. A kit for use in measuring the activity of CFTR or a fragment thereof in a biological sample in vitro or in vivo, comprising:

(i) a composition comprising a compound of Formula I according to claim 1;

(ii) instructions for:
  a) contacting the composition with the biological sample;
  b) measuring activity of said CFTR or a fragment thereof.

4. The kit of claim 3, further comprising instructions for:
  a) contacting an additional compound with the biological sample;
  b) measuring the activity of said CFTR or a fragment thereof in the presence of said additional compound, and c) comparing the activity of said CFTR or a fragment thereof in the presence of said additional compound with the activity of said CFTR or a fragment thereof in the presence of a composition of Formula I.

5. The kit according to claim 4, wherein the step of comparing the activity of said CFTR or a fragment thereof provides a measure of the density of said CFTR or a fragment thereof.

6. The method according to claim 1, wherein $Ar^1$ is selected from:

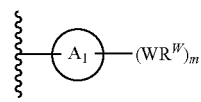

a-i wherein ring $A_1$ 5-6 membered aromatic monocyclic ring having 0-4 heteroatoms independently selected from nitrogen, oxygen, or sulfur.

7. The method according to claim 6, wherein $A_1$ is an optionally substituted 6 membered aromatic ring having 0-4 heteroatoms, wherein said heteroatom is nitrogen.

8. The method according to claim 6, wherein $A_1$ is phenyl.

9. The method according to claim 6, wherein said compound has Formula IIA:

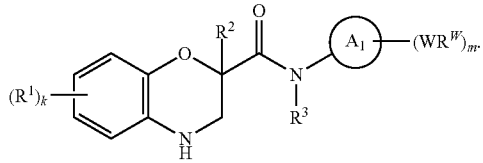

IIA

10. The method according to claim 6, wherein said compound has Formula IIIA,

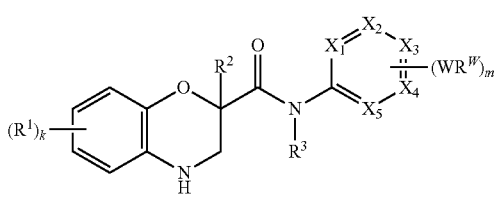

IIIA wherein:
each of $X_1$, $X_2$, $X_3$, $X_4$, and $X_5$ is independently selected from CH or N.

11. The method according to claim 10, wherein $X_1$, $X_2$, $X_3$, $X_4$, and $X_5$ taken together in compound of Formula IIIA is a ring selected from pyridyl, pyrazinyl, or pyrimidinyl.

12. The method according to claim 10, wherein said compound has Formula IIIA-1:

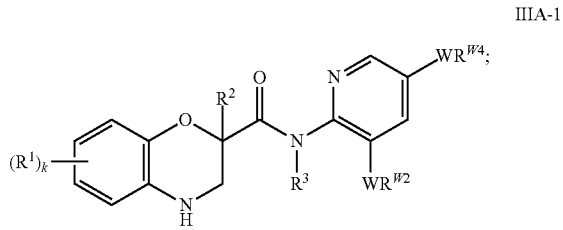

IIIA-1 wherein each of $WR^{W2}$ and $WR^{W4}$ is independently selected from CN, $CF_3$, $OCF_3$, $-OC_1-C_3$ aliphatic, $-C\equiv CCH_2N(R')(R')$, halo, $C_1$-$C_6$ straight or branched aliphatic, 3-12 membered cycloaliphatic, phenyl, 3-12 membered bicyclic, $C_5$-$C_{10}$ heteroaryl or $C_3$-$C_7$ heterocyclic, wherein said bicyclic, heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')(R')$, —$(CH_2)_2OR'$, —$(CH_2)OR'$, $CH_2CN$, —$N(R')(R')$, —$NR'C(O)OR'$, —$NR'C(O)R'$, —$(CH_2)_2N(R')(R')$, —$(CH_2)N(R')(R')$ optionally substituted phenyl or phenoxy, or optionally substituted $C_3$-$C_7$ heterocyclic, wherein said heterocyclic has up to 3 heteroatoms selected from O, S, or N.

13. The method according to claim 10, wherein said compound has the Formula IIIA-2:

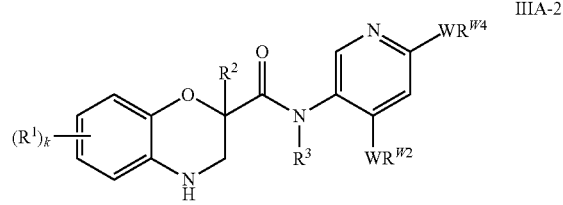

IIIA-2 wherein each of $WR^{W2}$ and $WR^{W4}$ is independently selected from CN, $CF_3$, $OCF_3$, —$OC_1$—$C_3$ aliphatic, —$C\equiv CCH_2N(R')(R')$, halo, $C_1$-$C_6$ straight or branched aliphatic, 3-12 membered cycloaliphatic, phenyl, 3-12 membered bicyclic, $C_5$-$C_{10}$ heteroaryl or $C_3$-$C_7$ heterocyclic, wherein said bicyclic, heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')(R')$, —$(CH_2)_2OR'$, —$(CH_2)OR'$, $CH_2CN$, —$N(R')(R')$, —$NR'C(O)OR'$, —$NR'C(O)R'$, —$(CH_2)_2N(R')(R')$, —$(CH_2)N(R')(R')$ optionally substituted phenyl or phenoxy, or optionally substituted $C_3$-$C_7$ heterocyclic, wherein said heterocyclic has up to 3 heteroatoms selected from O, S, or N.

14. The method according to claim 10, wherein said compound has the Formula IIIA-3:

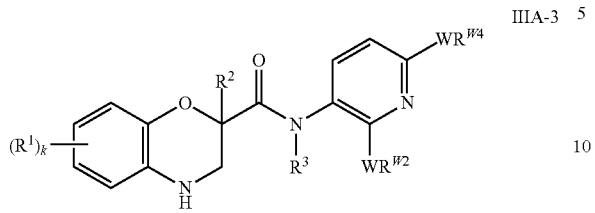

wherein each of $WR^{W2}$ and $WR^{W4}$ is independently selected from CN, $CF_3$, $OCF_3$, —$OC_1$—$C_3$ aliphatic, —C≡$CCH_2N(R')(R')$, halo, $C_1$-$C_6$ straight or branched aliphatic, 3-12 membered cycloaliphatic, phenyl, 3-12 membered bicyclic, $C_5$-$C_{10}$ heteroaryl or $C_3$-$C_7$ heterocyclic, wherein said bicyclic, heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')(R')$, —$(CH_2)_2OR'$, —$(CH_2)OR'$, $CH_2CN$, —$N(R')(R')$, —NR'C(0)OR', —NR'C(O)R', —$(CH_2)_2N(R')(R')$, —$(CH_2)N(R')(R')$ optionally substituted phenyl or phenoxy, or optionally substituted $C_3$-$C_7$ heterocyclic, wherein said heterocyclic has up to 3 heteroatoms selected from O, S, or N.

15. The method according to claim 6, wherein said compound has Formula IVA.

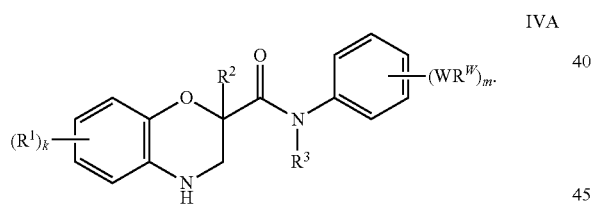

16. The method according to claim 15, wherein said compound has Formula VA-1A:

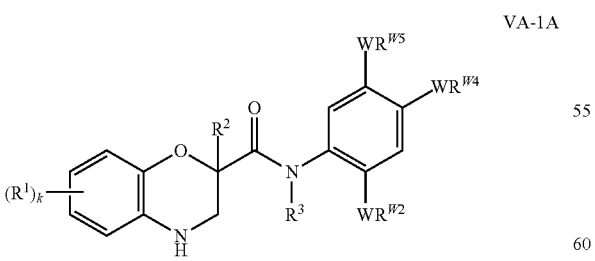

wherein each of $WR^{W2}$ and $WR^{W4}$ is independently selected from CN, $CF_3$, $OCF_3$, —$SO_2R'$, —$OC_1$-$C_3$ aliphatic, —C≡$CCH_2N(R')(R')$, halo, $C_1$-$C_6$ straight or branched aliphatic, 3-12 membered cycloaliphatic, phenyl, $C_5$-$C_{10}$ heteroaryl or $C_3$-$C_7$ heterocyclic, wherein said heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(0)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')$ (R'), —$(CH_2)_2OR'$, —$(CH_2)OR'$, $CH_2CN$, —$N(R')(R')$, —NR'C(0)OR', —NR'C(0)R', —$(CH_2)_3N(R')(R')$, —$(CH_2)_2N(R')(R')$, —$(CH_2)N(R')(R')$, optionally substituted phenyl or phenoxy, or optionally substituted $C_3$-$C_7$ heterocyclic, wherein said heterocyclic has up to 1 heteroatom selected from O, S, or N and $WR^{W5}$ is selected from halo, —OH, OR', —$OCF_3$, $NH_2$, CN, $CHF_2$, NHR', $N(R')_2$, —NHC(O)R', —NHC(O)OR', $NHSO_2R'$, —OR', $CH_2OH$, $CH_2N(R')_2$, C(O)OR', $C(O)N(R')_2$, $SO_2NHR'$, $SO_2N(R')_2$, $OSO_2N(R')_2$, $OSO_2CF_3$, optionally substituted $C_1$-$C_6$ straight or branched aliphatic, optionally substituted 3-12 membered cycloaliphatic, or $CH_2NHC(O)OR'$.

17. The method according to claim 16, wherein $WR^{W4}$ is a $C_1$-$C_6$ straight or branched aliphatic, or a 3-12 membered cycloaliphatic, $WR^{W5}$ is —OH or OR' and $WR^{W2}$ is —C≡$CCH_2N(R')(R')$, —$(CH_2)_3N(R')(R')$, —$(CH_2)_2N(R')$ (R'), —$(CH_2)N(R')(R')$ or —$N(R')(R')$.

18. The method according to claim 15, wherein said compound has the Formula VA-1B:

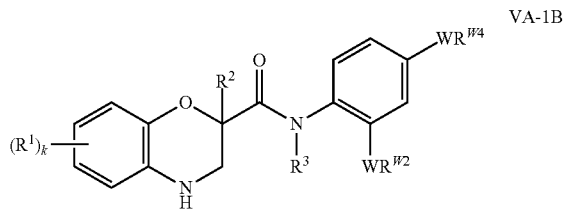

wherein each of $WR^{W2}$ and $WR^{W4}$ is independently selected from CN, $CF_3$, $OCF_3$, —$OC_1$—$C_3$ aliphatic, —C≡$CCH_2N(R')(R')$, halo, $C_1$-$C_6$ straight or branched aliphatic, 3-12 membered cycloaliphatic, phenyl, 3-12 membered bicyclic, $C_5$-$C_{10}$ heteroaryl or $C_3$-$C_7$ heterocyclic, wherein said bicyclic, heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, $C_1$-$C_6$ straight or branched aliphatic, CN, —COOR', —COR', —$O(CH_2)_2N(R')(R')$, —$O(CH_2)N(R')(R')$, —$CON(R')(R')$, —$(CH_2)_2OR'$, —$(CH_2)OR'$, $CH_2CN$, —$N(R')(R')$, —NR'C(O)OR', —NR'C(O)R', —$(CH_2)_2N(R')(R')$, —$(CH_2)N(R')(R')$ optionally substituted phenyl or phenoxy, or optionally substituted $C_3$-$C_7$ heterocyclic, wherein said heterocyclic has up to 1 heteroatom selected from O, S, or N.

19. The method according to claim 18, wherein $WR^{W4}$ is a substituted $C_1$-$C_6$ straight or branched aliphatic, $C_3$-$C_7$ heterocyclic, 3-12 membered cycloaliphatic, or 3-12 membered bicyclic and $WR^{W2}$ is —C≡$CCH_2N(R)(R)$, —$(CH_2)_3N(R')$ (R'), —$(CH_2)_2N(R')(R')$, —$(CH_2)N(R')(R')$ or —$N(R')(R')$.

20. The method according to claim 15, wherein said compound has the Formula VA-1C:

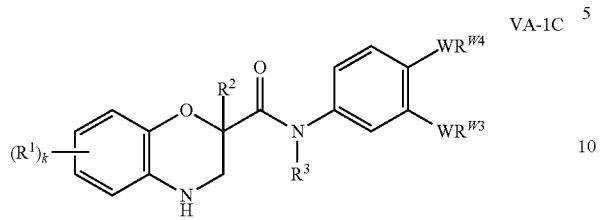

wherein WR$^{W3}$ is selected from halo, —OH, —OCF$_3$, NH$_2$, CN, CHF$_2$, NHR', N(R)$_2$, —NHC(O)R', —NHC(O)OR', NHSO$_2$R', —OR', CH$_2$OH, CH$_2$N(R')$_2$, C(O)OR', C(O)N(R')$_2$, SO$_2$NHR', SO$_2$N(R')$_2$, OSO$_2$N(R')$_2$, OSO$_2$CF$_3$, C$_1$-C$_6$ straight or branched aliphatic, 3-12 membered cycloaliphatic, or CH$_2$NHC(O)OR' and WR$^{W4}$ is independently selected from CN, CF$_3$, OCF$_3$, —SO$_2$R', —OC$_1$-C$_3$ aliphatic, halo, C$_1$-C$_6$ straight or branched aliphatic, 3-12 membered cycloaliphatic, phenyl, C$_5$-C$_{10}$ heteroaryl or C$_3$-C$_7$ heterocyclic, wherein said heteroaryl or heterocyclic has up to 3 heteroatoms selected from O, S, or N, wherein said WR$^{W4}$ is independently and optionally substituted with up to three substituents selected from —OR', —CF$_3$, —OCF$_3$, SR', S(O)R', SO$_2$R', —SCF$_3$, halo, C$_1$-C$_6$ straight or branched aliphatic, CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', CH$_2$CN, optionally substituted phenyl or phenoxy, —N(R')(R'), —NR'C(O)OR', —NR'C(O)R', —(CH$_2$)$_2$N(R')(R'), or —(CH$_2$)N(R')(R').

21. The method according to claim 20, wherein WR$^{W4}$ is a substituted C$_1$-C$_6$ straight or branched aliphatic, C$_3$-C$_7$ heterocyclic, 3-12 membered cycloaliphatic, or 3-12 membered bicyclic and WR$^{W2}$ is —C≡CCH$_2$N(R')(R'), —(CH$_2$)$_3$N(R')(R'), —(CH$_2$)$_2$N(R')(R'), —(CH$_2$)N(R')(R') or —N(R')(R').

22. The method according to claim 15, wherein said compound has the Formula VA—1D:

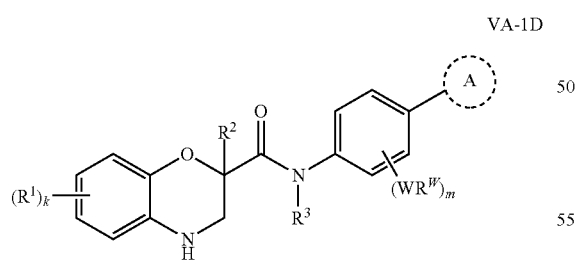

ring A is a 5-7 membered monocyclic or bicyclic, heterocyclic or heteroaryl ring optionally substituted with up to n occurrences of -Q—R$^Q$, Q is W;

R$^Q$ is R$^W$; and m is 0-4; and n is 0-4.

23. The method according to claim 15, wherein said compound has the Formula VA—2:

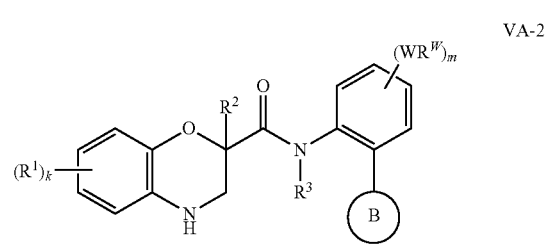

wherein:

ring B is a 5-7 membered monocyclic or bicyclic, heterocyclic or heteroaryl ring optionally substituted with up to n occurrences of -Q-R$^Q$, Q is W;

R$^Q$ is R$^w$; and m is 0-4; and n is 0-4.

24. The method according to claim 1, wherein said compound is selected from the group consisting of:

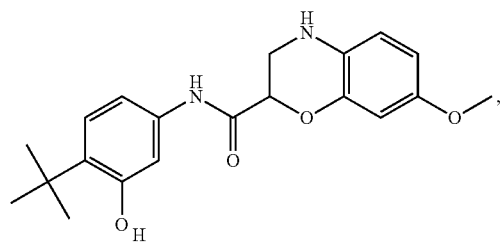

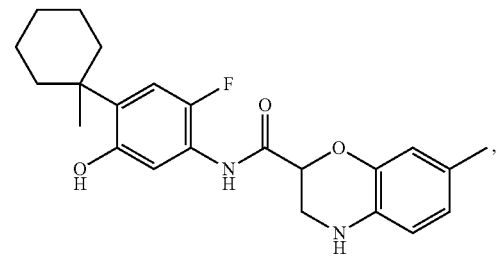

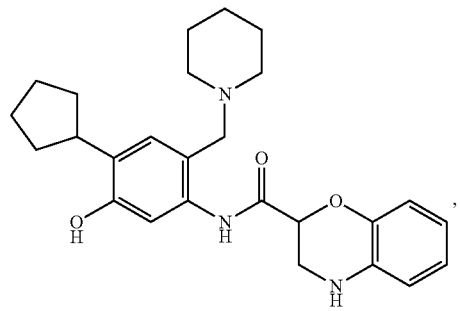

215
-continued
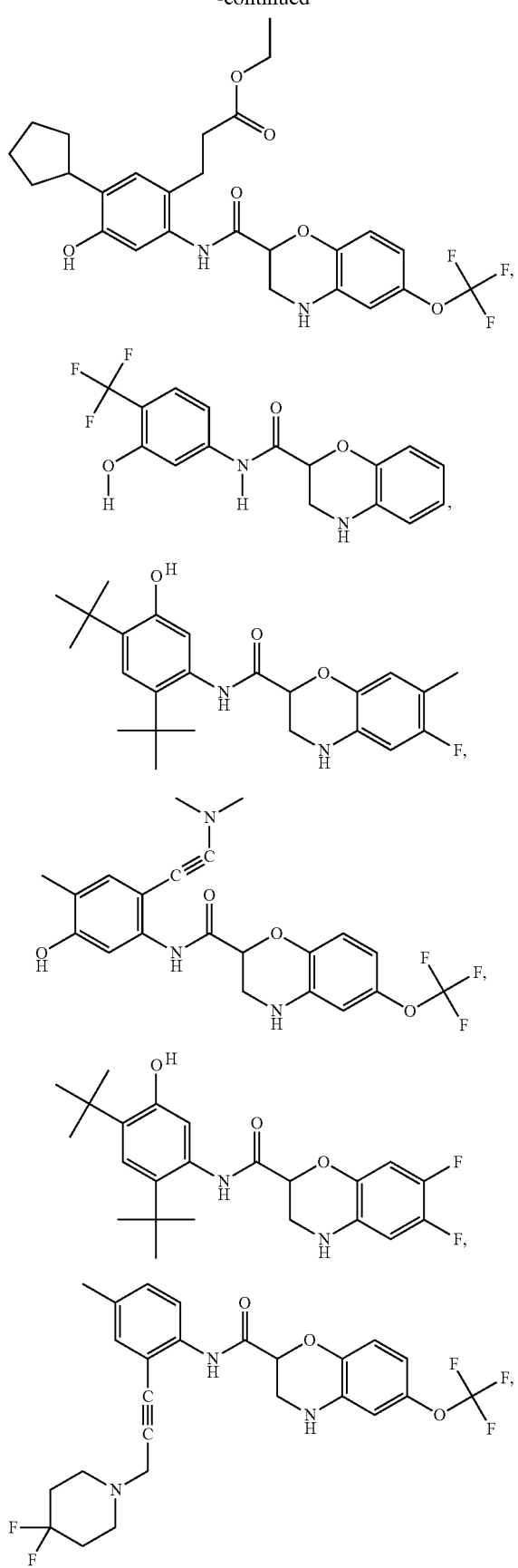
216
-continued
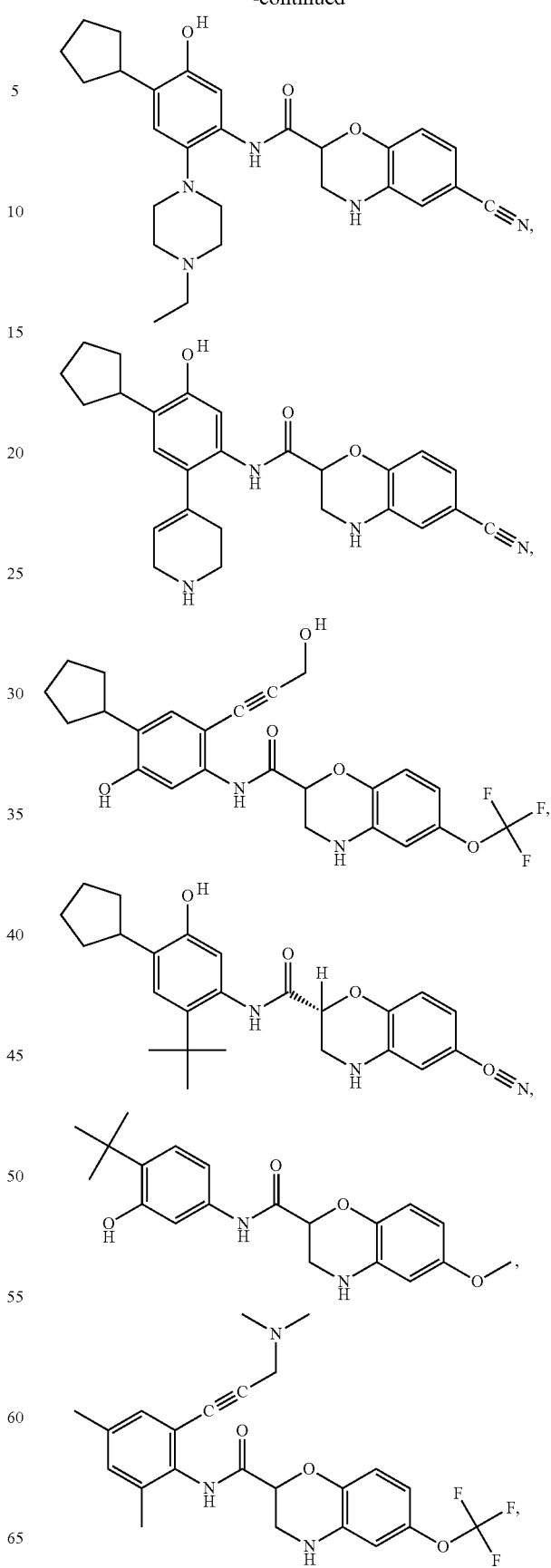

217
-continued
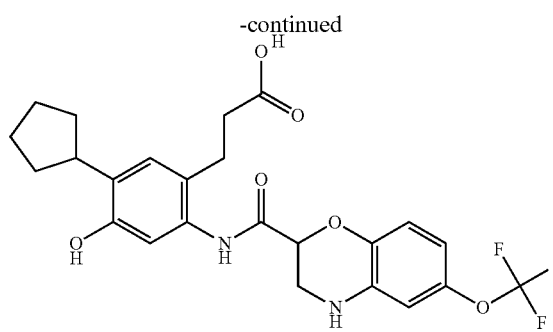
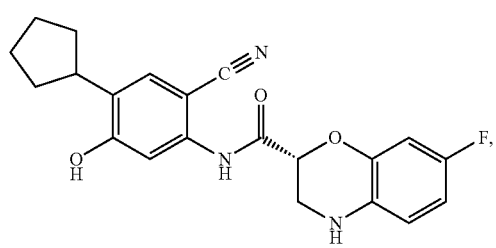
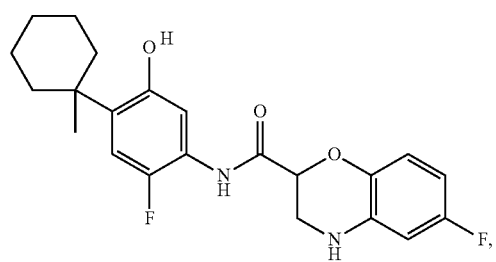
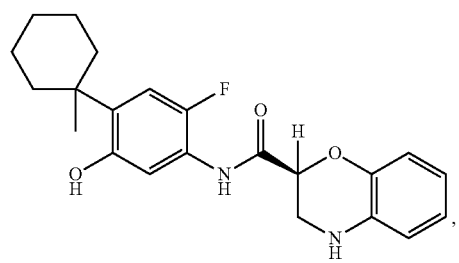
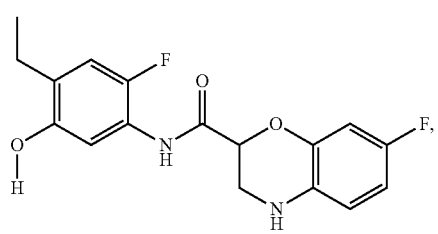
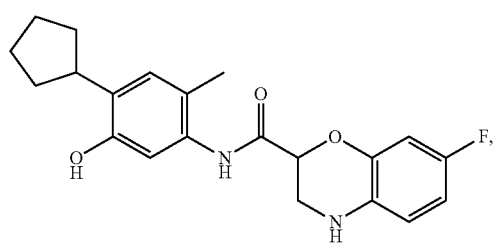
218
-continued
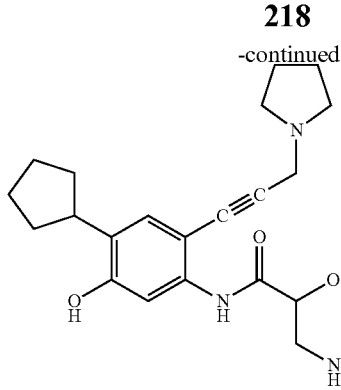
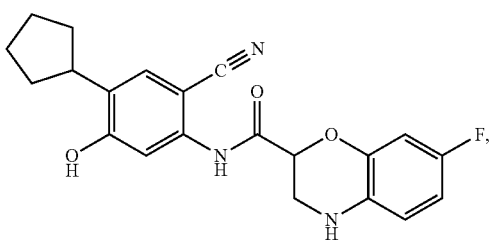
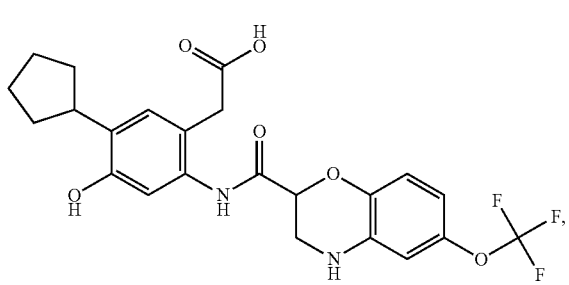
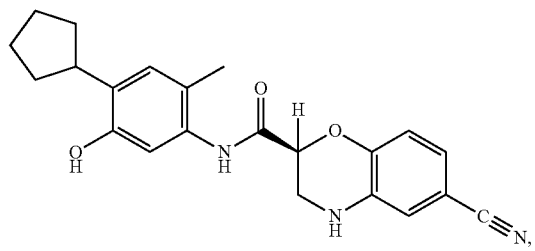
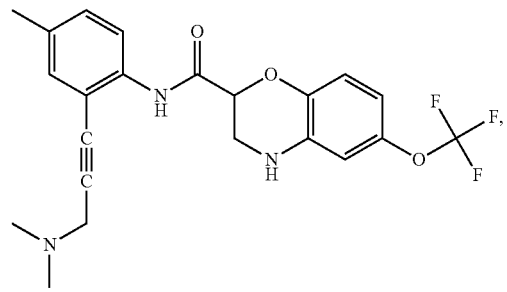
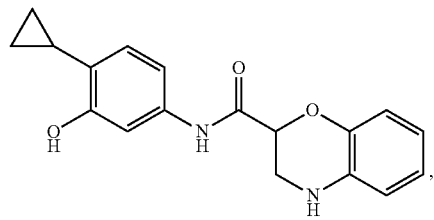

219
-continued
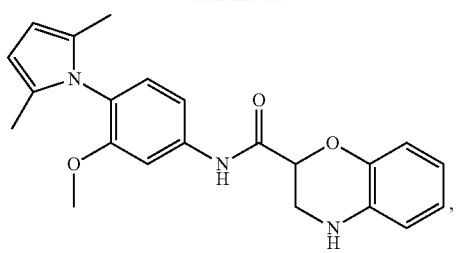
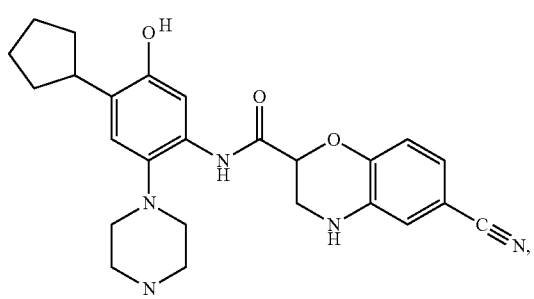
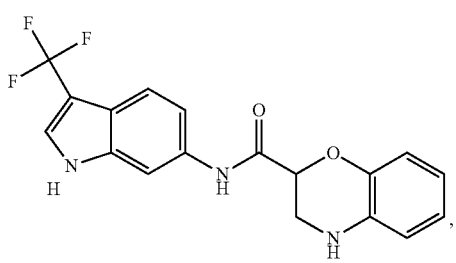
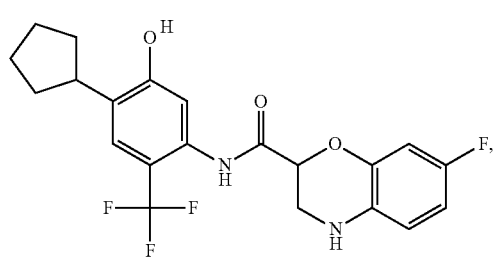
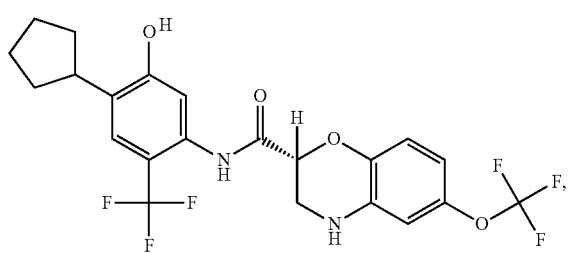
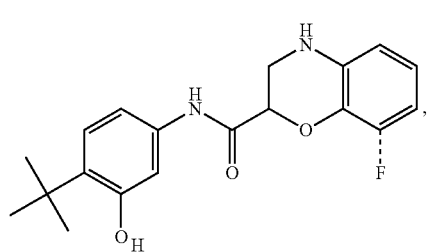
220
-continued
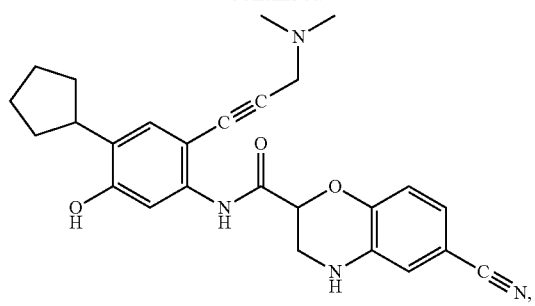
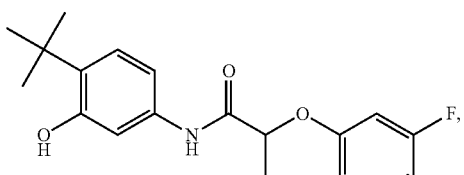
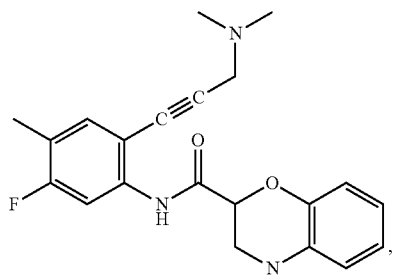
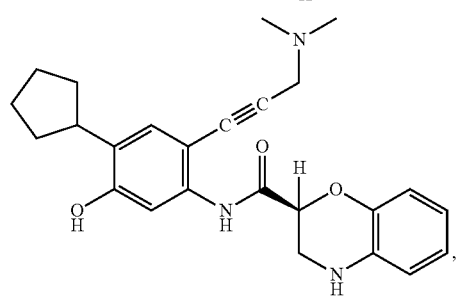
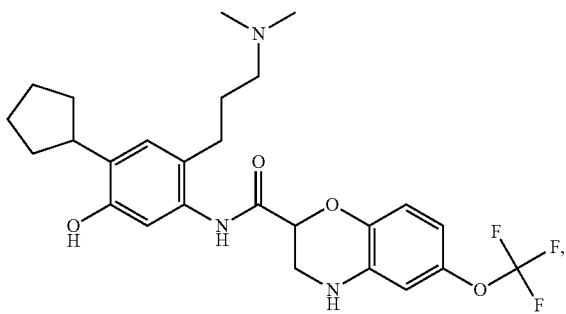
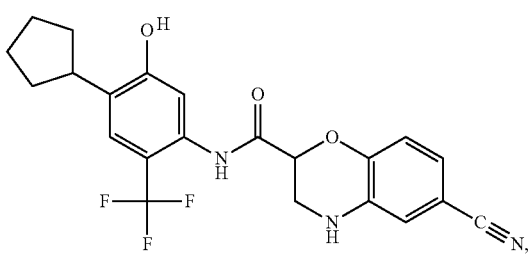

221
-continued
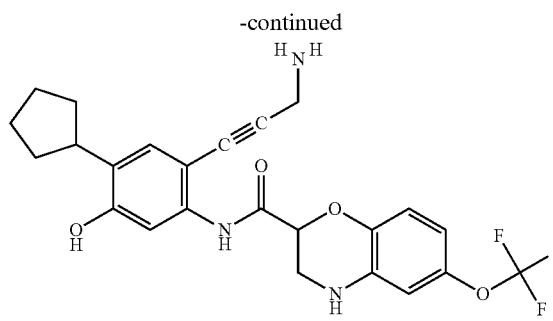
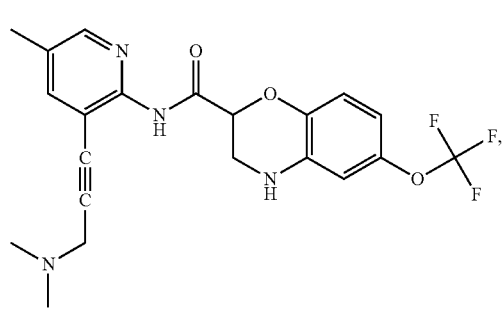
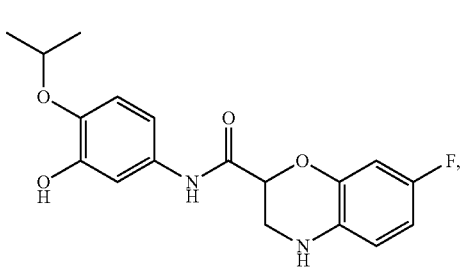
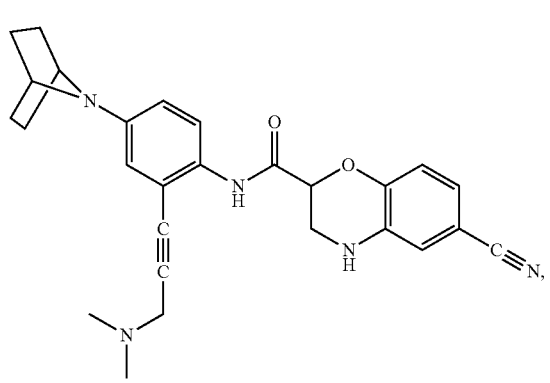
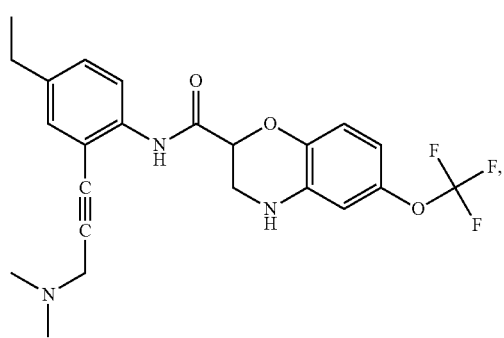
222
-continued
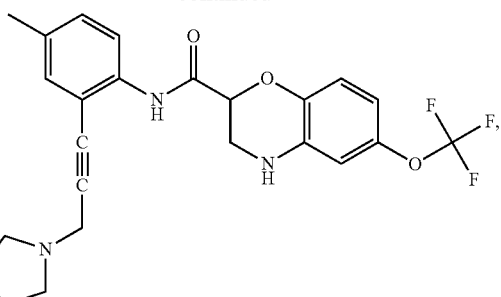
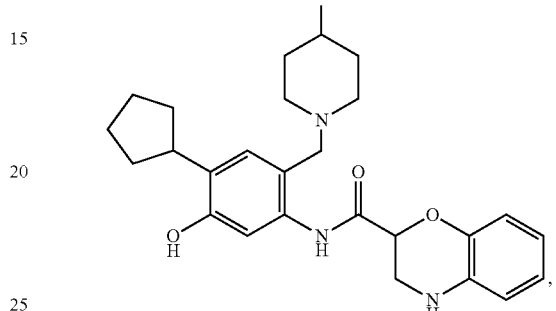
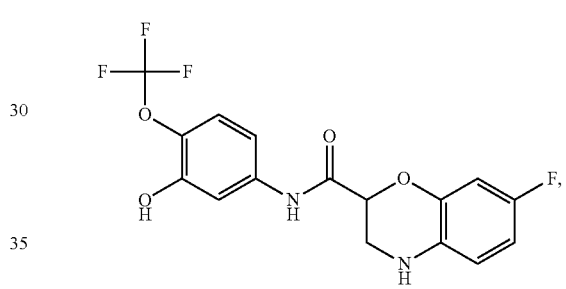
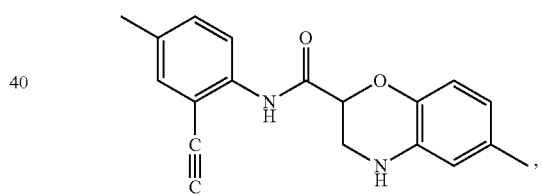
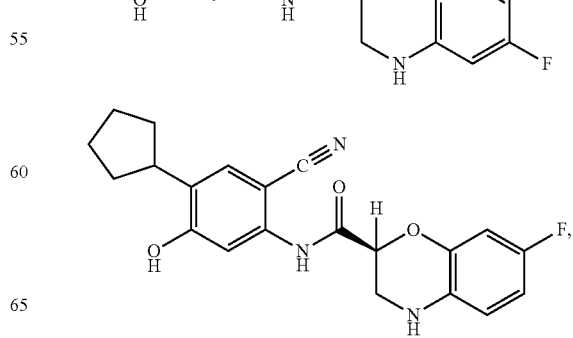

223
-continued
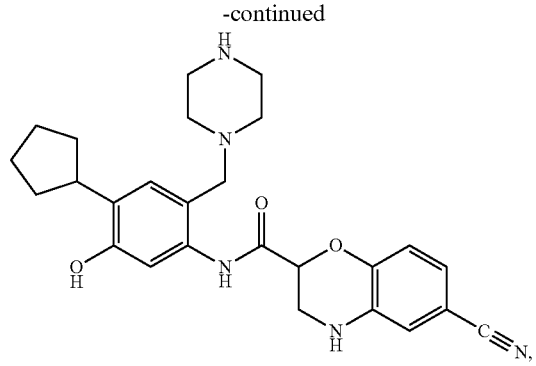
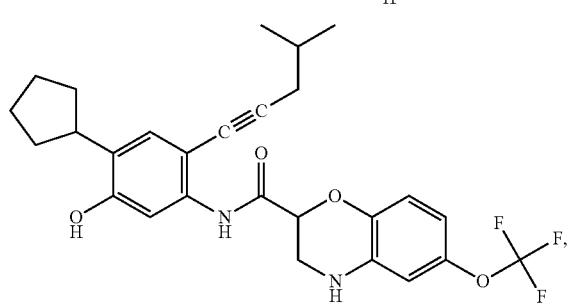
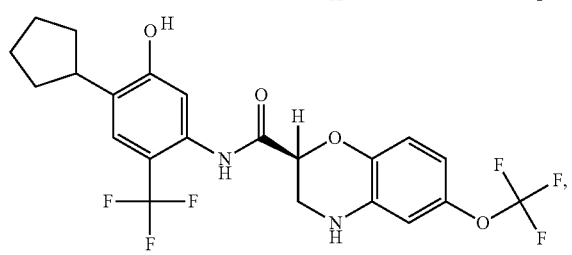
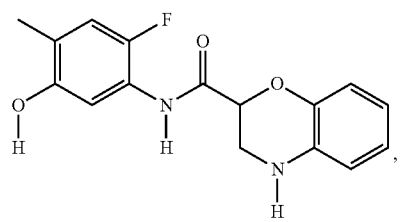
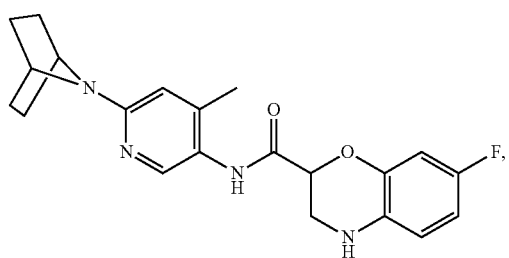
224
-continued
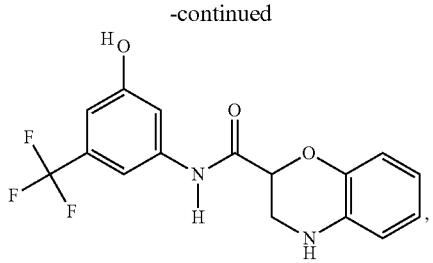
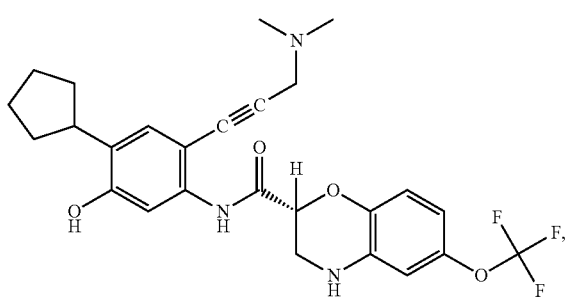
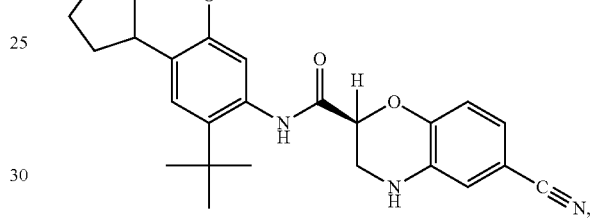
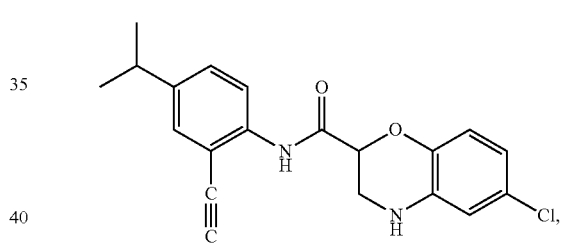
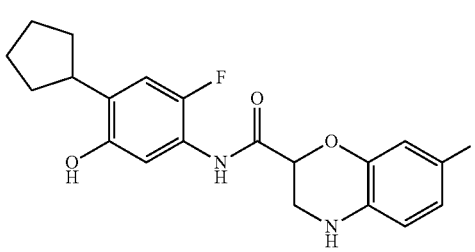
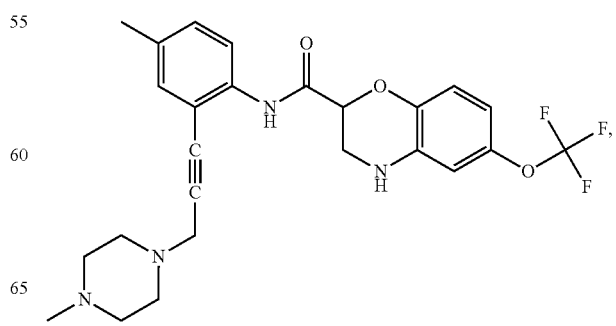

225
-continued
226
-continued
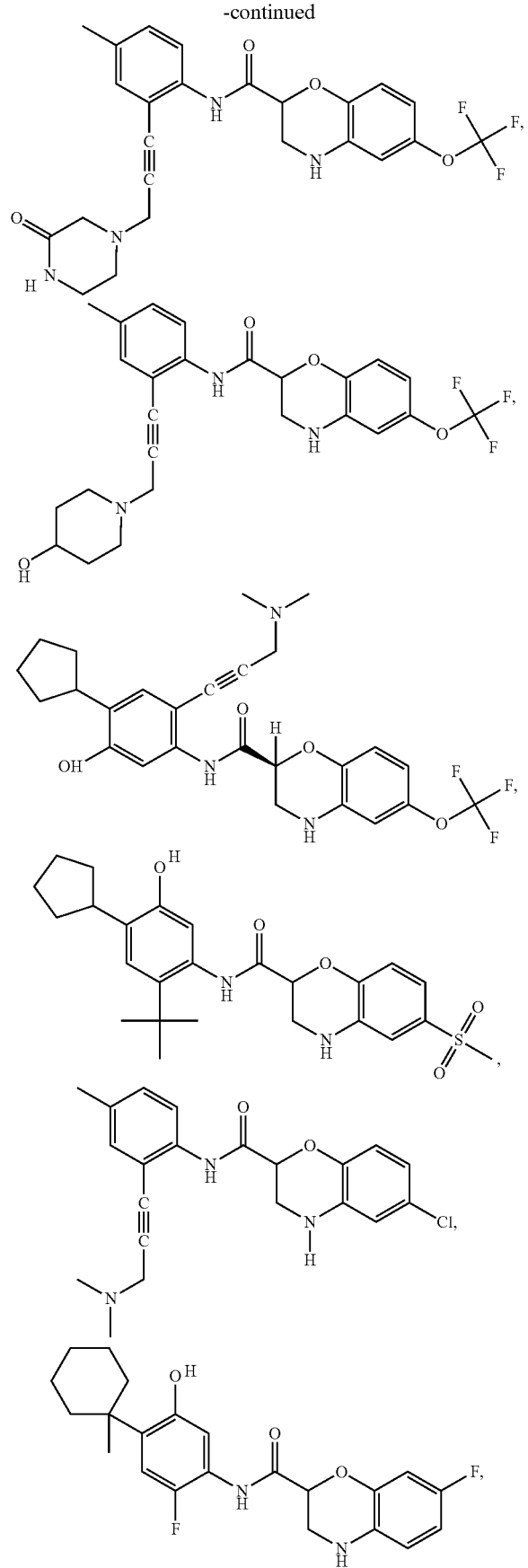
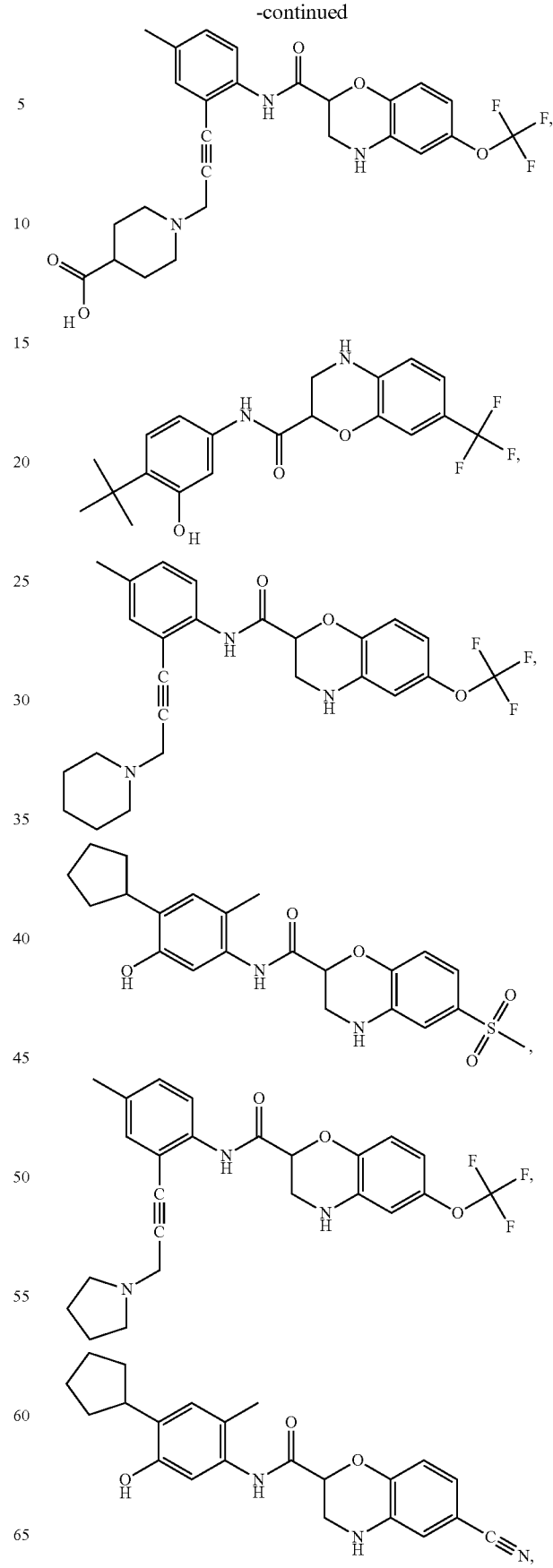

227
-continued
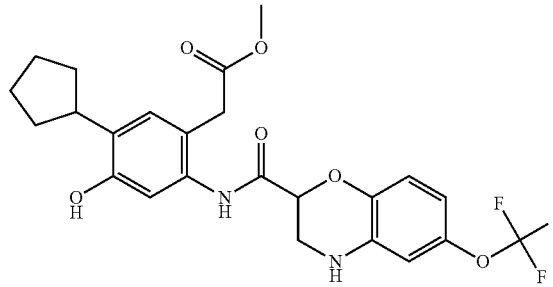
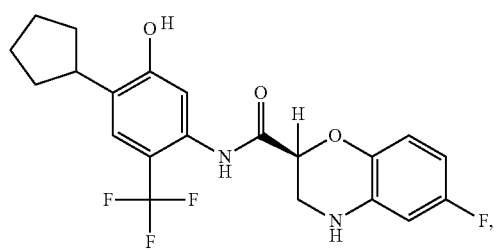
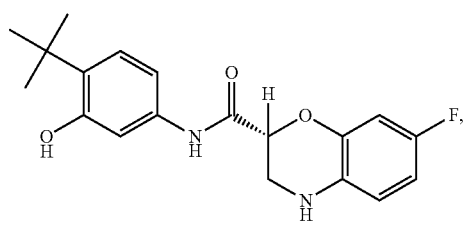
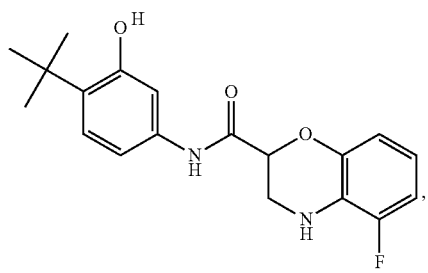
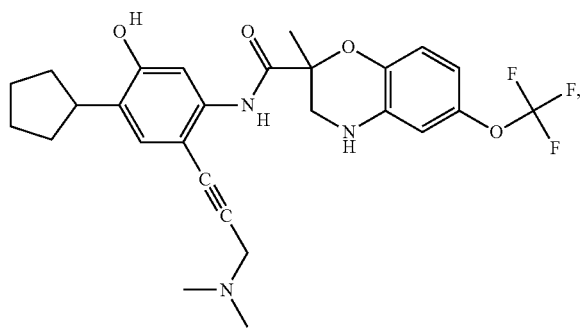
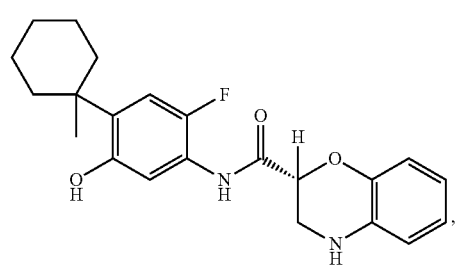
228
-continued
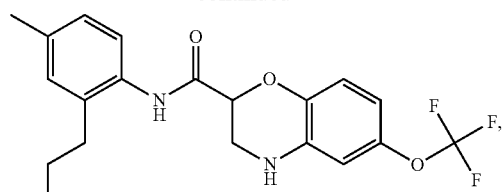
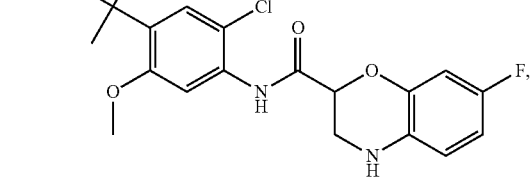
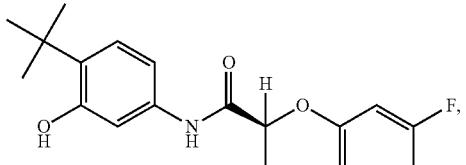
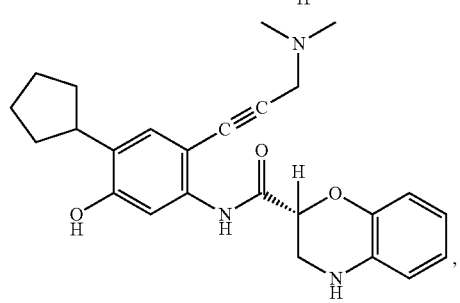
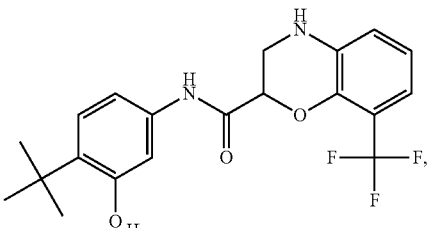
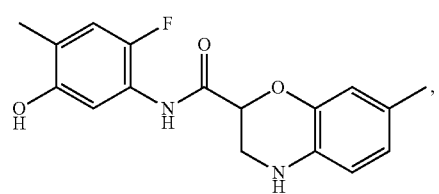
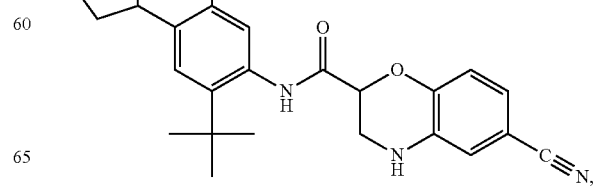

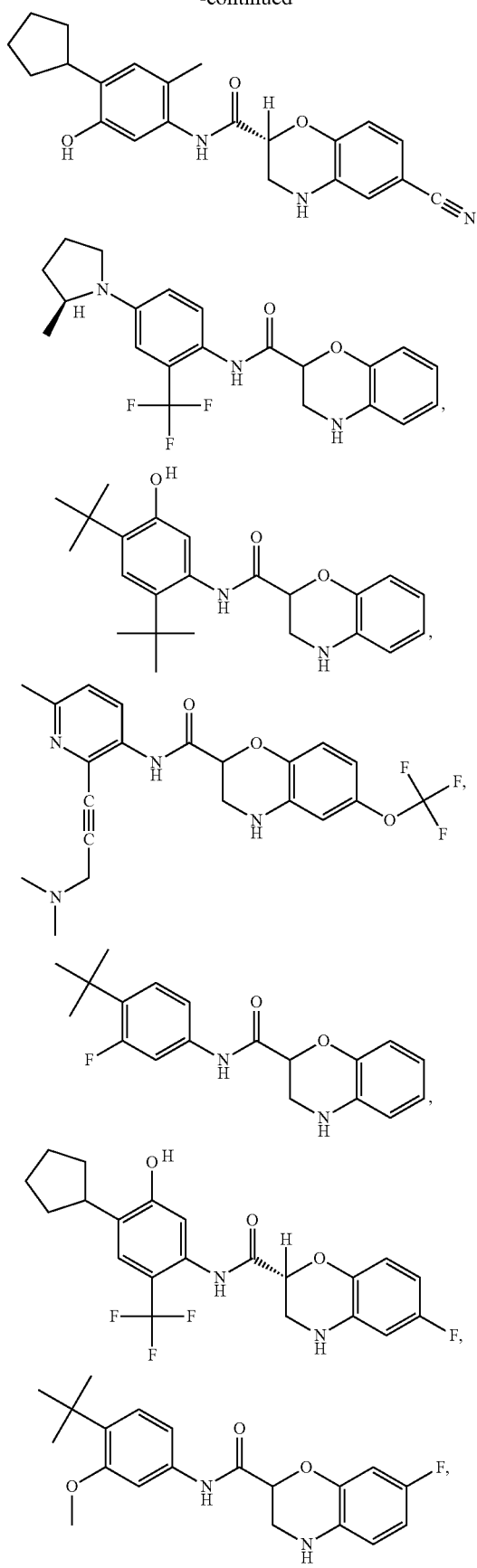
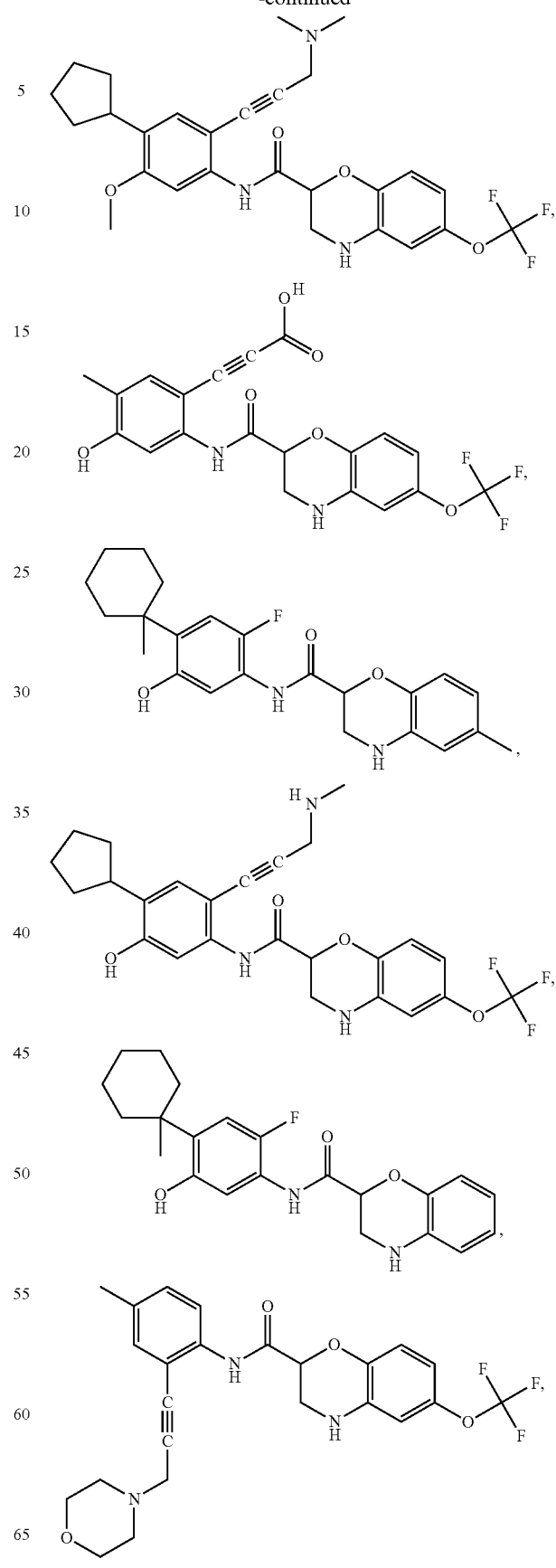

231
-continued
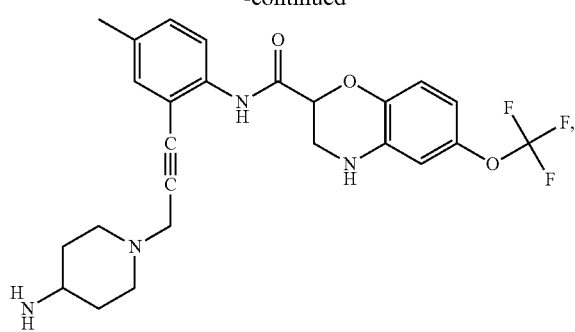
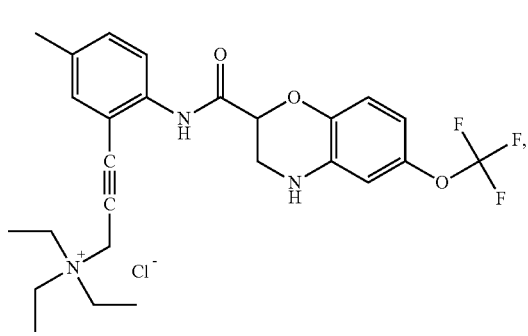
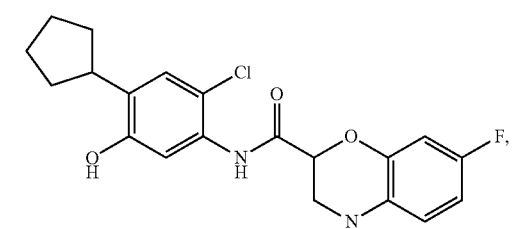
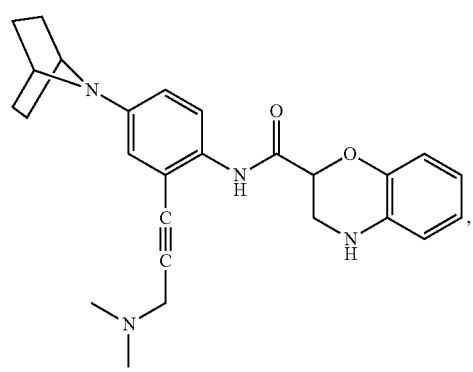
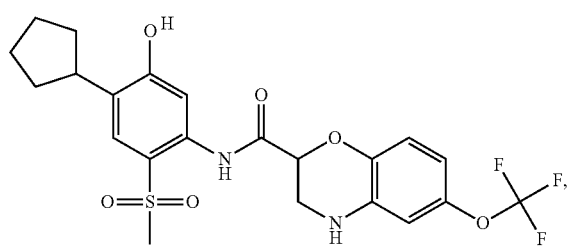
232
-continued
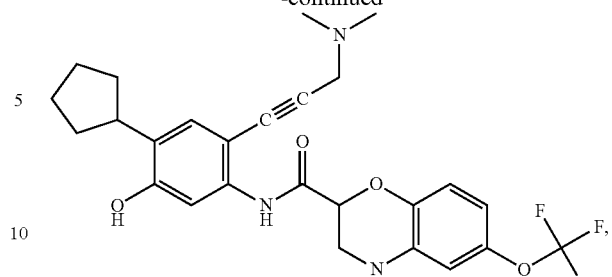
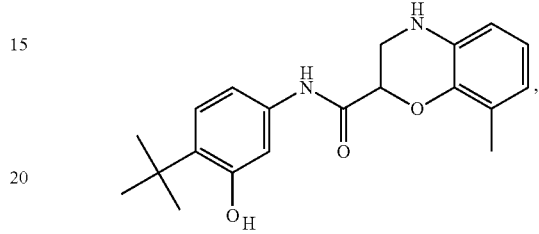
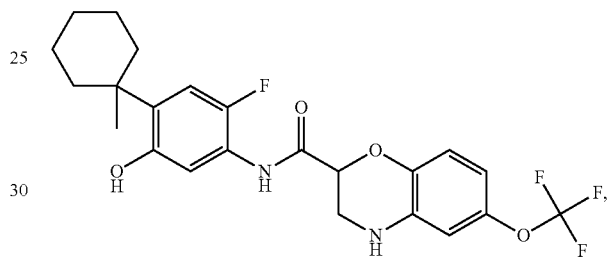
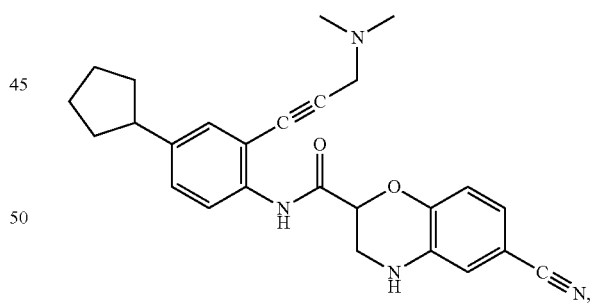
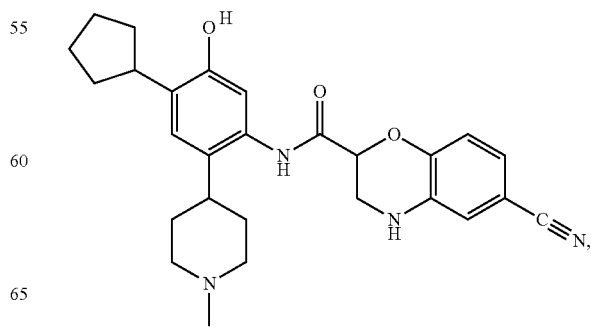

233
-continued
234
-continued
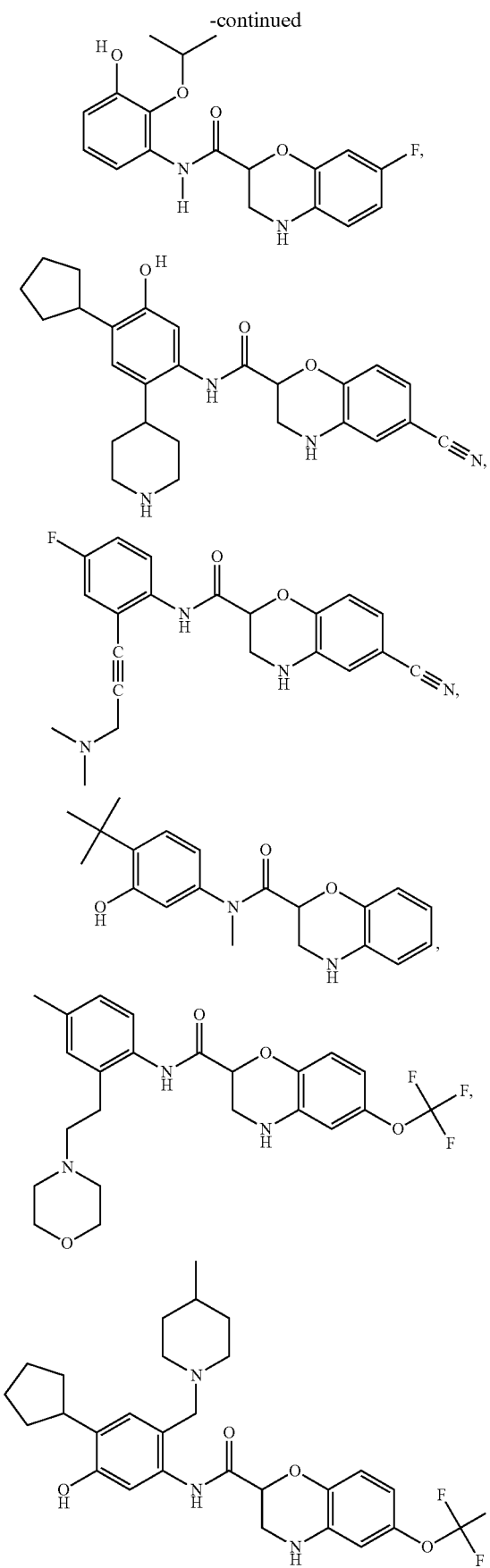
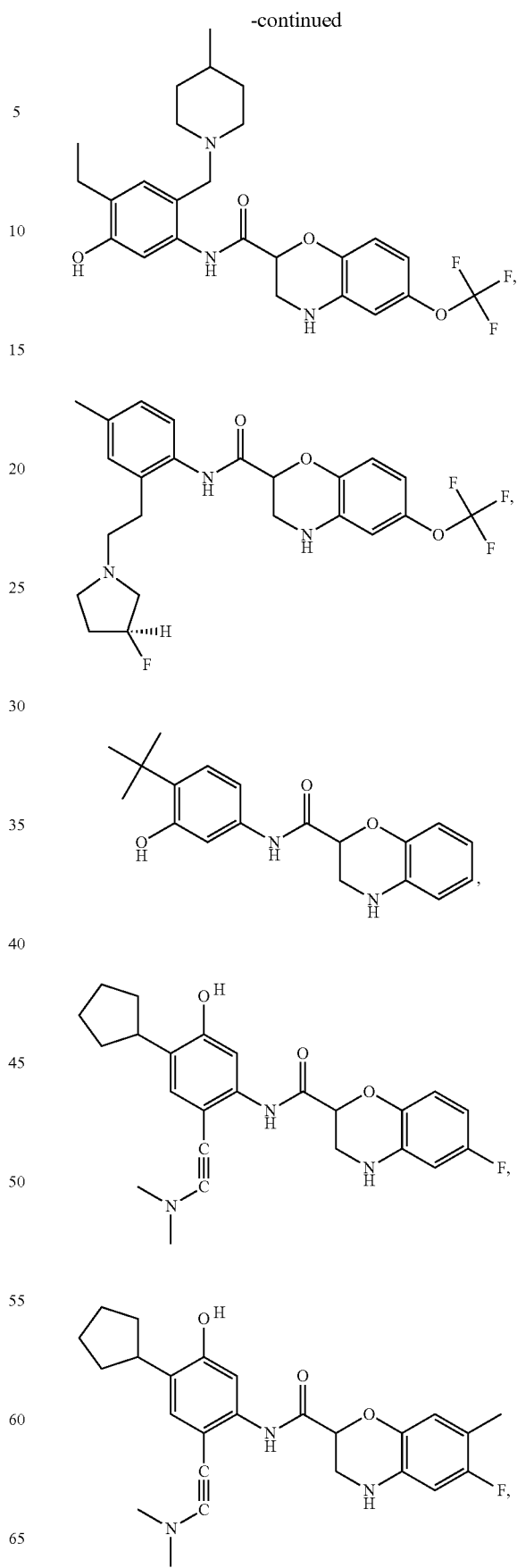

235
-continued
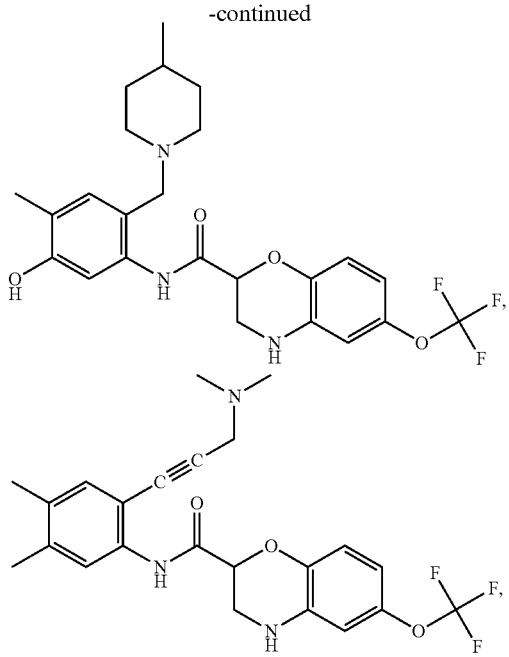
236
-continued
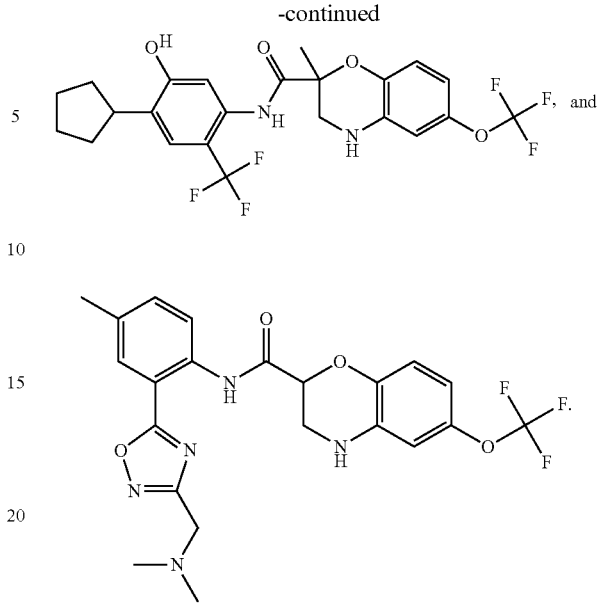
* * * * *